(12) United States Patent
Shair et al.

(10) Patent No.: US 10,508,121 B2
(45) Date of Patent: Dec. 17, 2019

(54) CORTISTATIN ANALOGUES AND SYNTHESES AND USES THEREOF

(71) Applicant: President and Fellows of Harvard College, Cambridge, MA (US)

(72) Inventors: Matthew D. Shair, Lexington, MA (US); Juergen Ramharter, Vienna (AT); Henry Efrem Pelish, Newton, MA (US); Brian Bor-Jen Liau, Belmont, MA (US); Jae Young Ahn, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/293,410

(22) Filed: Mar. 5, 2019

(65) Prior Publication Data
US 2019/0185484 A1    Jun. 20, 2019

Related U.S. Application Data

(60) Continuation of application No. 15/981,575, filed on May 16, 2018, now Pat. No. 10,273,241, which is a (Continued)

(51) Int. Cl.
C07D 493/08 (2006.01)
C07K 14/575 (2006.01)
(Continued)

(52) U.S. Cl.
CPC .......... *C07D 493/08* (2013.01); *C07D 493/22* (2013.01); *C07D 519/00* (2013.01); *C07K 14/575* (2013.01); *C07K 16/26* (2013.01)

(58) Field of Classification Search
CPC .................................................. C07D 493/08
(Continued)

(56) References Cited

U.S. PATENT DOCUMENTS 2,886,589 A   5/1959  Novello et al.
4,853,224 A   8/1989  Wong
(Continued)

FOREIGN PATENT DOCUMENTS

EP            0562849 A2    9/1993
WO    WO 1997/043417 A1   11/1997
(Continued)

OTHER PUBLICATIONS

U.S. Pat. No. 9,127,019, B2, U.S. Appl. No. 14/293,743, Flyer et al., Sep. 8, 2015.
(Continued)

*Primary Examiner* — Nizal S Chandrakumar
(74) *Attorney, Agent, or Firm* — Knowles Intellectual Property Strategies, LLC

(57) ABSTRACT

Provided herein are compounds of Formula (A), (B), (C), (D) and (E), pharmaceutically acceptable salts, quaternary amine salts, and N-oxides thereof, and pharmaceutical compositions thereof.

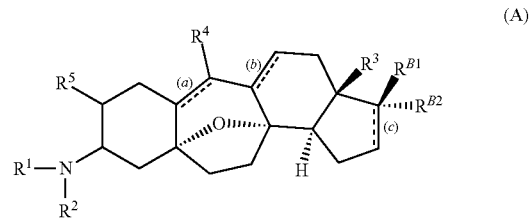

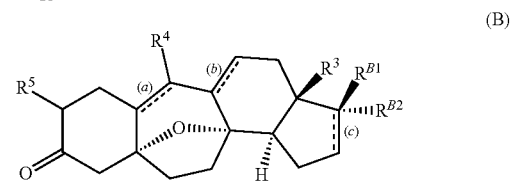

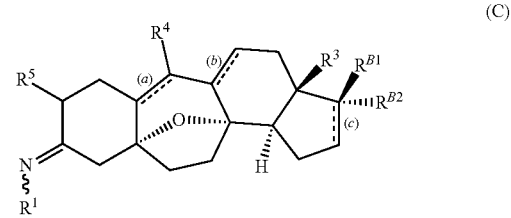

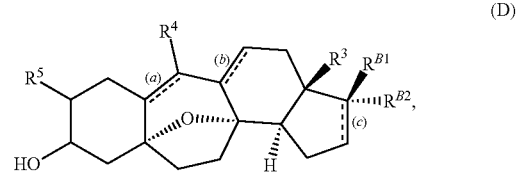

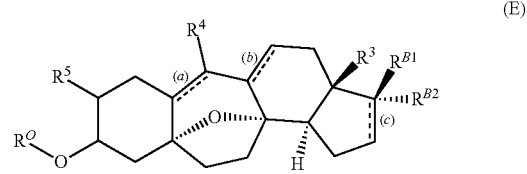

Compounds of Formula (A), (B), (C), (D), and (E) are contemplated useful as therapeutics for treating a wide variety of conditions, e.g., including but not limited to, conditions associated with angiogenesis and with CDK8 and/or CDK19 kinase activity. Further provided are methods of inhibiting CDK8 and/or CDK19 kinase activity, methods of modulating the □-catenin pathway, methods of modulating STAT 1 activity, methods of modulating the TGFβ/BMP pathway, methods of modulating HIF-1-alpha activity in a cell, and methods of increasing BIM expression to induce apoptosis, using a compound of Formula (A), (B), (C), (D),
(Continued)

or (E). Further provided are CDK8 and CDK19 point mutants and methods of use thereof.

12 Claims, 46 Drawing Sheets

Specification includes a Sequence Listing.

Related U.S. Application Data division of application No. 15/192,629, filed on Jun. 24, 2016, now Pat. No. 9,994,582, which is a continuation of application No. PCT/US2014/072365, filed on Dec. 24, 2014.

(60) Provisional application No. 61/993,329, filed on May 15, 2014, provisional application No. 61/935,240, filed on Feb. 3, 2014, provisional application No. 61/920,674, filed on Dec. 24, 2013.

(51) Int. Cl.
  *C07D 493/22* (2006.01)
  *C07K 16/26* (2006.01)
  *C07D 519/00* (2006.01)

(58) Field of Classification Search
  USPC .......................................................... 546/139
  See application file for complete search history.

(56) References Cited

U.S. PATENT DOCUMENTS

| | | | |
|---|---|---|---|
| 4,863,457 | A | 9/1989 | Lee |
| 4,997,652 | A | 3/1991 | Wong |
| 5,098,443 | A | 3/1992 | Parel et al. |
| 5,185,152 | A | 2/1993 | Peyman |
| 5,378,475 | A | 1/1995 | Smith et al. |
| 5,410,016 | A | 4/1995 | Hubbell et al. |
| 5,443,505 | A | 8/1995 | Wong et al. |
| 5,554,187 | A | 9/1996 | Rizzo, III |
| 5,710,182 | A | 1/1998 | Reunamaki et al. |
| 5,725,493 | A | 3/1998 | Avery et al. |
| 6,177,095 | B1 | 1/2001 | Sawhney et al. |
| 6,632,457 | B1 | 10/2003 | Sawhney |
| 6,803,031 | B2 | 10/2004 | Rabinowitz et al. |
| 8,642,766 | B2 | 2/2014 | Shenvi et al. |
| 8,791,263 | B2 | 7/2014 | Kobayashi et al. |
| 9,127,019 | B2 | 9/2015 | Flyer et al. |
| 2003/0060425 | A1 | 3/2003 | Ahlem et al. |
| 2003/0149287 | A1 | 8/2003 | Zasloff et al. |
| 2004/0220161 | A1 | 11/2004 | Ahlem et al. |
| 2005/0014737 | A1 | 1/2005 | Agoston et al. |
| 2006/0014727 | A1 | 1/2006 | Karsan et al. |
| 2006/0094696 | A1 | 5/2006 | Leese et al. |
| 2007/0004689 | A1 | 1/2007 | Agoston et al. |
| 2007/0225256 | A1 | 9/2007 | Leese et al. |
| 2009/0023666 | A1 | 1/2009 | Gardiner et al. |
| 2010/0168141 | A1 | 7/2010 | Evans et al. |
| 2011/0190323 | A1 | 8/2011 | Flyer et al. |
| 2012/0083484 | A1 | 4/2012 | Castro et al. |
| 2012/0190659 | A1 | 7/2012 | Corey et al. |
| 2014/0038958 | A1 | 2/2014 | Ronnison et al. |
| 2014/0155376 | A1 | 6/2014 | Hendricks et al. |
| 2016/0016971 | A1 | 1/2016 | Valente |

FOREIGN PATENT DOCUMENTS

| | | |
|---|---|---|
| WO | WO 1998/029438 A2 | 7/1998 |
| WO | WO 2000/041545 A2 | 7/2000 |
| WO | WO 2000/066611 A1 | 11/2000 |
| WO | WO 2001/023405 A2 | 4/2001 |
| WO | WO 2001/027135 A2 | 4/2001 |
| WO | WO 2001/030802 A2 | 5/2001 |
| WO | WO 2003/004518 A2 | 1/2003 |
| WO | WO 2003/063791 A2 | 8/2003 |
| WO | WO 2006/093993 A1 | 9/2006 |
| WO | WO 2007/082980 A1 | 7/2007 |
| WO | WO 2007/103162 A2 | 9/2007 |
| WO | WO 2008/064425 A1 | 6/2008 |
| WO | WO 2010/024930 A2 | 4/2010 |
| WO | WO 2010/123545 A2 | 10/2010 |
| WO | WO 2012/096934 A2 | 7/2012 |
| WO | WO 2013/122609 A1 | 8/2013 |
| WO | WO 2014/123900 A1 | 8/2014 |
| WO | WO 2014/134169 A1 | 9/2014 |
| WO | WO 2014/199377 A1 | 12/2014 |
| WO | WO 2015/040089 A1 | 3/2015 |
| WO | WO 2015/100420 A1 | 7/2015 |

OTHER PUBLICATIONS

U.S. Pat. No. 9,714,255, B2, U.S. Appl. No. 14/848,086, Flyer et al., Jul. 25, 2017.
U.S. Pat. No. 9,994,582, B2, U.S. Appl. No. 15/192,629, Shair et al., Jun. 12, 2018.
U.S. Pat. No. 10,202,400, B2, U.S. Appl. No. 15/658,201, Flyer et al., Feb. 12, 2019.
2018/0118778, A1, U.S. Appl. No. 15/852,178, Shair et al., May 3, 2018.
2018/0134725, A1, U.S. Appl. No. 15/807,301, Shair et al., May 17, 2018.
2018/0135134, A1, U.S. Appl. No. 15/807,277, Shair et al., May 17, 2018.
2018/0298024, A1, U.S. Appl. No. 16/016,199, Shair et al., Oct. 18, 2018.
2018/0319814, A1, U.S. Appl. No. 15/981,575, Shair et al., Nov. 8, 2018.
2018/0369230, A1, U.S. Appl. No. 16/016,242, Shair et al., Dec. 27, 2018.
2019-0062340, A1, U.S. Appl. No. 16/078,569, Shair et al., Feb. 28, 2019.
Abushanab et al., 9(10 leads to 19)abeo steriods. Total synthesis of abeo-estradiol, abeo-estradiol 3-methyl ether, and 17 alpha-ethynyl abeo-estradiol-3-methyl ether. JOC Apr. 30, 1976;41(9):1601-3.
Aguayo et al. Angiogenesis in acute and chronic leukemias and myelodysplastic syndromes. Blood. Sep. 15, 2000;96(6):2240-5.
Aoki et al., Cortistatins A, B, C, and D, anti-angiogenic steroidal alkaloids, from the marine sponge Corticum simplex. JACS Mar. 15, 2006;128(10):3148-9.
Aoki et al., Cortistatins J, K, L, novel abeo-0(10-19)-androstane-type steroidal alkaloids with isoquinoline unit, from marine sponge Carticium simplex. Tetrahedron Lett. 2007;48(26)4485-88.
Aoki et al., Structure-activity relationship and biological property of cortistatins, anti-angiogenic spongean steoidal alkaloids. Bioorg. Med. Chem. Nov. 1, 2007;15(21):6758-62. Epub Aug. 21, 2007.
Arefolov V. Presidents and Fellows of Harvard College and Matthew Shair, Case No. 1:17-cv-10785 (D. Mass.).
Atta et al., New Steroidal Alkaloids from the Roots of Buxus sempervirens. J. Nat. Prod. 1999; 62(5):665-69.
Berge et al., Pharmaceutical salts. J. Pharm. Sci. Jan. 1977;66(1):1-19.
Boeckman et al., The Dess-Martin Periodinane: 1,1,1-Triacetoxy-1,1-Dihydro-1,2-Benziodoxol-3(1H)-One. J. Org. Synth. 2000 77:141-52.
Brown, The Pomeranz-Fritsch Reaction, Isoquinoline vs Oxazoles. J. Org. Chem. 1977;42:3208-09.
Brown et al., 1986, Caplus an 1986:627117.
Cassoni et al., Ghrelin and cortistatin in lung cancer: expression of peptides and related receptors in human primary tumors and in vitro effect on the H345 small cell carcinoma cell line. J. Endocrinol. Invest. Oct. 2006; 29(9):781-90—Abstract.
Chen et al., Eryhtropoietin deficiency decreases vascular stability in mice. J. Clin. Invest. Feb. 2008.p. 118(2):526-33.
Cheson et al., National Cancer Institute-sponsored Working Group guidelines for chronic lymphocytic leukemia:revised guidelines for diagnosis and treatment. Blood. Jun. 15, 1996;87(12):4990-7.

(56) References Cited

OTHER PUBLICATIONS

Czako et al. "Discovery of Potent and Practical Antiangiogenic Agents Inspired by Cortistatin A", J. Am. Chem. Soc. vol. 131, No. 25, Apr. 1, 2009.
De Marino et al., A new steroidal alkaloid from a marine sponge *Corticium* sp. Tetrahedron Lett. 1998;39(41):7611-14.
Du Bois et al. Nitrogen Transfer from Nitrodomanganese (v) Complex: Amination of Silyl Enol Ethers. JACS 1996;118(4)915-16.
Duboudin et al., Evidence for [2+2] and [4+2] cycloadditions of allylic Grignard-reagents to benzyne. J. Chem. Soc-Chem Commun. 1977;13:454-55.
Evans et al., New silicon-phosphorous reagents in organic synthesis-carbonyl and conjugate addition-reactions of silicon phosphate esters and related systems. JACS 1978;100(11):3467-77.
Extended European Search Report for EP 09810384.9, dated Mar. 30, 2012.
Ferrara, Vascular endothelial growth factor as a target for anticancer therapy. Oncologist. 2004;9 Suppl 1:2-10.
Folkman, Angiogenesis: an organizing principle for drug discovery? Nat. Rev. Drug Discov. Apr. 2007;6(4):273-86.
Folkman, Antiangiogenesis in cancer therapy—endostatin and its mechanisms of action. Exp. Cell Res. Mar. 10, 2006;312(5):594-607. Epub Dec. 22, 2005.
Folkman, Tumor angiogenesis: therapeutic implications. N. Engl. J. Med. Nov. 18, 1971;285(21):1182-6.
Furrow et al., Practical procedures for the preperation of N-tert-butyldimethylsilylhydrazones and their use in modified Wolff-Kishner reductions and in the synthesis of vinyl halides and gem-dihalides. JACS May 5, 2004;126(17):5436.
Gerber et al., The role of VEGF in normal and neoplastic hematopoiesis. J. Mol. Med. Jan. 2003;81(1):20-31. Epub Dec. 14, 2002.
Grant et al., Matrigel induces thymosin beta 4 gene in differentiating endothelial cells. J. Cell Sci. Dec. 1995;108(Pt 12):3685-94.
Hajos et al., Synthesis and Conversion of 2-Methyl-2-(30oxobutyl)-1,3-cyclopentanedione to the Isomeric Racemic Ketols of the [3.2.1]Bicyclooctane and of the Perhydroindan Series. J. Org. Chem. 1974;39:1612-15.
Hajos et al., Total Synthesis of (+−)-17B-Hydroxy-d9(10)-des-A-Androsten-5-one-[(+−)-2,3,4a,4,5,7,8,9,9aB,9ba-Decahydro-3B-hydroxy-3aB,6-dimethyl-1H-benz[e]inden=7-one]. J. Org. Chem. 1967;32:3008-10.
Hanahan et al., Patterns and emerging mechanisms of the angiogenic switch during tumorigenesis. Cell. Aug. 9, 1996;86(3):353-64.
Huang et al., Control of cyclin D1, p27(Kip1), and cell cycle progression in human capillary endothelial cells by cell shape and cytoskeletal tension. Mol. Biol. Cell. Nov. 9, 1998(11):3179-93.
Hurwitz et al., Bevacizumab plus irinotecan, fluorouracil, and leucoviorin for metastatic colorectal cancer. N. Engl. J. Med. Jun. 3, 2004;350(23):2335-42.
Hussong et al., Evidence of increased angiogenesis in patients with acute myeloid leukemia. Blood. Jan. 1, 2000;95(1):309-13.
International Preliminary Report on Patentability for PCT/US2009/04911, dated Nov. 3, 2011.
International Search Report and Written Opinion for PCT/US2016/40482, dated Sep. 26, 2016.
International Search Report and Written Opinion for PCT/US2009/04911, dated May 4, 2010.
International Search Report and Written Opinion for PCT/US2014/072365 dated May 19, 2015.
International Search Report and Written Opinion for PCT/US2016/31188, dated Aug. 18, 2016.
International Search Report and Written Opinion for PCT/US2016/31279, dated Aug. 25, 2016.
International Search Report and Written Opinion for PCT/US16/68125 dated Mar. 16, 2017.
International Search Report and Written Opinion for PCT/US16/68137 dated Mar. 16, 2017.
International Search Report and Written Opinion for PCT/US16/68143 dated Mar. 23, 2017.
Isaacs et al., Synthesis of an Enantiomerically Pure Intermediate Containing the CD Substructure of Taxol. J. Org. Chem. 1993;58:3938-41.
Jain, Normalizing tumor vaculature with anti-angiogenic therapy:a new paradigm for combination therapy. Nat. Med. Sep. 2001;7(9):987-9.
Kerbel et al., Clinical translation of angiogenesis inhibitors. Nat. Rev. Cancer. Oct. 2002;2(10):727-39.
Khurana et al., Angiogenesis-dependent and independent phases of intimal hyperplasia. Circulation. Oct. 19, 2004;110(16):2436-43. Epub Oct. 11, 2004.
Klagsbrun et al., Molecular angiogenesis. Chem. Biol. Aug. 1999;6(8):R127-24.
Kohen et al., Solvolysis of 19-substituted androstane derivaties. J. Org. Chem. Jul. 1970;35(7):2272-5.
Kolb et al., Catalytic Asymmetric Dihydroxylation. J. Chem. Rev. 1994;94:2483-547.
Kolonin et al., Reversal of obesity by targeted ablation of adipose tissue. Nat. Med. Jun. 2004;10(6);625-32. Epub May 9, 2004.
Kotoku et al., "Synthetic Stufies of Cortistatin A Analogue from the CD-Ring Fragment of Vitamin D2", Chem. Pharm. Bull. 61(1) 1024-1029, May 13, 2013.
Kozikowski et al., Phosphoniosilyation—an efficient and practical method for the beta-functionalization of enones. J. Org. Chem. 1986;51(17):3400-02.
Kunding, Low temperature Grignard reactions with pure Mg slurries. Trapping of cyclopropylmethyl and benzocyclobutenylmethyl Grignard reagents with CO2. Helvetica Chimica Acta. 1981;64(8):2606-13.
Kupchan et al., Buxus alkaloids. 13. A synthetic approach to the 9(10-19) abeo-pregnane system. JACS. Nov. 22, 1967;89(24):6327-32.
Lee et al., Entantioselective synthesis of (+)-cortistatin A, a potent and selective inhibitor of endothelial cell proliferation. JACS Dec. 17, 2008;130(50):16864-6.
Liu et al., 5-(Trimethylstannyl)-2H-pyran-2-one and 3-(Trimethylstannyl)-2H-pyran-2-one: New 2H-Pyran-2-one Synthons. JOC Sep. 20, 1996;61(19):6693-6699.
Magnus et al., Oxidative addition of azide anion to triisopropylsilyl enol ethers: Synthesis of [alpha]-azido ketones and 2-amino(methoxycarbonyl)alk-2-en-1-ones. Tetrahedron 1995;51(41):11075-86.
Mammoto et al., A mechanosensitivie transcriptional mechanism that controls angiogenesis. Nature. Feb. 26, 2009;457(7233)1103-8.
Mayer, Two steps forward in the treatment of colorectal cancer. N. Engl. J. Med. Jun. 3, 2004;350(23):2406-8.
Molica et al., Prognostic value of enhanced bone marrow angiogenesis in early B-cell chronic lymphocytic leukemia. Blood. Nov. 1, 2002;100(9):3344-51.
Moses, The regulation of neovascularization of matrix metalloproteinases and their inhibitors. Stem Cells. 1997;15(3):180-9.
Moulton et al., Angiogenesis inhibitors endostatin or TNP-470 reduce intimal neovascularization and plaque growth in apolipoprotein E-deficient mice. Circulation. Apr. 6, 1999;99(13):1726-32.
Mousseau et al., An analog of the natural steroidal alkaloid Cortistatin A potently suppresses Tat dependent HIV transcription, Cell Host Microbe. Jul. 19, 2012; 12(1): 97-108. doi:10.1016/j.chom.2012.05.016.
Neef et al., A radical approach to the synthesis of 9(10-19)abeosteroids. Tetrahedron. 1993;49(4):833-40.
Neef et al., New steroids by Simmons-Smith methylenation and subsequent rearrangement. J. Org. Chem. 1987;52(18):4143-46.
Nicolaou et al., Total synthesis of (+)-cortistatin A. (Supportive Information) Angew. Chem. Int. Ed. Engl. 2008;47(38):1-57.
Nicolaou et al., Total synthesis of (+)-cortistatin A. Angew. Chem. Int. Ed. Engl. 2008;47(38):7310-3.
Ohtani et al., Blockade of vascular endothelial growth factor suppresses experimental restenosis after intraluminal injury by inhibiting recruitment of monocye lineage cells. Circulation. Oct. 19, 2004;110(16):2444-52. Epub Oct. 11, 2004.
Ottow et al., Highly diastereoselective synthesis of 11 beta, 17 beta-diaryl-18a-homo-19-nor steroids. Journal Fur Praktishche Chemie-Chemiker-Zeitung. 1997;339(4):365-70.

(56) References Cited

OTHER PUBLICATIONS

Peacock et al., Angiogenesis inhibition suppresses collagen arthritis. J. Exp. Med. Apr. 1, 1992;175(4):1135-8.

Pelish et al. Mediator Kinase Inhibition Further Activates Super-Enhancer Associated Genes in AML. Nature. Oct. 8, 2015; 526(7572): 273-276.

Perez-Atayde et al., Spectrum of tumor angiogenesis in the bone marrow of children with acute lymphoblastic leukemia. Am. J. Pathol. Mar. 1997;150(3):815-21.

Puckett et al., The structure of buxenine-G. Tetrahedron Lett. 1966;7(32):3815-18.

Rastinejad et al., Regulation of the activity of a new inhibitor of angiogenesis by a cancer suppressor gene. Cell. Feb. 10, 1989;56(3):345-55.

Rigby et al., A general approach to the synthesis of C8-Oxygenated Guaianolides. JOC. 1987;52:34-44.

Shenvi et al., Synthesis of (+)-cortistatin A (Supporting Information). JACS Jun. 11, 2008; 130(23):SI-1-SI-22. Epub May 14, 2008.

Shenvi et al., Synthesis of (+)-cortistatin A JACS Jun. 11, 2008; 130(23):7241-3. Epub May 14, 2008.

Shih et al., Selective stimulation of VEGFR-1 prevents oxygen-induced retinal vascular degeneration in retinopathy of prematurity. J. Clin. Invest. Jul. 2003;112(1):50-7.

Shimizu et al., ABL2/ARG tyrosine kinase mediates SEMA3F-induced RhoA inactivation and cytoskeleton collapse in human glioma cells. J. Biol. Chem. Oct. 3, 2008;283(40):27230-8. Epub Jul. 25, 2008.

Shojima et al., The role of vascular endothelial growth factor in restenosis: the controversy continues. Circulation. Oct. 19, 2004;110(16):2283-6.

Smith et al., Organometallic reagents in synthesis: A new protocol for construction of the indole nucleus. Tetrahedron. 1986;42:2957.

Still et al., Rapid Chromatographic Technique for Perparative Seperations with Moderate Resolution. J. Org. Chem. 1978;43:2923-25.

Street et al., Vascular endothelial growth factor stimulates bone repair by promoting angiogenesis and bone turnover. Proc. Natl. Acad. Sci. USA. Jul. 23, 2002;99(15):9656-61. Epub Jul. 12, 2002.

Tamao et al., (Diisopropoxymethylsilyl)methyl Grignard Reagent: A New, Practically Useful Nucleophilic Hydroxymethylating Agent. J. Org. Chem. 1983;48:2120-22.

Teicher et al., Antiangiogenic agents can increase tumor oxygenation and response to radiation therapy. Radiat. Oncol. Investig. 1994;2(6):269-276.

Vacca et al., Bone marrow angiogenesis and progression in multiple myeloma. Br. J. Haematol. Jul. 1994;87(3):503-8.

Wang et al., Marine-Derived Angiogenesis Inhibitors for Cancer Therapy. Mar. 15, 2013; 11(3): 903-933.

Watanabe et al., Cortistatins E, F, G, and H, four novel steroidal alkaloids from marine sponge Corticium simplex. Tetrahedron. 2007;63(19):4074-79.

Williams et al., Isocyanide addition to pyridinium salts. Efficient entry into substituted nicotinonitrile derivatives. Org. Lett. Dec. 7, 2006;8(25):5789-92.

Yamashita et al., A concise synthesis of the pentacyclic framework of Cortistatins. Org. Lett., Jul. 17, 2008; 10(16): 3413-3415.

Molecular structure of ent-dimethylamine (14B) in the crystal

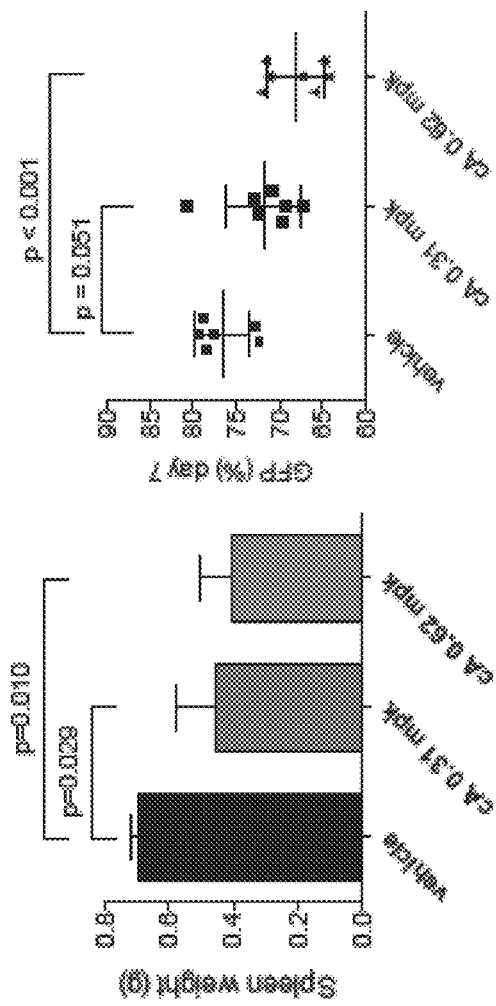
FIG. 14A
FIG. 14B
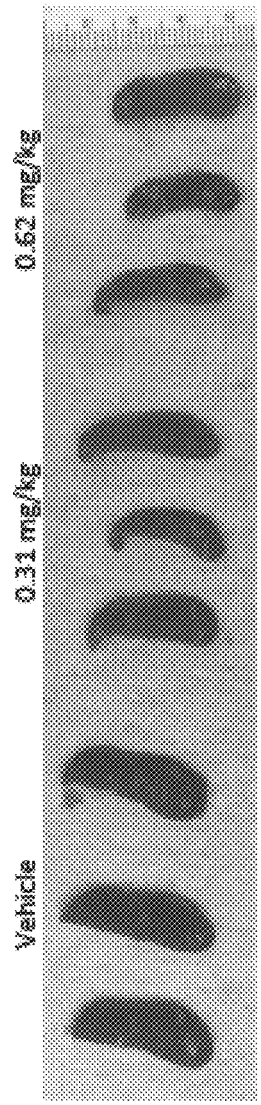
FIG. 14C

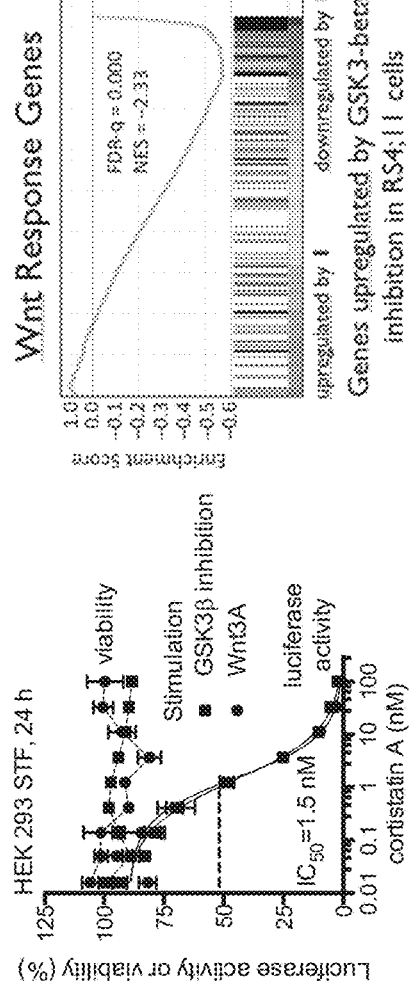
FIG. 15A
FIG. 15B
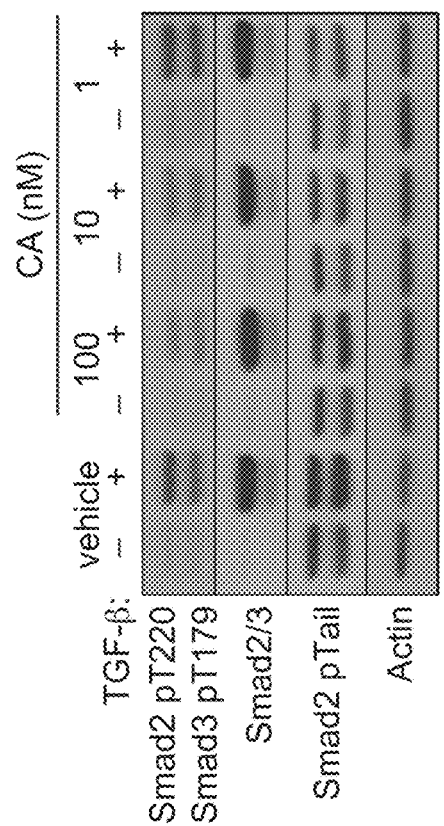
FIG. 15C

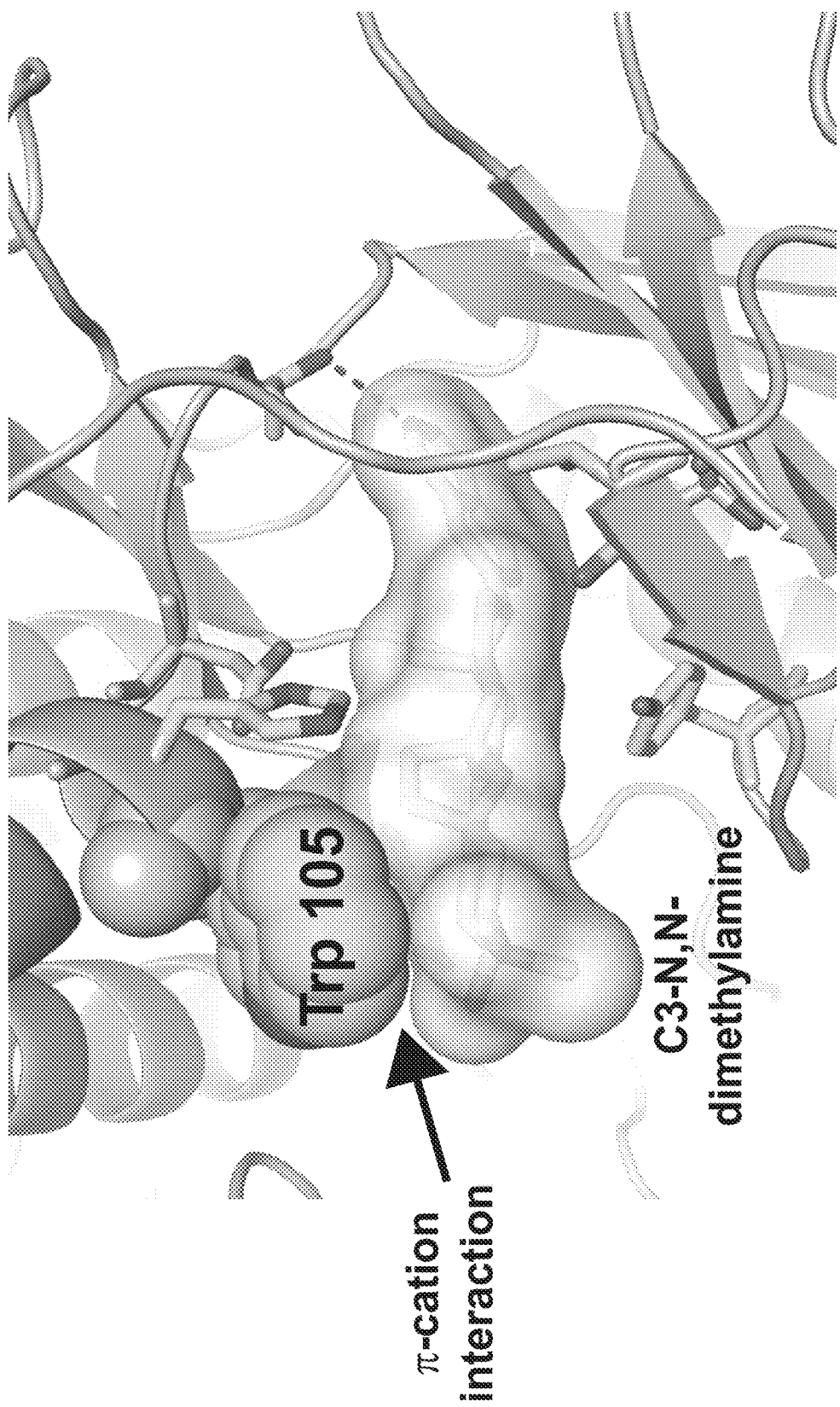

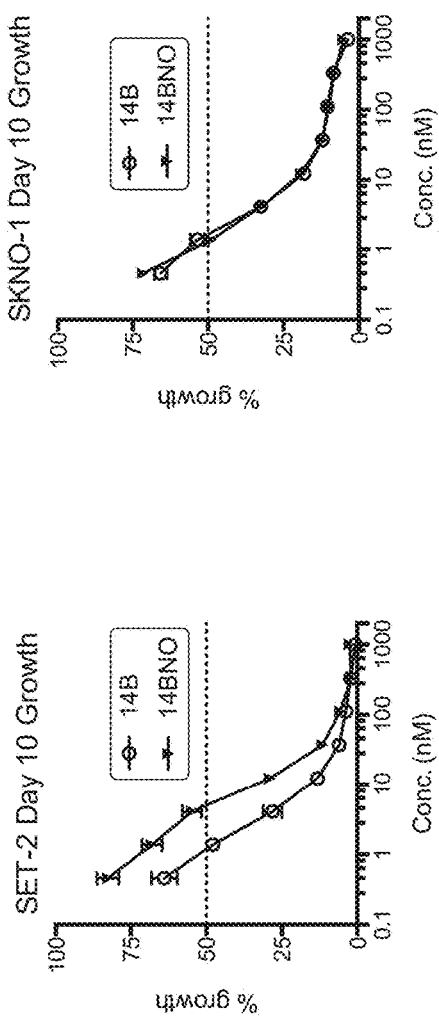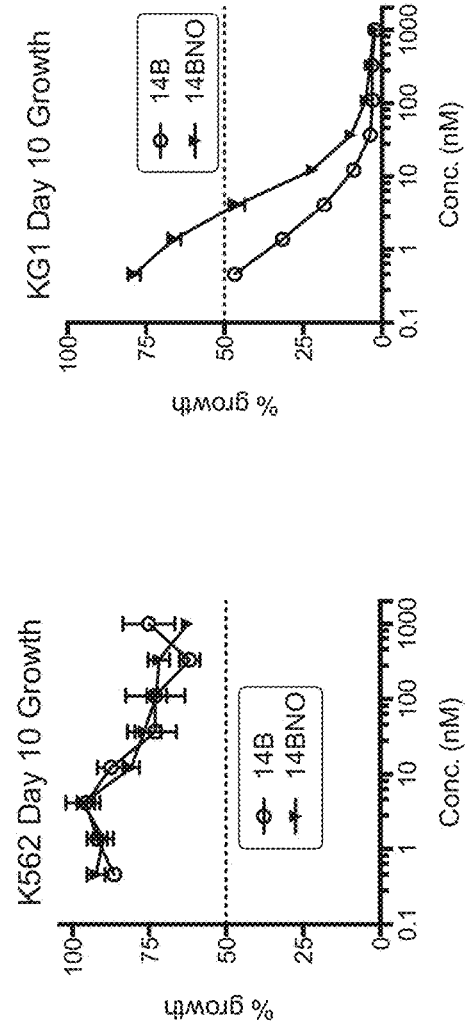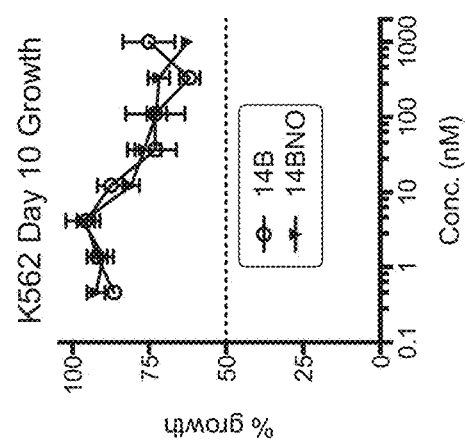

| Test Article | Species | CL$_{int}$ (µL/min/10⁶ cells)$^a$ | T$_{1/2}$ (min)$^b$ | % remaining parent at last time point |
|---|---|---|---|---|
| verapamil | Human | 7.3 | 95.3 | 41.8% |
| warfarin | Human | 0.46 | >240 | 94.6% |
| 14BNO | Human | 0.50 | >240 | 88.8% |
| 14BNO | Human (Heat-Inactivated) | N/A | N/A | 100% |

$^a$Hepatocyte Intrinsic Clearance
$^b$Half-life

CORTISTATIN ANALOGUES AND SYNTHESES AND USES THEREOF

STATEMENT OF RELATED APPLICATIONS

This application continuation of U.S. application Ser. No. 15/981,575, filed May 16, 2018, which is a Divisional of U.S. application Ser. No. 15/192,629, filed Jun. 24, 2016, now U.S. Pat. No. 9,994,582, issued Jun. 12, 2018, which is a continuation of International Application No. PCT/US2014/072365, filed Dec. 24, 2014, which is related to and claims priority benefit of U.S. Provisional Patent Application No. 61/920,674, filed Dec. 24, 2013; U.S. Provisional Patent Application No. 61/935,240, filed Feb. 3, 2014; and U.S. Provisional Patent Application No. 61/993,329, filed May 15, 2014, the entire contents of each of which is incorporated herein by reference.

REFERENCE TO SEQUENCE LISTING

The sequence listing submitted on Mar. 5, 2019, bearing the file number 15020-009US3_2019-03-05_Sequence-Listing_ST25 was created on Mar. 5, 2019 with a byte size of 11,871 is being submitted under 37 C.F.R. § 1.821(e).

BACKGROUND

The cortistatins are a group of anti-angiogenic steroidal alkaloids first isolated in 2006 from the marine sponge *Corticium simplex*. See, e.g., Aoki, et al., *JACS* (2006) 128: 3148-9. From the date of isolation to the present, these natural products have been the subject of much study, especially in the development of total syntheses and of new unnatural biologically active analogs. See, e.g., Aoki et al., *Bioorganic & Medicinal Chemistry* (2007) 15: 6758-62. Mousseau et al., *Cell Host & Microbe* (2012) 12: 97-108; Chen et al., *Organic & Biomolecular Chemistry* (2010) 8: 2900; Hardin et al., *European Journal of Organic Chemistry* (2010) 19: 3553. Thus, there is an active interest in the development of new cortistatin analogs and methods of their preparation.

SUMMARY OF THE INVENTION

Provided herein are new cortistatin analogs of Formula (A), (B), and (C), and pharmaceutically acceptable salts, quaternary amine salts, and N-oxides thereof, synthesized, in part, by reductive amination of a ketone of Formula (B) to provide the aminated product of Formula (A), as depicted in Scheme 1, optionally via an imine intermediate of Formula (C).

Further provided are new cortistatin analogs prepared by reduction of the ketone of Formula (B) to provide a C3-hydroxyl compound of Formula (D). Still yet further provided is a compound of Formula (E), prepared by substitution of the compound of Formula (D). Such compounds may also be converted to a compound of Formula (A) upon treatment with an amine under suitable conditions.

It has been surprisingly found that the beta isomers of Formula (A), referred to as Formula (A-1), have been found to be equipotent, or more potent, than cortistatin A at inhibiting CDK8 kinase activity and the proliferation of AML cells, and it has also been found that the corresponding alpha isomers of Formula (A), referred to as Formula (A-2), are also very potent. Furthermore, it has been discovered that compounds of Formula (B) have been found active against the growth of AML cell lines in culture and CDK8 kinase activity in cells.

Further provided are pharmaceutical compositions comprising a cortistatin analogs of Formula (A), (B), (C), (D), or (E) or a pharmaceutically acceptable salt, quaternary amine salt, or N-oxide thereof, and a pharmaceutically acceptable excipient. Further provided are methods of use and treatment.

Scheme 1.

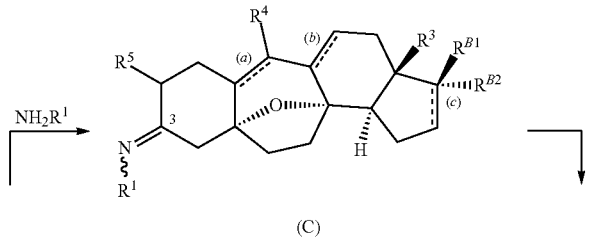

(C)

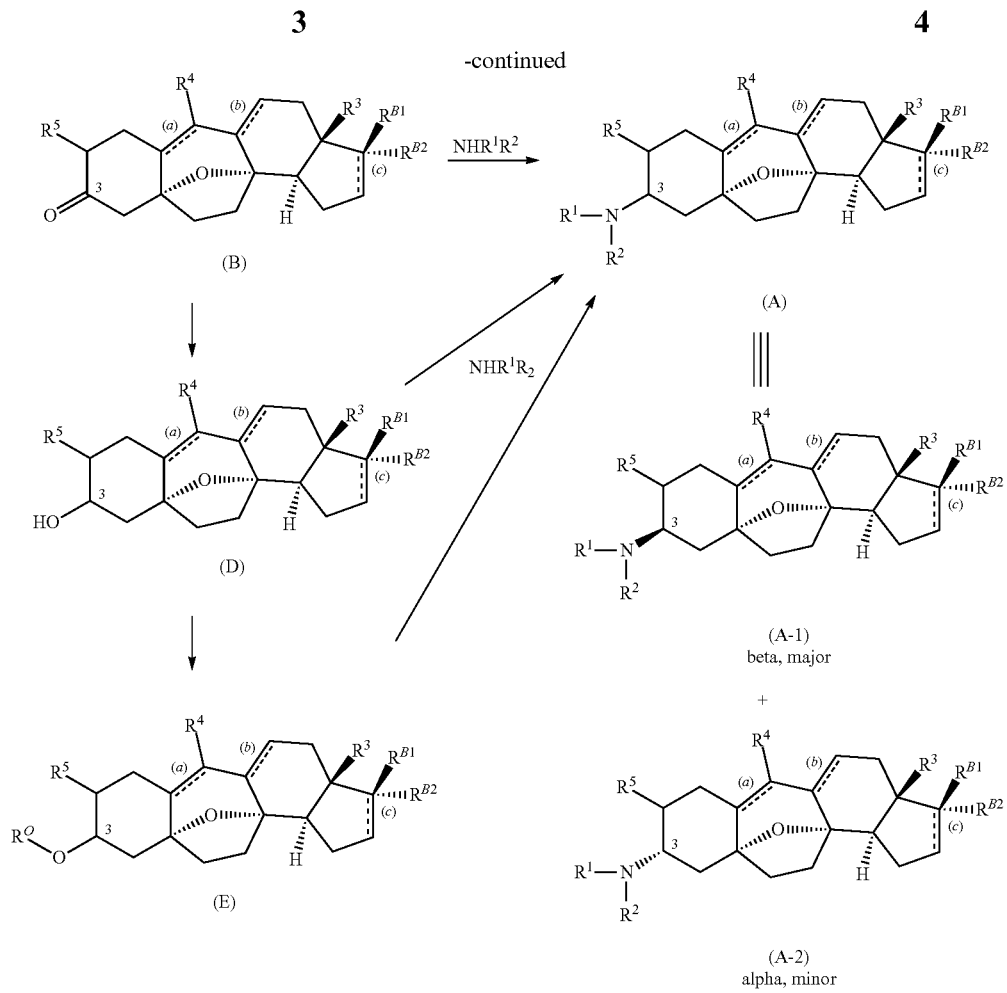

Thus, as further described herein, in one aspect, provided is a method of preparing a compound of Formula (A), or a pharmaceutically acceptable salt, quaternary amine salt, or N-oxide thereof; the method comprising contacting a compound of Formula (B), or a pharmaceutically acceptable salt, provided $R^{B1}$ and $R^{B2}$ are not joined to form an oxo group; with an amine of formula $HNR^1R^2$, or salt thereof, under reductive amination conditions.

In another aspect, provided is a method of preparing a compound of Formula (D), or a pharmaceutically acceptable salt thereof; the method comprising contacting a compound of Formula (B), or a pharmaceutically acceptable salt, with a reducing agent, to provide a compound of Formula (D).

In another aspect, provided is a method of preparing a compound of Formula (E), or a pharmaceutically acceptable salt thereof; the method comprising contacting a compound of Formula (D), or a pharmaceutically acceptable salt thereof, with a compound of formula $R^O$-LG, wherein LG is a leaving group, to provide a compound of Formula (E).

In another aspect, provided is a method of preparing a compound of Formula (A), or a pharmaceutically acceptable salt, quaternary amine salt, or N-oxide thereof; the method comprising contacting a compound of Formula (E), wherein $R^O$ is $C(=O)R^A$, or a pharmaceutically acceptable salt thereof, with a compound of formula $NHR^1R^2$, to provide a compound of Formula (A).

In another aspect, provided are pharmaceutical compositions comprising a compound of Formula (A), (B), (C), (D), or (E), or a pharmaceutically acceptable salt, quaternary amine, or N-oxide thereof.

In another aspect, provided is a method of treating a condition associated with angiogenesis comprising administering to a subject in need thereof a compound of Formula (A), (B), (C), (D), or (E), or a pharmaceutically acceptable salt, quaternary amine, or N-oxide thereof, or a pharmaceutical composition thereof. In certain embodiments, the condition is a diabetic condition, an inflammatory condition, macular degeneration, obesity, atherosclerosis, or a proliferative disorder.

In yet another aspect, provided is a method of treating a condition associated with CDK8 and/or CDK19 kinase activity, comprising administering to a subject in need thereof a compound of Formula (A), (B), (C), (D), or (E), or a pharmaceutically acceptable salt, quaternary amine, or N-oxide thereof, or a pharmaceutical composition thereof. In certain embodiments, the condition is a proliferative disorder. In certain embodiments, the proliferative disorder is cancer. In certain embodiments, the cancer is a hematopoietic cancer. In certain embodiments, the hematopoietic cancer is lymphoma. In certain embodiments, the hematopoietic cancer is leukemia. In certain embodiments, the hematopoietic cancer is multiple myeloma. In certain embodiments, the leukemia is acute myelocytic leukemia (AML). In certain embodiments, the proliferative disorder is a myeloproliferative neoplasm. In certain embodiments, the myeloproliferative neoplasm is primary myelofibrosis (PMF). In certain embodiments, the cancer is a solid tumor.

In yet another aspect, provided is a method of inhibiting CDK8 and/or CDK19 kinase activity in a cell comprising contacting a compound of Formula (A), (B), (C), (D), or (E), or a pharmaceutically acceptable salt, quaternary amine, or N-oxide thereof, or a pharmaceutical composition thereof, with the cell.

In yet another aspect, provided is a method of modulating the β-catenin pathway in a cell comprising contacting a compound of Formula (A), (B), (C), (D), or (E), or a pharmaceutically acceptable salt, quaternary amine, or N-oxide thereof, or a pharmaceutical composition thereof, with the cell.

In yet another aspect, provided is a method of modulating STAT1 activity in a cell comprising contacting a compound of Formula (A), (B), (C), (D), or (E), or a pharmaceutically acceptable salt, quaternary amine, or N-oxide thereof, or a pharmaceutical composition thereof, with the cell.

In yet another aspect, provided is a method of modulating the TGFβ/BMP pathway in a cell comprising contacting a compound of Formula (A), (B), (C), (D), or (E), or a pharmaceutically acceptable salt, quaternary amine, or N-oxide thereof, or a pharmaceutical composition thereof, with the cell.

In yet another aspect, provided is a method of modulating HIF-1-A (HIF-1-alpha) activity in a cell comprising contacting a compound of Formula (A), (B), (C), (D), or (E), or a pharmaceutically acceptable salt, quaternary amine, or N-oxide thereof, or a pharmaceutical composition thereof, with the cell.

In yet another aspect, provided is a method of increasing BIM expression to induce apoptosis in a cell comprising contacting a compound of Formula (A), (B), (C), (D), or (E), or a pharmaceutically acceptable salt, quaternary amine, or N-oxide thereof, or a pharmaceutical composition thereof, with the cell.

In any of the above recited methods, the method is an in vitro method or an in vivo method.

Further provided are CDK8 or CDK19 Tpr105 point mutants, and methods of use thereof. For example, in one aspect, provided is a method of validating CDK8 and/or CDK19 kinase activity in a cell by contacting a CDK8 or CDK19 Trp105 point mutant and a cortistatin or cortistatin analog. In another aspect, provided is a CDK8 Trp105 point mutant. In certain embodiments, the CDK8 Trp105 point mutant has an amino acid sequence that a degree of homology to the amino acid sequence of SEQ ID NO: 1 of at least about 80%. Further provided is a protein that has a degree of homology to the amino acid sequence of SEQ ID NO: 1 of at least about 80%. In yet another aspect, provided is a CDK19 Trp105 point mutant. In certain embodiments, the CDK19 Trp105 point mutant has an amino acid sequence that a degree of homology to the amino acid sequence of SEQ ID NO: 2 of at least about 80%. Further provided is a protein that has a degree of homology to the amino acid sequence of SEQ ID NO: 2 of at least about 80%.

The details of one or more embodiments of the invention are set forth in the accompanying Figures. Other features, objects, and advantages of the invention will be apparent from the Detailed Description, the Examples, and from the claims.

BRIEF DESCRIPTION OF THE DRAWINGS

FIG. 11A: Cortistatin A was administered IP in a 10% DMSO/phosphate buffered saline at a pH6 and at 10 mg/kg to male CD-1 mice and serial blood plasma samples were collected and analyzed for the presence of cortistatin A.

As indicated, the $C_{max}$ was 1.4 microM at 1 hour and the calculated T ½ was 6.06 hours. Based on this PK study and the in vitro potency of cortistatin A, it is predicted that cortistatin A may maintain an efficacious dose in mice with at least 0.16 mg/kg once daily treatment. FIG. 11B: Male CD-1 mice dosed with single IP injection of 1 mg/kg cortistatin A in 20% hydroxypropyl-beta-cyclodextrin (HPCD). The $C_{max}$ was 762 nM at 30 minutes and the calculated T½ between 0.5-2 h was 33 minutes.

FIG. 12A shows bioluminescent images of the mouse with the median bioluminescence for each timepoint, indicating a lower disease burden over time. FIG. 12B shows the mean bioluminescence±s.e.m., n=1, P<0.0001, determined by two-way ANOVA. FIG. 12C shows the Kaplan-Meier survival analysis (n=8, P<0.0001, log-rank test). FIGS. 12D-12F depict the day 30 spleen weight (D) and percentage of MV4; 11 cells (mCherry-positive) in the spleen (E) and femur bone marrow (F) are shown for the mouse in each group with the highest, lowest, and median day 29 bioluminescence. *, P<0.05, , P<0.01, *, P<0.001, determined by one-way ANOVA vehicle vs. treatment. Dotted lines in FIG. 12D mark the range within 1 standard deviation of mean for healthy 8-week old female NSG mice. FIG. 12G shows that the mean body weight did not decrease upon treatment with cortistatin A, suggesting that cortistatin A treatment is tolerated. Mean body weight±s.e.m., n=11.

FIG. 13A, Mean body weight±s.e.m., n=3. FIG. 13B, CBC data collected 2 hours after the last dose on day 15. CBC analysis indicates no significant differences between vehicle and 0.16 mg kg$^1$. RBC, red blood cells (×10$^6$ cells/μl); HGB, hemoglobin (g/dl); HCT, hematocrit (%); MCV, mean corpuscle volume (fl); MCH, mean corpuscle hemoglobin (pg); MCHC, mean corpuscle hemoglobin (g/dl); PLT, platelets (×10$^5$ platelets/μl); WBC, white blood cells (×10$^3$ cells/μl); LYMPH, lymphocytes (×10$^3$ cells/μl).

FIG. 14A, FIG. 14B, and FIG. 14C, demonstrate cortistatin A shows promise as a therapeutic in the treatment of primary myelofibrosis (PMF). The results are from a pilot study in a murine model of PMF. In this model, MPLW515L overexpression in hematopoietic stem cells leads to myeloproliferation in vivo, with marked bone marrow fibrosis, splenomegaly, and megakaryocyte proliferation (See, e.g., Pikman et al., PLoS Med. (2006) 3:e270). In this model, mice were transplanted with MPLW515L-transduced bone marrow. After 14 days to allow for engraftment and development of severe MPN (including thrombocytosis, leukocytosis, and myelofibrosis), mice were randomized to receive vehicle or cortistatin A i.p. once daily. Sacrifice of 3 mice per group after 6 doses of daily cortistatin A shows significant reduction of spleen weights at 0.31 mg/kg and 0.62 mg/kg (A). Macroscopic reduction of splenomegaly is shown in (C). Analysis of blood counts after 4 doses of daily treatment shows significant reduction of allele burden as reflected by GFP percentage in peripheral blood (the MPLW515L mutant is expressed using a MSCV-IRES-GFP retrovirus) (B).

FIG. 15A, FIG. 15B, FIG. 15C, FIG. 15D, and FIG. 15E, demonstrates cortistatin A can modulate Wnt/beta-catenin (A,B) and TGF-beta (C) pathways and can induce BCL2L11 expression (D and E) in cells. FIG. 15A indicates cortistatin A inhibits Wnt/beta-catenin pathway-stimulated reporter gene expression. HEK-293 cells stably transfected with a luciferase reporter under the control of several TCF binding sites (referred to as SuperTOPflash)(See, e.g., Xu, et al., Cell 2004, 116, 883-895). Upon 24 hour treatment with either Wnt3A or 10 μM GSK30 inhibitor azakenpaullone to stimulate the Wnt/beta-catenin pathway, cortistatin A inhibited expression of luciferase as measured by luminescence ($IC_{50}$=1.5 nM, without affecting HEK-293 cell viability. Vertical bars=SEM, n=3. FIG. 15B indicates that cortistatin A inhibits putative Wnt/beta-catenin response genes in the AML cell line MV4; 11. MV4; 11 cells were treated with cortistatin A for 24 h and gene expression analysis and Gene Set Enrichment Analysis (GSEA) was performed. The GSEA revealed that cortistatin A downregulated a set of genes that are upregulated upon GSK3-beta inhibition. Since GSK3-beta inhibition can stimulate beta-catenin driven transcription, these genes represent putative Wnt/beta-catenin pathway genes. FIG. 15C indicates cortistatin A (CA) dose-dependently inhibited TGF-beta-stimulated SMAD2/3 phosphorylation. HaCat cells were treated with vehicle or CA for 1 hour followed by TGF-beta for 1 hour. Cells were then washed, lysed, and analyzed by Western blot. FIGS. 15D and E indicate cortistatin A dose-dependently increases mRNA levels of BCL2L11 upon 24 h treatment of MV4; 11 and MOLM-14 cells.

FIG. 16A, FIG. 16B, FIG. 16C, and FIG. 16D, depict binding of cortistatin A to the CDK8/cyclin C ATP binding site. FIG. 16A depicts the X-ray crystal structure of cortistatin A/CDK8/cyclin C ternary complex at 2.4 Angstrom resolution. FIG. 16B depicts the binding pocket showing equisite shape complementarity. FIG. 16C depicts the key contact residues between CDK8 and cortistatin A. The dotted line indicates an H-bond between the isoquinoline N of cortistatin A and the main chain amide N—H of CDK8. Electron density of cortistatin A also shown. FIG. 16C also includes the structural alignment of ATP (cyan/orange, from CDK2-ATP structure) with X-ray structure of cortistatin A (yellow) in CDK8. Note that Trp105 does not contact ATP. FIG. 16D depicts a closer view of the contact between Trp105 and the N,N-dimethyl group of cortistatin A. As further described herein, a Trp105 mutation (replacement with Met) confers resistance to cortistatin A.

FIG. 17B depicts the sensitivity of HUVECs to treatment with cortistatin A and cortistatin A N-oxide and shows that the 2 compounds are equipotent. Growth inhibition after 96 hour treatment of HUVECs was measured by fluorescence signal using Cell-titer Blue (Promega) with vehicle (DMSO) representing maximal growth and 10 μM doxorubicin representing maximal growth inhibition.

FIG. 21A, FIG. 21B, FIG. 21C, FIG. 21D, and FIG. 21E, demonstrate equipotency of the N-oxide of compound 14B and compound 14B in cell lines tested. Cells were passaged and fresh compounds were added on days 3 and 7 (mean+/− standard error, n=3).

FIG. 23 demonstrates that the N-oxide of compound 14B (14BNO) has an acceptable half-life and clearance rate upon mixing with pooled human hepatocytes.

DEFINITIONS

Chemical Definitions

Figure 1:
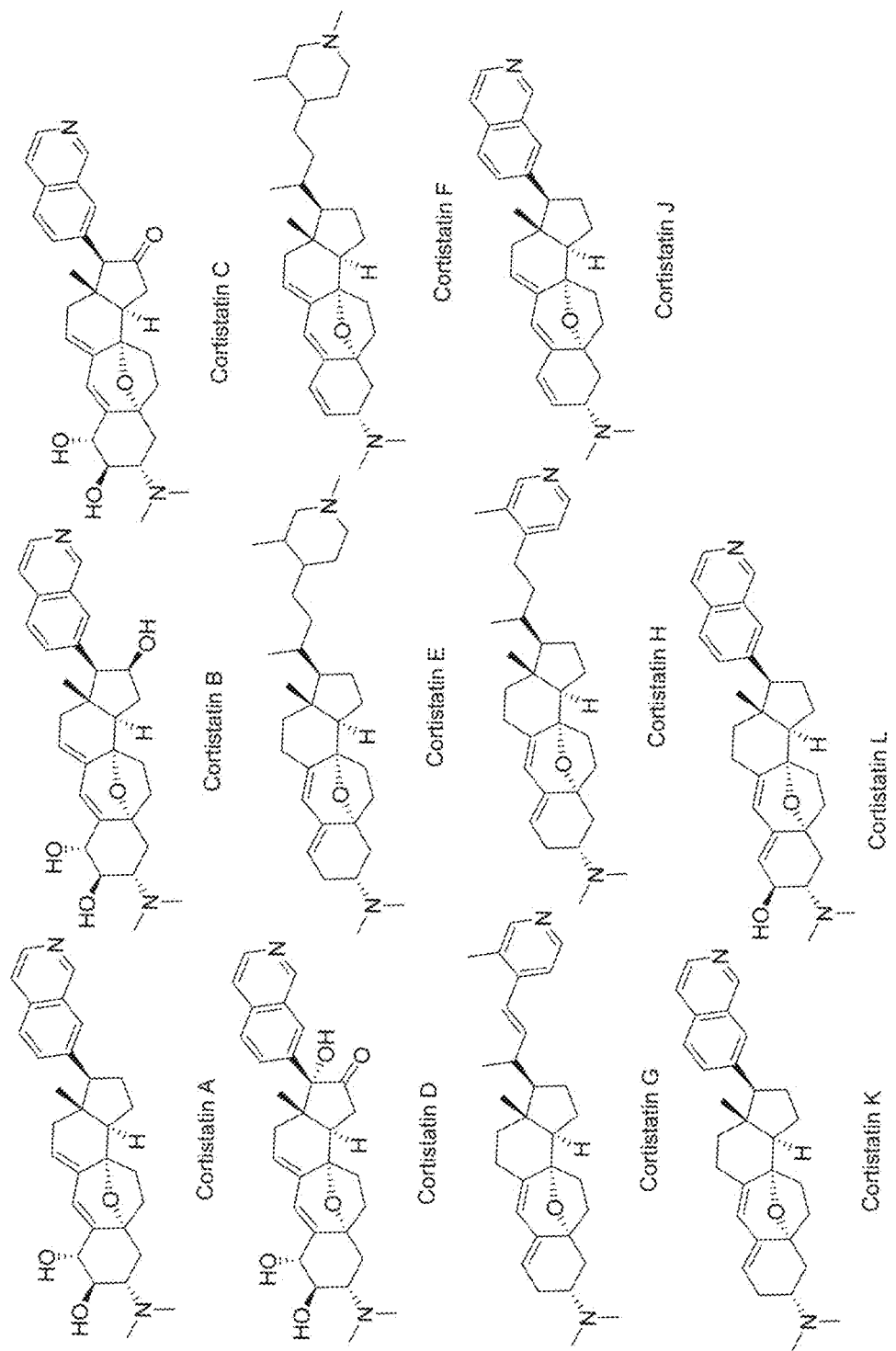
FIG. 1 depicts the structure of cortistatin A and other known cortistatins.
Figure 2A:
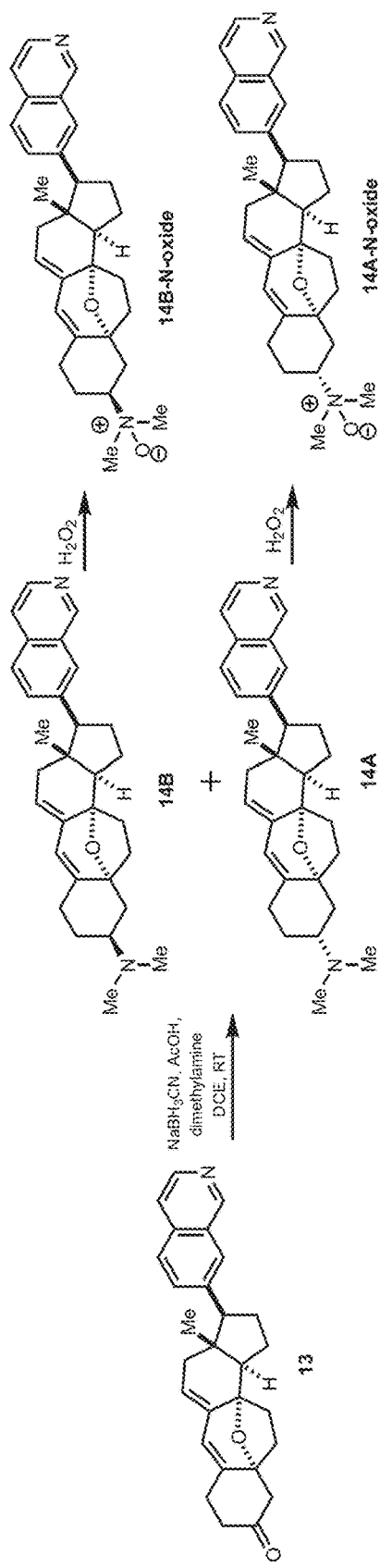
FIG. 2A and FIG. 2B depict an exemplary reductive amination of ketone 13 to provide compounds 14A and 14B, and their corresponding N-oxides (FIG. 2A) and the molecular structure of compound 14B, wherein the dimethylamine is beta (axial) (FIG. 2B).
Figure 2B:
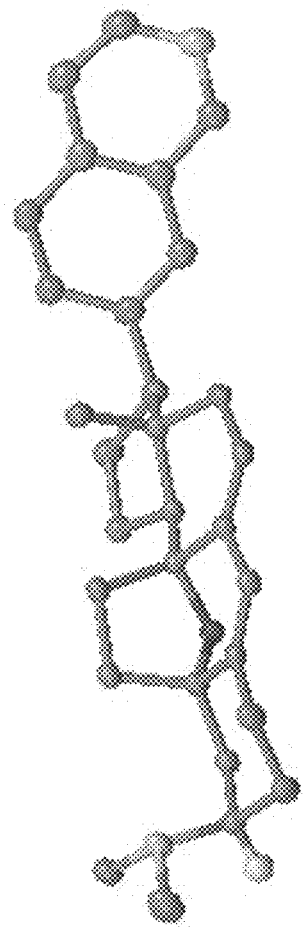
Figure 3A:
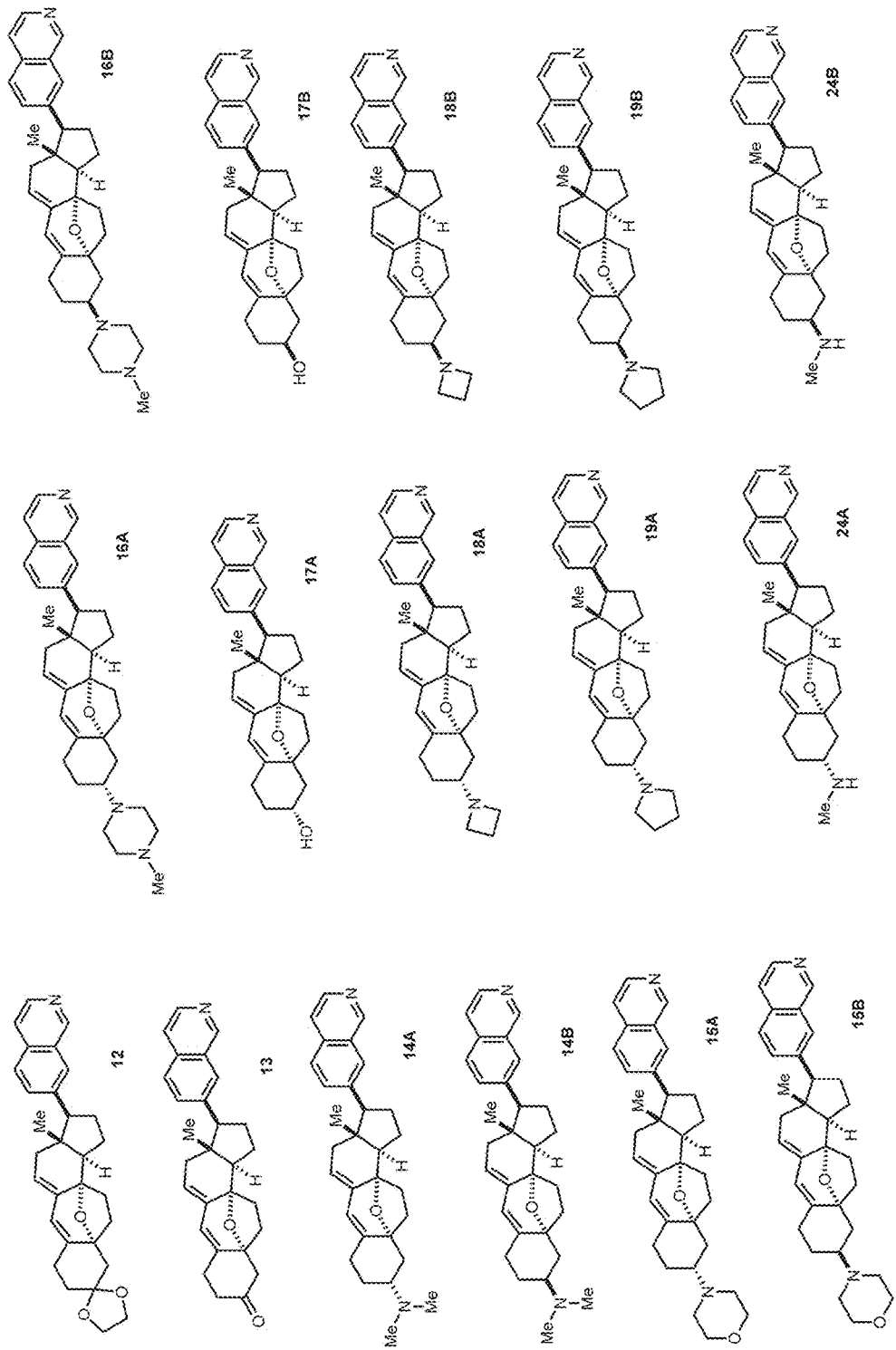
FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, and FIG. 3M depict exemplary compounds of the present invention. Additional compounds are further described herein.
Figure 3B:
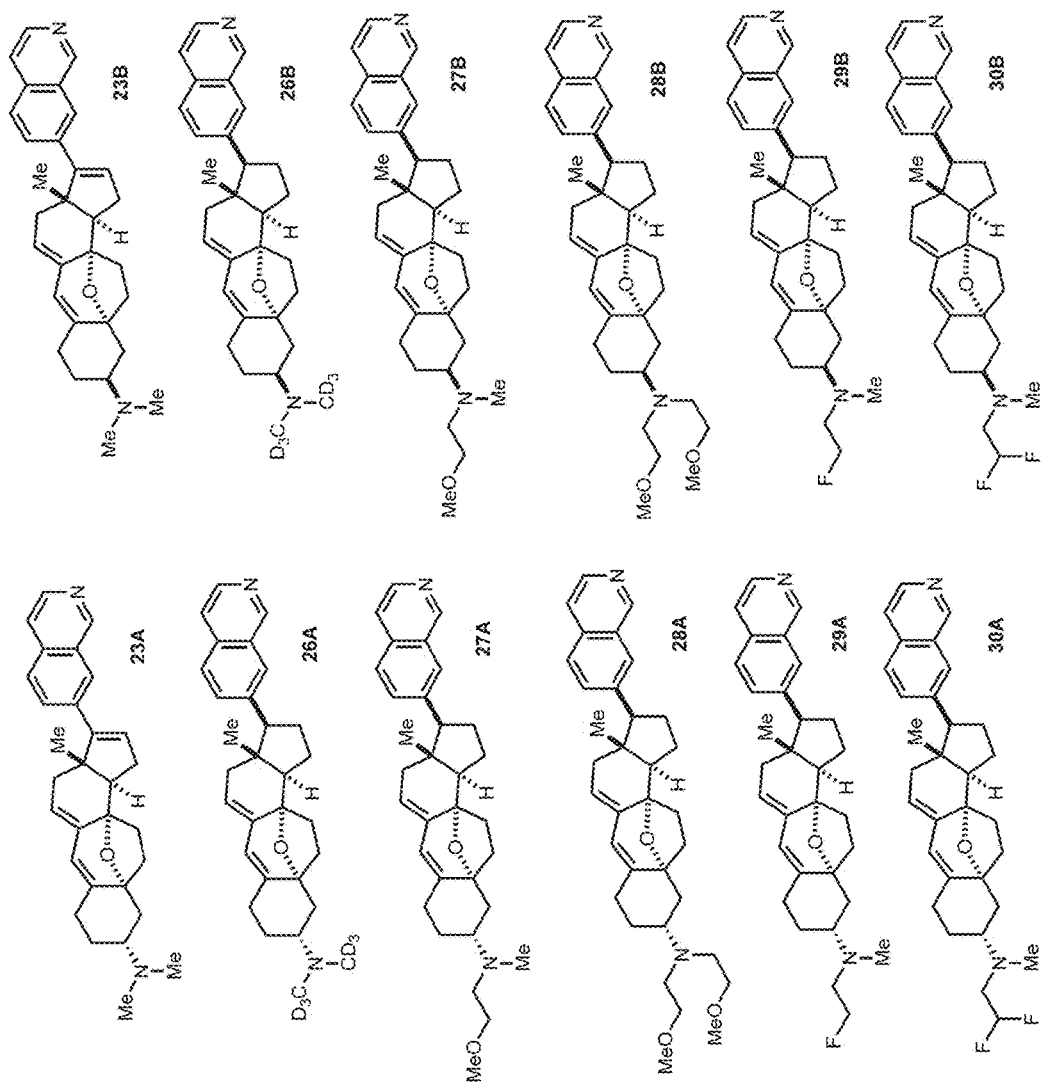
Figure 3C:
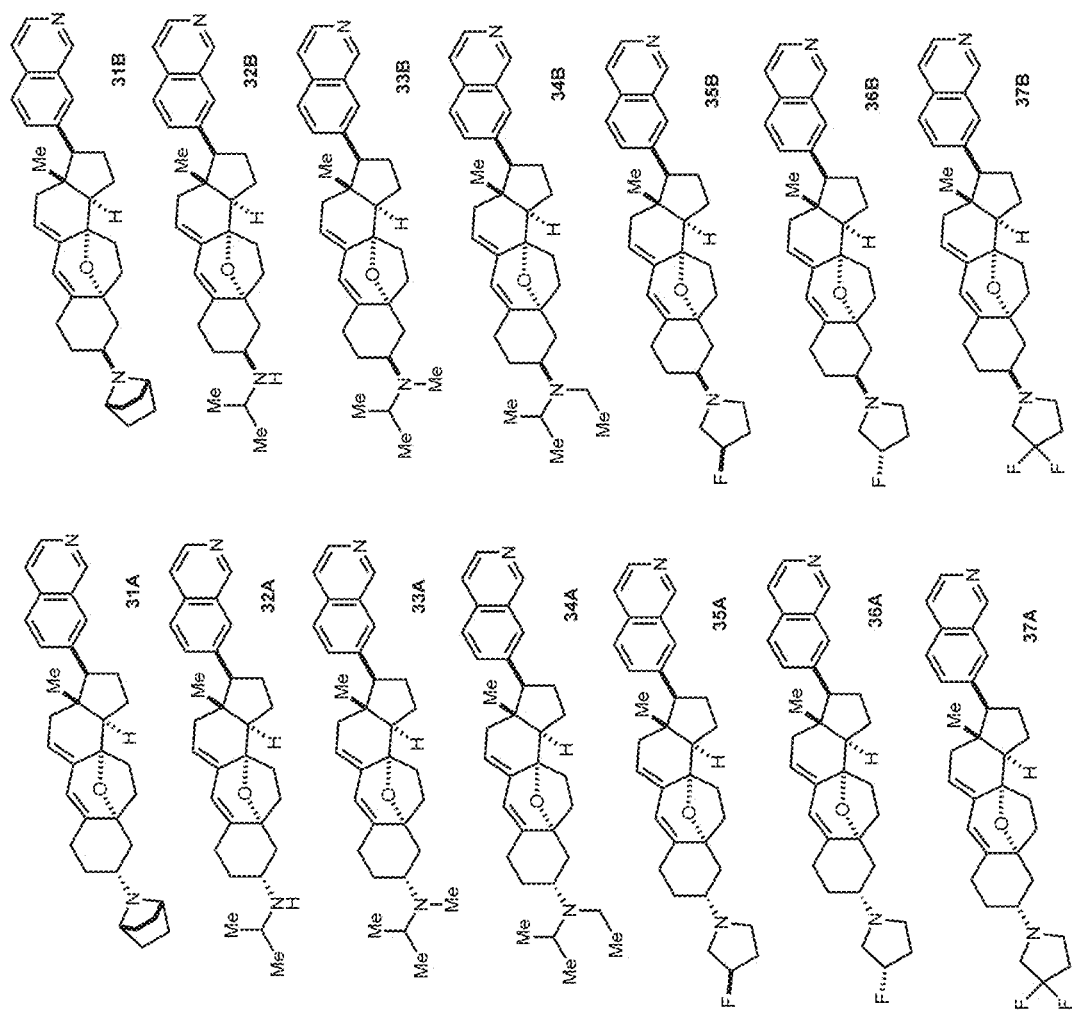
Figure 3D:
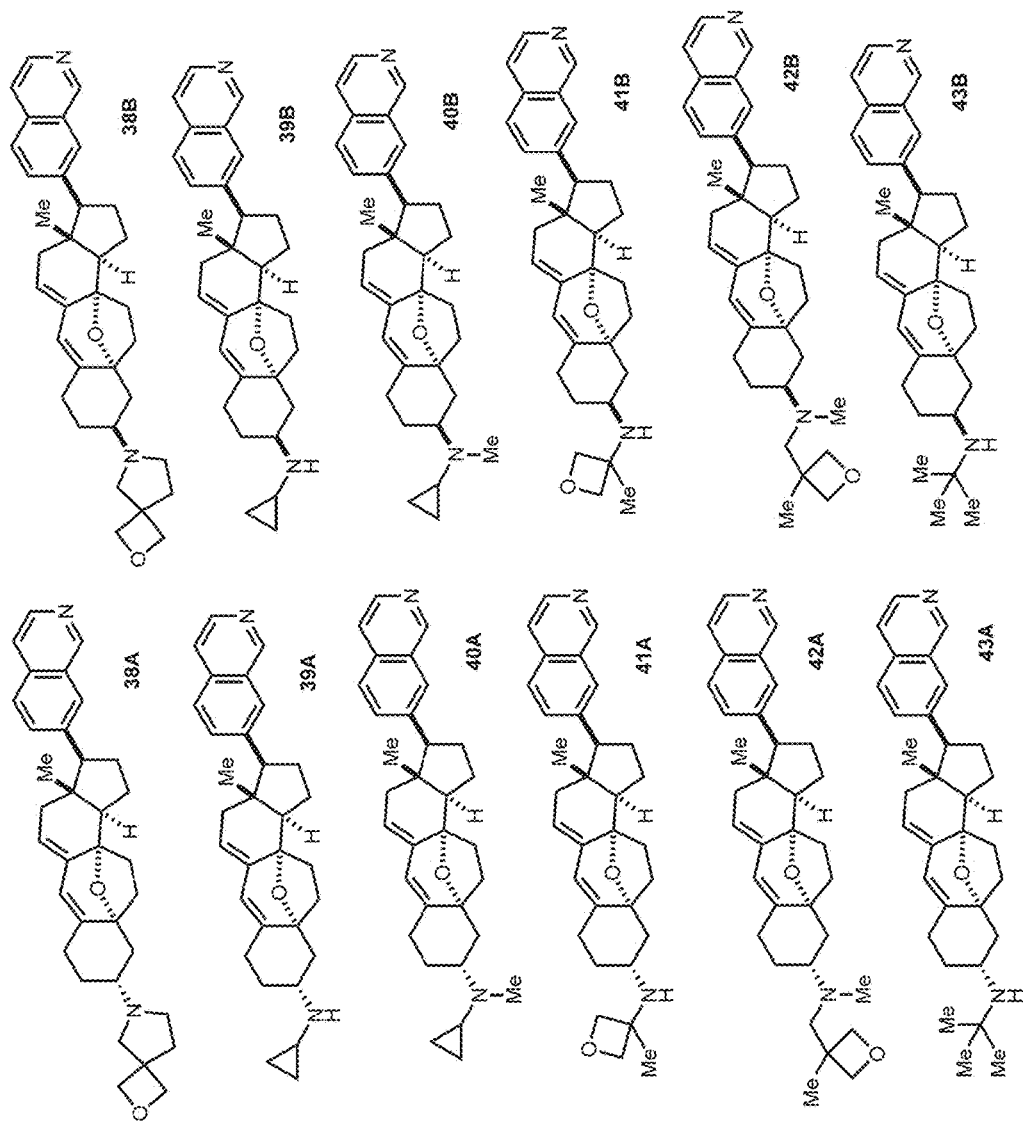
Figure 3E:
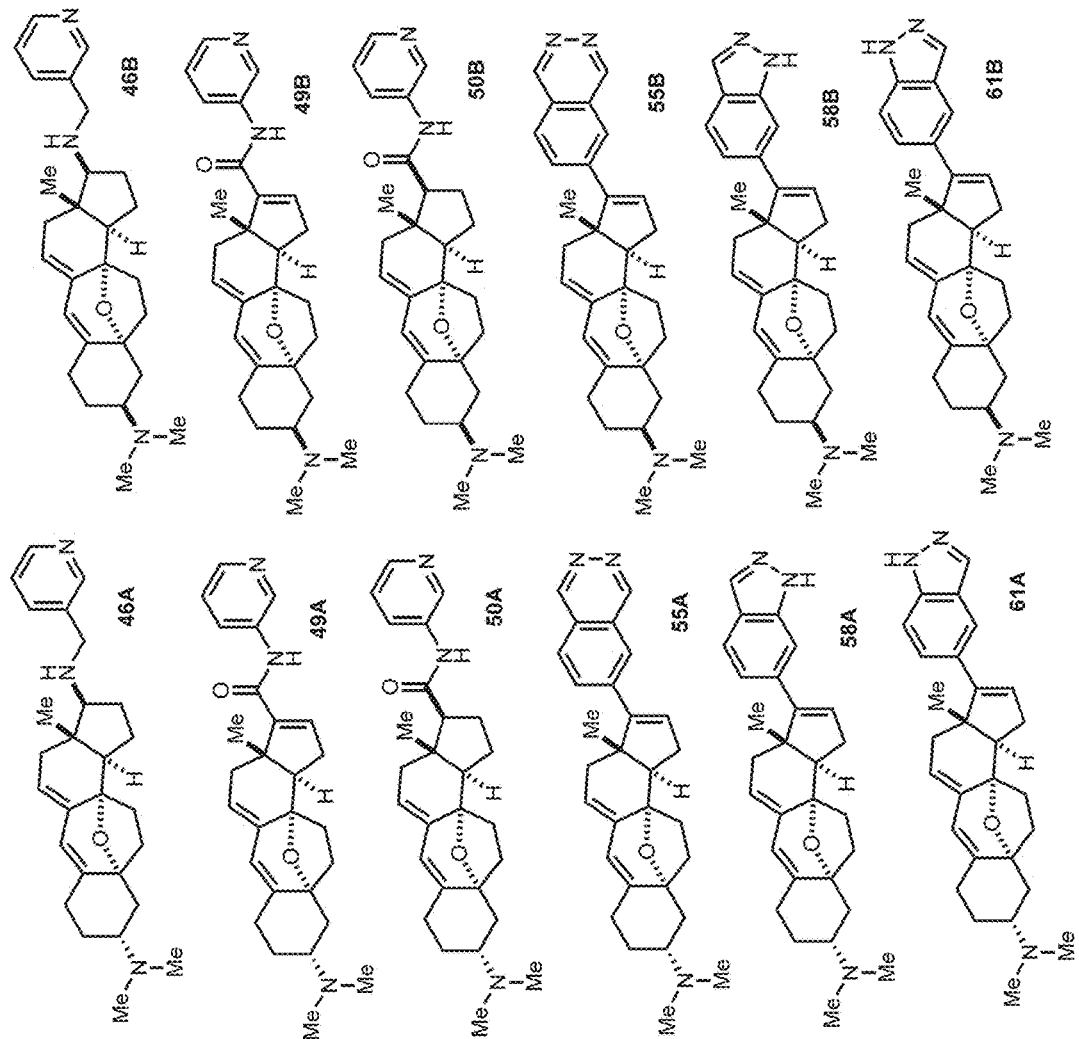
Figure 3F:
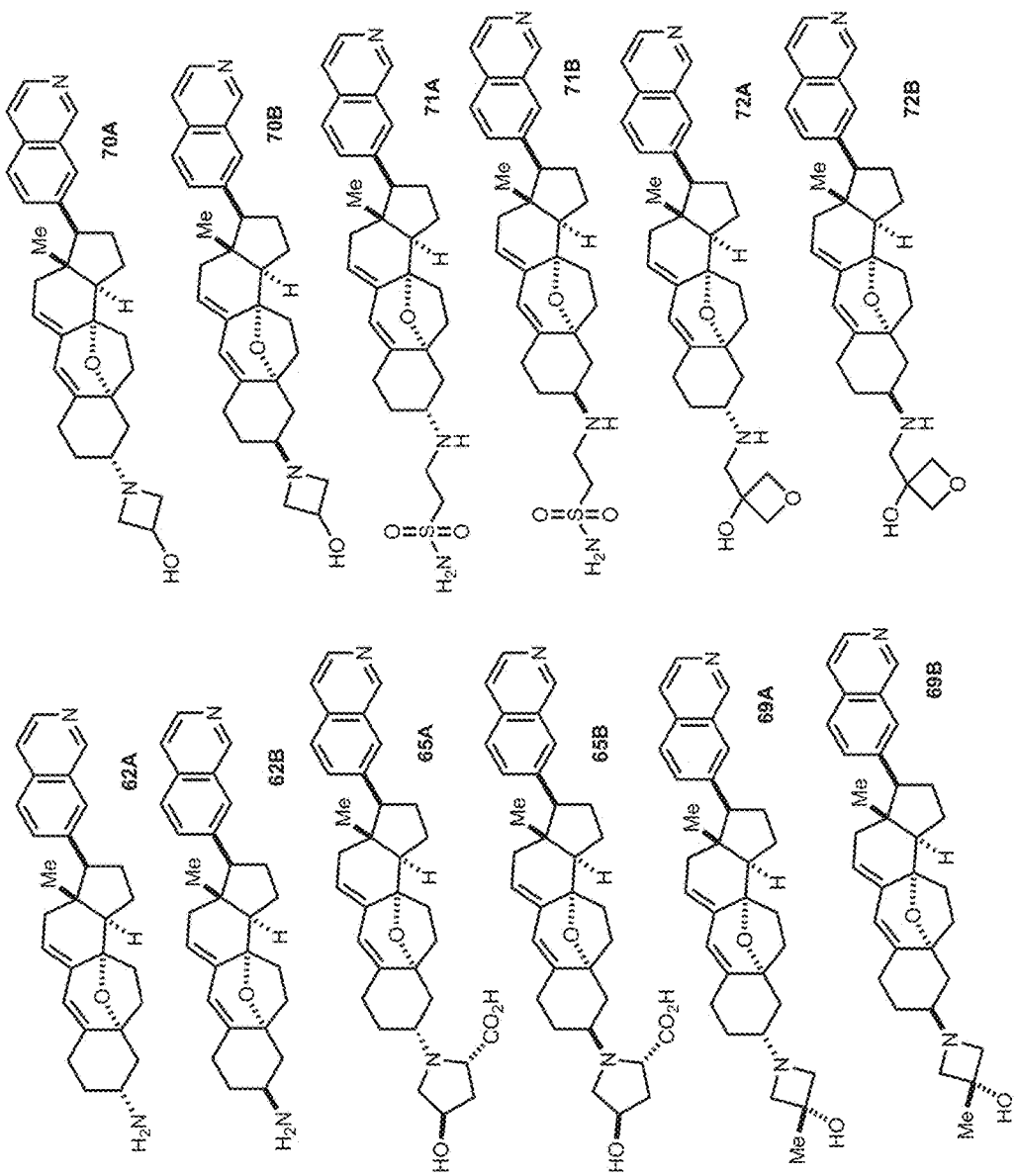
Figure 3G:
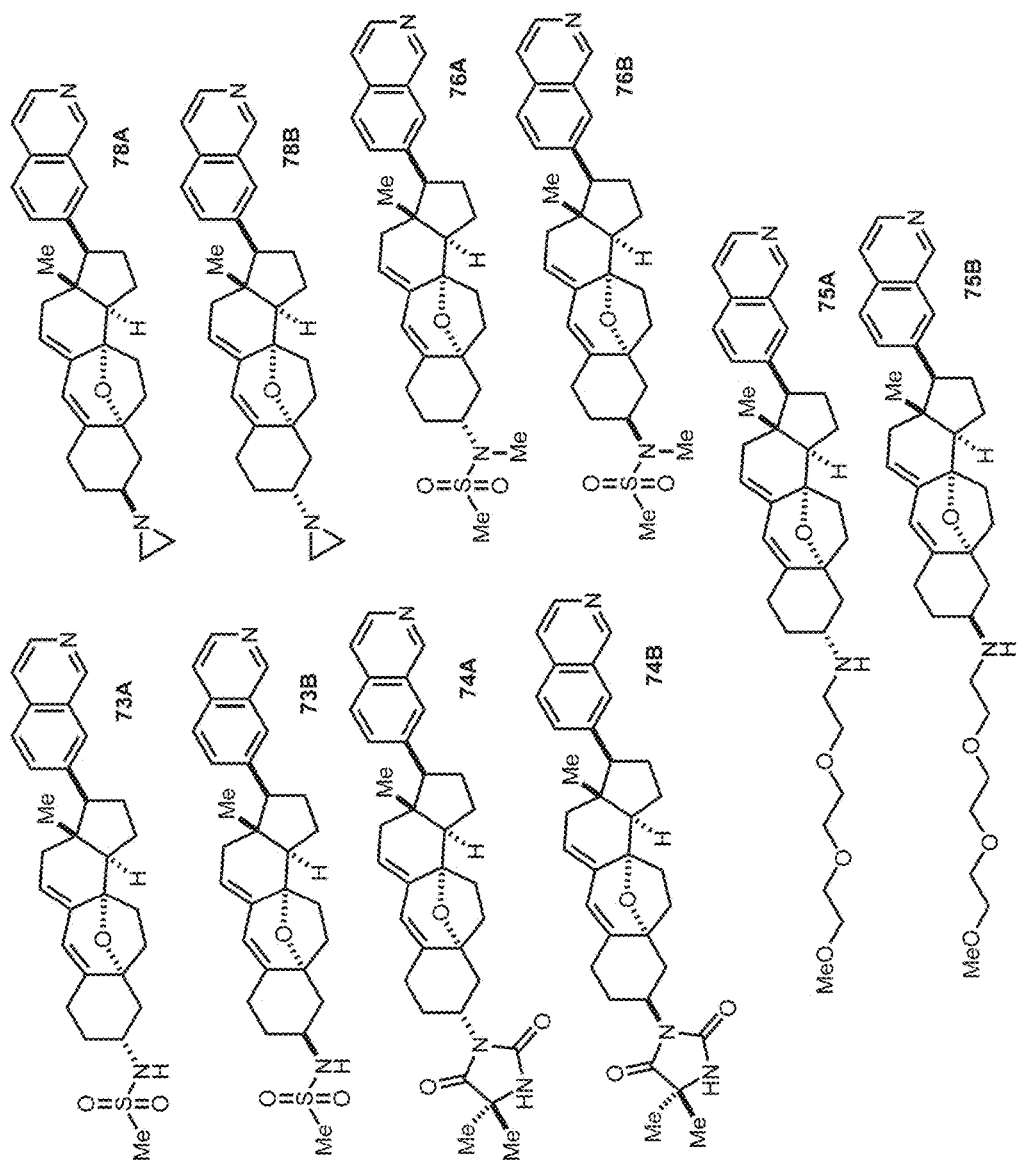
Figure 3H:
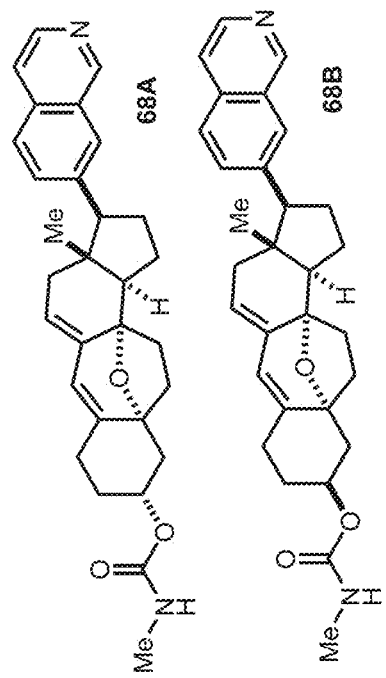
Figure 3H:
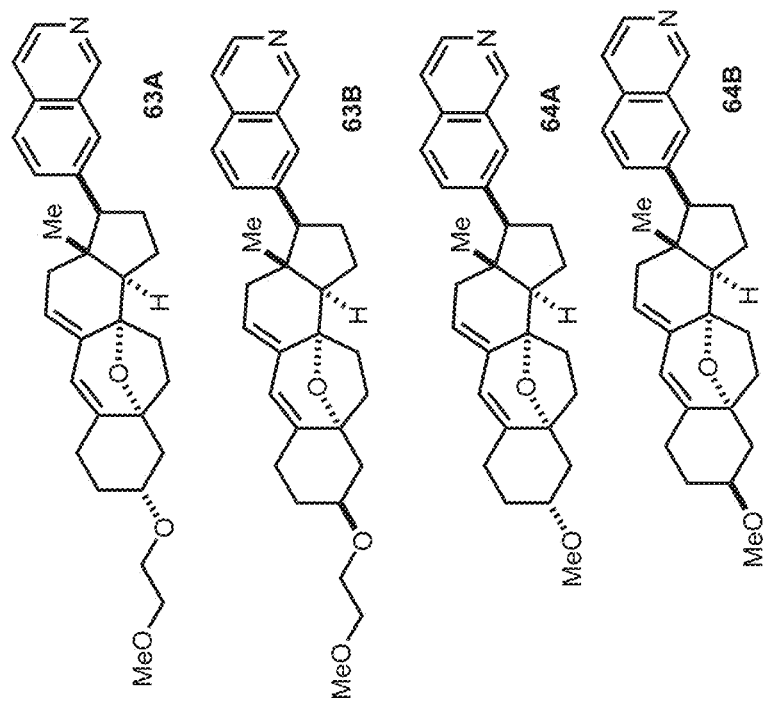
Figure 3I:
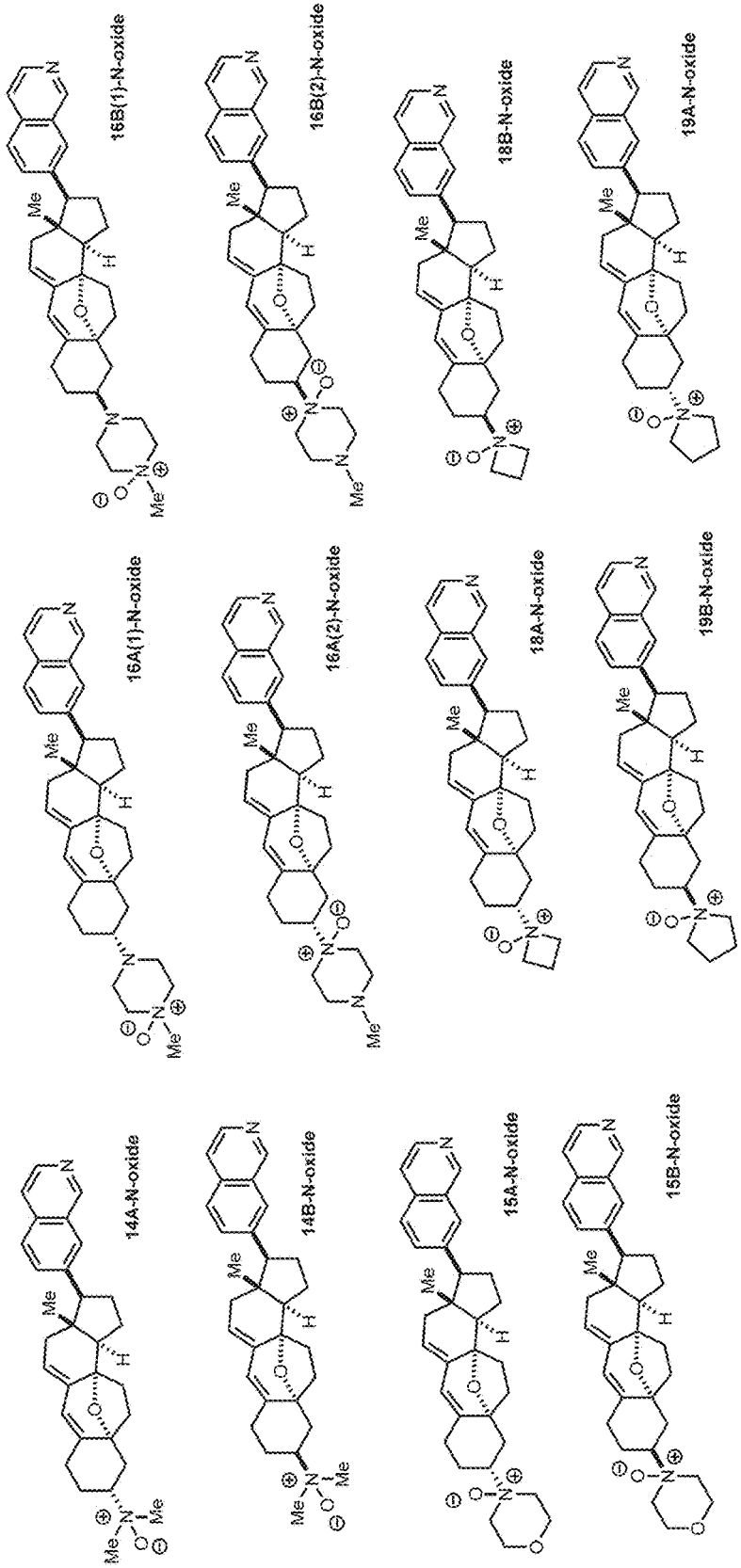
Figure 3J:
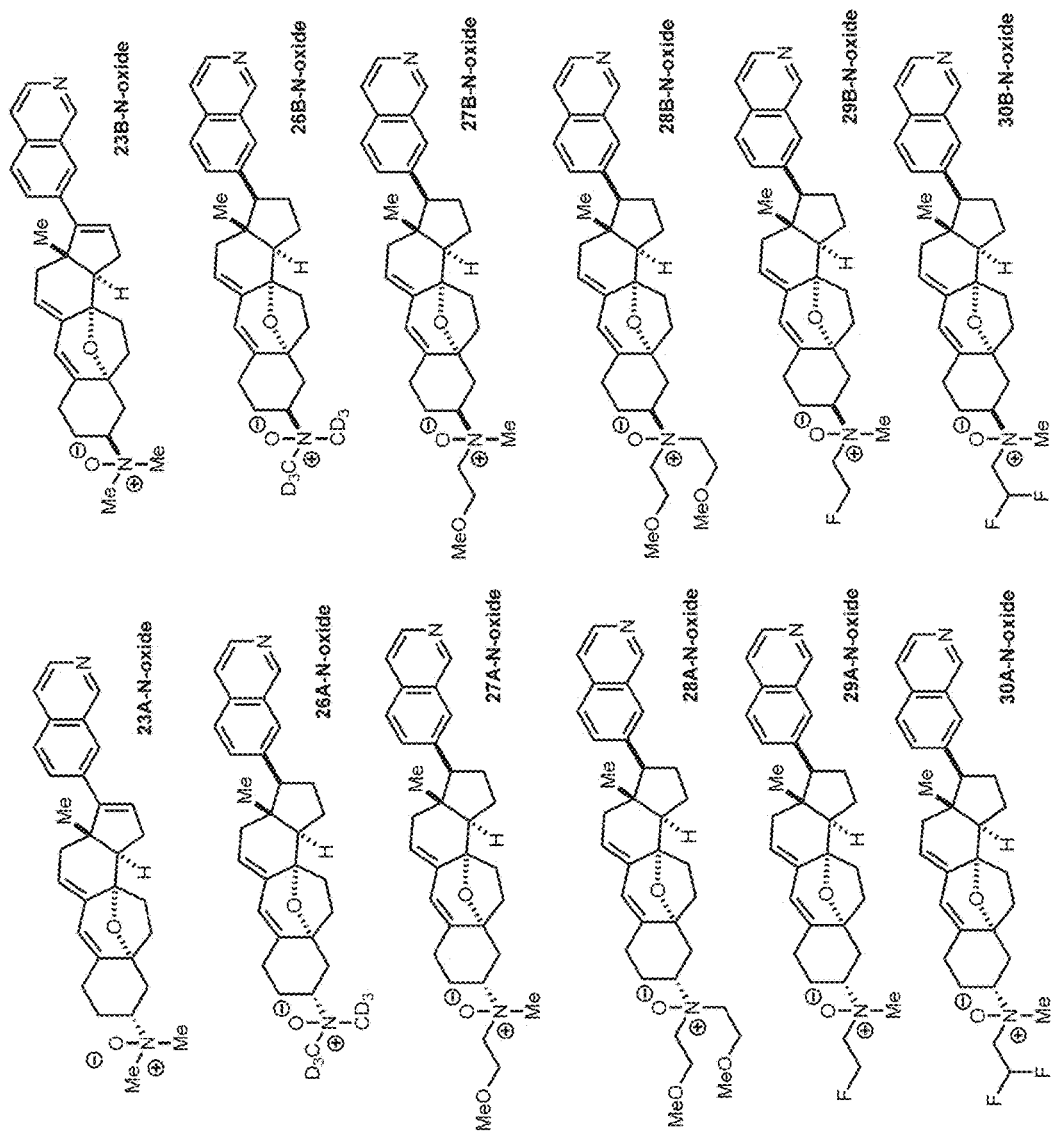
Figure 3K:
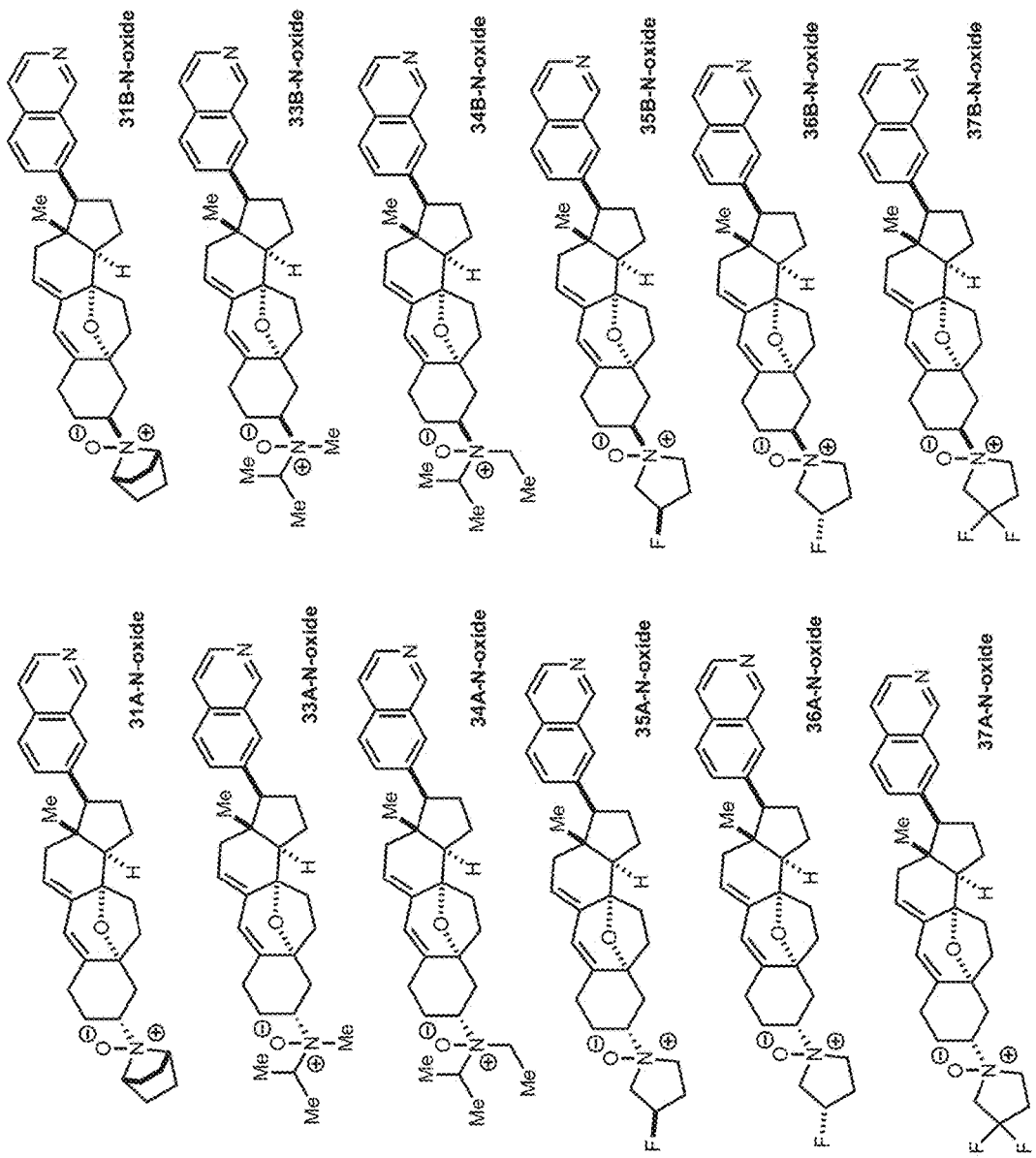
Figure 3L:
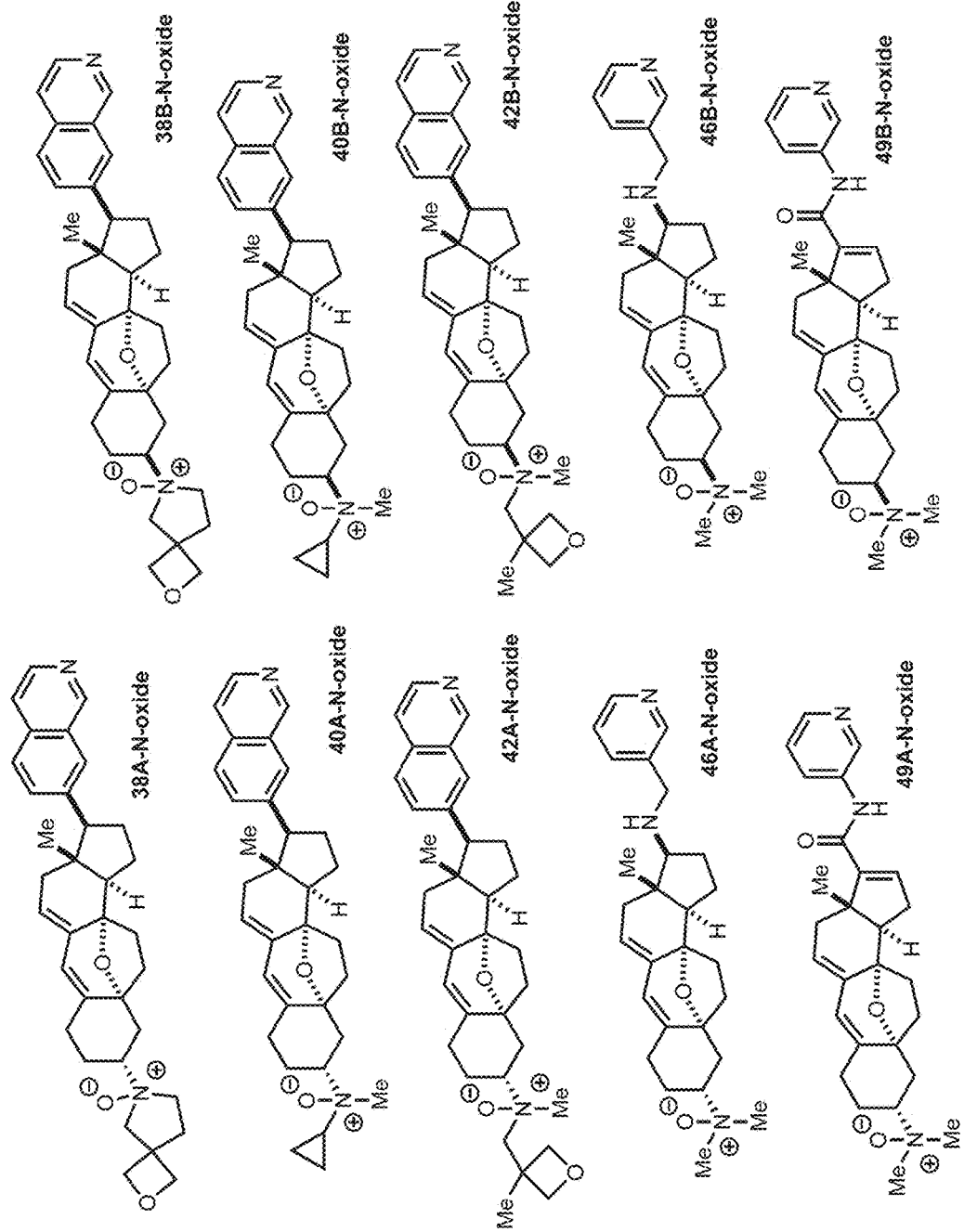
Figure 3M:
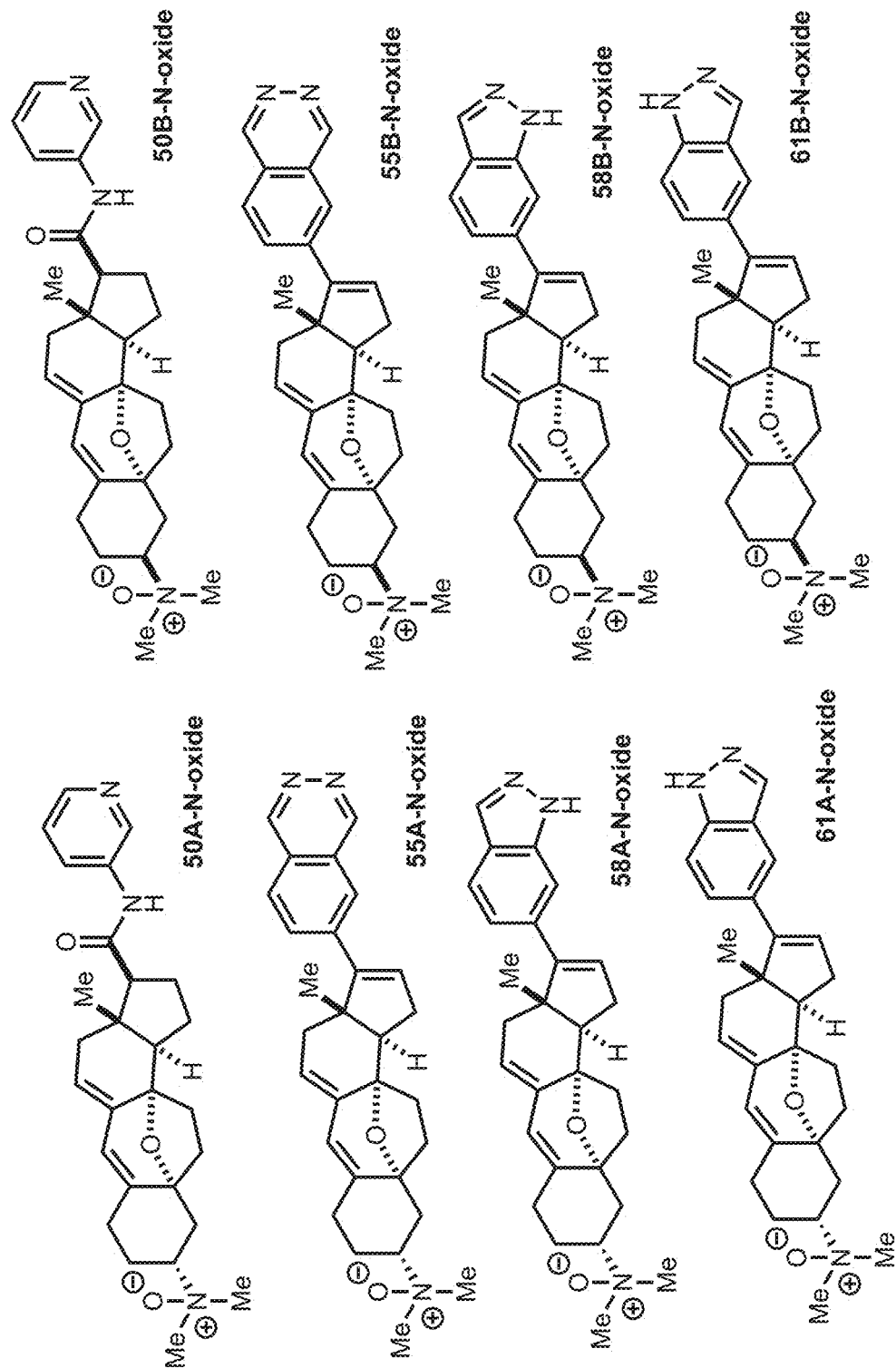
Figures 4A, 4B:
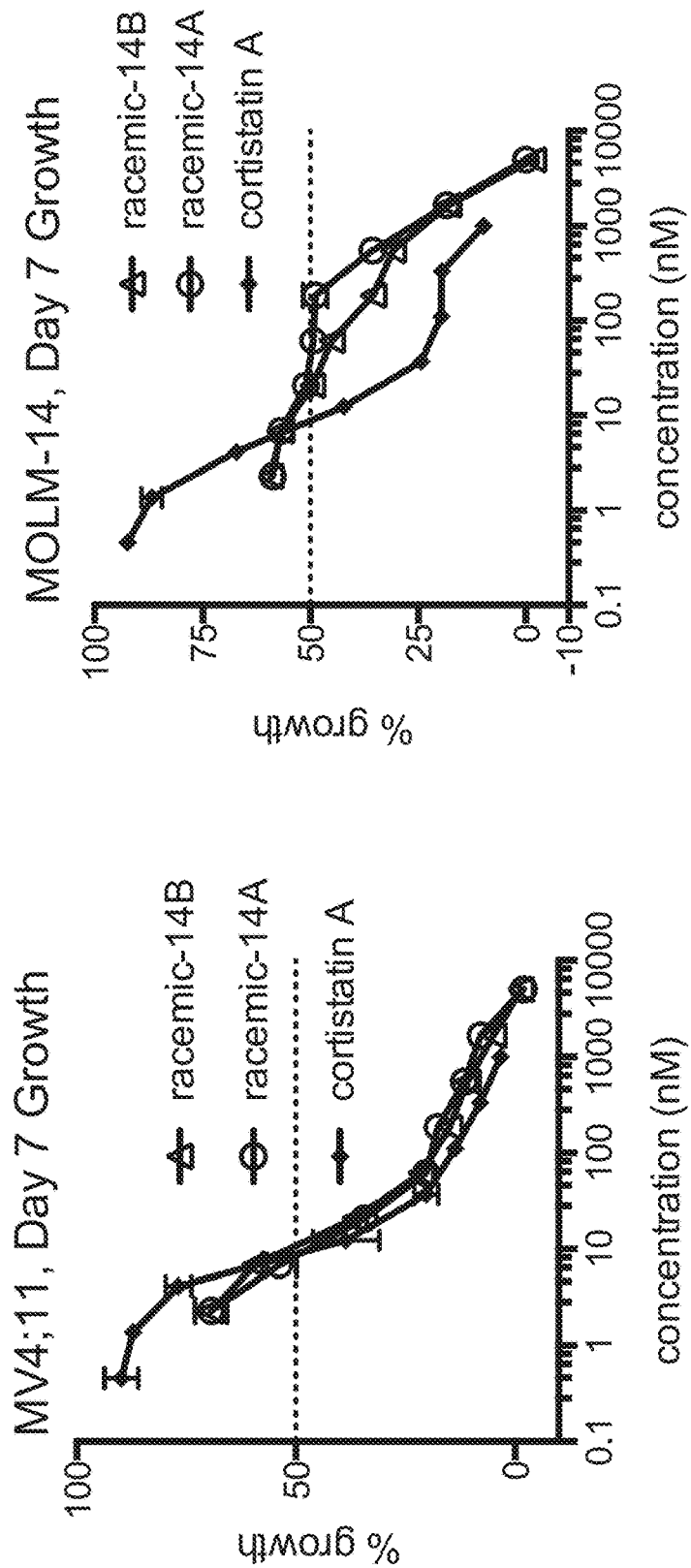
FIG. 4A and FIG. 4B depict the dose-dependent inhibition of proliferation of AML cell lines MV4; 11 (4A) and MOLM-14 (4B) upon 7-day treatment with cortistatin A and the indicated analogs. Cells were passaged and fresh compounds were added on day 3 (mean+/−standard error, n=3).
Figures 5A, 5B:
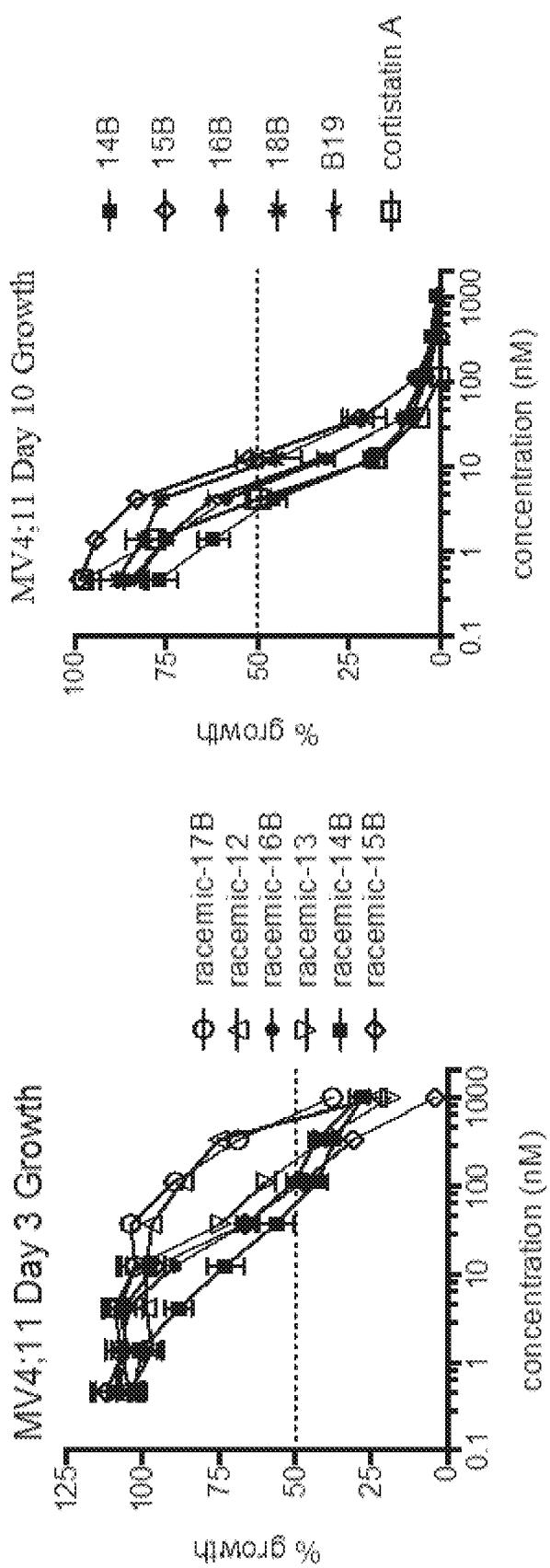
FIG. 5A and FIG. 5B depict the dose-dependent inhibition of proliferation of AML cell line MV4; 11 upon 3-day or 10-day treatment with the indicated cortistatin analogs. Cells were passaged and fresh compounds were added on days 3 and 7 (mean+/−standard error, n=3).
Figures 6A, 6B:
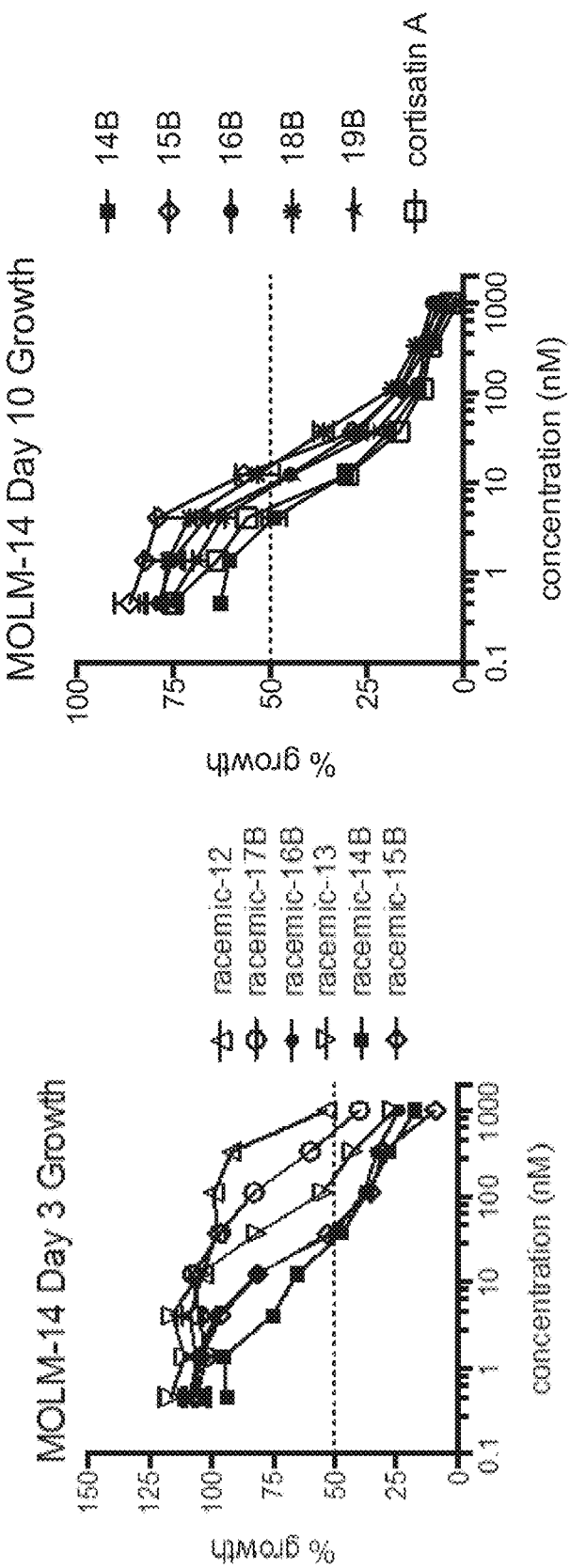
FIG. 6A and FIG. 6B depict the dose-dependent inhibition of proliferation of AML cell line MOLM-14 upon 3-day or 10-day treatment with the indicated cortistatin analogs. Cells were passaged and fresh compounds were added on days 3 and 7 (mean+/−standard error, n=3).

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 9 ring carbon atoms ("$C_{3-9}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N (R$^{bb}$)$_2$, —C(=NR$^{bb}$)R$^{aa}$, —C(=NR$^{bb}$)OR$^{aa}$, —OC (=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_1$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, an exemplary substituent is selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —SSR$^{cc}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N ($R^{bb}$)$_2$, —C(=O)NR$^{bb}$ SO$_2$R$^{aa}$, —NR$^{bb}$SO$_2$R$^{aa}$, —SO$_2$N($R^{bb}$)$_2$, —SO$_2$R$^{aa}$, —S(=O)R$^{aa}$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and —OSO$_2$R$^{aa}$, wherein R$^{aa}$ as defined herein. The group —OSO$_2$R$^{aa}$ encompasses leaving groups such as tosyl, mesyl, and besyl, wherein R$^{aa}$ is optionally substituted alkyl (e.g., —CH$_3$) or optionally substituted aryl (e.g., phenyl, tolyl).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON($R^{bb}$)$_2$, —OC(=O)SR$^{aa}$, —OC(=O)R$^{aa}$, —OCO$_2$R$^{aa}$, —OC(=O)N($R^{bb}$)$_2$, —OC(=NR$^{bb}$)R$^{aa}$, —OC(=NR$^{bb}$)OR$^{aa}$, —OC(=NR$^{bb}$)N($R^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N($R^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino or a disubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N($R^{bb}$)$_2$, —NHC(=NR$^{bb}$)N($R^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —NR$^{bb}$C(=O)R$^{aa}$, —NR$^{bb}$CO$_2$R$^{aa}$, —NR$^{bb}$C(=O)N($R^{bb}$)$_2$, —NR$^{bb}$C(=NR$^{bb}$)N($R^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "sulfonyl" refers to a group selected from —SO$_2$N($R^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N($R^{bb}$)$_2$, —C(=O)NR$^{bb}$SO$_2$R, —C(=S)N($R^{bb}$)$_2$), and imines (—C(=NR$^{bb}$)R$^{aa}$, —C(=NR$^{bb}$)OR$^{aa}$, —C(=NR$^{bb}$)N($R^{bb}$)$_2$), wherein R$^{aa}$ and R$^{bb}$ are as defined herein.

As used herein, the term "silyl" refers to the group —Si(R$^{aa}$)$_3$, wherein R$^{aa}$ is as defined herein.

As used herein, the term "oxo" refers to the group =O, and the term "thiooxo" refers to the group =S.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R, —SO$_2$OR, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R)$_2$, —C(=O)R$^{aa}$, —C(=O)N(R$^{cc}$)$_2$, —CO$_2$R, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzi soxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N($R^{bb})_2$, —C(=$NR^{bb}$)$R^{aa}$, —C(=$NR^{bb}$)$OR^{aa}$, —C(=$NR^{bb}$)N($R^{bb})_2$, —S(=O)$R^{aa}$, —$SO_2R^{aa}$, —Si($R^{aa})_3$, —P($R^{cc})_2$, —P($R^{cc})_3$, —P(=O)$_2R^{aa}$, —P(=O)($R^{aa})_2$, —P(=O)($OR^{cc})_2$, —P(=O)$_2$N($R^{bb})_2$, and —P(=O)(N$R^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxido, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —Si($R^{aa})_3$, —P($R^{cc})_2$, —P($R^{cc})_3$, —P(=O)$_2R^{aa}$, —P(=O)($R^{aa})_2$, —P(=O)($OR^{cc})_2$, —P(=O)$_2N(R^{bb})_2$, and —P(=O)(N$R^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein "modulating" refers to the ability of a compound to increase or inhibit a particular biological process (e.g., kinase activity, overexpression), e.g., for example in a cell (e.g., in vitro such as a cell in a cell culture, or in vivo such as a cell in a subject) relative to vehicle.

As used herein "inhibition", "inhibiting", "inhibit" and "inhibitor", and the like, refer to the ability of a compound to reduce, slow, halt or prevent activity of a particular biological process (e.g., kinase activity, overexpression), e.g., for example in a cell (e.g., in vitro such as a cell in a cell culture, or in vivo such as a cell in a subject) relative to vehicle.

As used herein "increasing" or "increase", and the like, refer to the ability of a compound to stimulate activity of a particular biological process (e.g., kinase activity), e.g., for example in a cell (e.g., in vitro such as a cell in a cell culture, or in vivo such as a cell in a subject) relative to vehicle.

Detailed Description of Certain Embodiments of the Invention

As generally described herein, provided are new cortistatin analogs which may be synthesized, in part, by reductive amination of a ketone of Formula (B) to provide an aminated product of Formula (A), optionally via an imine intermediate of Formula (C). Further provided are new cortistatin analogs of Formulae (D) and (E). See, e.g., Scheme 1, supra.

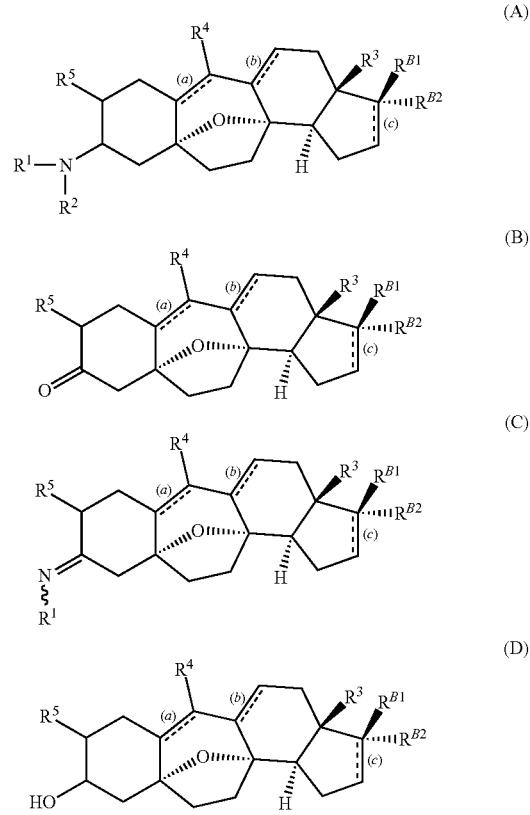

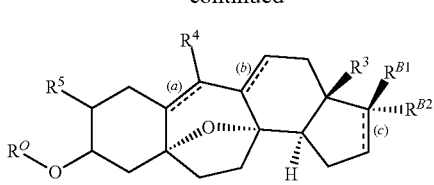

(E)

and pharmaceutically acceptable salts, quaternary amine salts, or N-oxides thereof, wherein:

$R^1$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —$SR^A$, —$N(R^A)_2$, —$C(=O)R^A$, —$C(=O)OR^A$, —$C(=O)N(R^A)_2$, —$S(=O)_2R^A$, or a nitrogen protecting group;

$R^2$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$C(=O)R^A$, —$C(=O)OR^A$, —$C(=O)N(R^A)_2$, —$S(=O)_2R^A$, or a nitrogen protecting group;

or $R^1$ and $R^2$ are joined to form an optionally substituted heterocyclyl or optionally substituted heteroaryl;

$R^3$ is hydrogen or optionally substituted alkyl;

$R^4$ is hydrogen, halogen, optionally substituted alkyl, or —$Si(R^A)_3$;

$R^5$ is hydrogen, halogen, or optionally substituted alkyl;

each instance of ⸺, designated as (a), (b), and (c), represents a single or double bond, provided that when ⸺ designated as (c) represents a double bond, then one of $R^{B1}$ and $R^{B2}$ is absent, and provided that when ⸺ designated as (c) represents a single bond, then both $R^{B1}$ and $R^{B2}$ are present;

each instance of $R^{B1}$ and $R^{B2}$ is, independently, hydrogen, -$L_1$-$R^{B3}$, or —$X^A R^A$ wherein $X^A$ is —O—, —S—, or —$N(R^A)$—; or $R^{B1}$ and $R^{B2}$ are joined to form an oxo group, provided that at least one of $R^{B1}$ and $R^{B2}$ is not hydrogen;

$L_1$ is a bond, —$C(=O)$—, —$C(=O)O$—, —$C(=O)S$—, —$C(=O)N(R^L)$—, or —$N(R^L)$—$(C(R^{LL})_2)_p$—, wherein $R^L$ is hydrogen, optionally substituted alkyl, or a nitrogen protecting group, each instance of $R^{LL}$ is independently hydrogen, halogen, or optionally substituted alkyl, and p is 0, 1, or 2;

$R^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that when $L_1$ is a bond, then $R^{B3}$ is not hydrogen;

each instance of $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, an oxygen protecting group when attached to oxygen, a sulfur protecting group when attached to sulfur, or a nitrogen protecting group when attached to nitrogen, optionally when attached to N the two $R^A$ groups may be joined to form an optionally substituted heterocyclyl or optionally substituted heteroaryl ring, and optionally when $R^{B1}$ and $R^{B2}$ are each —$X^A R^A$ then two $R^A$ groups may be joined to form an optionally substituted heterocyclyl ring; and $R^O$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —$C(=O)R^A$, —$C(=O)OR^A$, —$C(=O)N(R^A)_2$, or an oxygen protecting group.

It is generally understood that any atom encompassed by any of the formula described herein may be replaced with an isotope of that atom, e.g., for example, a hydrogen atom ($^1H$) may be replaced with a deuterium ($^2H$, D) or tritium ($^3H$, T) atom, a carbon atom ($^{12}C$) may be replaced with its $^{14}C$ isotope, and a fluorine atom ($^{18}F$) may be replaced by its $^{19}F$ isotope.

In general, reductive amination of Formula (B) generally provides both alpha and beta aminated isomers encompassed by Formula (A), referred to herein as Formula (A-1), the beta isomer, and Formula (A-2), the alpha isomer, and the beta isomer is typically the major product of the reaction. The alpha isomer shares $C_3$ stereochemistry with other cortistatin natural products. See, e.g., FIG. 1. Furthermore, reduction of the ketone generally provides both alpha and beta reduced isomers encompassed by Formula (D), referred to herein as Formula (D-1), the beta isomer, and Formula (D-2), the alpha isomer. Subsequent protection of these isomers of Formula (D) respectively provides Formula (E-1), the beta isomer, and Formula (E-2), the alpha isomer.

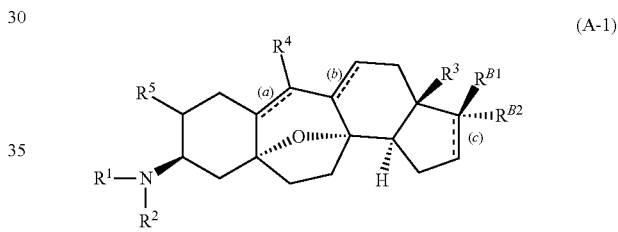

(A-1)

(A-2)

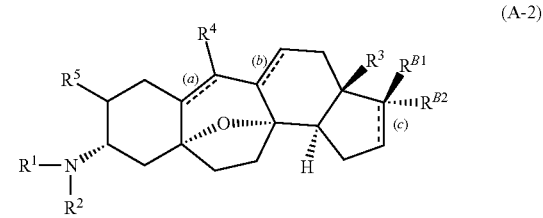

(D-1)

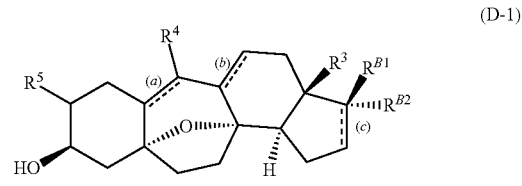

(D-2)

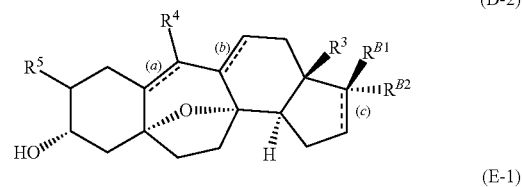

(E-1)

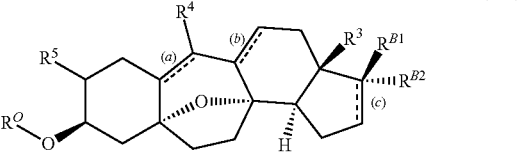

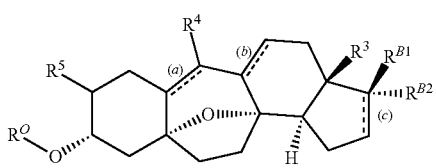

(E-2)

The (2.4 Å) crystal structure of a cortistatin A/CDK8/cyclin C ternary complex (see, e.g., FIG. 16) reveals that cortistatin A exhibits remarkable shape complementarity with the ATP-binding pocket of CDK8 and there is an apparent cation-π interaction between the charged N,N-dimethylammonium ion of cortistatin A and Trp105 of CDK8, which are within close contact (3.4 Å). CDK8 and CDK19 are the only CDKs with Trp at amino acid 105, suggesting that the cation-π interaction as well as hydrophobic contacts between cortistatin A and Trp105 might be important for the high affinity and selectivity of cortistatin A for CDK8. Based on this crystal structure, the beta isomer was predicted to sterically clash with Trp105.

The crystal structure also revealed that the A ring hydroxyl groups on cortistatin A might be dispensible for binding, as they do not form hydrogen bonds with CDK8 and orient away from CDK8, outside of the cortistatin A binding pocket. In addition, cortistatin J, which lacks the hydroxyl groups present in cortistatin A, is only 8-fold less potent at inhibiting HUVEC proliferation (see, e.g., Aoki, et al., *Bioorg. Med. Chem.* (2007) 15:6758-6762) and certain synthetic cortistatin A analogs with replacement of both the amine and hydroxyl substituents retained potent HUVEC antiproliferative activity (see, e.g., Nicolaou, et al., *J. Am. Chem. Soc.* (2009) 131: 10587-10597).

However, and most surprisingly, beta isomers of Formula (A), which do not contain any hydroxyl groups on the A ring, have been found to be equipotent, or more potent, than cortistatin A at inhibiting CDK8 kinase activity and the proliferation of AML cells, and it has also been found that the corresponding alpha isomers, also which do not contain any hydroxyl groups on the A ring, are also very potent.

It has also been discovered that compounds of Formula (B) have been found active against the growth of AML cell lines in culture and CDK8 kinase activity in cells. It is envisioned that the imine of Formula (C), such as an oxime wherein $R_1$ is —$OR^A$, will also be active.

Furthermore, despite the loss of the charged N,N-dimethylammonium ion cation-pi interaction, the compounds of Formula (D) and (E) are also surprisingly highly active.

Quaternary Amine Salts and N-Oxides

In certain embodiments, as provided herein, a compound of Formula (A), (B), (C), (D), or (E) may comprise a quaternary amine salt and/or an N-oxide.

A "quaternary amine salt" as used herein refers to an amino group wherein the nitrogen atom comprises four valence bonds (e.g., is substituted with four groups which may be hydrogen and/or non-hydrogen groups) such that the nitrogen atom is positively charged and the charge is balanced (neutralized) with a counteranion (e.g., $X^C$ as defined herein).

An "N-oxide" as used herein refers to an amino group wherein the nitrogen atom comprises four valence bonds (e.g, is substituted with four groups which may be hydrogen and/or non-hydrogen groups, wherein one group directly attached to the nitrogen atom is an oxidyl group (—$O^⊖$)) such that the nitrogen atom is positively charged, and wherein the oxidyl group balances (neutralizes) the positive charge of the nitrogen atom.

It should be understood that any one of Formula (A), (B), (C), (D), or (E) may comprise quaternary amine salt and/or N-oxide groups at any position where an amino group may be located.

In particular, compounds of Formula (A) may comprise a quaternary amine salt or N-oxide group at the $C_3$ position (also referred to as a "quaternary C3-amine salt" and "C3-N-oxide"), which comprises the amino group —$NR_1R_2$ attached to Ring A.

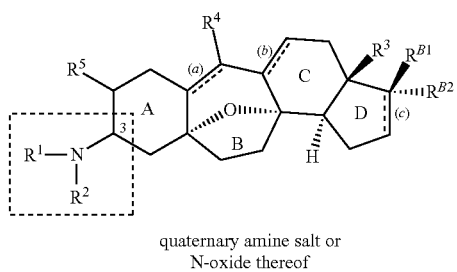

quaternary amine salt or
N-oxide thereof

In certain embodiments, the amino group

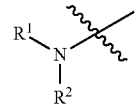

at the $C_3$ position may be an quaternary amine salt formula

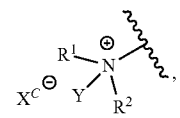

e.g., to provide a compound of Formula (A-QA):

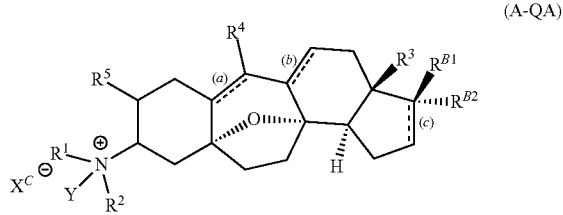

(A-QA)

wherein ~~~, $R^1$, $R^2$, $R^3$, $R^4$, $R^5$, $R^{B1}$, and $R^{B2}$ are as defined herein; and wherein:

Y is optionally substituted alkyl, optionally substituted alkenyl, optionally substituted alkynyl, optionally substituted carbocyclyl, optionally substituted heterocyclyl, optionally substituted aryl, or optionally substituted heteroaryl; and $X^C$ is a counteranion.

A quaternary C3-amine salt may be formed by reaction of the free C3-amine with a group Y—$X^C$, wherein Y is defined above (e.g., optionally substituted alkyl, optionally substituted alkenyl, optionally substituted alkynyl, optionally substituted carbocyclyl, or optionally substituted heterocyclyl), and $X^C$ is a leaving group as defined herein. The counterion $X^C$ resulting therefrom may be exchanged with another counterion $X^C$ by ion exchange methods, e.g., ion exchange chromatography. Exemplary $X^C$ counterions include but are not limited to halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like). In certain embodiments, Y is optionally substituted alkyl (e.g., methyl). In certain embodiments, $X^C$ is a halide ion.

In certain embodiments, the quaternary amine salt of Formula (A-QA) is the beta (A-1-QA) or alpha (A-2-QA) isomer of the following Formula:

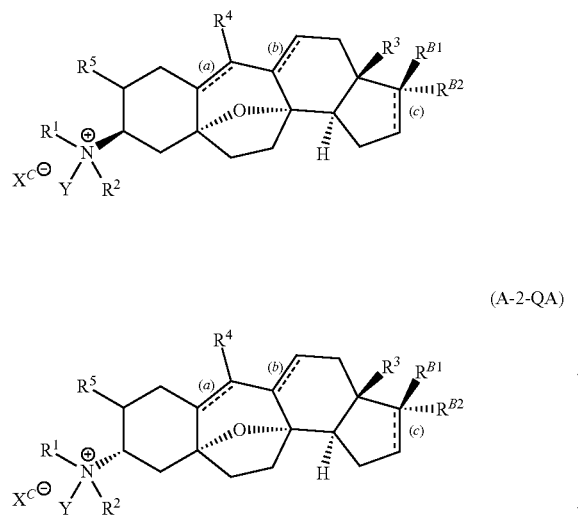

(A-1-QA)

(A-2-QA)

wherein ~~~~, R$^1$, R$^2$, R$^3$, R$^4$, R$^5$, R$^B$1, and R$^{B2}$ are as defined herein.

Alternatively, in certain embodiments, the amino group

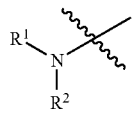

at the C$_3$ position may be an N-oxide of formula

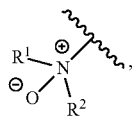

e.g., to provide a compound of Formula (A-NO):

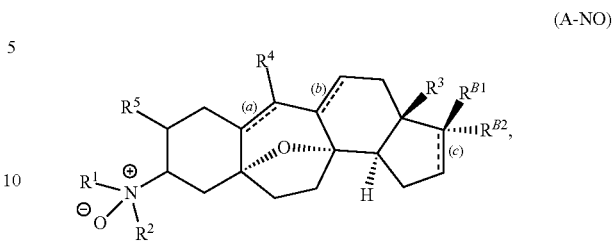

(A-NO)

wherein ~~~~, R$^1$, R$^2$, R$^3$, R$^4$, R$^5$, R$^{B1}$, and R$^{B2}$ are as defined herein.

In certain embodiments, the N-oxide of Formula (A-NO) is the beta (A-1-NO) or alpha (A-2-NO) isomer of the following Formula:

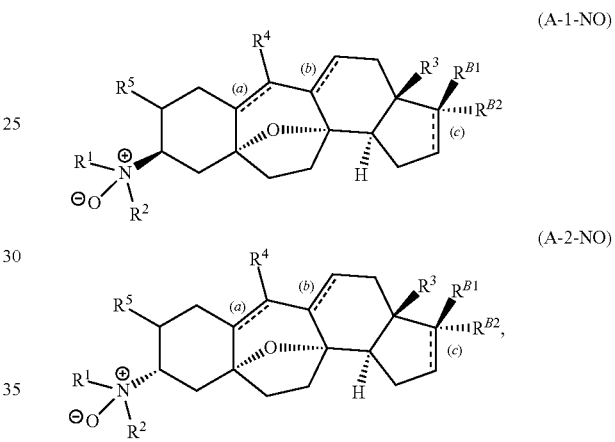

(A-1-NO)

(A-2-NO)

wherein ~~~~, R$^1$, R$^2$, R$^3$, R$^4$, R$^5$, R$^{B1}$, and R$^{B2}$ are as defined herein.

Figure 17A:
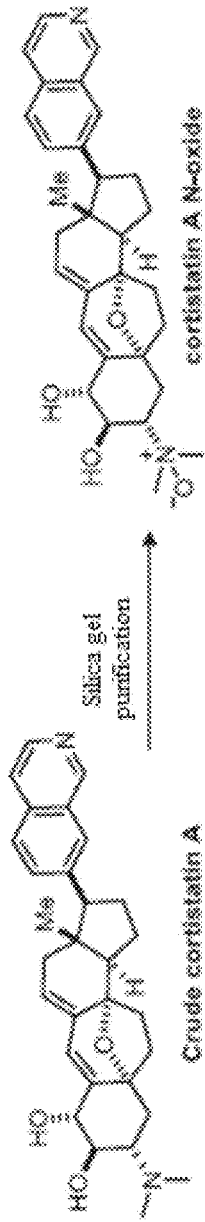
FIG. 17A and FIG. 17B, FIG. 17A depicts the synthesis of the C3-N-oxide of cortistatin A upon exposure of cortistatin A to silica gel, in contrast to treatment of cortistatin A with triethylamine treated silica gel.
Figure 17B:
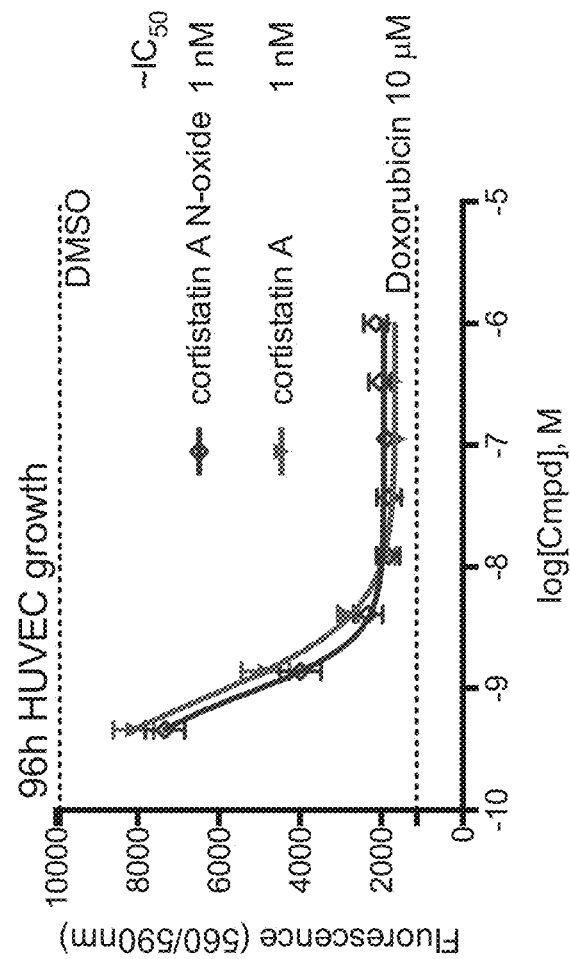
Figure 18:
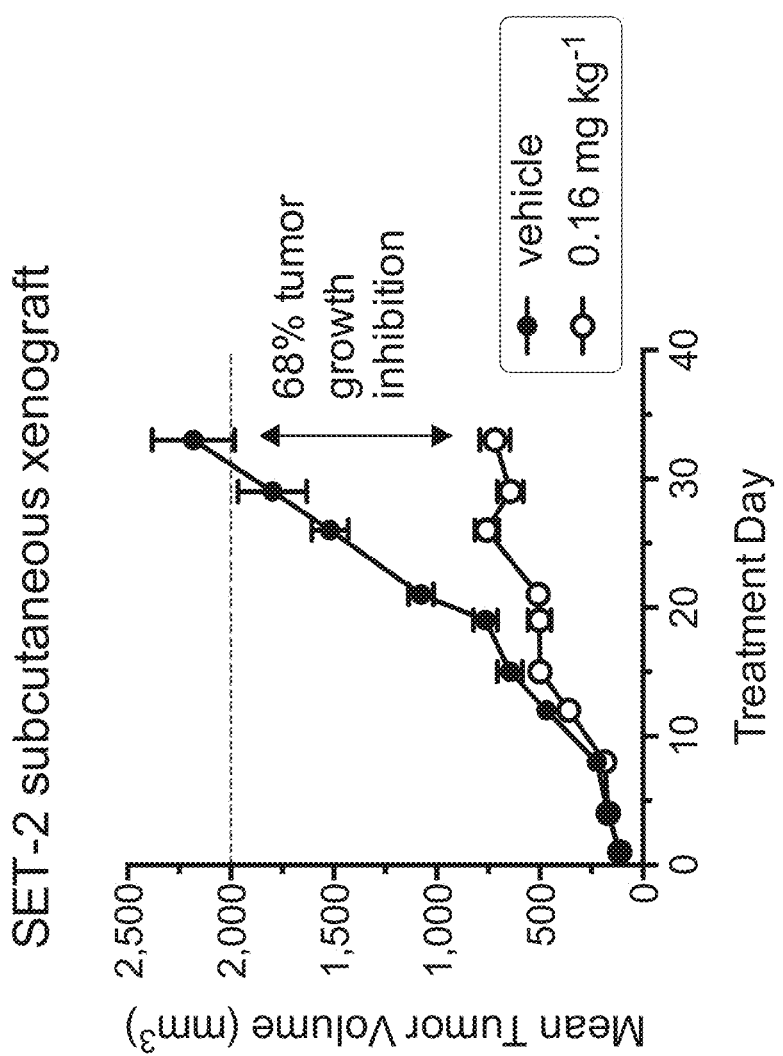
FIG. 18 demonstrates that cortistatin A is effective in SET-2 subcutaneous xenograft model of JAK2V617F-driven proliferation. 1×10$^7$ SET-2 cells tumor cells in 50% matrigel were injected subcutaneously into the flank of 8 to 12 week old female SCID Beige mice. Once tumors reached an average size of 80-120 mm³, the mice were treated with vehicle or 0.16 mg kg⁻¹ daily for the duration of the study, resulting in 68% tumor growth inhibition (n=10, P<0.001, 2way ANOVA).

It has been discovered that C$_3$ N-oxide of cortistatin A is equipotent with cortistatin A in inhibition of HUVEC proliferation. See, e.g., FIGS. 17A and 17B.

Figure 19:
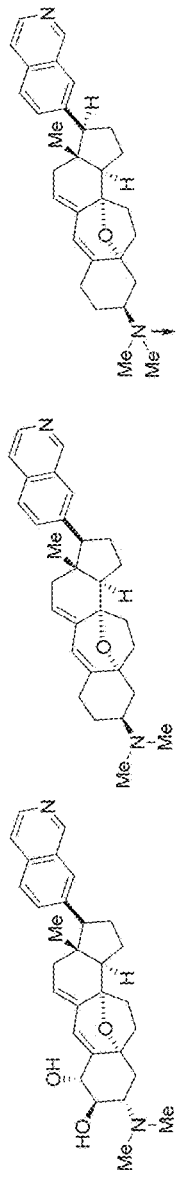
FIG. 19 depicts in vitro liver microsome metabolic stability assay demonstrating the N-oxide of compound 14B demonstrates improved stability.
Figure 20:
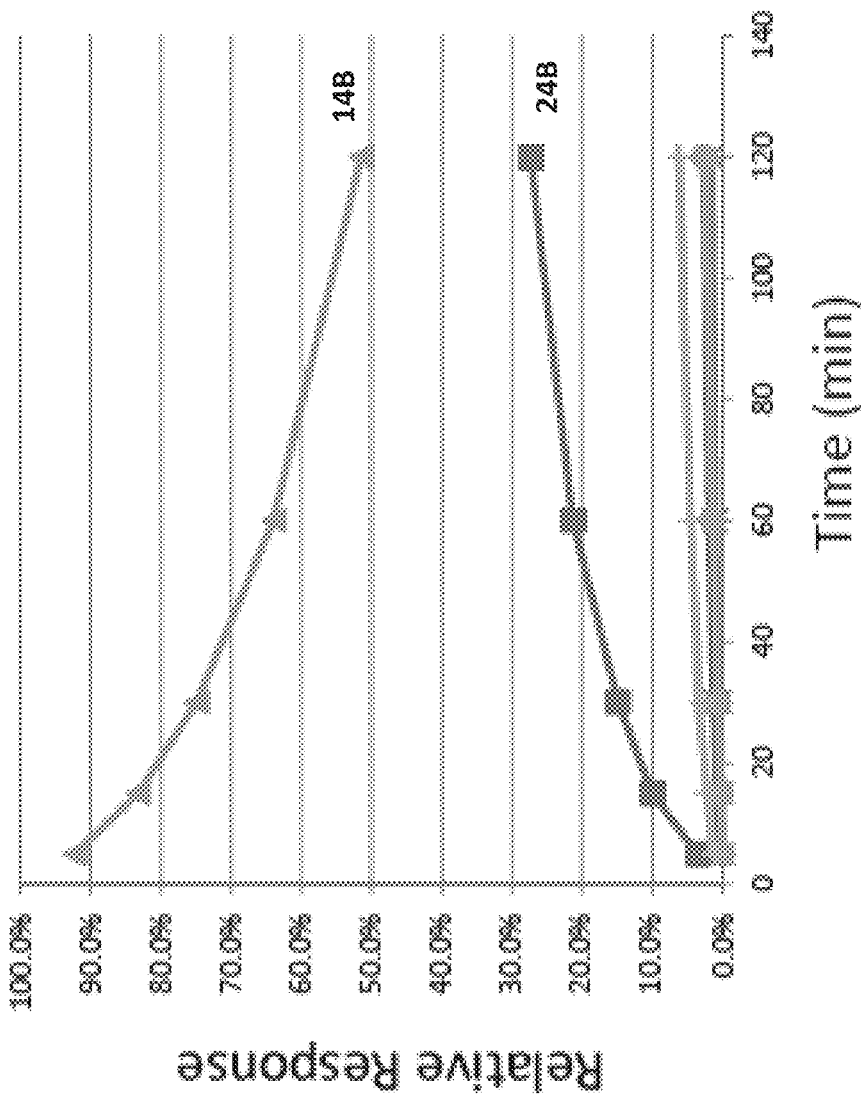
FIG. 20 depicts the results of an in vitro liver microsome assay demonstrating compound 14B undergoes N-monodemethylation at $C_3$ in human liver microsomes to compound 24B.
Figure 21A:
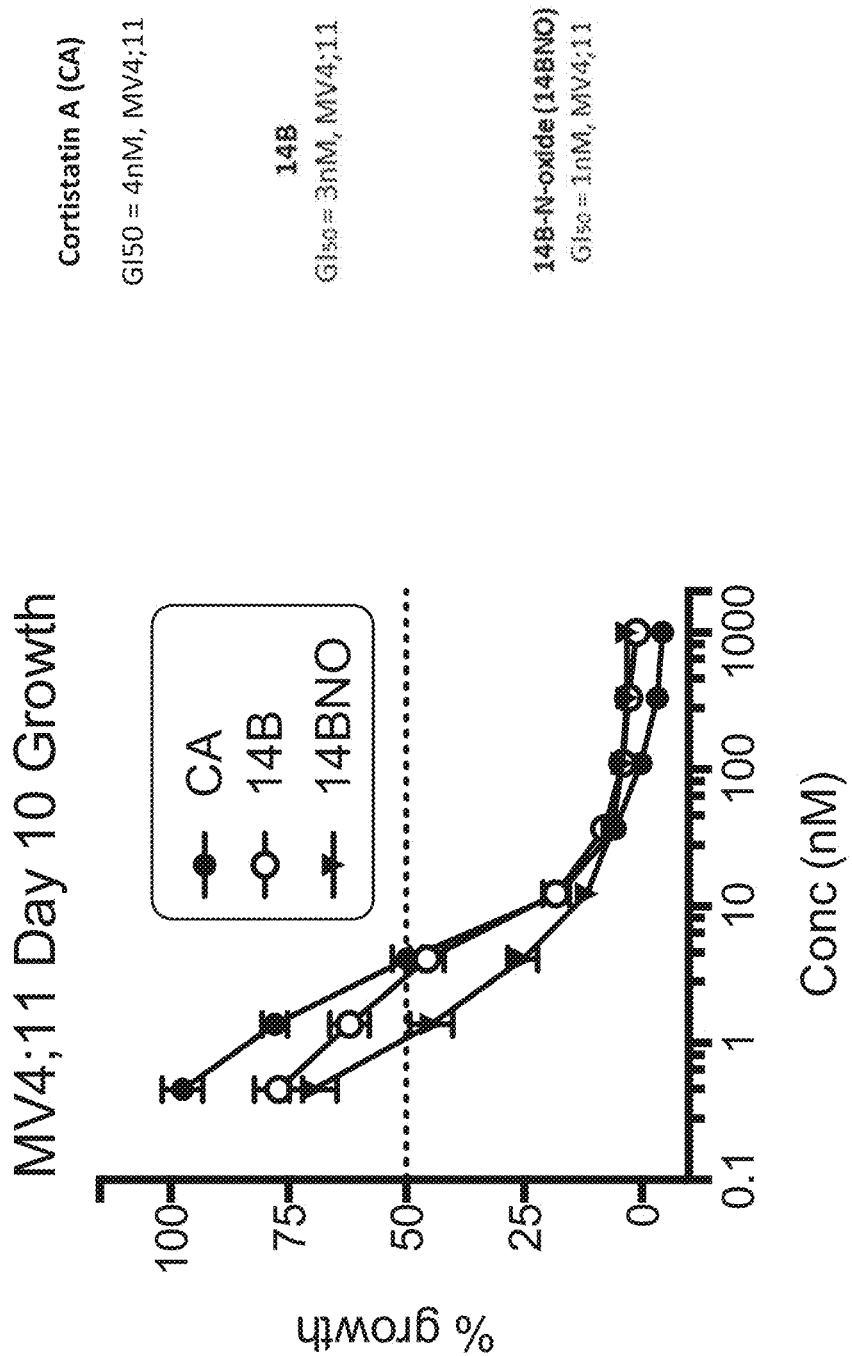

It has further been discovered that beta N-oxides of Formula (A-1-NO), as described herein, have increased stability in liver microsomes compared to the corresponding free beta amino analog of Formula (A-1). See, e.g., FIG. 19, demonstrating increased stability of 14B-N-oxide compared to compound 14B.

Groups R$^1$ and R$^2$

As generally defined herein, in certain embodiments of Formula (A) and (C), R$^1$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —SR$^A$, —N(R$^A$)$_2$, —C(=O)R$^A$, —C(=O)OR$^A$, —C(=O)N(R$^A$)$_2$, —S(=O)$_2$R$^A$, or a nitrogen protecting group.

Furthermore, in certain embodiments of Formula (A), R$^2$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^A$, —C(=O)OR$^A$, —C(=O)N(R$^A$)$_2$, —S(=O)$_2$R, S(=O)$_2$R$^A$ or a nitrogen protecting group.

For example, in certain embodiments of Formula (A), at least one of R$^1$ and R$^2$ is hydrogen. In certain embodiments of Formula (A), both of R$^1$ and R$^2$ is hydrogen. In certain embodiments of Formula (A), one of $R^1$ and $R^2$ is hydrogen and the other is a non-hydrogen group, e.g, optionally substituted alkyl. In certain embodiments of Formula (C), $R^1$ is hydrogen.

In certain embodiments of Formula (A), at least one of $R^1$ and $R^2$ is optionally substituted alkyl, e.g., optionally substituted $C_{1-6}$alkyl. In certain embodiments of Formula (A), each instance of $R^1$ and $R^2$ is independently optionally substituted alkyl. In certain embodiments of Formula (C), $R^1$ is optionally substituted alkyl, e.g., optionally substituted $C_{1-6}$alkyl. In certain embodiments, $R^1$ and/or $R^2$ is optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments, $R^1$ and/or $R^2$ is optionally substituted methyl ($C_1$), optionally substituted ethyl ($C_2$), optionally substituted n-propyl ($C_3$), optionally substituted isopropyl ($C_3$), optionally substituted n-butyl ($C_4$), or optionally substituted t-butyl ($C_4$). In certain embodiments, $R^1$ and/or $R^2$ is alkyl substituted with one or more halogen substitutents (e.g., fluoro). In certain embodiments, $R^1$ and/or $R^2$ is —$CH_3$ or —$CF_3$. In certain embodiments, each instance of $R^1$ and $R^2$ is independently —$CH_3$ or —$CF_3$. In certain embodiments, $R^1$ and/or $R^2$ is alkyl substituted with one or more halogen (e.g., fluoro), amino (—$NH_2$), substituted amino, hydroxyl (—OH), substituted hydroxyl, thiol (—SH), substituted thiol, or sulfonyl substituents. In certain embodiments, $R^1$ and/or $R^2$ is alkyl substituted with an optionally substituted carbocyclyl (e.g., cyclopropyl) or optionally substituted heterocyclyl (e.g., oxetanyl) ring.

For example, in certain embodiments, at least one of $R^1$ and $R^2$ is a group of formula:

e.g., to provide a compound of Formula (A-f), (A-1-f) or (A-2-f):

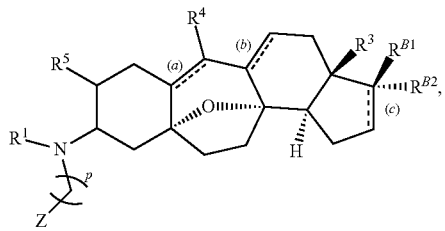
(A-f)

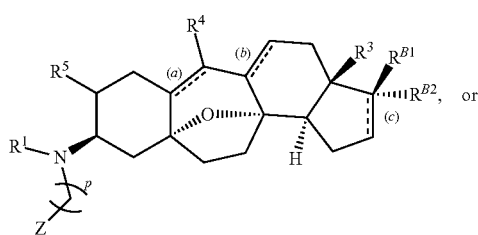
(A-1-f) or

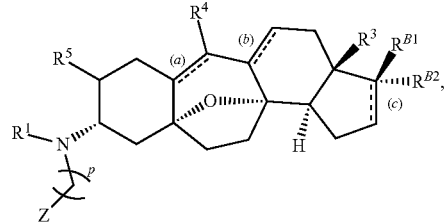
(A-2-f)

or a pharmaceutically acceptable salt, quaternary amine salt, or N-oxide thereof,
wherein ====, $R^1$, $R^3$, $R^4$, $R^5$, $R^{B1}$, and $R^{B2}$ are as defined herein; and
wherein:
p is 1, 2, 3, 4, 5, or 6; and
Z is —$CH_2X^Z$, —$CH(X^Z)_2$, —$C(X^Z)_3$, —$OR^Z$, —$SR^Z$, —$N(R^Z)_2$, —$S(O)_2N(R^Z)_2$,

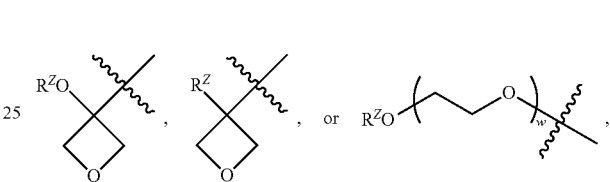

wherein each instance of $R^Z$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^Z$, —C(=O)$OR^Z$, —C(=O)N($R^Z$)$_2$, an oxygen protecting group when attached to oxygen, a sulfur protecting group when attached to sulfur, or a nitrogen protecting group when attached to nitrogen, optionally when attached to N the two $R^Z$ groups may be joined to form an optionally substituted heterocyclyl or optionally substituted heteroaryl ring;
each instance of $X_Z$ is independently fluoro, chloro, bromo, or iodo; and
w is an integer between 1 and 10, inclusive.

In certain embodiments, both instances of $R^1$ and $R^2$ are independently a group of formula

In certain embodiments, p is 1. In certain embodiments, p is 2. In certain embodiments, p is 3. In certain embodiments, w is 1, 2, 3, or 4. In certain embodiments, $R^Z$ is hydrogen or optionally substituted alkyl (e.g., —$CH_3$). In certain embodiments, Z is —$OR^Z$, e.g., —OH or —$OR^Z$ wherein $R^Z$ is a non-hydrogen group, e.g., wherein $R^Z$ is optionally substituted alkyl such as —$CH_3$. In certain embodiments, Z is —N($R^Z$)$_2$, e.g., —$NH_2$, —$NHR^Z$, or —N($R^Z$)$_2$ wherein $R^Z$ is a non-hydrogen group, e.g., wherein $R^Z$ is optionally substituted alkyl such as —$CH_3$. In certain embodiments, Z is —$CH_2X^Z$, —$CH(X^Z)_2$, —$C(X^Z)_3$, e.g., wherein $X^Z$ is fluoro. In certain embodiments, Z is —$S(O)_2N(R^Z)_2$, e.g., —$S(O)_2NH_2$ or —$S(O)_2NHCH_3$.

In certain embodiments of Formula (A), at least one of $R^1$ and $R^2$ is optionally substituted alkenyl, e.g., optionally substituted $C_{2-6}$alkenyl. In certain embodiments of Formula (A), both of $R^1$ and $R^2$ is optionally substituted alkenyl. In certain embodiments of Formula (C), $R^1$ is optionally substituted alkenyl, e.g., optionally substituted $C_{2-6}$alkenyl. In certain embodiments, $R^1$ and/or $R^2$ is optionally substituted $C_2$alkenyl, optionally substituted $C_3$alkenyl, optionally substituted $C_4$alkenyl, optionally substituted $C_5$alkenyl, or optionally substituted $C_6$alkenyl. In certain embodiments, $R^1$ and/or $R^2$ is optionally substituted vinyl ($C_2$) or optionally substituted allyl ($C_3$).

In certain embodiments of Formula (A), at least one of $R^1$ and $R^2$ is optionally substituted alkynyl, e.g., optionally substituted $C_{2-6}$alkynyl. In certain embodiments of Formula (A), both of $R^1$ and $R^2$ is optionally substituted alkynyl. In certain embodiments of Formula (C), $R^1$ is optionally substituted alkynyl, e.g., optionally substituted $C_{2-6}$alkynyl. In certain embodiments, $R^1$ and/or $R^2$ is optionally substituted $C_2$alkynyl, optionally substituted $C_3$alkynyl, optionally substituted $C_4$alkynyl, optionally substituted $C_5$alkynyl, or optionally substituted $C_6$alkynyl. In certain embodiments, $R^1$ and/or $R^2$ is optionally substituted acetylenyl ($C_2$) or optionally substituted propargyl ($C_3$).

In certain embodiments of Formula (A), at least one of $R^1$ and $R^2$ is optionally substituted carbocyclyl, e.g., optionally substituted $C_{3-6}$carbocyclyl. In certain embodiments of Formula (A), both of $R^1$ and $R^2$ is optionally substituted carbocyclyl. In certain embodiments of Formula (C), $R^1$ is optionally substituted carbocyclyl, e.g., optionally substituted $C_{3-6}$carbocyclyl. In certain embodiments, $R^1$ and/or $R^2$ is optionally substituted $C_3$ carbocyclyl, optionally substituted $C_4$ carbocyclyl, optionally substituted $C_5$ carbocyclyl, or optionally substituted $C_6$ carbocyclyl. In certain embodiments, $R^1$ and/or $R^2$ is optionally substituted cyclopropyl ($C_3$), optionally substituted cyclobutyl ($C_4$), optionally substituted cyclopenyl ($C_5$), or optionally substituted cyclohexyl ($C_6$).

In certain embodiments of Formula (A), at least one of $R^1$ and $R^2$ is optionally substituted heterocyclyl, e.g., optionally substituted 3-6 membered heterocyclyl. In certain embodiments of Formula (A), both of $R^1$ and $R^2$ is optionally substituted heterocyclyl. In certain embodiments of Formula (C), $R^1$ is optionally substituted heterocyclyl, e.g., optionally substituted 3-6 membered heterocyclyl. In certain embodiments, $R^1$ and/or $R^2$ is optionally substituted 3-membered heterocyclyl (e.g., optionally substituted oxetanyl), optionally substituted 4-membered heterocyclyl, optionally substituted 5-membered heterocyclyl, or optionally substituted 6-membered heterocyclyl, e.g., optionally substituted 6-membered heterocyclyl comprising 1 or 2 heteroatoms selected from oxygen, sulfur, or nitrogen.

In certain embodiments of Formula (A), at least one of $R^1$ and $R^2$ is optionally substituted aryl, e.g., optionally substituted phenyl. In certain embodiments of Formula (A), both of $R^1$ and $R^2$ is optionally substituted phenyl. In certain embodiments of Formula (C), $R^1$ is optionally substituted aryl, e.g., optionally substituted phenyl.

In certain embodiments of Formula (A), at least one of $R^1$ and $R^2$ is optionally substituted heteroaryl, e.g., optionally substituted 5-6 membered heteroaryl. In certain embodiments of Formula (A), both of $R^1$ and $R^2$ is optionally substituted heteroaryl. In certain embodiments of Formula (C), $R^1$ is optionally substituted heteroaryl, e.g., optionally substituted 5-6 membered heteroaryl.

In certain embodiments of Formula (A) and (C), $R^1$ is —$OR^A$, e.g., —OH or —$OCH_3$. In certain embodiments of Formula (A) and (C), $R^1$ is —$SR^A$. In certain embodiments of Formula (A) and (C), $R^1$ is —$N(R^A)_2$.

In certain embodiments of Formula (A), at least one of $R^1$ and $R^2$ is —$C(=O)R^A$, —$C(=O)OR^A$, or —$C(=O)N(R^A)_2$. In certain embodiments of Formula (C), $R^1$ is —$C(=O)R^A$, —$C(=O)OR^A$, or —$C(=O)N(R^A)_2$.

In certain embodiments of Formula (A), at least one of $R^1$ and $R^2$ is a nitrogen protecting group. In certain embodiments of Formula (C), $R^1$ is a nitrogen protecting group.

Furthermore, as generally defined herein, in certain embodiments of Formula (A), $R^1$ and $R^2$ are joined to form an optionally substituted heterocyclyl or optionally substituted heteroaryl.

In certain embodiments of Formula (A), at least one of $R^1$ and $R^2$ is —$S(O)_2R^A$. In certain embodiments, $R^A$ optionally substituted alkyl (e.g., —$CH_3$). In certain embodiments of Formula (A), one of $R^1$ and $R^2$ is —$S(O)_2R^A$ and the other is optionally substituted alkyl (e.g., —$CH_3$). In certain embodiments of Formula (C), $R^1$ is —$S(O)_2R^A$.

In certain embodiments of Formula (A), $R^1$ and $R^2$ are joined to form an optionally substituted heterocyclyl, e.g., an optionally substituted 3-6 membered heterocyclyl. In certain embodiments of Formula (A), $R^1$ and $R^2$ are joined to form an optionally substituted 3-membered heterocyclyl, an optionally substituted 4-membered heterocyclyl, optionally substituted 5-membered heterocyclyl, or an optionally substituted 6-membered heterocyclyl. In certain embodiments, $R^1$ and $R^2$ are joined to form an optionally substituted 3-membered heterocyclyl, i.e., an optionally substituted aziridinyl. In certain embodiments, $R^1$ and $R^2$ are joined to form an optionally substituted 4-membered heterocyclyl, e.g., an optionally substituted azetidinyl. In certain embodiments, $R^1$ and $R^2$ are joined to form an optionally substituted 5-membered heterocyclyl, e.g., an optionally substituted pyrrolidinyl or optionally substituted imidazolidine-2,4-dione. In certain embodiments, $R^1$ and $R^2$ are joined to form an optionally substituted 6-membered heterocyclyl, e.g., an optionally substituted piperidinyl, optionally substituted tetrahydropyranyl, optionally substituted dihydropyridinyl, optionally substituted thianyl, optionally substituted piperazinyl, optionally substituted morpholinyl, optionally substituted dithianyl, optionally substituted dioxanyl, or optionally substituted triazinanyl.

For example, in certain embodiments, $R^1$ and $R^2$ are joined to form a group of formula:

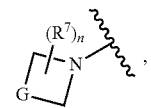

e.g., to provide a compound of Formula (A-a), (A-1-a) or (A-2-a):

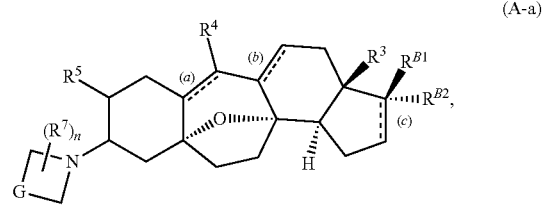

-continued (A-1-a)

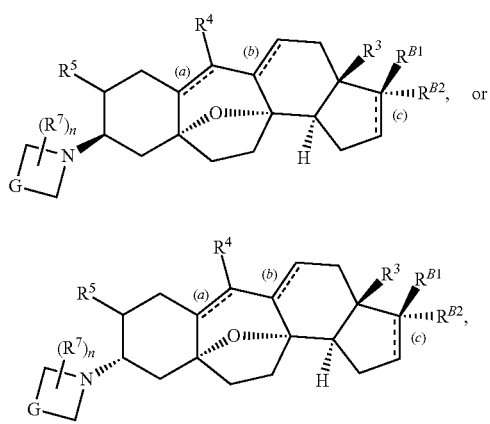

(A-2-a)

or a pharmaceutically acceptable salt, quaternary amine salt, or N-oxide thereof, wherein ≈≈≈,
$R^3$, $R^4$, $R^5$, $R^{B1}$, and $R^{B2}$ are as defined herein; and wherein:

G is —O—, —S—, —NH—, —NR$^7$—, —CH$_2$—, —CH(R$^7$)—, or —C(R$^7$)$_2$—;

each instance of $R^7$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, amino, substituted amino, hydroxyl, substituted hydroxyl, thiol, substituted thiol, carbonyl, sulfonyl, sulfinyl, or a nitrogen protecting group when attached to a nitrogen atom;

optionally wherein two $R^7$ groups are joined to form an optionally substituted carbocyclyl, optionally substituted heterocyclyl, optionally substituted aryl, an optionally substituted heteroaryl ring, or an oxo (=O) group; and n is 0, 1, 2, 3, or 4.

In certain embodiments, $R^1$ and $R^2$ are joined to form a group of formula:

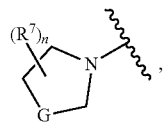

e.g., to provide a compound of Formula (A-b), (A-1-b), or (A-2-b):

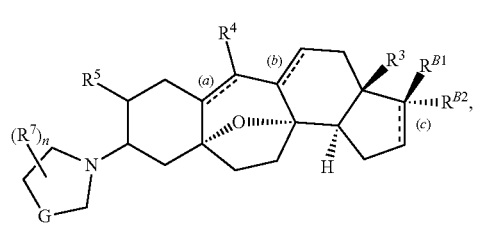

(A-b)

-continued (A-1-b)

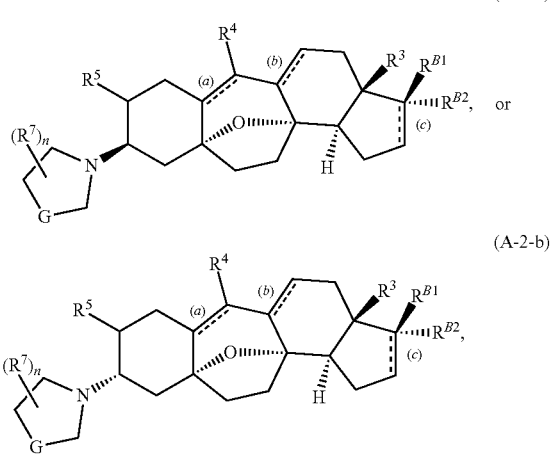

(A-2-b)

or a pharmaceutically acceptable salt, quaternary amine salt, or N-oxide thereof, wherein ≈≈≈,
$R^3$, $R^4$, $R^5$, $R^{B1}$, and $R^{B2}$ are as defined herein; and wherein:

G is —O—, —S—, —NH—, —NR$^7$—, —CH$_2$—, —CH(R$^7$)—, or —C(R$^7$)$_2$—;

each instance of $R^7$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, amino, substituted amino, hydroxyl, substituted hydroxyl, thiol, substituted thiol, carbonyl, sulfonyl, sulfinyl, or a nitrogen protecting group when attached to a nitrogen atom;

optionally wherein two $R^7$ groups are joined to form an optionally substituted carbocyclyl, optionally substituted heterocyclyl, optionally substituted aryl, an optionally substituted heteroaryl ring, or an oxo (=O) group; and n is 0, 1, 2, 3, or 4.

In certain embodiments, $R^1$ and $R^2$ are joined to form a group of formula:

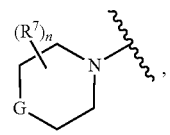

e.g., to provide a compound of Formula (A-c), (A-1-c), (A-2-c):

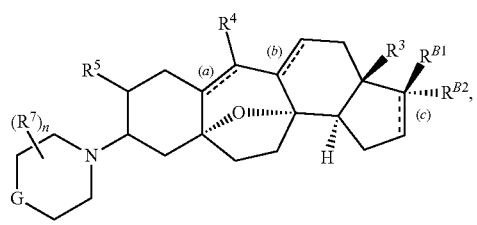

(A-c)

-continued

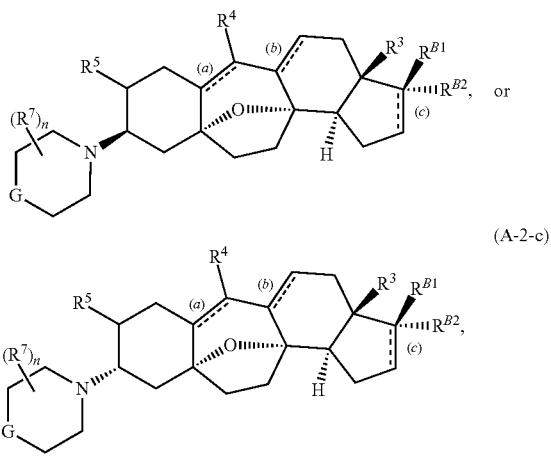

(A-1-c)

(A-2-c)

or a pharmaceutically acceptable salt, quaternary amine salt, or N-oxide thereof, wherein ~~~~,
$R^3$, $R^4$, $R^5$, $R^{B1}$, and $R^{B2}$ are as defined herein; and wherein:

G is —O—, —S—, —NH—, —$NR^7$—, —$CH_2$—, —CH($R^7$)—, or —C($R^7$)$_2$—;

each instance of $R^7$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, amino, substituted amino, hydroxyl, substituted hydroxyl, thiol, substituted thiol, carbonyl, sulfonyl, sulfinyl, or a nitrogen protecting group when attached to a nitrogen atom;

optionally wherein two $R^7$ groups are joined to form an optionally substituted carbocyclyl, optionally substituted heterocyclyl, optionally substituted aryl, an optionally substituted heteroaryl ring, or an oxo (=O) group; and n is 0, 1, 2, 3, or 4.

In certain embodiments, n is 0, and the ring system formed by the joining of $R^1$ and $R^2$ is not substituted with an $R^7$ group as defined herein. In certain embodiments, n is 1, 2, 3, or 4, and the ring system is substituted with 1, 2, 3, or 4 $R^7$ groups as defined herein. In certain embodiments, n is 1. In certain embodiments, n is 2. In certain embodiments, n is 3. In certain embodiments, n is 4.

In certain embodiments, wherein n is not 0 (i.e., n is 1, 2, 3, or 4) and at least one $R^7$ is attached to a carbon atom, the $R^7$ is halogen (e.g., fluoro), hydroxyl, substituted hydroxyl, or carbonyl (e.g., —$CO_2H$). In certain embodiments, wherein n is not 0 (i.e., n is 1, 2, 3, or 4) and two $R^7$ groups are attached to the same carbon atom, the two $R^7$ groups are each halogen, e.g., fluoro. In certain embodiments, wherein n is not 0 (i.e., n is 1, 2, 3, or 4) and two $R^7$ groups are attached to the same carbon atom, the two $R^7$ groups are joined to form an optionally substituted carbocyclyl ring or optionally substituted heterocyclyl ring (e.g., optionally substituted oxetanyl ring). In certain embodiments, wherein n is not 0 (i.e., n is 1, 2, 3, or 4) and two $R^7$ groups are attached to a different carbon atom, the two $R^7$ groups are joined to form an optionally substituted carbocyclyl ring or optionally substituted heterocyclyl ring.

In certain embodiments, G is —O—. In certain embodiments, G is —$NR^7$—, e.g., wherein $R^7$ is optionally substituted alkyl (e.g., —$CH_3$). In certain embodiments, G is —CH($R^7$)— or —C($R^7$)$_2$— wherein at least one $R^7$ is hydroxyl, substituted hydroxyl, or carbonyl (e.g., —$CO_2H$).

In certain embodiments, the group

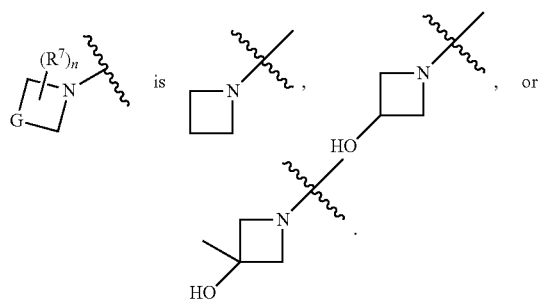

In certain embodiments, the group

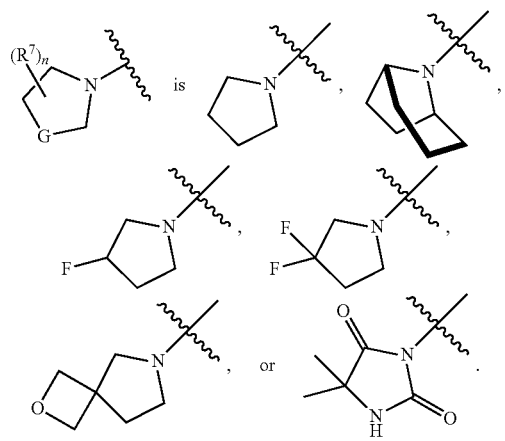

In certain embodiments, the group

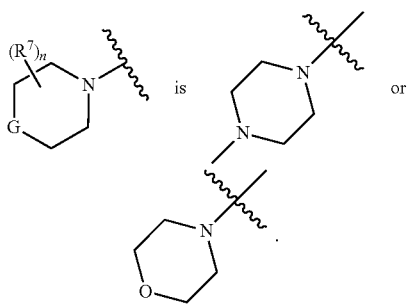

In certain embodiments of Formula (A), $R^1$ and $R^2$ are joined to form an optionally substituted heteroaryl, e.g., an optionally substituted 5-membered heteroaryl or optionally substituted 6-membered heteroaryl.

Group $R^O$

As generally defined herein, for Formula (E), $R^O$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^A$, —C(=O)O$R^A$, —C(=O)N($R^A$)$_2$, or an oxygen protecting group.

In certain embodiments of Formula (E), $R^O$ is optionally substituted alkyl, e.g., optionally substituted $C_{1-6}$alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments, $R^O$ is optionally substituted methyl ($C_1$), optionally substituted ethyl ($C_2$), optionally substituted n-propyl ($C_3$), optionally substituted isopropyl ($C_3$), optionally substituted n-butyl ($C_4$), or optionally substituted t-butyl ($C_4$). In certain embodiments, $R^O$ is alkyl substituted with one or more halogen substitutents (e.g., fluoro). In certain embodiments, $R^O$ is —$CH_3$ or —$CF_3$. In certain embodiments, $R^O$ is alkyl substituted with one or more halogen (e.g., fluoro), amino (—$NH_2$), substituted amino, hydroxyl (—OH), substituted hydroxyl, thiol (—SH), substituted thiol, or sulfonyl substituents. In certain embodiments, $R^O$ is alkyl substituted with an optionally substituted carbocyclyl (e.g., cyclopropyl) or optionally substituted heterocyclyl (e.g., oxetanyl) ring.

For example, in certain embodiments, $R^O$ is a group of formula:

e.g., to provide a compound of Formula (E-f), (E-1-f) or (E-2-f):

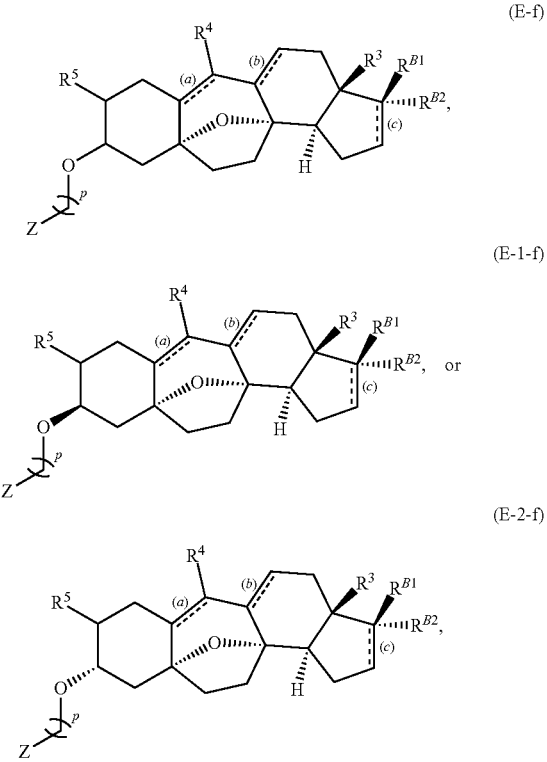

or a pharmaceutically acceptable salt, quaternary amine salt, or N-oxide thereof, wherein ═══ $R^3$, $R^4$, $R^5$, $R^{B1}$, and $R^{B2}$ are as defined herein; and
wherein:
p is 1, 2, 3, 4, 5, or 6; and
Z is —$CH_2X^Z$, —$CH(X^Z)_2$, —$C(X^Z)_3$, —$OR^Z$, —$SR^Z$, —$N(R^Z)_2$, —$S(O)_2N(R^Z)_2$,

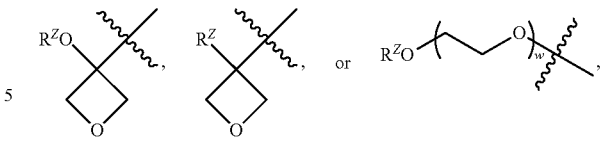

wherein each instance of $R^Z$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)$R^Z$, —C(═O)O$R^Z$, —C(═O)N($R^Z$)$_2$, an oxygen protecting group when attached to oxygen, a sulfur protecting group when attached to sulfur, or a nitrogen protecting group when attached to nitrogen, optionally when attached to N the two $R^Z$ groups may be joined to form an optionally substituted heterocyclyl or optionally substituted heteroaryl ring;
each instance of $X^Z$ is independently fluoro, chloro, bromo, or iodo; and
w is an integer between 1 and 10, inclusive.

In certain embodiments, p is 1. In certain embodiments, p is 2. In certain embodiments, p is 3. In certain embodiments, w is 1, 2, 3, or 4. In certain embodiments, $R^Z$ is hydrogen or optionally substituted alkyl (e.g., —$CH_3$). In certain embodiments, Z is —$OR^Z$, e.g., —OH or —$OR^Z$ wherein $R^Z$ is a non-hydrogen group, e.g., wherein $R^Z$ is optionally substituted alkyl such as —$CH_3$. In certain embodiments, Z is —N($R^Z$)$_2$, e.g., —$NH_2$, —$NHR^Z$, or —N($R^Z$)$_2$ wherein $R^Z$ is a non-hydrogen group, e.g., wherein $R^Z$ is optionally substituted alkyl such as —$CH_3$. In certain embodiments, Z is —$CH_2X^Z$, —$CH(X^Z)_2$, —$C(X^Z)_3$, e.g., wherein $X^Z$ is fluoro. In certain embodiments, Z is —$S(O)_2N(R^Z)_2$, e.g., —$S(O)_2NH_2$ or —$S(O)_2NHCH_3$.

In certain embodiments of Formula (E), $R^O$ is optionally substituted alkenyl, e.g., optionally substituted $C_{3-6}$alkenyl, e.g., optionally substituted $C_3$alkenyl, optionally substituted $C_4$alkenyl, optionally substituted $C_5$alkenyl, or optionally substituted $C_6$alkenyl.

In certain embodiments of Formula (E), $R^O$ is optionally substituted alkynyl, e.g., optionally substituted $C_{3-6}$alkynyl, e.g., optionally substituted $C_3$alkynyl, optionally substituted $C_4$alkynyl, optionally substituted $C_5$alkynyl, or optionally substituted $C_6$alkynyl.

In certain embodiments of Formula (E), $R^O$ is optionally substituted carbocyclyl, e.g., optionally substituted $C_{3-6}$carbocyclyl, e.g., optionally substituted $C_3$ carbocyclyl, optionally substituted $C_4$ carbocyclyl, optionally substituted $C_5$ carbocyclyl, or optionally substituted $C_6$ carbocyclyl. In certain embodiments, $R^O$ is optionally substituted cyclopropyl ($C_3$), optionally substituted cyclobutyl ($C_4$), optionally substituted cyclopenyl ($C_5$), or optionally substituted cyclohexyl ($C_6$).

In certain embodiments of Formula (E), $R^O$ is optionally substituted heterocyclyl, e.g., optionally substituted 3-6 membered heterocyclyl, e.g., optionally substituted 3-membered heterocyclyl (e.g., optionally substituted oxetanyl), optionally substituted 4-membered heterocyclyl, optionally substituted 5-membered heterocyclyl, or optionally substituted 6-membered heterocyclyl, e.g., optionally substituted 6-membered heterocyclyl comprising 1 or 2 heteroatoms selected from oxygen, sulfur, or nitrogen.

In certain embodiments of Formula (E), at least one of $R^1$ and $R^2$ is optionally substituted aryl, e.g., optionally substituted phenyl.

In certain embodiments of Formula (A), $R^O$ is optionally substituted heteroaryl, e.g., optionally substituted 5-6 membered heteroaryl.

In certain embodiments of Formula (E), $R^O$ is —C(=O)$R^A$, —C(=O)O$R^A$, or —C(=O)N($R^A$)$_2$. In certain embodiments, $R^A$ is hydrogen or optionally substituted alkyl (e.g., —CH$_3$). For example, in certain embodiments, $R^O$ is —C(=O)CH$_3$, —C(=O)OCH$_3$, —C(=O)N(CH$_3$)$_2$, or —C(=O)NHCH$_3$.

In certain embodiments of Formula (E), $R^O$ is an oxygen protecting group.

Group $R^3$, $R^4$, $R^5$, and Bonds (a), (b), and (c) of Formula ⁝⁝⁝⁝

As generally defined herein, for Formula (A), (B), (C), (D), and (E), $R^3$ is hydrogen or optionally substituted alkyl.

In certain embodiments, $R^3$ is hydrogen. Such compounds are possible using starting materials such as 18-nor estrone.

In certain embodiments, $R^3$ is optionally substituted alkyl, e.g., methyl (—CH$_3$). Such compounds are possible by using starting materials such as estrone and tetralone for methyl.

As generally defined herein, for Formula (A), (B), (C), (D), and (E), $R^4$ is hydrogen, halogen, optionally substituted alkyl, or —Si($R^A$)$_3$.

For example, in certain embodiments, $R^4$ is hydrogen. In certain embodiments, $R^4$ is optionally substituted alkyl, e.g., methyl. In certain embodiments, $R^4$ is —Si($R^A$)$_3$, e.g., wherein each instance of $R^A$ is independently optionally substituted alkyl or optionally substituted phenyl.

As generally defined herein, $R^5$ is hydrogen, halogen, or optionally substituted alkyl. In certain embodiments, $R^5$ is hydrogen. In certain embodiments, $R^5$ is halogen (e.g., bromo, iodo, chloro). In certain embodiments, $R^5$ is optionally substituted alkyl, e.g., methyl.

As generally defined herein, each instance of ⁝⁝⁝⁝, designated as (a), (b), and (c), represents a single or double bond, provided that when ⁝⁝⁝⁝ designated as (c) represents a double bond, then one of $R^{B1}$ and $R^{B2}$ is absent, and provided that when ⁝⁝⁝⁝ designated as (c) represents a single bond, then both $R^{B1}$ and $R^{B2}$ are present.

In certain embodiments, the bond ⁝⁝⁝⁝ designated as (a) is a single bond. In certain embodiments, the bond ⁝⁝⁝⁝ designated as (a) is a double bond.

In certain embodiments, the bond ⁝⁝⁝⁝ designated as (b) is a single bond. In certain embodiments, the bond ⁝⁝⁝⁝ designated as (b) is a double bond.

In certain embodiments, the bond ⁝⁝⁝⁝ designated as (c) is a single bond. In certain embodiments, the bond ⁝⁝⁝⁝ designated as (c) is a double bond, and $R^{B2}$ is absent.

In certain embodiments, the bond ⁝⁝⁝⁝ designated as (a) is double bond, and the bond ⁝⁝⁝⁝ designated as (b) is a double bond. In this instance, in certain embodiments, the bond ⁝⁝⁝⁝ designated as (c) is a double bond, and $R^{B2}$ is absent. However, in this instance, in other embodiments, the bond ⁝⁝⁝⁝ designated as (c) is a single bond.

For example, in certain embodiments of Formula (A), (B), (C), (D), and (E), wherein $R^3$ is methyl, $R^4$ is hydrogen, $R^5$ is hydrogen, and the bond designated (c) is a single bond, provided are compounds of Formula (A-d), (A-1-d), (A-2-d), (B-d), (C-d), (D-d), (D-1-d), (D-2-d), (E-d), (E-1-d), and (E-2-d):

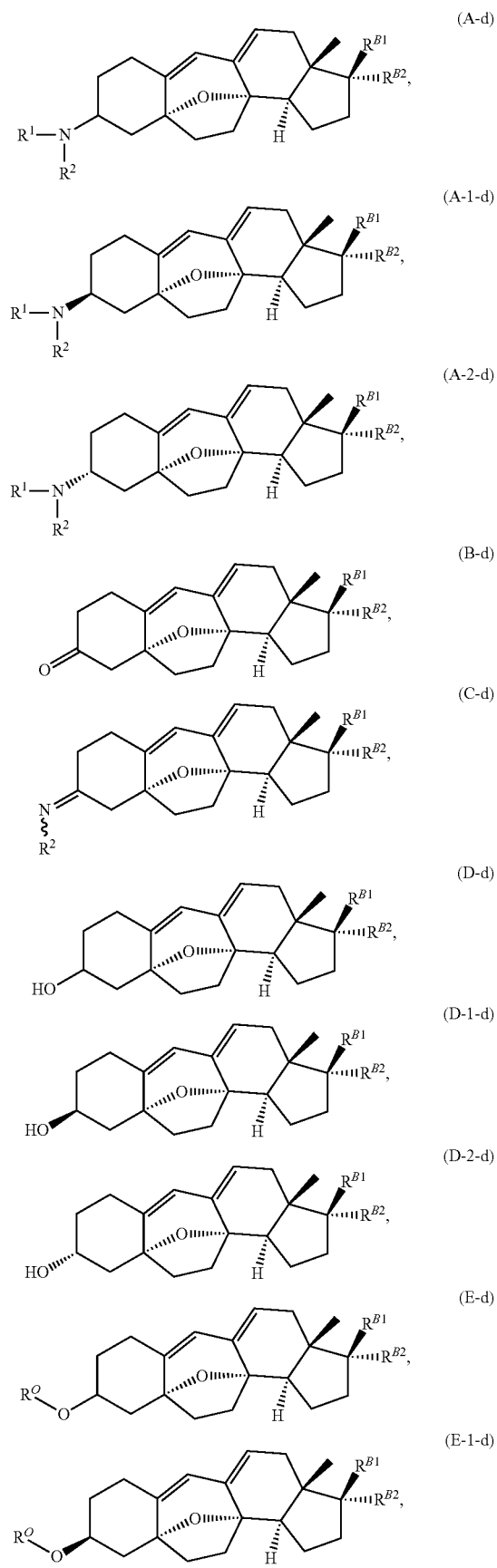

(E-2-d)
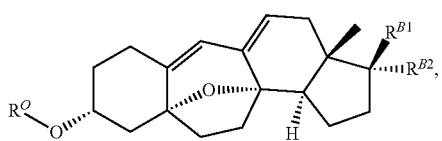

or a pharmaceutically acceptable salt, quaternary amine salt, or N-oxide thereof; wherein $R^1$, $R^2$, $R^O$, $R^{B1}$, and $R^{B2}$ are as defined herein.

In other embodiments of Formula (A), (B), (C), (D), and (E), wherein $R^3$ is methyl, $R^4$ is hydrogen, the bond designated (c) is a double bond, and $R^{B2}$ is absent, provided are compounds of Formula (A-e), (A-1-e), (A-2-e), (B-e), (C-e), (D-e), (D-1-e), (D-2-e), (E-e), (E-1-e), (E-2-e):

(A-e)
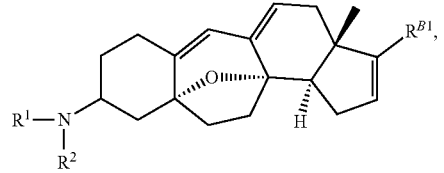

(A-1-e)
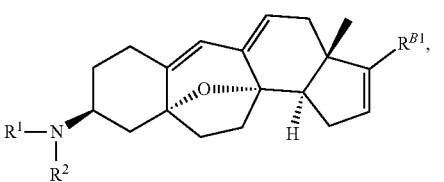

(A-2-e)
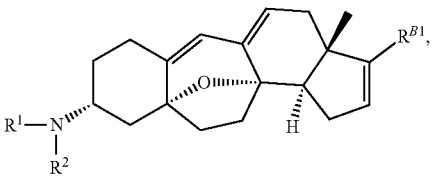

(B-e)
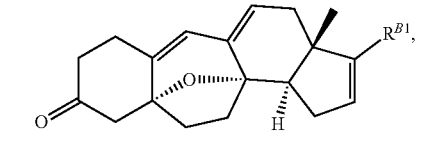

(C-e)
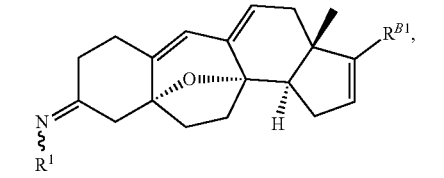

(D-e)
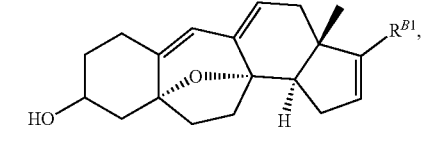

(D-1-e)
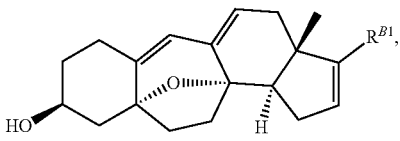

(D-2-e)
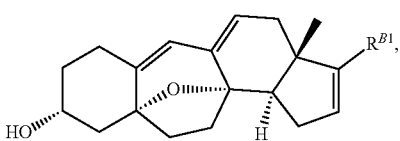

(E-e)
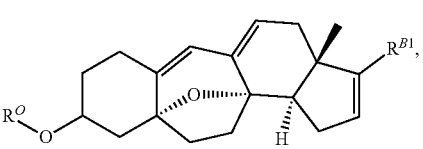

(E-1-e)
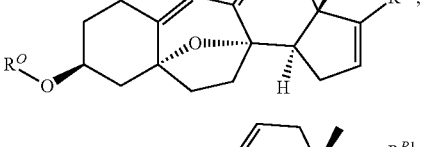

(E-2-e)
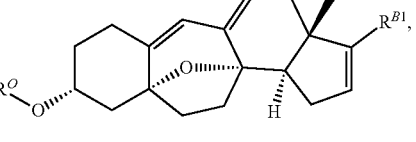

or a pharmaceutically acceptable salt, quaternary amine salt, or N-oxide thereof; wherein $R^1$, $R^2$, $R^O$, $R^5$, and $R^{B1}$, are as defined herein.

Groups $R^{B1}$ and $R^{B2}$

As generally defined herein, each instance of $R^{B1}$ and $R^{B2}$ is, independently, hydrogen, -L$_1$-$R^{B3}$, or —$X^A R^A$ wherein $X^A$ is —O—, —S—, or —N($R^A$)—, provided that at least one of $R^{B1}$ and $R^{B2}$ is not hydrogen; or $R^{B1}$ and $R^{B2}$ are joined to form an oxo group;

$L^1$ is a bond, —C(=O)—, —C(=O)O—, —C(=O)S—, —C(=O)N($R^L$)—, or —N($R^L$)—(C($R^{LL}$)$_2$)$_p$—, wherein $R^L$ is hydrogen, optionally substituted alkyl, or a nitrogen protecting group, each instance of $R^{LL}$ is independently hydrogen, halogen, or optionally substituted alkyl, and p is 0, 1, or 2;

$R^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that when $L_1$ is a bond, then $R^{B3}$ is not hydrogen;

each instance of $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, an oxygen protecting group when attached to oxygen, a sulfur protecting group when attached to sulfur, or a nitrogen protecting group when attached to nitrogen; optionally when attached to N the two $R^A$ groups may be joined to form an optionally substituted heterocyclyl or optionally substituted heteroaryl ring; and optionally when $R^{B1}$ and $R^{B2}$ are each —$X^A R^A$ then two $R^A$ groups may be joined to form an optionally substituted heterocyclyl ring.

In certain embodiments, at least one instance of $R^{B1}$ and $R^{B2}$ is -$L_1$-$R^{B3}$. In this instance, in certain embodiments, the other of $R^{B1}$ and $R^{B2}$ is hydrogen or —$X^A R^A$ (e.g., —$OR^A$). For example, in certain embodiments, when ≈≈≈≈ designated as (c) represents a single bond, then $R^{B1}$ is -$L_1$-$R^{B3}$ and $R^{B2}$ is hydrogen or —$X^A R^A$ (e.g., —$OR^A$). In other embodiments, when ≈≈≈≈ designated as (c) represents a single bond, then $R^{B2}$ is -$L_1$-$R^{B3}$ and $R^{B1}$ is hydrogen or —$X^A R^A$ (e.g., —$OR^A$). Alternatively, in certain embodiments, when ≈≈≈≈ designated as (c) represents a double bond, then $R^{B1}$ is -$L_1$-$R^{B3}$ and $R^{B2}$ is absent.

For example, in certain embodiments of Formula (A), (B), (C), (D), and (E), wherein $R^{B1}$ is -$L_1$-$R^{B3}$, provided are compounds of Formula (A-g), (A-1-g), (A-2-g), (B-g), (C-g), (D-g), (D-1-g), (D-2-g), (E-g), (E-1-g), (E-2-g):

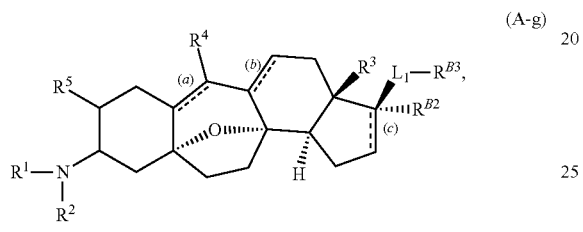
(A-g)

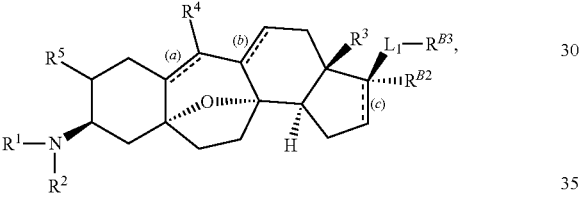
(A-1-g)

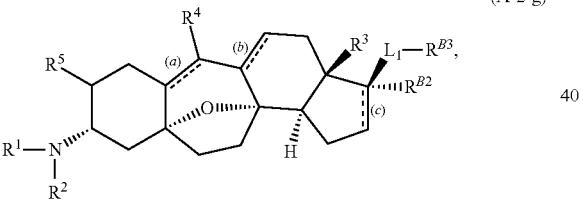
(A-2-g)

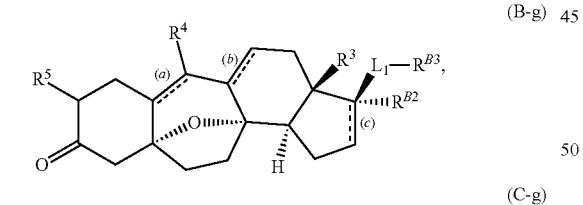
(B-g)

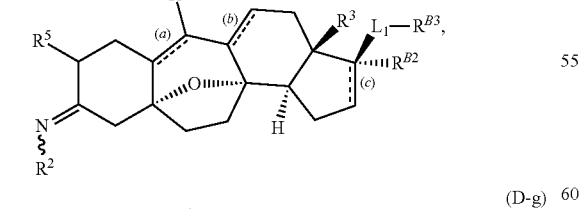
(C-g)

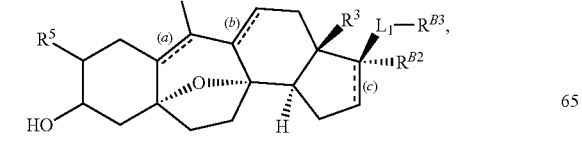
(D-g)

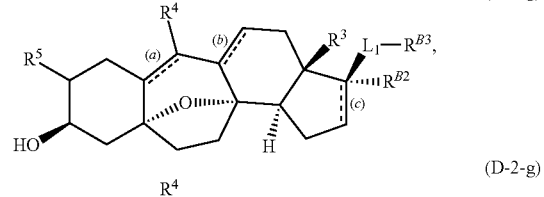
(D-1-g)

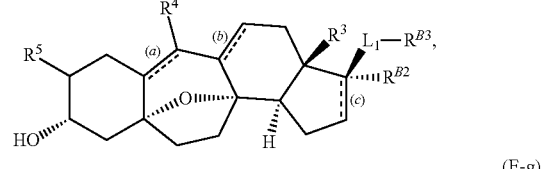
(D-2-g)

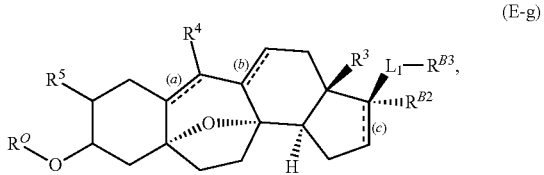
(E-g)

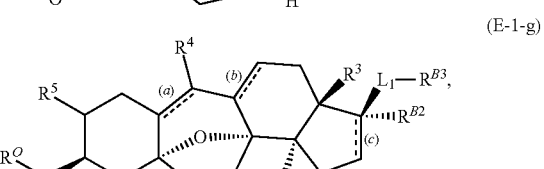
(E-1-g)

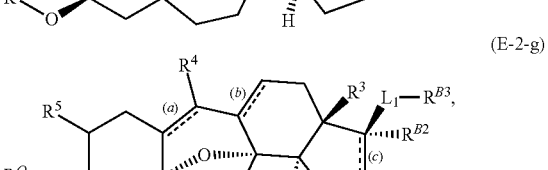
(E-2-g)

or a pharmaceutically acceptable salt, quaternary amine salt, or N-oxide thereof; wherein ≈≈≈≈, $R^1$, $R^2$, $R^O$, $R^3$, $R^4$, $R^5$, $R^{B2}$, $L_1$, and $R^{B3}$ are as defined herein.

In certain embodiments, $L_1$ is a bond, and $R^{B3}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $L_1$ is —C(=O)—, —C(=O)O—, —C(=O)S—, —C(=O)N($R^L$)—, or —N($R^L$)—(C($R^{LL}$)$_2$)$_p$—, wherein $R^L$ is hydrogen, optionally substituted alkyl, or a nitrogen protecting group, each instance of $R^{LL}$ is independently hydrogen, halogen, or optionally substituted alkyl, and $R^{B3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $L_1$ is —C(=O)—. In certain embodiments, $L_1$ is —C(=O)O—. In certain embodiments, $L_1$ is —C(=O)S—. In certain embodiments, $L_1$ is —C(=O)N($R^L$)—. In certain embodiments, $L_1$ is —N($R^L$)—C($R^{LL}$)$_2$—. In certain embodiments, $R^L$ is hydrogen or optionally substituted alkyl, e.g., methyl. In certain embodiments, each instance of $R^{LL}$ is independently hydrogen, optionally substituted alkyl, e.g., methyl, or fluoro. In certain embodiments, p is 0. In certain embodiments, p is 1. In certain embodiments, p is 2.

In certain embodiments, when $L_1$ is —C(=O)—, —C(=O)O—, —C(=O)S—, —C(=O)N($R^L$)—, or —N($R^L$)—(C($R^{LL}$)$_2$)$_p$—, and $R^{B3}$ is hydrogen, provided is a group of formula —C(=O)H, —C(=O)OH, —C(=O)SH, —C(=O)N(R^L)H, or —N(R^L)H.

However, in certain embodiments when L₁ is a bond or —C(=O)—, —C(=O)O—, —C(=O)S—, —C(=O)N(R^L)—, or —N(R^L)—(C(R^{LL})₂)ₚ—, R^{B3} is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, R^{B3} is an acyclic group, e.g., R^{B3} is an optionally substituted alkyl, optionally substituted alkenyl, or optionally substituted alkynyl. In certain embodiments, R^{B3} is optionally substituted alkyl, e.g., optionally substituted C₁₋₆alkyl. In certain embodiments, R^{B3} is optionally substituted alkenyl, e.g., optionally substituted C₂₋₆alkenyl. In certain embodiments, R^{B3} is optionally substituted alkynyl, e.g., optionally substituted C₂₋₆alkynyl.

However, in certain embodiments, R^{B3} is a cyclic group, e.g., R^{B3} is optionally substituted carbocyclyl, optionally substituted heterocyclyl, optionally substituted aryl, or optionally substituted heteroaryl. In certain embodiments, R^{B3} is a nonaromatic cyclic group, e.g., in certain embodiments, R^{B3} is optionally substituted carbocyclyl or optionally substituted heterocyclyl. In certain embodiments, R^{B3} is an aromatic cyclic group, e.g., in certain embodiments, R^{B3} is optionally substituted aryl or optionally substituted heteroaryl.

In certain embodiments, R^{B3} is optionally substituted carbocyclyl, e.g., optionally substituted C₃₋₆carbocyclyl. In certain embodiments R^{B3} is optionally substituted C₃ carbocyclyl, optionally substituted C₄ carbocyclyl, optionally substituted C₅ carbocyclyl, or optionally substituted C₆ carbocyclyl. In certain embodiments, R^{B3} is optionally substituted cyclopenyl (C₅) or optionally substituted cyclohexyl (C₆).

In certain embodiments, R^{B3} is optionally substituted carbocyclyl fused to an optionally substituted aryl or optionally substituted heteroaryl ring, wherein the point of attachment is on the carbocyclyl ring. In certain embodiments, R^{B3} is optionally substituted carbocyclyl, e.g., optionally substituted C₃₋₆carbocyclyl, fused to an optionally substituted aryl or optionally substituted heteroaryl ring. In certain embodiments R^{B3} is optionally substituted C₃ carbocyclyl, optionally substituted C₄ carbocyclyl, optionally substituted C₅ carbocyclyl, or optionally substituted C₆ carbocyclyl, fused to an optionally substituted aryl or optionally substituted heteroaryl ring. In certain embodiments, R^{B3} is optionally substituted cyclopenyl (C₅) or optionally substituted cyclohexyl (C₆) fused to an optionally substituted aryl or optionally substituted heteroaryl ring. In certain embodiments, the fused aryl ring is an optionally substituted phenyl ring. In certain embodiments, the fused heteroaryl ring is an optionally substituted 6-membered heteroaryl ring, e.g., an optionally substituted pyridinyl ring.

In certain embodiments, R^{B3} is optionally substituted heterocyclyl, e.g., optionally substituted 3-6 membered heterocyclyl. In certain embodiments R^{B3} is optionally substituted 3-membered heterocyclyl, optionally substituted 4-membered heterocyclyl, optionally substituted 5-membered heterocyclyl, or optionally substituted 6-membered heterocyclyl, e.g., comprising 1 or 2 heteroatoms selected from oxygen, sulfur, or nitrogen.

In certain embodiments, R^{B3} is optionally substituted heterocyclyl fused to an optionally substituted aryl or optionally substituted heteroaryl ring, wherein the point of attachment is on the heterocyclyl ring. In certain embodiments, R^{B3} is optionally substituted heterocyclyl, e.g., optionally substituted 3-6 membered heterocyclyl, fused to an optionally substituted aryl or optionally substituted heteroaryl ring. In certain embodiments R^{B3} is optionally substituted 3-membered heterocyclyl, optionally substituted 4-membered heterocyclyl, optionally substituted 5-membered heterocyclyl, or optionally substituted 6-membered heterocyclyl, e.g., comprising 1 or 2 heteroatoms selected from oxygen, sulfur, or nitrogen, fused to an optionally substituted aryl or optionally substituted heteroaryl ring. In certain embodiments, the fused aryl ring is a fused optionally substituted phenyl ring. In certain embodiments, the fused heteroaryl ring is a 6-membered heteroaryl ring, e.g., an optionally substituted pyridinyl ring. In certain embodiments, the point of attachment of R^{B3} is via a nitrogen atom. In certain embodiments, R^{B3} is an optionally substituted 1,2,3,4-tetrahydro-2,7-naphthyridinyl ring, a 3,4-dihydropyrido[4,3-d]pyrimidinyl ring, a 3,4-dihydropyrido[4,3-d]pyrimidin-2-one ring, or a 3,4-dihydro-2H-pyrido[3,4-e][1,3]oxazin-2-one ring, wherein the point of attachment is on the non-aromatic heterocyclyl ring.

In certain embodiments, R^{B3} is optionally substituted aryl, e.g., optionally substituted C₆₋₁₄aryl. In certain embodiments, R^{B3} is optionally substituted phenyl. In certain embodiments, R^{B3} is optionally substituted naphthyl. In certain embodiments, R^{B3} is optionally substituted phenyl fused to an optionally substituted heterocyclyl ring; such as an optionally substituted phenyl tetrahydroisoquinolinyl. It is understood in reference to optionally substituted aryl ring systems comprising a fused heterocyclyl ring that the point of attachment to the parent molecule is on the aryl (e.g., phenyl) ring.

In certain embodiments, R^{B3} is optionally substituted heteroaryl, e.g., optionally substituted 5-14 membered heteroaryl. In certain embodiments, R^{B3} is an optionally substituted 5-membered heteroaryl or an optionally substituted 6-membered heteroaryl. In certain embodiments, R^{B3} is an optionally substituted bicyclic heteroaryl, e.g., an optionally substituted 5,6-bicyclic heteroaryl, or optionally substituted 6,6-bicyclic heteroaryl. In certain embodiments, R^{B3} is an optionally substituted 5,6-bicyclic heteroaryl or optionally substituted 6,6-bicyclic heteroaryl ring system selected from the group consisting of optionally substituted naphthyridinyl, optionally substituted pteridinyl, optionally substituted quinolinyl, optionally substituted isoquinolinyl, optionally substituted cinnolinyl, optionally substituted quinoxalinyl, optionally substituted phthalazinyl, and optionally substituted quinazolinyl. In certain embodiments, the point of attachment of R^{B3} is via a nitrogen atom.

In certain embodiments, wherein R^{B3} is an optionally substituted heterocyclyl, -L₁-R^{B3} is selected from the group consisting of:

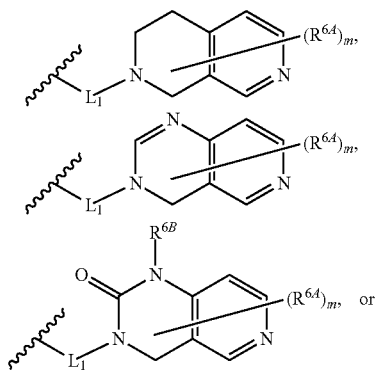

-continued

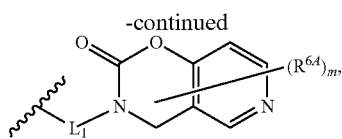

wherein:
each instance of $R^{6A}$ is independently halogen, —NO$_2$, —CN, —OR$^{6C}$, —SR$^{6C}$, —N(R$^{6C}$)$_2$, —C(=O)R$^{6C}$, —C(=O)OR$^{6C}$, —C(=O)N(R$^{6C}$)$_2$, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each instance of $R^{6B}$ is independently hydrogen, optionally substituted alkyl, or a nitrogen protecting group when attached to nitrogen;
wherein each instance of $R^{6C}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a nitrogen protecting group when attached to nitrogen, optionally when attached to N the two $R^{6C}$ groups may be joined to form an optionally substituted heterocyclyl or optionally substituted heteroaryl ring; and
m is 0 or an integer between 1 and 4, inclusive,
provided $L^1$ is not —N(R$^L$)—(C(R$^{LL}$)$_2$)$_p$— wherein p is 0.

In certain embodiments, wherein $R^{B3}$ is an optionally substituted aryl or optionally substituted heteroaryl, -L$_1$-R$^{B3}$ is selected from the group consisting of:

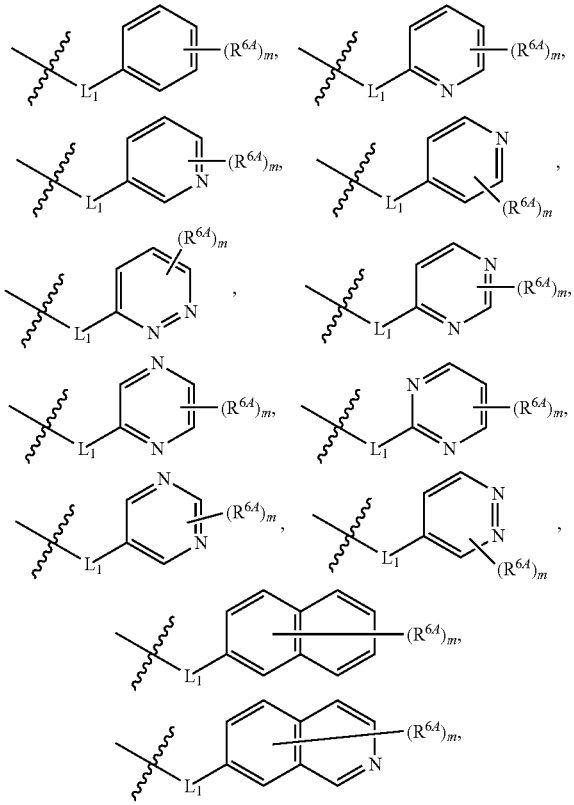

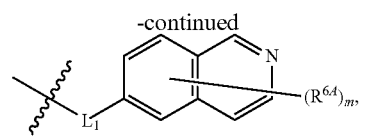
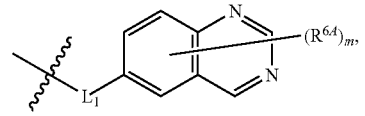
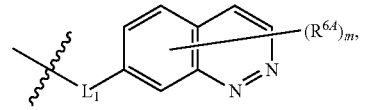
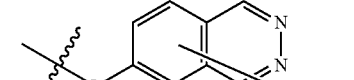
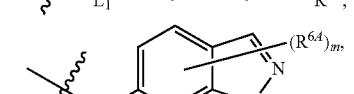
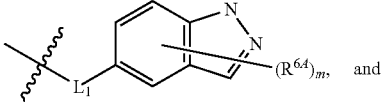, and
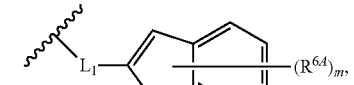

wherein:
each instance of $R^{6A}$ is independently halogen, —NO$_2$, —CN, —OR$^{6C}$, —SR$^{6C}$, —N(R$^{6C}$)$_2$, —C(=O)R$^{6C}$, —C(=O)OR$^{6C}$, —C(=O)N(R$^{6C}$)$_2$, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each instance of $R^{6B}$ is independently hydrogen, optionally substituted alkyl, or a nitrogen protecting group when attached to nitrogen;
wherein each instance of $R^{6C}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a nitrogen protecting group when attached to nitrogen, optionally when attached to N the two $R^{6C}$ groups may be joined to form an optionally substituted heterocyclyl or optionally substituted heteroaryl ring; and
m is 0 or an integer between 1 and 4, inclusive.

In certain embodiments, m is 0. In certain embodiments, m is 1, 2, 3, or 4. In certain embodiments, wherein m is 1, 2, 3, or 4, at least one $R^{6A}$ is halogen (e.g., fluoro), —OR$^{6C}$, —SR$^{6C}$, or —N(R$^{6C}$)$_2$.

In certain embodiments, $L_1$ is a bond or —C(=O)N($R^L$)—, wherein $R^L$ is hydrogen or an optionally substituted alkyl (e.g., methyl), and $R^{B3}$ is optionally substituted aryl or optionally substituted heteroaryl, as described herein.

For example, in certain embodiments of Formula (A), (B), (C), (D), and (E), wherein the group -$L_1$-$R^{B3}$ is a group of formula:

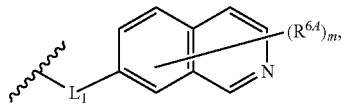

wherein $L_1$ is a bond, provided are compounds of Formula (A-h), (A-1-h), (A-2-h), (B-h), or (C-h), (D-h), (D-1-h), (D-2-h), (E-h), (E-1-h), (E-2-h):

(A-h)
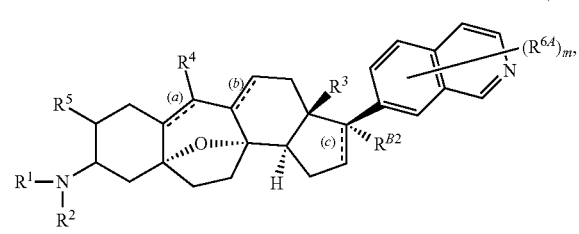

(A-1-h)
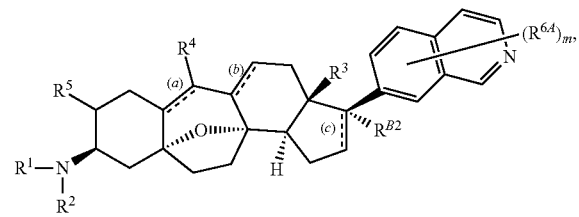

(A-2-h)
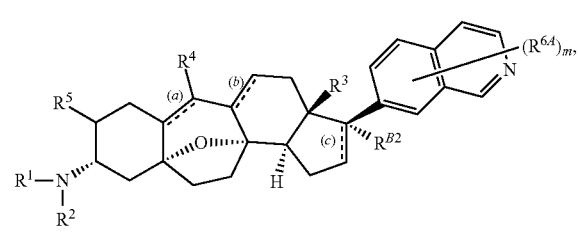

(B-h)
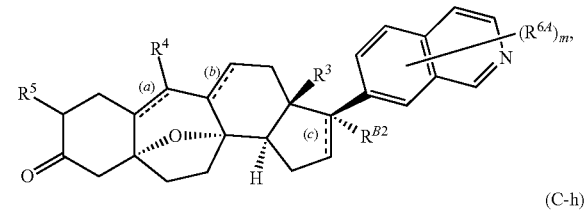

(C-h)
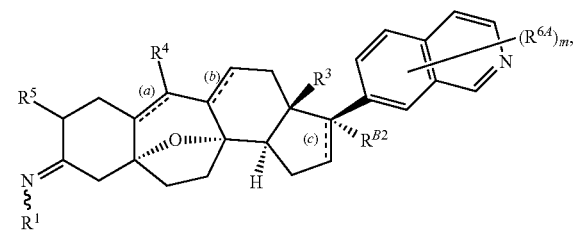

(D-h)
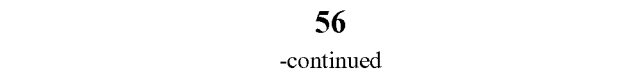

(D-1-h)
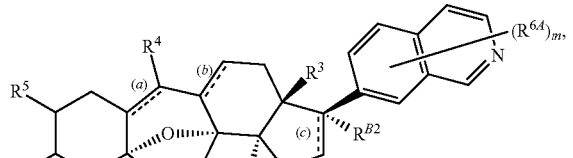

(D-2-h)
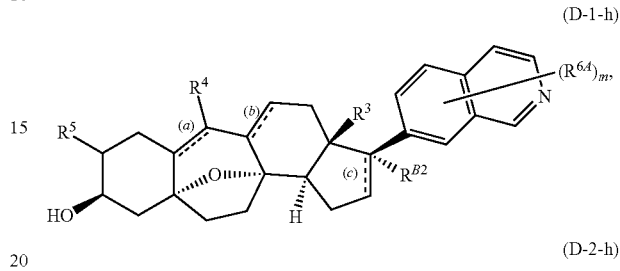

(E-h)
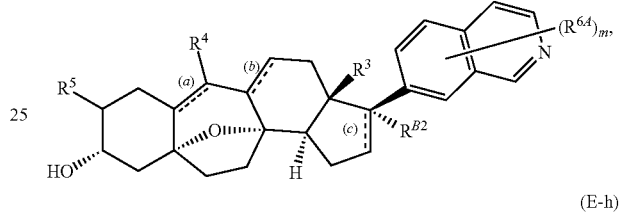

(E-1-h)
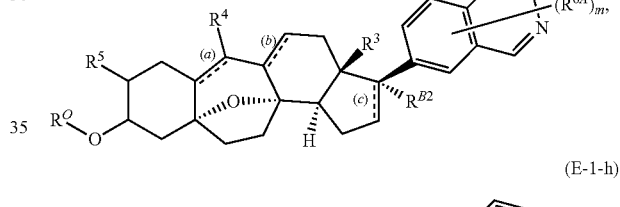

(E-2-h)
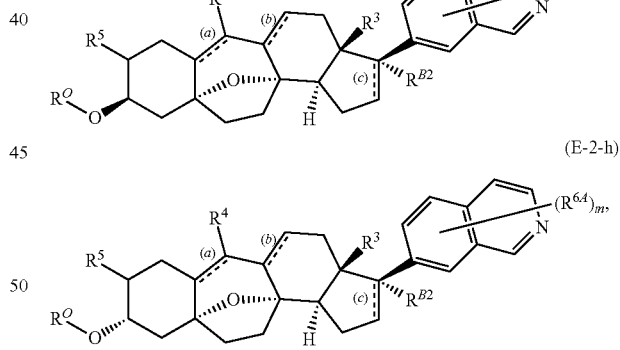

or a pharmaceutically acceptable salt, quaternary amine salt, or N-oxide thereof; wherein ⁓, $R^1$, $R^2$, $R^3$, $R^4$, $R^5$, $R^{6A}$, and m are as defined herein.

For example, in certain embodiments of Formula (A), (B), and (C) wherein the group -$L_1$-$R^{B3}$ is a group of formula:

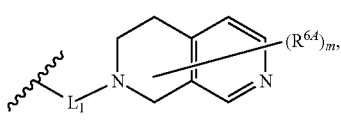

wherein L₁ is a bond, provided are compounds of Formula (A-i), (A-1-i), (A-2-i), (B-i), or (C-i):

wherein L₁ is a bond, provided are compounds of Formula (A-p), (A-1-p), (A-2-p), (B-p), or (C-p):

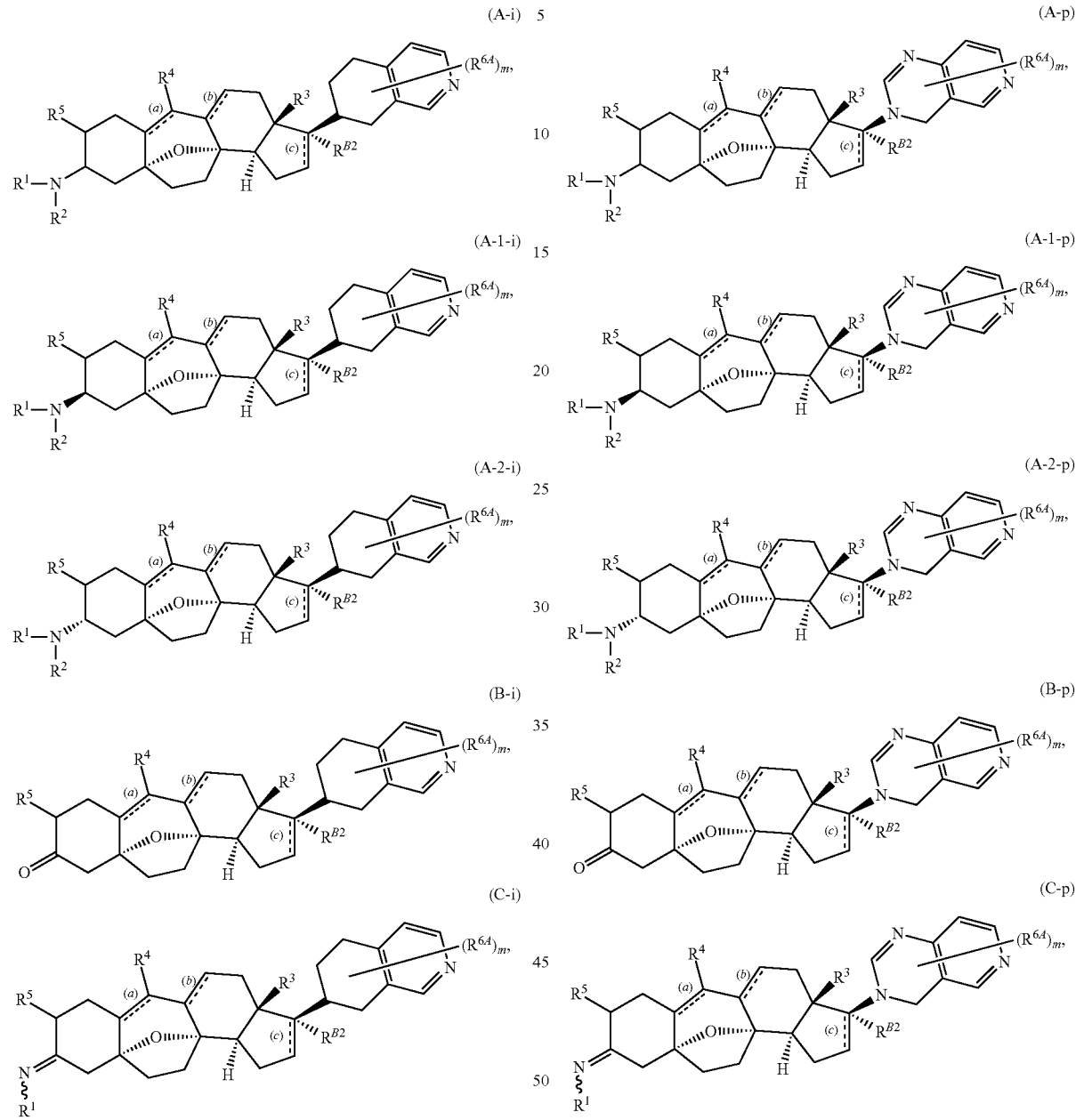

or a pharmaceutically acceptable salt, quaternary amine salt, or N-oxide thereof; wherein ~~~~, $R^1$, $R^2$, $R^3$, $R^4$, $R^5$, $R^{6A}$, and m are as defined herein.

In certain embodiments of Formula (A), (B), and (C), wherein the group -$L_1$-$R^{B3}$ is a group of formula:

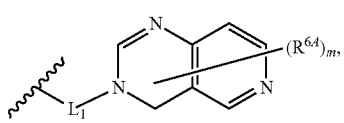

or a pharmaceutically acceptable salt, quaternary amine salt, or N-oxide thereof; wherein ~~~~, $R^1$, $R^2$, $R^3$, $R^4$, $R^5$, $R^{6A}$, and m are as defined herein.

In certain embodiments of Formula (A), (B), and (C), wherein the group -$L_1$-$R^{B3}$ is a group of formula:

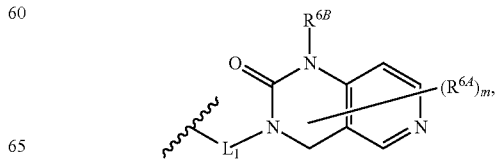

wherein L₁ is a bond, provided are compounds of Formula (A-q), (A-1-q), (A-2-q), (B-q), or (C-q):

In certain embodiments of Formula (A), (B), and (C), wherein the group -L₁-R$^{B3}$ is a group of formula:

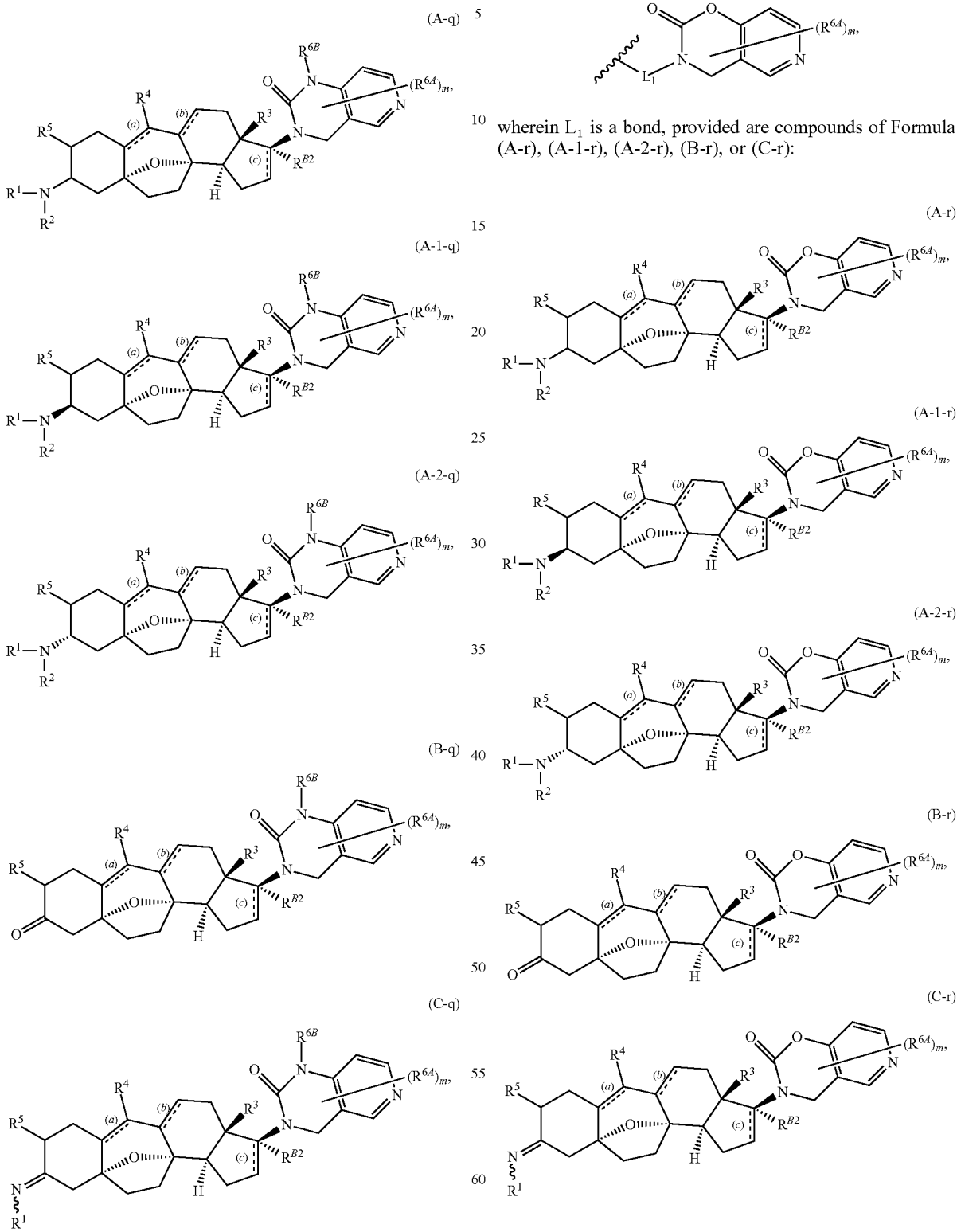

wherein L₁ is a bond, provided are compounds of Formula (A-r), (A-1-r), (A-2-r), (B-r), or (C-r):

or a pharmaceutically acceptable salt, quaternary amine salt, or N-oxide thereof; wherein ≈≈≈, R¹, R², R³, R⁴, R⁵, R$^{6A}$, and m are as defined herein.

or a pharmaceutically acceptable salt, quaternary amine salt, or N-oxide thereof; wherein ≈≈≈, R¹, R², R³, R⁴, R⁵, R$^{6A}$, and m are as defined herein.

Compounds of Formula (A-i), (A-1-i), (A-2-i), (B-i), (C-i), (A-p), (A-1-p), (A-2-p), (B-p), (C-p), (A-q), (A-1-q), (A-2-q), (B-q), (C-q), (A-r), (A-1-r), (A-2-r), (B-r), and (C-r) are designed to mimic the isoquinoline of cortistatin A and are envisioned to have improved metabolic stability.

In other embodiments of Formula (A), (B), and (C), wherein $R^{B1}$ is -$L_1$-$R^{B3}$, and $L_1$ is —C(=O)N($R^L$)—, provided are compounds of Formula (A-j), (A-1-j), (A-2-j), (B-j), or (C-j):

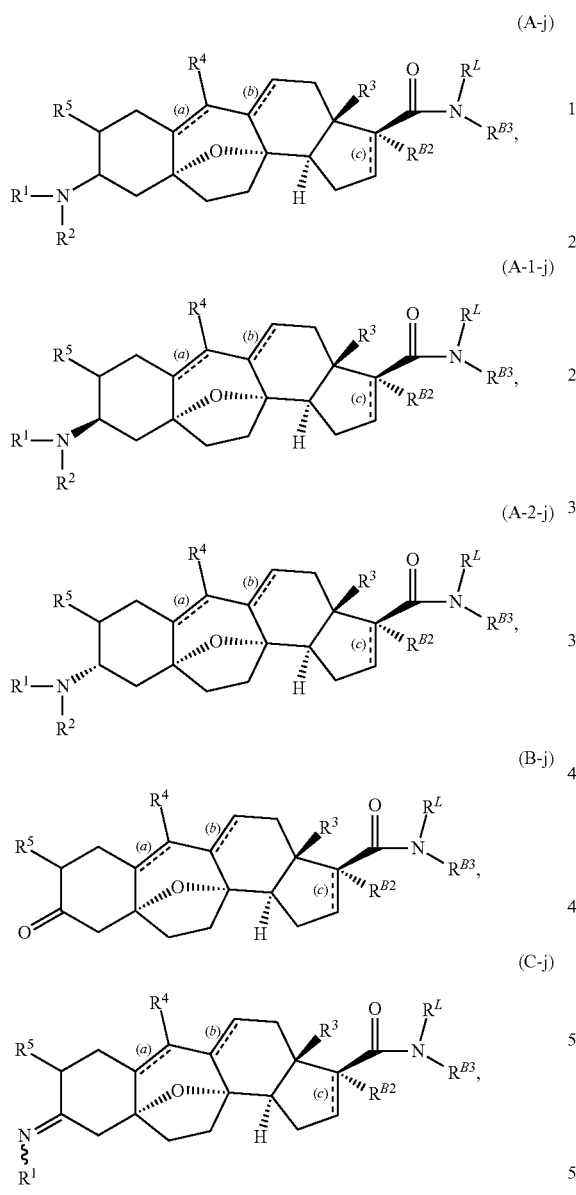

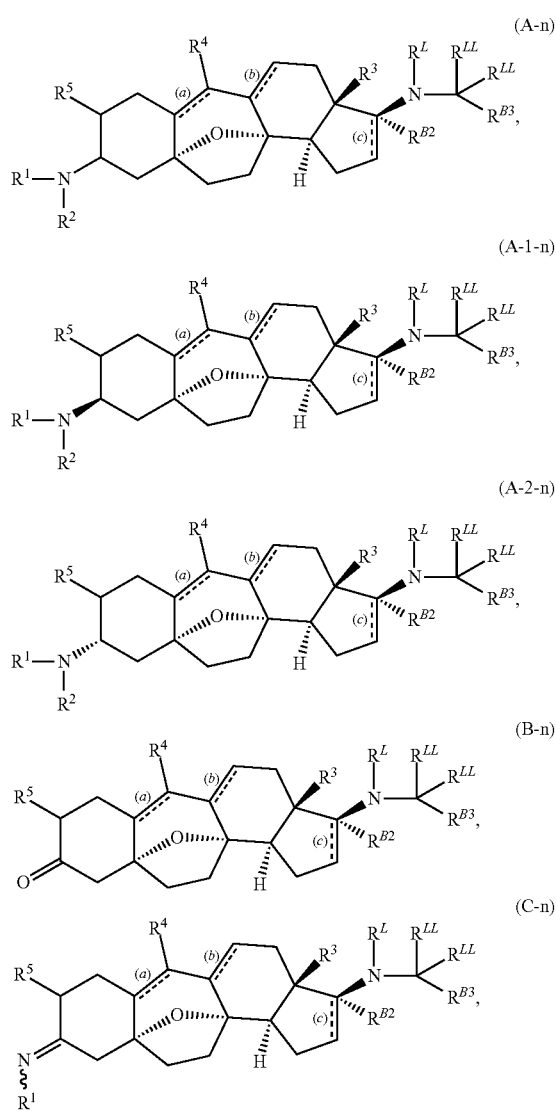

or a pharmaceutically acceptable salt, quaternary amine salt, or N-oxide thereof; wherein ----, $R^1$, $R^2$, $R^3$, $R^4$, $R^5$, $R^L$, and $R^{B3}$ are as defined herein.

In other embodiments of Formula (A), (B), and (C), wherein $R^{B1}$ is -$L_1$-$R^{B3}$, and $L_1$ is —N($R^L$)—(C($R^{LL}$)$_2$)$_p$—, wherein p is 1, provided are compounds of Formula (A-n), (A-1-n), (A-2-n), (B-n), or (C-n):

or a pharmaceutically acceptable salt, quaternary amine salt, or N-oxide thereof; wherein ----, $R^1$, $R^2$, $R^3$, $R^4$, $R^5$, $R^L$, and $R^{B3}$ are as defined herein.

Compounds of Formula (A-j), (A-1-j), (A-2-j), (B-j), (C-j), (A-n), (A-1-n), (A-2-n), (B-n), and (C-n) are designed to mimic the isoquinoline of cortistatin A and are envisioned to have improved pharmacokinetic properties. In particular, compounds wherein -$L_1$-$R^{B3}$ is a group of formula:

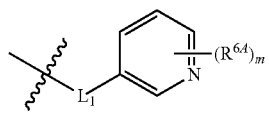

wherein $L_1$ is —C(O)N($R^L$)— or —N($R^L$)—((C$R^{LL}$)$_2$)$_p$—, wherein p is 1, are contemplated herein.

Alternatively, in certain embodiments, at least one instance of $R^{B1}$ and $R^{B2}$ is —$X^A R^A$. In this instance, in certain embodiments, the other of $R^{B1}$ and $R^{B2}$ is hydrogen or —$X^A R^A$ (e.g., —$OR^A$). For example, in certain embodiments, when ---- designated as (c) represents a single bond, then $R^{B1}$ is —$X^A R^A$ (e.g., —$OR^A$) and $R^{B2}$ is hydrogen or —$X^A R^A$ (e.g., —$OR^A$). In other embodiments, when ≈≈≈ designated as (c) represents a single bond, then $R^{B2}$ is —$X^A R^A$ (e.g., —$OR^A$) and $R^{B1}$ is hydrogen or —$X^A R^A$ (e.g., —$OR^A$). Alternatively, in certain embodiments, when ≈≈≈ designated as (c) represents a double bond, then $R^{B1}$ is —$X^A R^A$ (e.g., —$OR^A$ wherein $R^A$ is not hydrogen) and $R^{B2}$ is absent.

In certain embodiments, both instances of $R^{B1}$ and $R^{B2}$ is —$X^A R^A$. In this embodiments, in certain instances, the two $R^A$ groups may be joined to form an optionally substituted heterocyclyl ring, e.g., an optionally substituted 5-6 membered heterocyclyl ring. For example, in certain embodiments of Formula (A), (B), and (C), wherein both instances of $R^{B1}$ and $R^{B2}$ is —$X^A R^A$, provided are compounds of Formula (A-k), (A-1-k), (A-2-k), and (B-k), and (C-k):

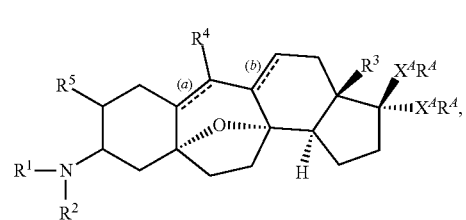
(A-k)

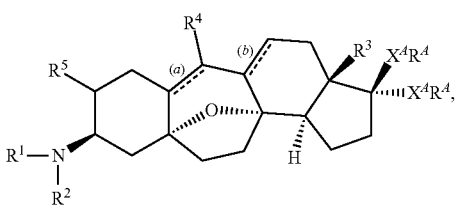
(A-1-k)

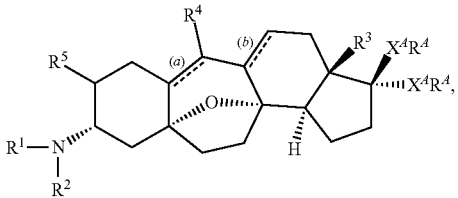
(A-2-k)

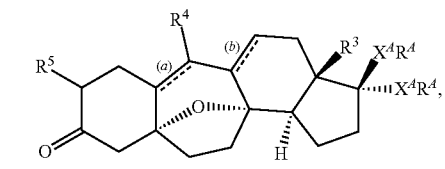
(B-k)

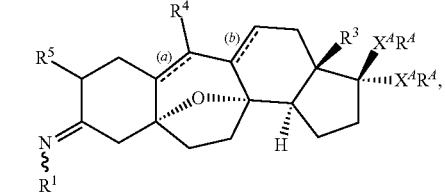
(C-k)

or a pharmaceutically acceptable salt, quaternary amine salt, or N-oxide thereof; wherein ≈≈≈, $R^1$, $R^2$, $R^3$, $R^4$, $R^5$, $X^A$ and $R^A$, are as defined herein.

In certain embodiments, $R^{B1}$ and $R^{B2}$ are joined to form an oxo group (=O). For example, in certain embodiments of Formula (A), (B), and (C), $R^{B1}$ and $R^{B2}$ are joined to form an oxo group (=O), provided are compounds of Formula (A-m), (A-1-m), (A-2-m), (B-m), or (C-m):

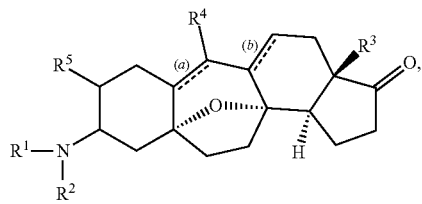
(A-m)

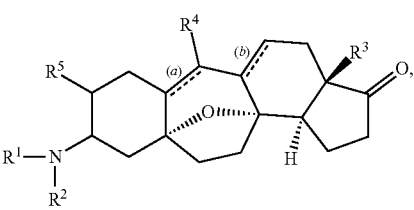
(A-1-m)

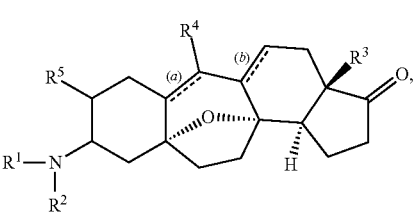
(A-2-m)

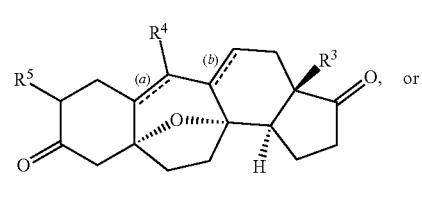
(B-m)

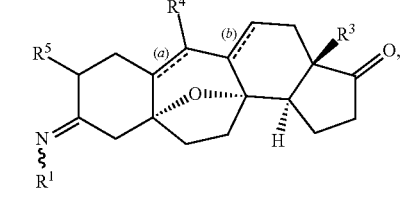
(C-m)

or a pharmaceutically acceptable salt, quaternary amine salt, or N-oxide thereof; wherein ≈≈≈, $R^1$, $R^2$, $R^3$, $R^4$, and $R^5$, are as defined herein.

Exemplary Compounds

Various combinations of certain embodiments are further contemplated herein.

For example, in certain embodiments of Formula (A-1-h), (A-1-i), (A-1-p), (A-1-q), (A-1-r), (A-1-j), (A-1-n), (A-2-h), (D-1-h), (D-2-h), (E-1-h), (E-2-h), and wherein the bond ≈≈≈ designated as (c) is a single bond, and $R^{B2}$ is hydrogen, provided is a compound of Formulae:

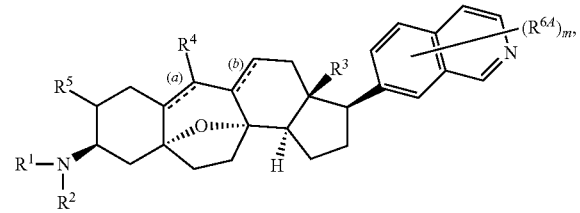
(A-1-h-i)

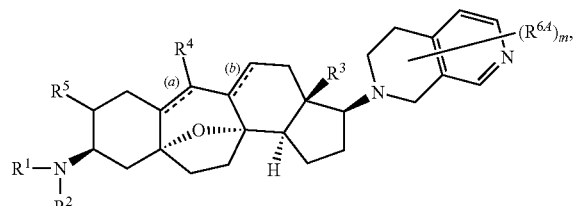
(A-1-i-i)

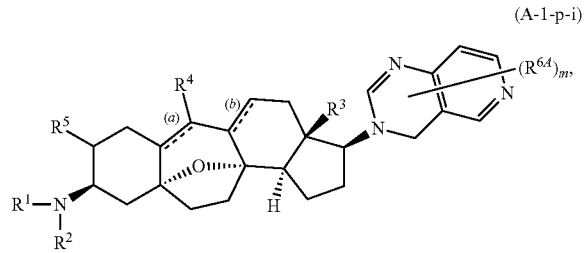
(A-1-p-i)

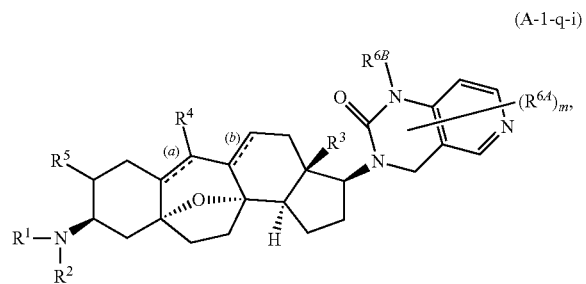
(A-1-q-i)

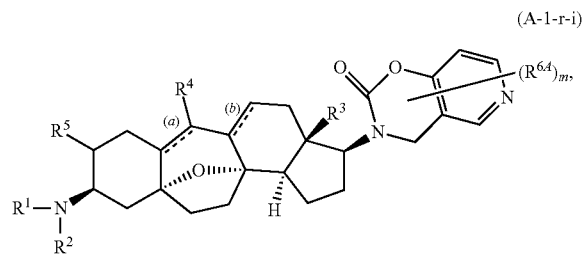
(A-1-r-i)

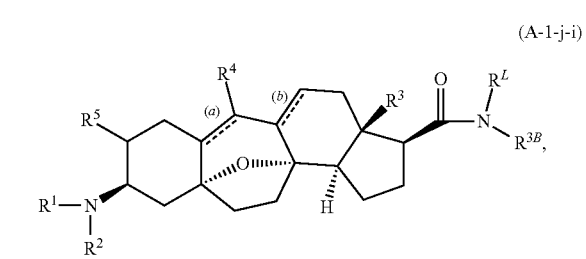
(A-1-j-i)

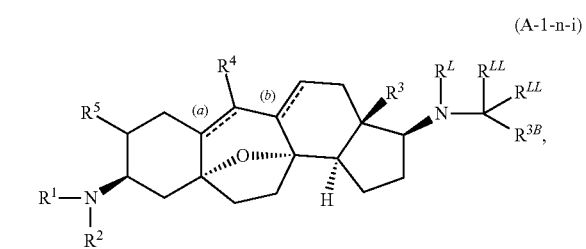
(A-1-n-i)

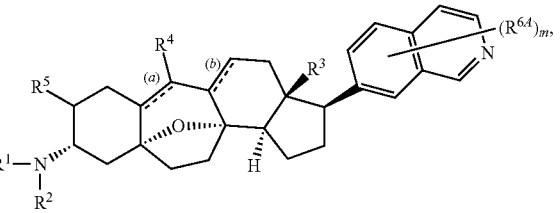
(A-2-h-i)

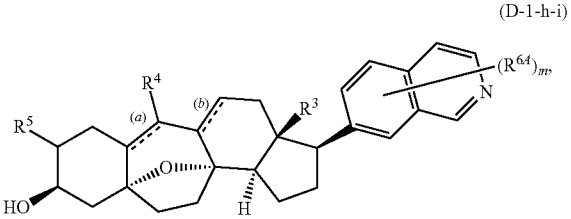
(D-1-h-i)

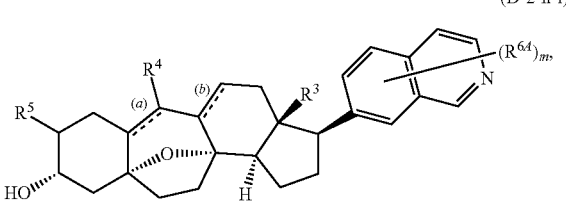
(D-2-h-i)

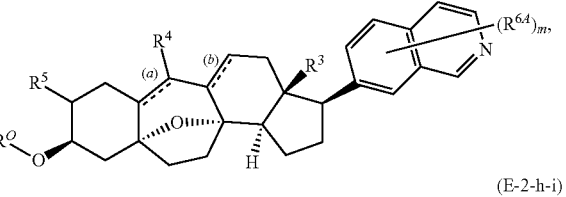
(E-1-h-i)

(E-2-h-i)

or a pharmaceutically acceptable salt, quaternary amine salt, or N-oxide thereof; wherein ====, $R^1$, $R^2$, $R^O$, $R^3$, $R^4$, $R^5$, $R^{6A}$, $R^{6B}$, $R^L$, $R^{LL}$, and m are as defined herein. In certain embodiments, $R^3$ is methyl. In certain embodiments, $R^4$ is hydrogen. In certain embodiments, $R^5$ is hydrogen. In certain embodiments the bonds ==== designated as (a) and (b) are double bonds. In certain embodiments, each instance of $R^1$ and $R^2$ is optionally substituted alkyl, e.g., —CH$_3$. In certain embodiments, at least one of $R^1$ and $R^2$ is a group of formula

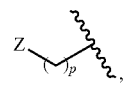

wherein p and Z are as defined herein. In certain embodiments, at least one of $R^1$ and $R^2$ is —S(=O)$_2$R$^A$. In certain embodiments, $R^1$ and $R^2$ are joined to form an optionally substituted heterocyclyl. In certain embodiments, $R^1$ and $R^2$ are joined to form a ring of formula:

wherein R⁷, n and G are as defined herein. In certain embodiments, the compound is an N-oxide, e.g., the group

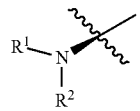

of formula

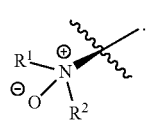

In certain embodiments, $R^O$ is an optionally substituted alkyl, e.g., —CH₃ or a group of formula

wherein Z and p are as defined herein. In certain embodiments, $R^O$ is —C(=O)$R^A$, —C(=O)O$R^A$, or —C(=O)N($R^A$)₂, e.g., —C(=O)CH₃, —C(=O)OCH₃, —C(=O)N(CH₃)₂, or —C(=O)NHCH₃.

In certain embodiments of Formula (A-1-h-i), (A-1-i-i), (A-1-p-i), (A-1-q-i), (A-1-r-i), (A-1-j-i), (A-1-n-i), (A-2-h-i), (D-1-h-i), (D-2-h-i), (E-1-h-i), and (E-2-h-i), wherein $R^3$ is methyl, $R^4$ and $R^5$ are hydrogen, and the bonds ═══ designated as (a) and (b) are double bonds, provided is a compound of Formulae:

(A-1-h-ii)

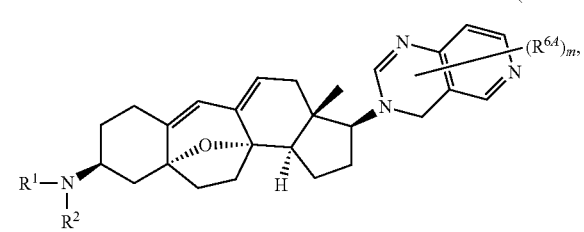

(A-1-q-ii)

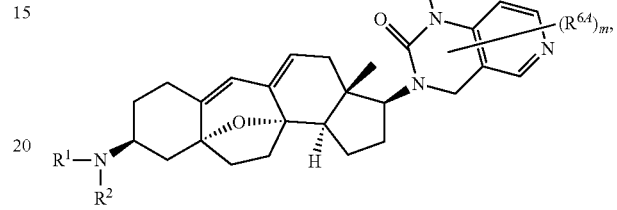

(A-1-r-ii)

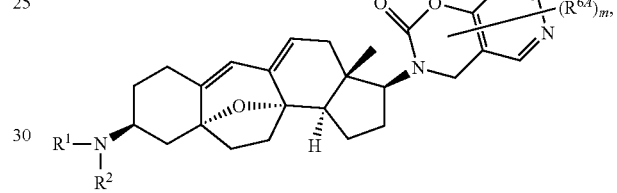

(A-1-j-ii)

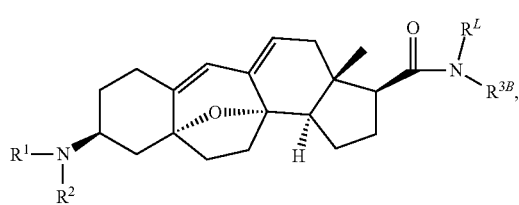

(A-1-h-ii)

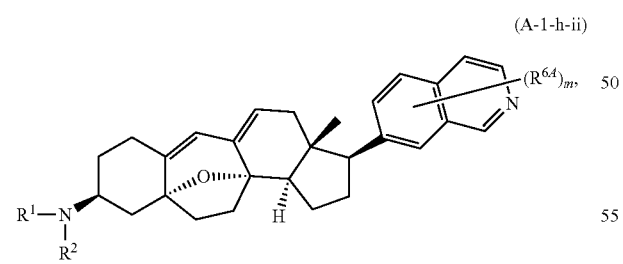

(A-1-n-ii)

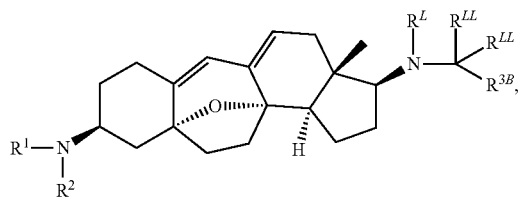

(A-1-h-ii)

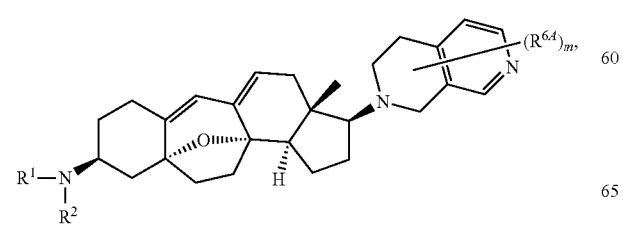

(A-2-h-ii)

-continued

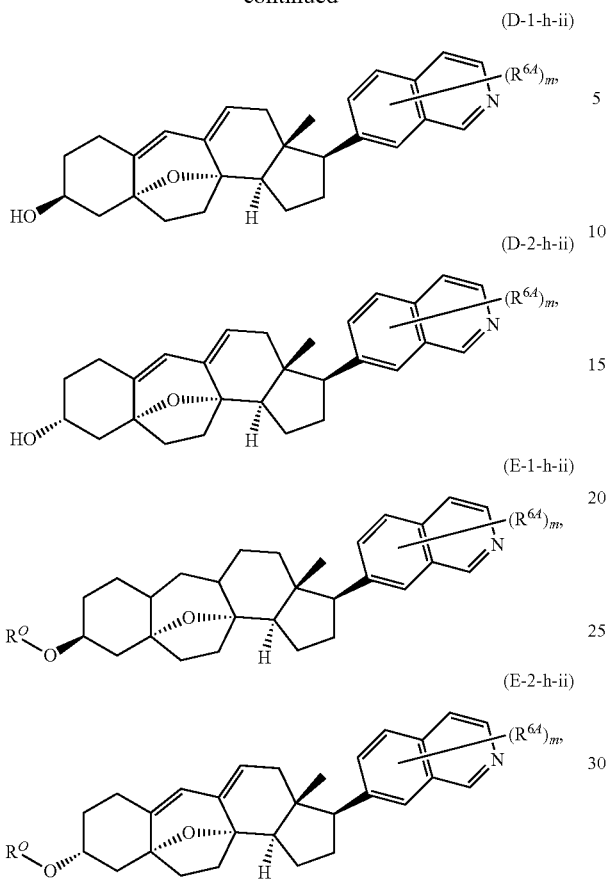

or a pharmaceutically acceptable salt, quaternary amine salt, or N-oxide thereof; wherein $R^1$, $R^2$, $R^O$, $R^{6A}$, $R^{6A}$, $R^{6B}$, $R^L$, $R^{LL}$ and m are as defined herein. In certain embodiments, each instance of $R^1$ and $R^2$ is optionally substituted alkyl, e.g., —$CH_3$. In certain embodiments, one of $R^1$ and $R^2$ is hydrogen, and one of $R^1$ and $R^2$ is optionally substituted alkyl, e.g., —$CH_3$. In certain embodiments, at least one of $R^1$ and $R^2$ is a group of formula

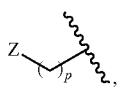

wherein p and Z are as defined herein. In certain embodiments, at least one of $R^1$ and $R^2$ is —$S(=O)_2R^A$. In certain embodiments, $R^1$ and $R^2$ are joined to form an optionally substituted heterocyclyl. In certain embodiments, $R^1$ and $R^2$ are joined to form a ring of formula:

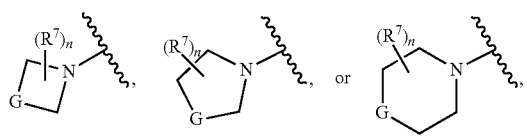

wherein $R^7$, n and G are as defined herein. In certain embodiments, the compound is an N-oxide, e.g., the group

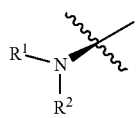

is of formula

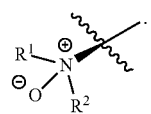

In certain embodiments, $R^O$ is an optionally substituted alkyl, e.g., —$CH_3$ or a group of formula

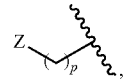

wherein Z and p are as defined herein. In certain embodiments, $R^O$ is —$C(=O)R^A$, —$C(=O)OR^A$, or —$C(=O)N(R^A)_2$, e.g., —$C(=O)CH_3$, —$C(=O)OCH_3$, —$C(=O)N(CH_3)_2$, or —$C(=O)NHCH_3$.

In certain embodiments of Formula (A-1-h-ii) and (A-2-h-ii), wherein $R^1$ and $R^2$ are joined to form an optionally substituted heterocyclyl, provided is a compound of Formula:

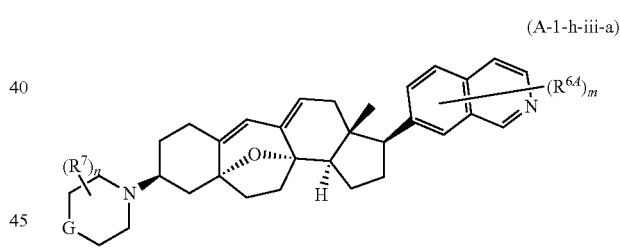

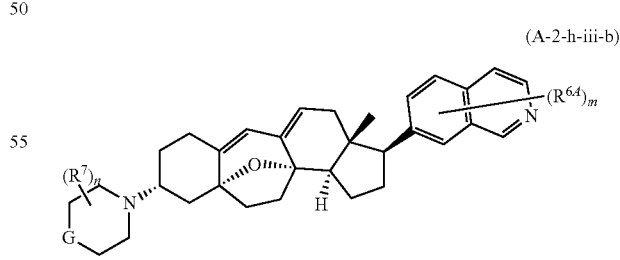

or a pharmaceutically acceptable salt, quaternary amine salt, or N-oxide thereof; wherein $R^7$, $R^{6A}$, n and m are as defined herein. In certain embodiments, G is O. In certain embodiments, G is N—$CH_3$. In certain embodiments, m is 0. In certain embodiments, m is 1. In certain embodiments, n is 0. In certain embodiments, n is 1.

In certain embodiments of Formula (A-1-h-ii) or (A-2-h-ii), wherein $R^1$ and $R^2$ are joined to form an optionally substituted heterocyclyl, provided is a compound of Formula:

(A-1-h-iii-c)

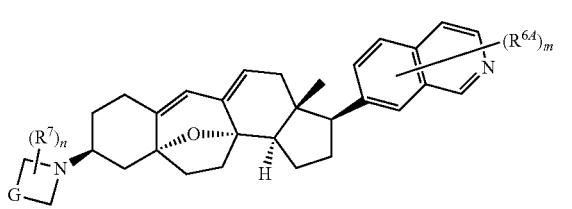

(A-2-h-iii-d)

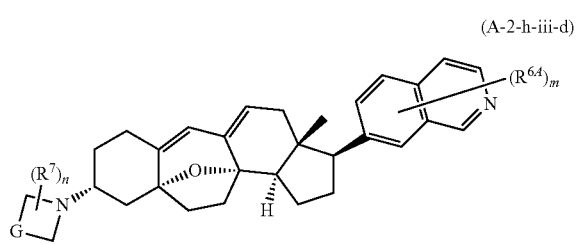

or a pharmaceutically acceptable salt, quaternary amine salt, or N-oxide thereof; wherein $R^7$, $R^{6A}$, n and m are as defined herein. In certain embodiments, G is —CH$_2$—. In certain embodiments, m is 0. In certain embodiments, m is 1. In certain embodiments, n is 0. In certain embodiments, n is 1.

In certain embodiments of Formula (A-1-h-ii), wherein each of $R^1$ and $R^2$ are —CH$_3$, provided is a compound of Formula:

(A-1-h-iii-e)

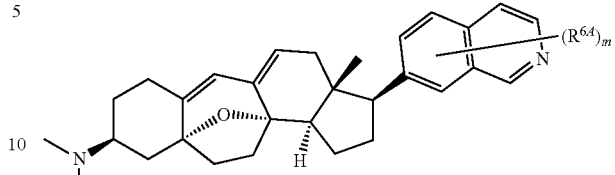

or a pharmaceutically acceptable salt, quaternary amine salt, or N-oxide thereof; wherein $R^{6A}$, and m are as defined herein. In certain embodiments, m is 0. In certain embodiments, m is 1.

In certain embodiments of Formula (A-2-h-ii), wherein one of $R^1$ and $R^2$ is hydrogen, and the other of $R^1$ and $R^2$ is —CH$_3$, provided is a compound of Formula:

(A-2-h-iii-e)

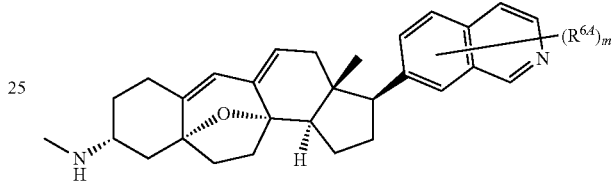

or a pharmaceutically acceptable salt, quaternary amine salt, or N-oxide thereof; wherein $R^{6A}$, and m are as defined herein. In certain embodiments, m is 0. In certain embodiments, m is 1.

Exemplary compounds of Formula (A) include, but are not limited to:

14B

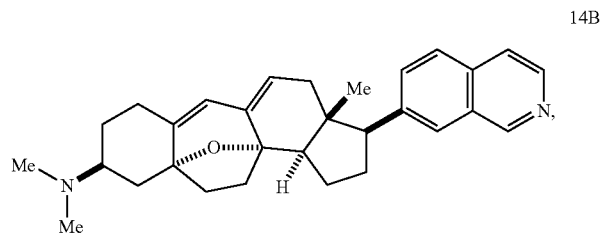

14A

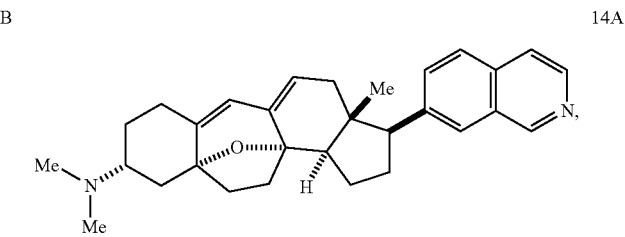

15B

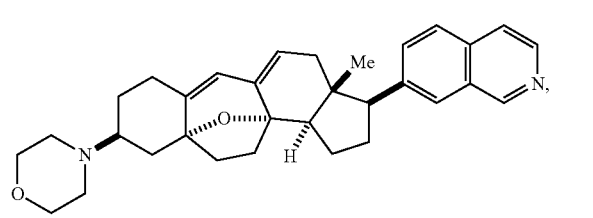

15A

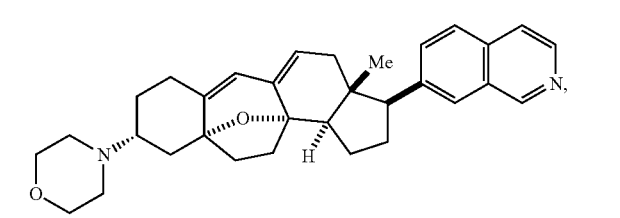

16B

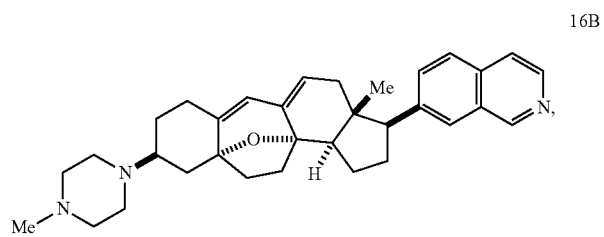

16A

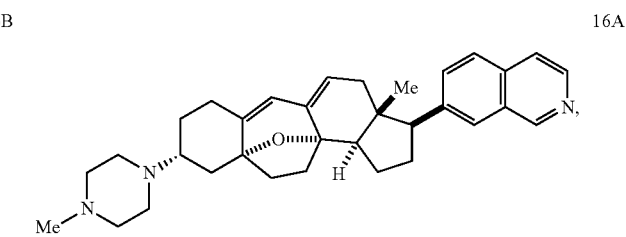

-continued
| 18B | 18A |
|---|---|
| 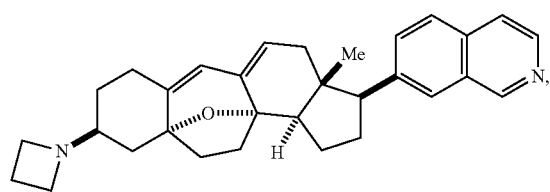 | |
| 19B | 19A |
|---|---|
| 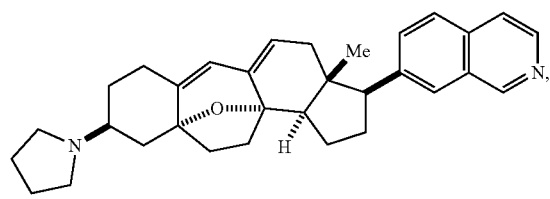 | 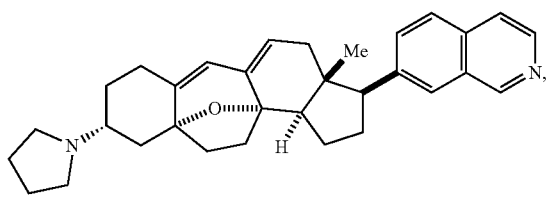 |
| 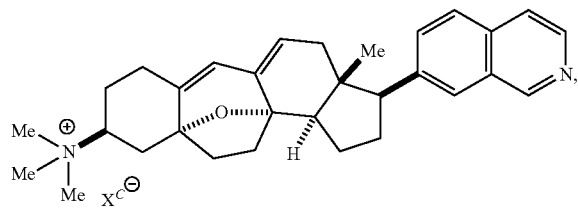 | 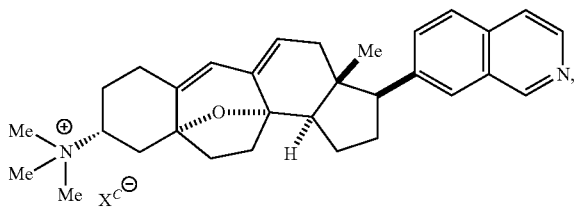 |
|---|---|
| 23B | 23A |
|---|---|
| 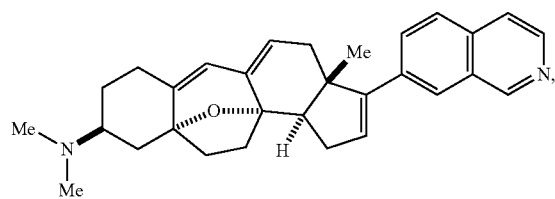 | 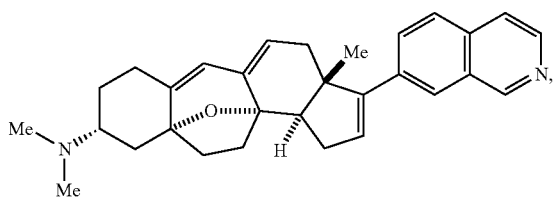 |
| 24B | 24A |
|---|---|
| 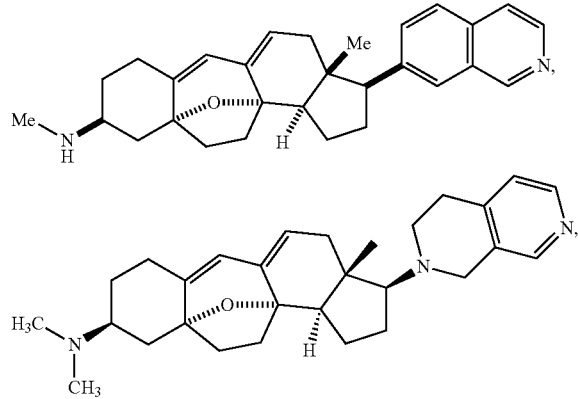 | 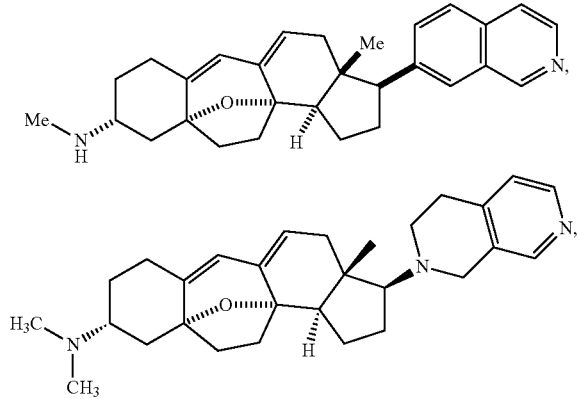 |
| 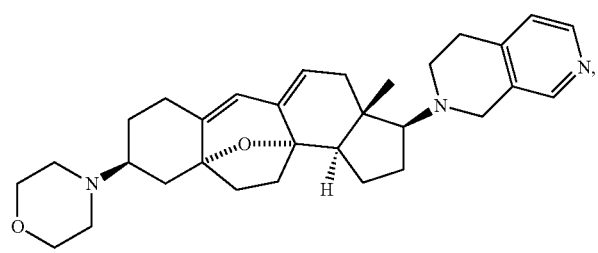 | 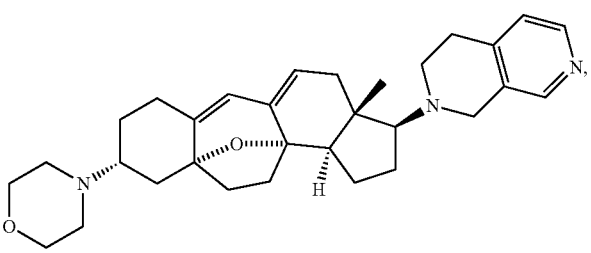 |
|---|---|

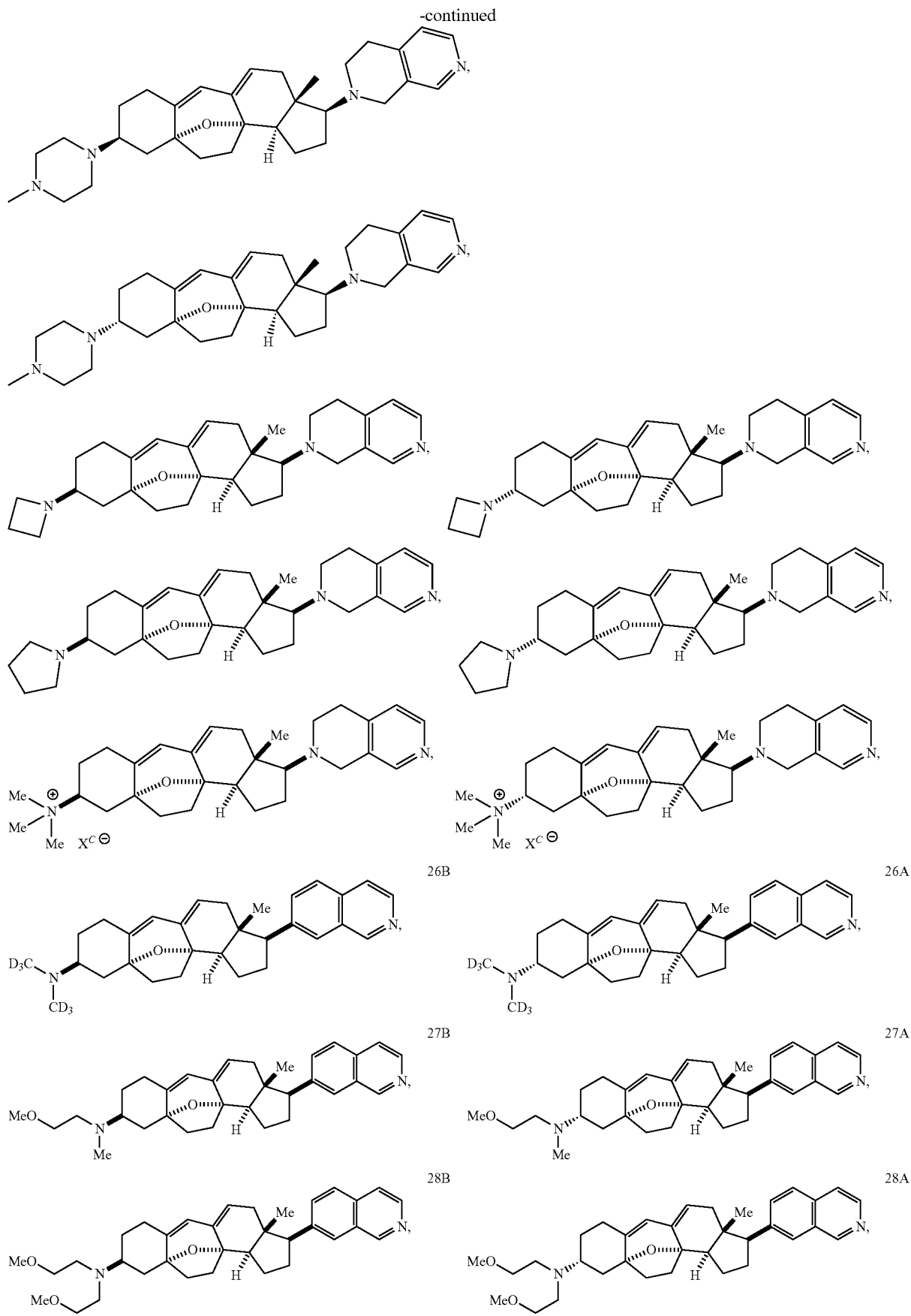

-continued
| | |
|---|---|
| 29B 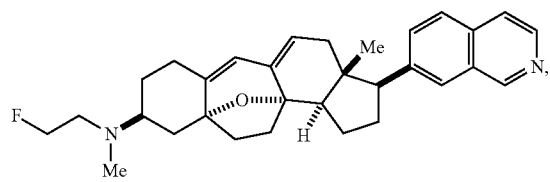 | 29A |
| 30B 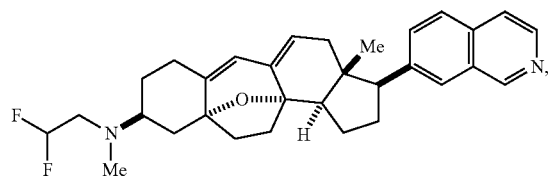 | 30A |
| 31B 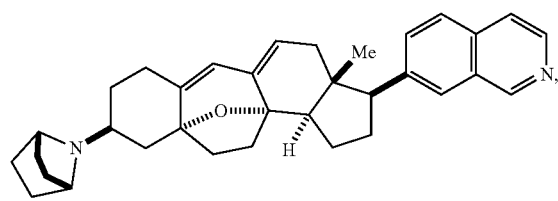 | 31A |
| 32B 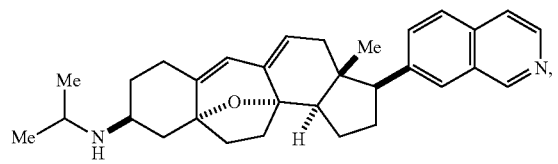 | 32A |
| 33B 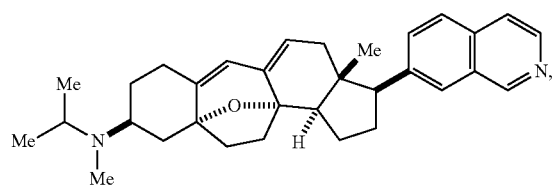 | 33A |
| 34B 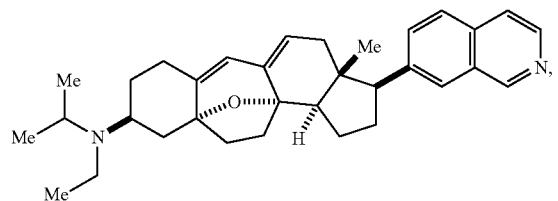 | 34A |
| 35B 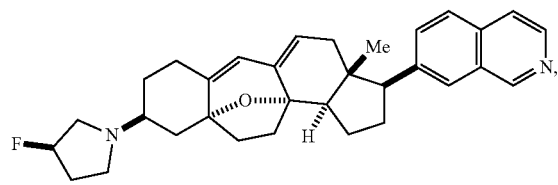 | 35A 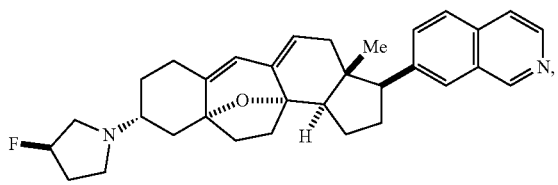 |

-continued
| 36B | 36A |
|---|---|
| 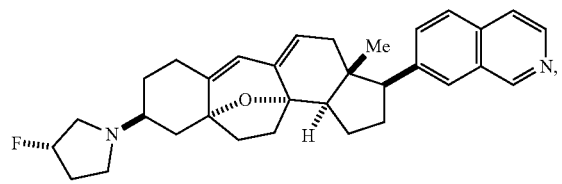 | 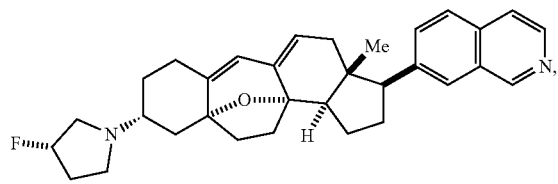 |
| 37B | 37A |
| 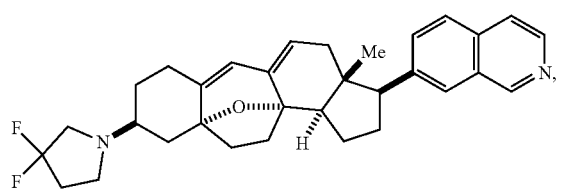 | 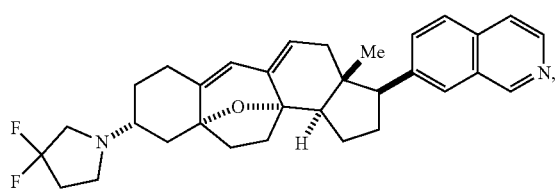 |
| 38B | 38A |
| 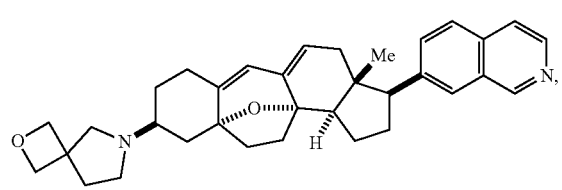 | 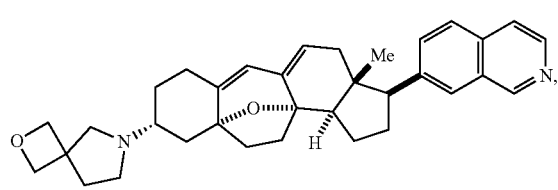 |
| 39B | 39A |
| 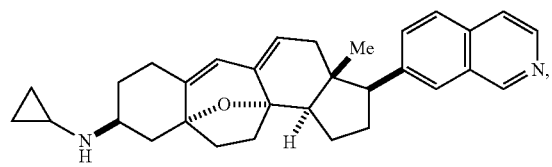 | 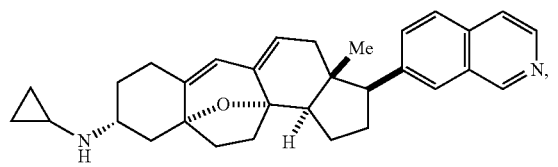 |
| 40B | 40A |
| 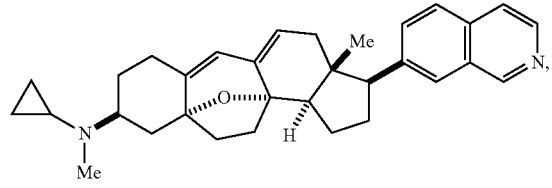 | 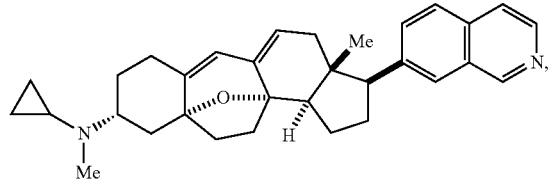 |
| 41B | 41A |
| 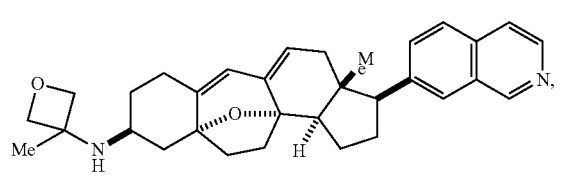 | 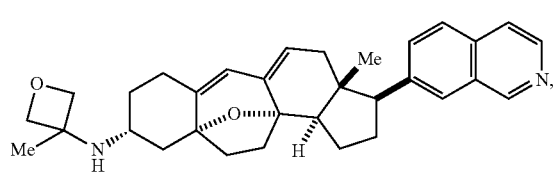 |
| 42B | 42A |
| 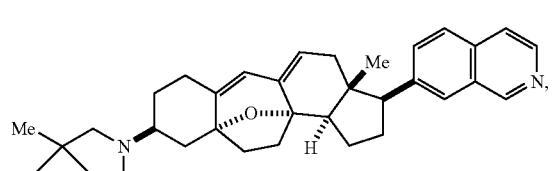 | 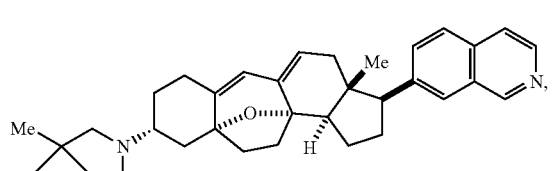 |
| 43B | 43A |
| 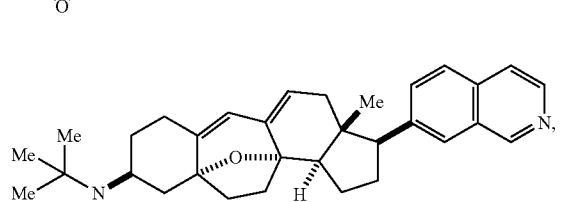 | 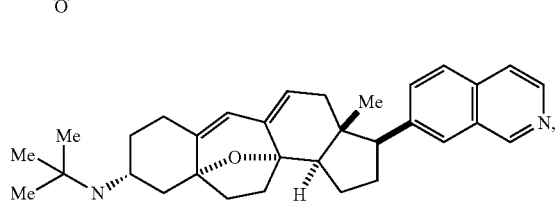 |

-continued
| 46B | 46A |
|---|---|
| 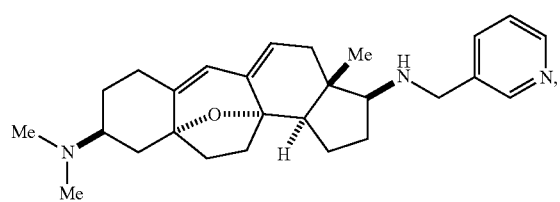 | 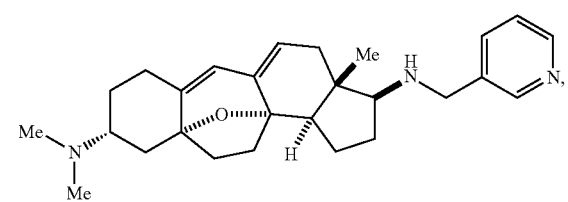 |
| 49B | 49A |
| 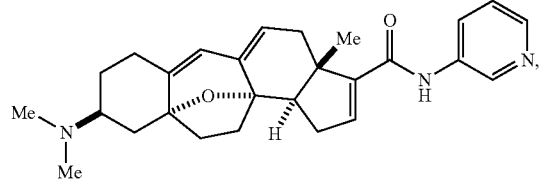 | 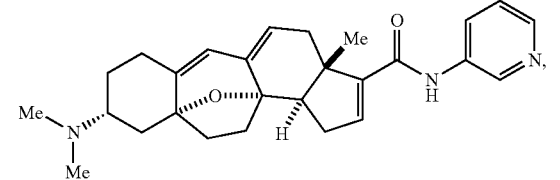 |
| 50B | 50A |
| 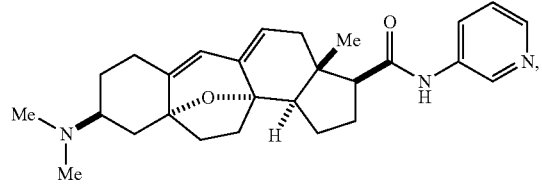 | 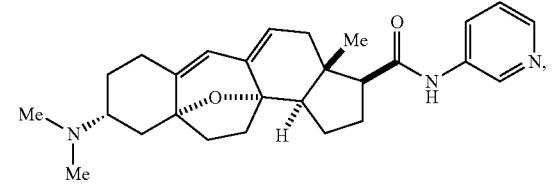 |
| 55B | 55A |
| 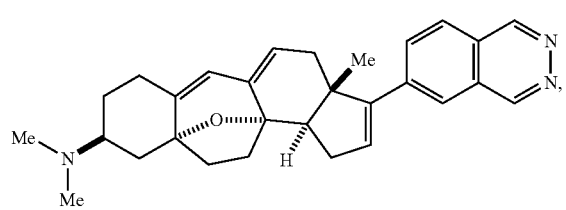 | 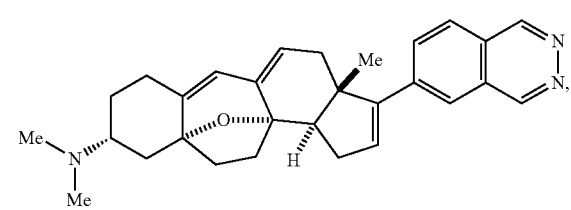 |
| 58B | 58A |
| 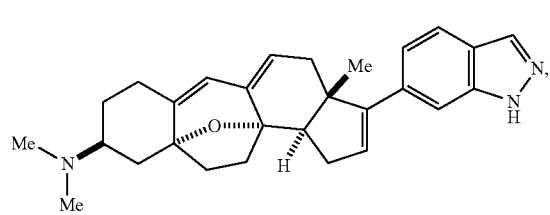 | 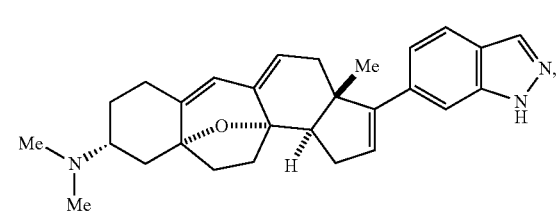 |
| 61B | 61A |
| 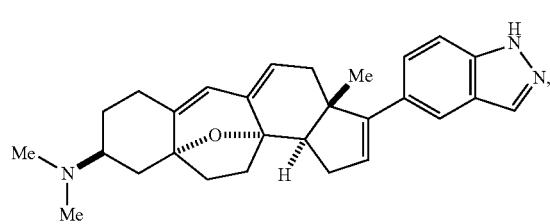 | 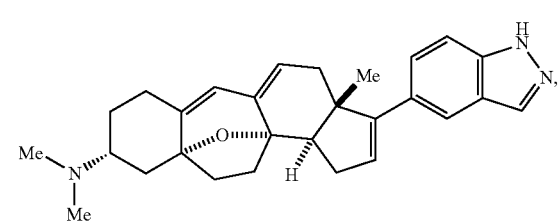 |
| 62B | 62A |
| 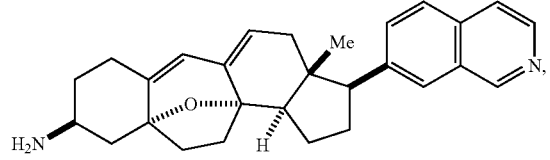 | 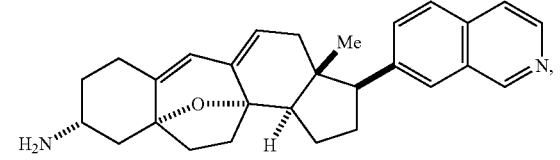 |

-continued
| | |
|---|---|
| 65B 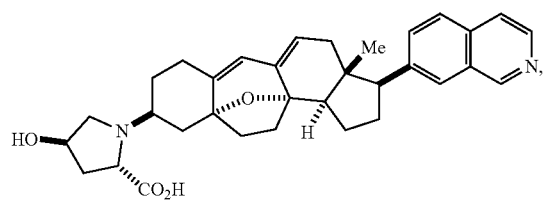 | 65A 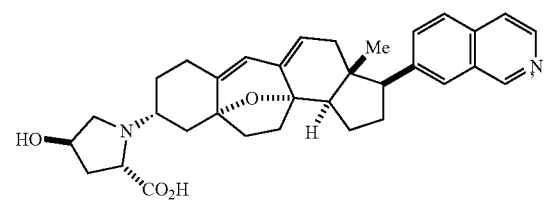 |
| 69B 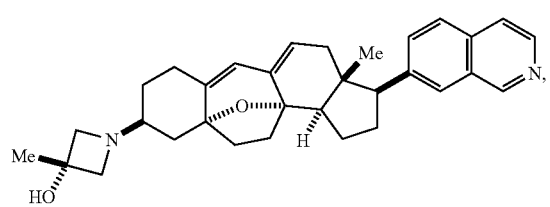 | 69A 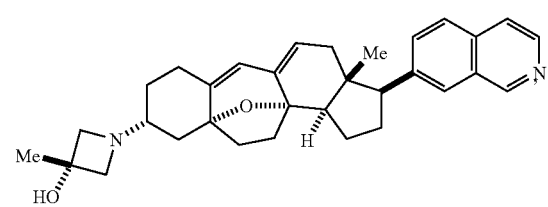 |
| 70B 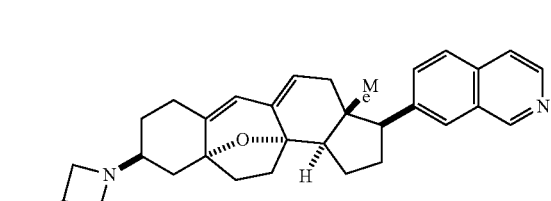 | 70A 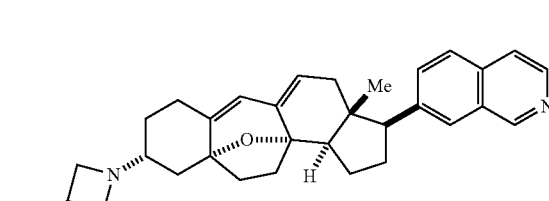 |
| 71B 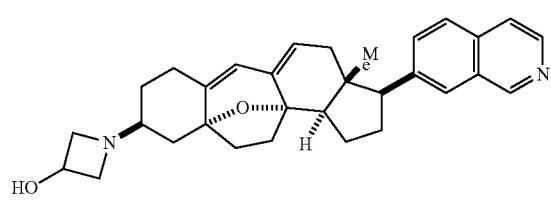 | 71A 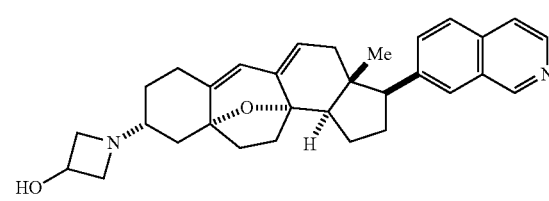 |
| 72B 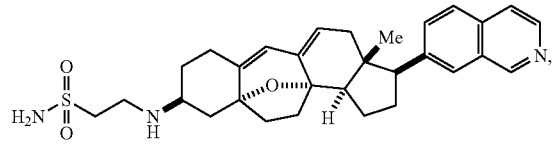 | 72A 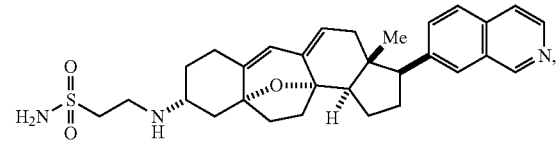 |
| 73B 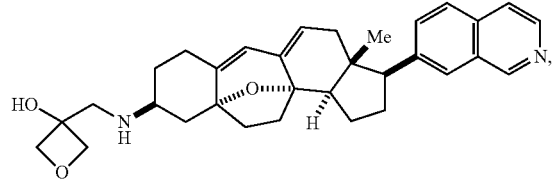 | 73A 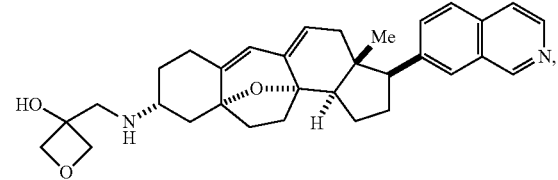 |
| 74B 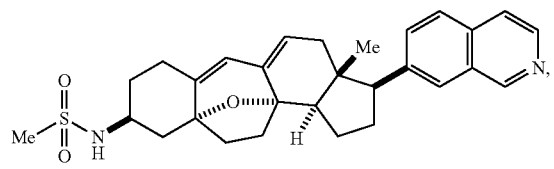 | 74A 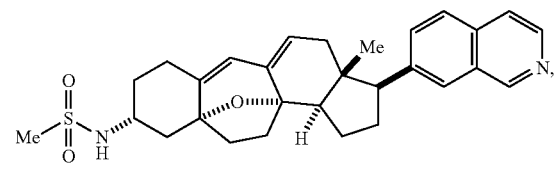 |
| | 75A 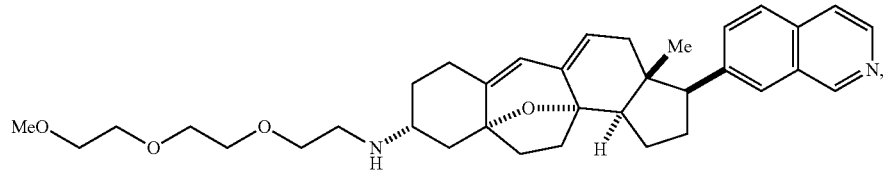 |

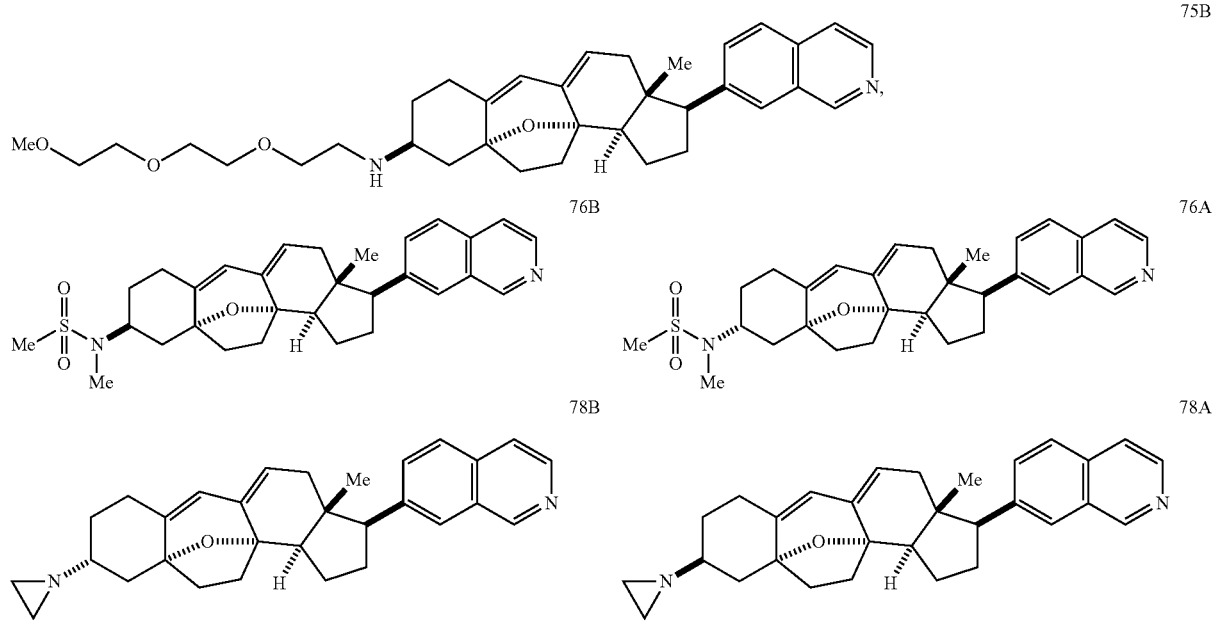
and pharmaceutically acceptable salts, quaternary amine salts thereof, and N-oxides thereof, e.g., N-oxides of formula:
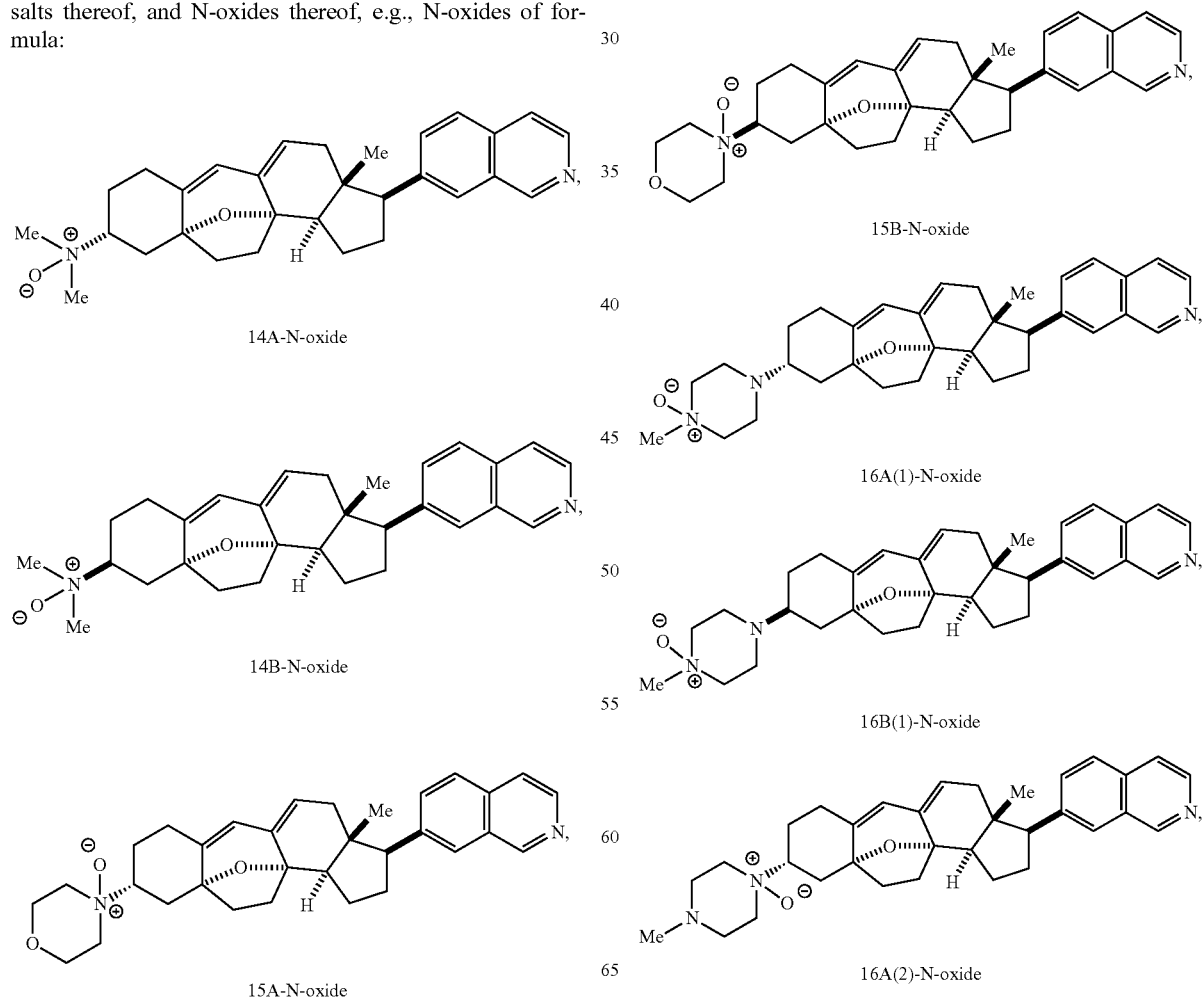

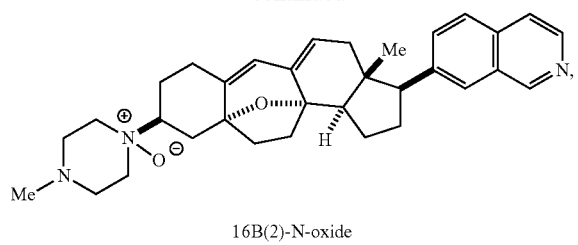
16B(2)-N-oxide
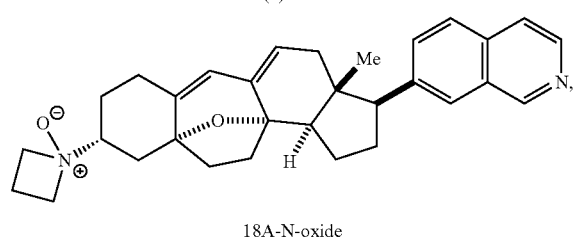
18A-N-oxide
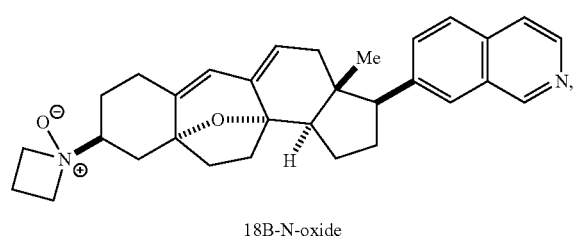
18B-N-oxide
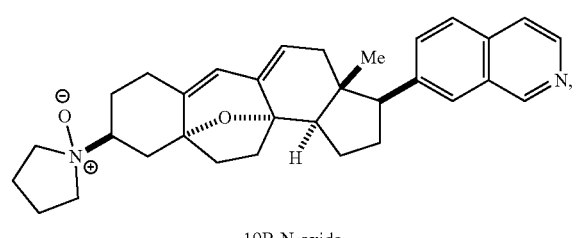
19B-N-oxide
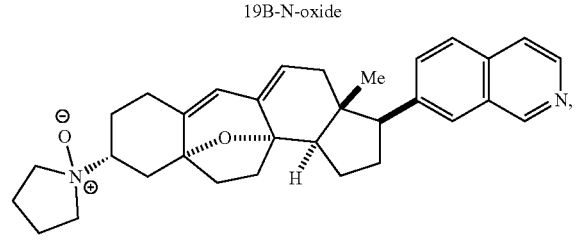
19A-N-oxide
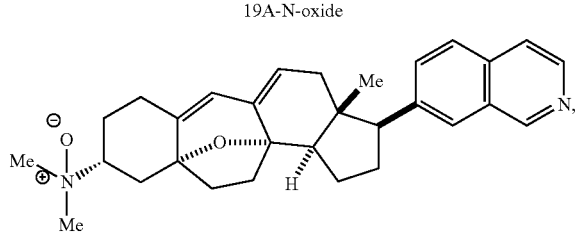
23A-N-oxide
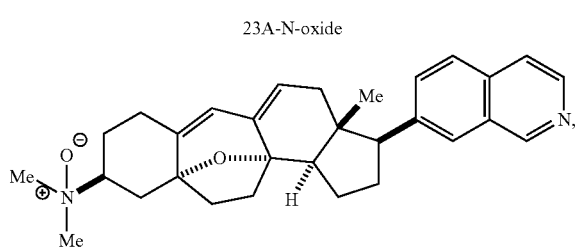
23B-N-oxide
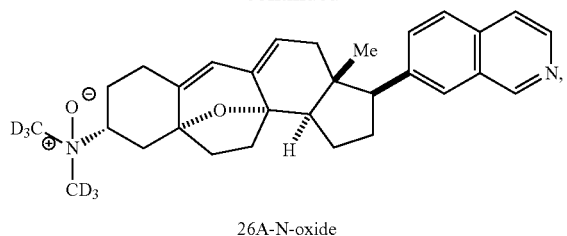
26A-N-oxide
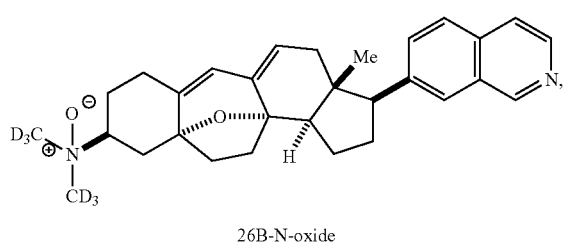
26B-N-oxide
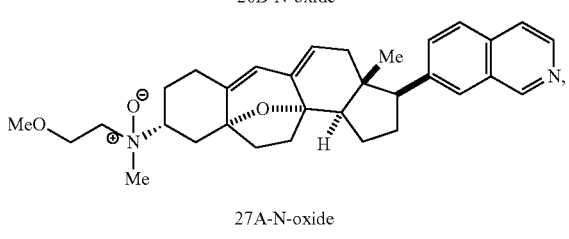
27A-N-oxide
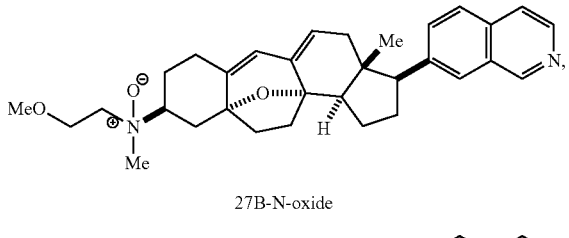
27B-N-oxide
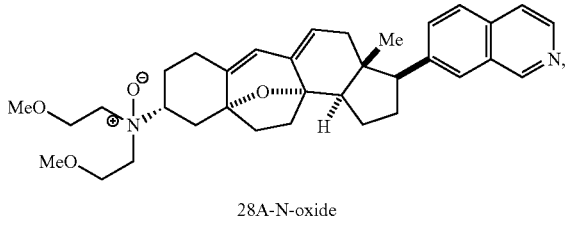
28A-N-oxide
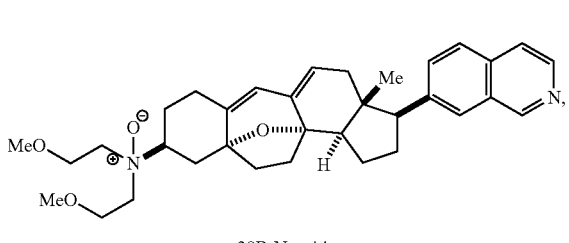
28B-N-oxide
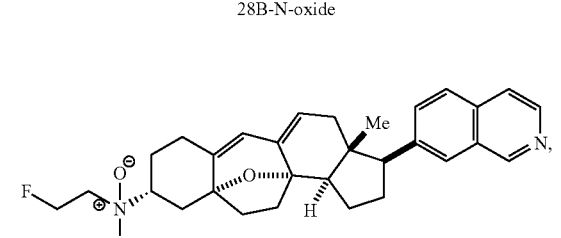
29A-N-oxide

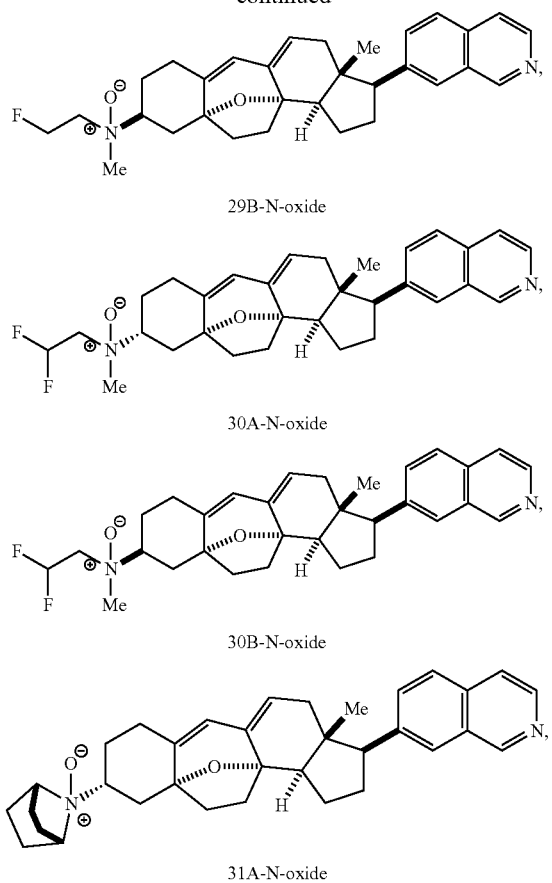
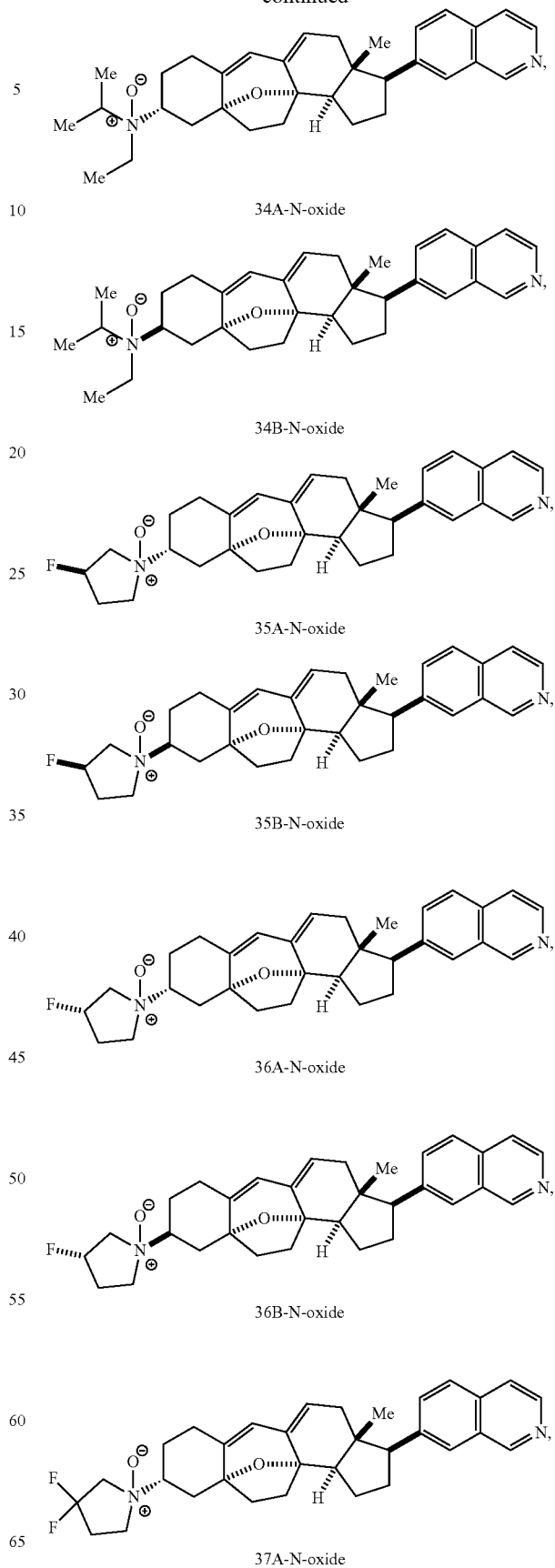

91
-continued
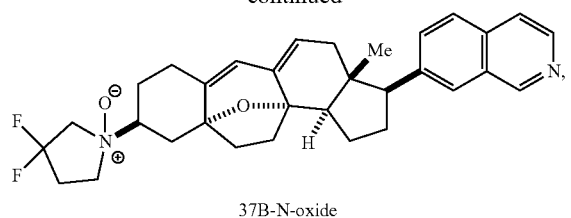
37B-N-oxide
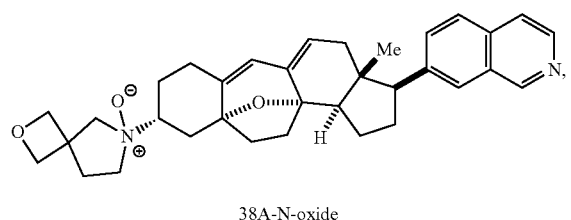
38A-N-oxide
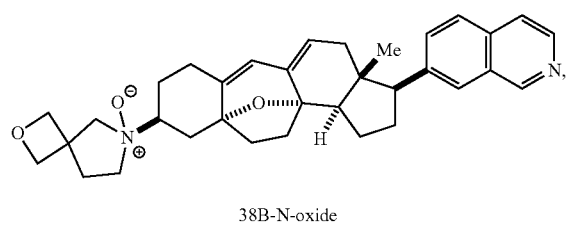
38B-N-oxide
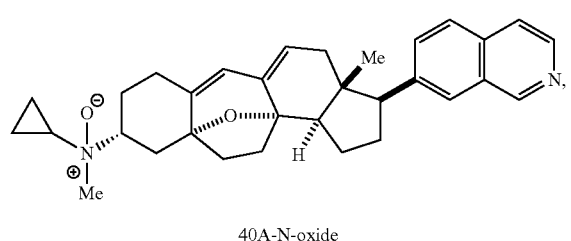
40A-N-oxide
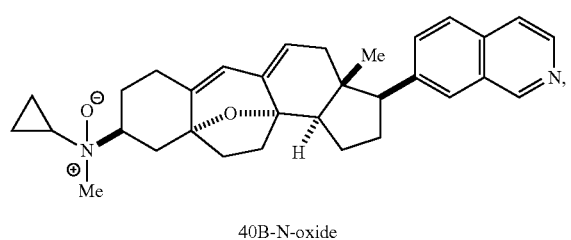
40B-N-oxide
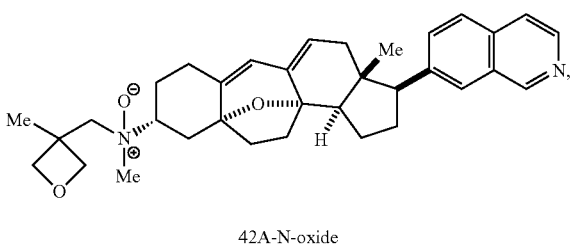
42A-N-oxide
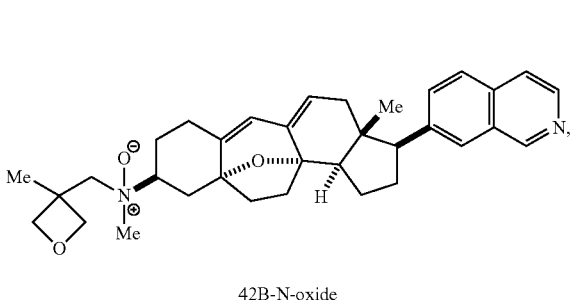
42B-N-oxide
92
-continued
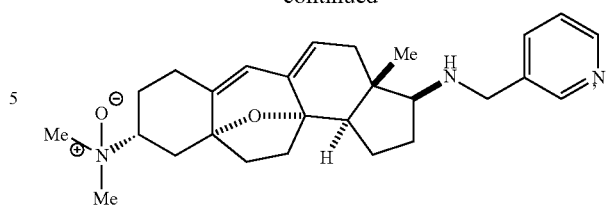
46A-N-oxide
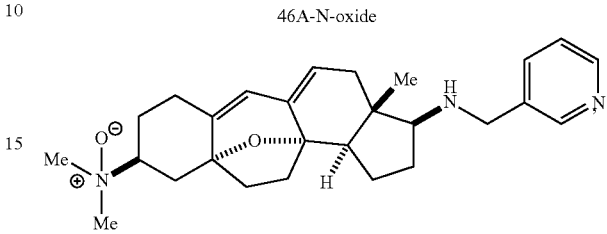
46B-N-oxide
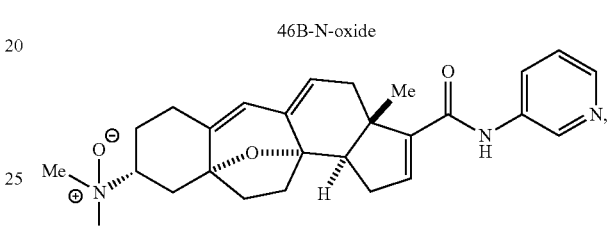
49A-N-oxide
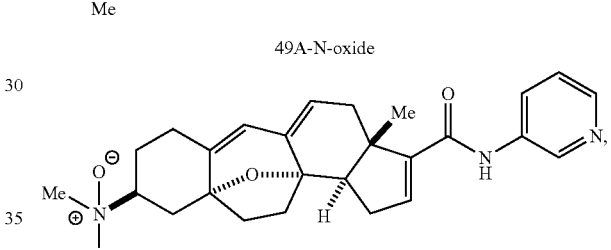
49B-N-oxide
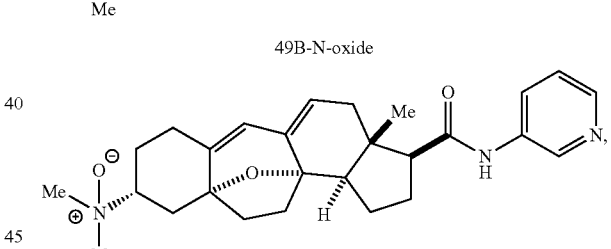
50A-N-oxide
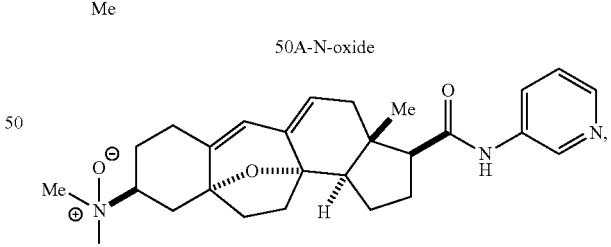
50B-N-oxide
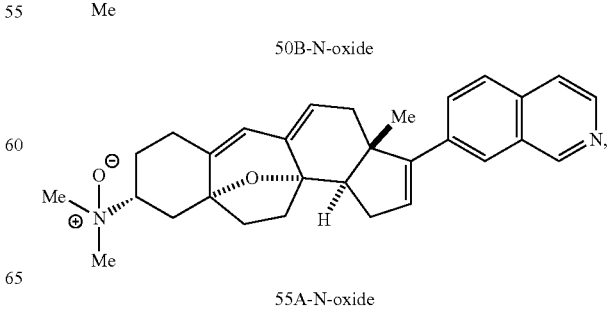
55A-N-oxide

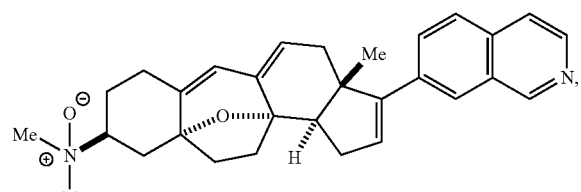

55B-N-oxide

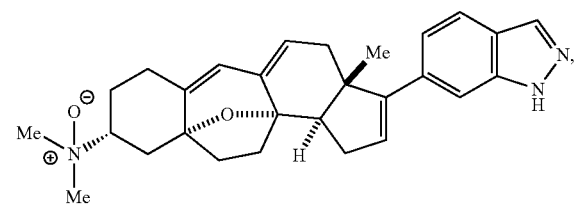

58A-N-oxide

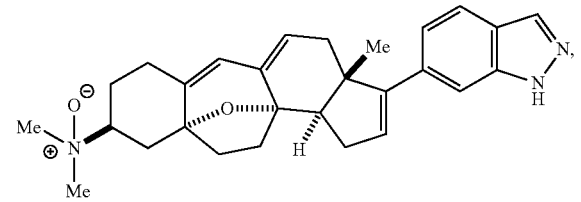

58B-N-oxide

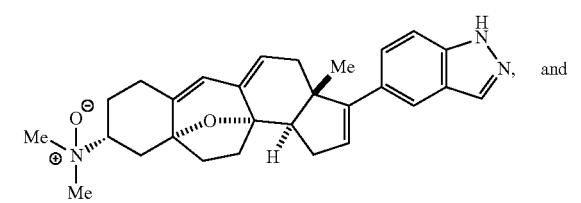

61A-N-oxide

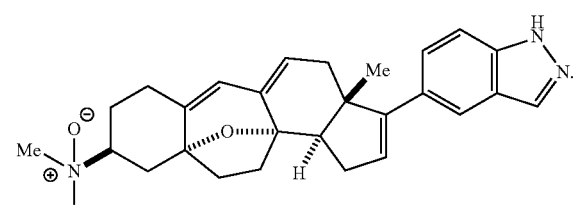

61B-N-oxide

However, in certain embodiments, the compound of Formula (A) is not:

14A

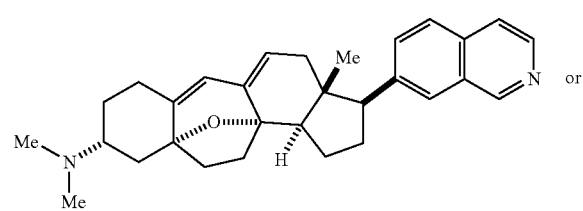

or

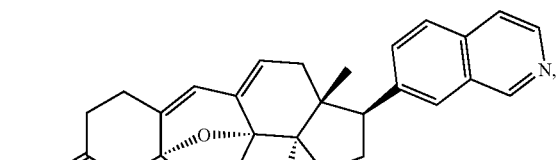

or a pharmaceutically acceptable salt or quaternary amine salt thereof, or an N-oxide thereof.

Exemplary compounds of Formula (B) include, but are not limited to:

(13)

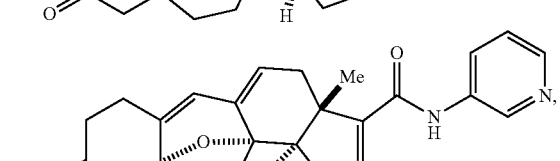

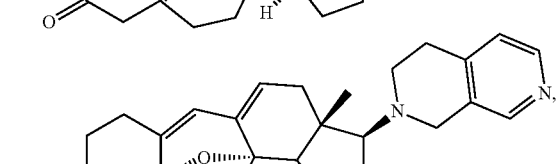

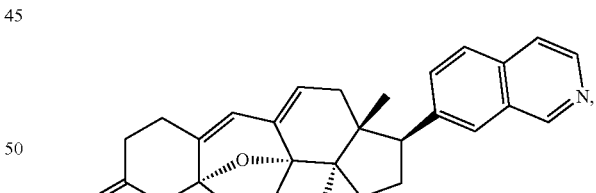

and pharmaceutically acceptable salts, quaternary amine salts, or N-oxides thereof.

Exemplary compounds of Formula (C) include, but are not limited to:

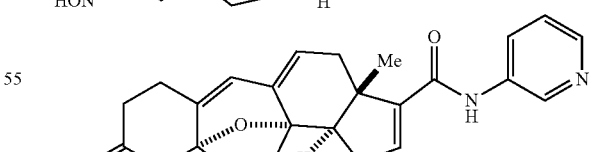

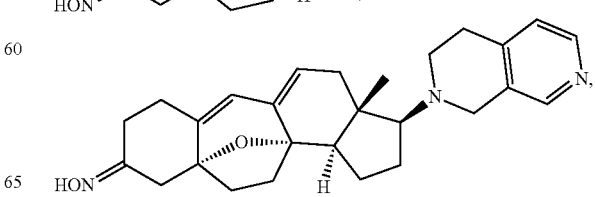

and pharmaceutically acceptable salts thereof.

Exemplary compounds of Formula (D) include, but are not limited to:

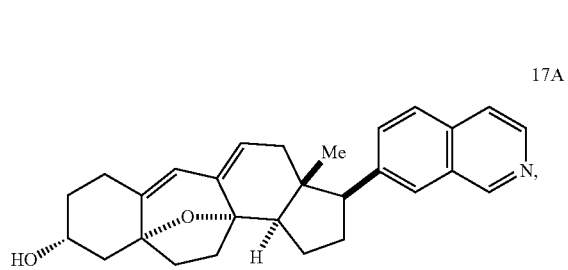

17A

17B and pharmaceutically acceptable salts thereof.

Exemplary compounds of Formula (E) include, but are not limited to:

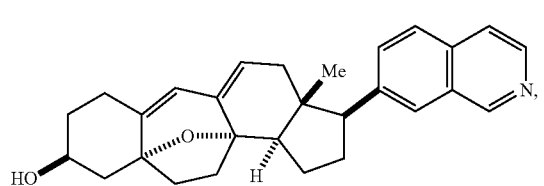

63A

63B

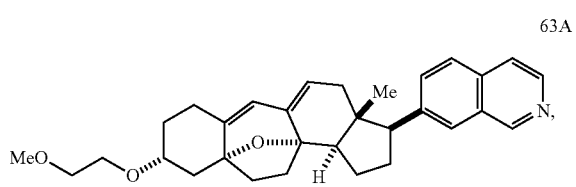

64A

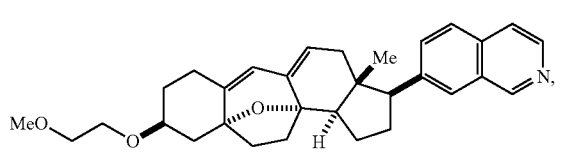

64B

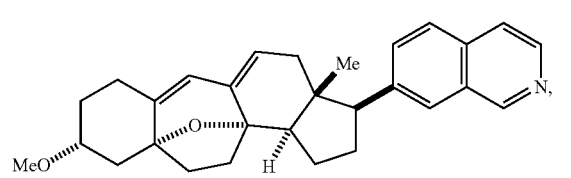

68A

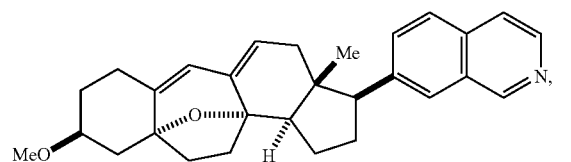

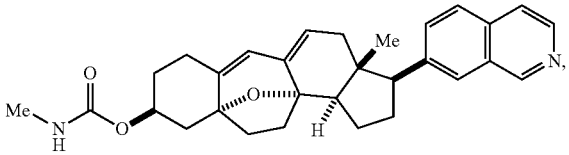

68B and pharmaceutically acceptable salts thereof.

Pharmaceutical Compositions

In certain embodiments, the present invention provides pharmaceutical compositions comprising a compound of Formula (A), (B), (C), (D), or (E) or a pharmaceutically acceptable salt, quaternary amine salt, or N-oxide thereof, and a pharmaceutically acceptable excipient. In certain embodiments, the compound is present in an effective amount, e.g., a therapeutically effective amount or a prophylactically effective amount.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, $21^{st}$ Edition (Lippincott Williams & Wilkins, 2005).

Pharmaceutical compositions described herein can be prepared by any method known in the art of pharmacology. In general, such preparatory methods include the steps of bringing the compound of Formula (A), (B), (C), (D), or (E) or a pharmaceutically acceptable salt, quaternary amine salt, or N-oxide thereof (the "active ingredient") into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredient(s), the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, polymer conjugates (e.g., IT-101/CLRX101), and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the active ingredient, it is often desirable to slow the absorption of the active ingredient from subcutaneous or intramuscular injection. This can be accomplished by the use of a liquid suspension of crystalline or amorphous material with poor water solubility. The rate of absorption of the active ingredient then depends upon its rate of dissolution which, in turn, may depend upon crystal size and crystalline form. Alternatively, delayed absorption of a parenterally administered form is accomplished by dissolving or suspending the active ingredient in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient(s) can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or atomized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w)

solution and/or suspension of the active ingredient in an aqueous or oily liquid carrier. Such drops may further comprise buffering agents, salts, and/or one or more other of the additional ingredients described herein. Other opthalmically administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Treatment

CDK8 and CDK19, referred to as "Mediator kinases", assemble in multi-protein complexes that reversibly bind the Mediator complex. The Mediator complex links enhancer-bound transcription factors to promoter-bound RNA pol II holoenzyme and it influences chromatin architecture to regulate transcription and gene expression through still poorly understood mechanisms. Recent comprehensive genome-wide sequencing of samples from 200 AML patients revealed that, remarkably, nearly all mutations in presumably cancer-driving proteins are associated with regulating gene expression. See, e.g., Aerts, et al., *Nature* (2013) 499:35-36; The Cancer Genome Atlas Research Network, 2013. Genomic and Epigenomic Landscapes of Adult De Novo Acute Myeloid Leukemia. *N. Engl. J. Med.* 368, 2059-2074. Therefore, specific inhibition of Mediator kinases might be a new means to disrupt the ability of some AML mutations to deregulate gene expression programs that drive AML cell growth. Specific small molecule inhibition of CDK8/CDK19 may also prove beneficial for treating other cancers that rely on deregulated gene expression. CDK8/cyclin C was further observed to be more highly expressed in neurons and astrocytes of Alzheimer's disease (AD) patients, and thus specific small molecule inhibition of CDK8 may also prove beneficial for treating degenerative disorders, such as AD. See, e.g., Hessel et al., *Neurobiology of Aging* (2003) 24:427-435, wherein. Cortistatin A has been reported to bind to CDK8 and CDK19. See, e.g., Cee et al., *Angew Chem Int Ed* (2009) 48:8952 and US 20120071477. Furthermore, as FIGS. 7, 10A-10C, and 16A-16D demonstrate, cortistatin A inhibits CDK8 kinase activity, in part due to this binding. CDK8 and CDK19 have very similar sequences and catalytic domains suggesting that inhibiting CDK8 will likely also inhibit CDK19. See, e.g., Ries et al., *Semin. Cell Dev. Biol.* (2011) 22:735-740. Blast alignment of CDK8 vs. CDK19 also indicate that the amino acids are 70% identical and 82% similar.

Thus, in one aspect, provided is a method of inhibiting CDK8 and/or CDK19 kinase activity in a cell comprising contacting a compound of Formula (A), (B), (C), (D), or (E) or a pharmaceutically acceptable salt, quaternary amine, or N-oxide thereof, with the cell. In certain embodiments, the method is an in vitro method. In certain embodiments, the method is an in vivo method. In another aspect, provided is a method of treating a condition associated with CDK8 and/or CDK19 kinase activity, comprising administering to a subject in need thereof a compound Formula (A), (B), (C), (D), or (E) or a pharmaceutically acceptable salt, quaternary amine salt, or N-oxides thereof.

In certain embodiments, the condition associated with CDK8 and/or CDK19 kinase activity is a proliferative disorder, e.g., cancer. CDK8 kinase activity has been linked to colon cancer. See, e.g., Firestein, et al., *Nature* (2008) 455:547-551.

In certain embodiments, the condition associated with CDK8 and/or CDK19 kinase activity is a diabetic condition, e.g., diabetes.

In certain embodiments, the condition associated with CDK8 and/or CDK19 kinase activity is a degenerative disorder, e.g., Alzheimer's disease (AD).

CDK8 has been linked to regulation of a number of signaling pathways and transcriptional programs that have been implicated in maintaining and driving diseases such as cancer. These pathways and programs include Wnt/beta-catenin pathway, Notch pathway, TGF-beta/BMP signaling, JAK-STAT pathway, p53 pathway, and hypoxia response. Aberrant Wnt/beta-catenin signaling is associated with leukemias and many other cancers. For instance, the most common mutations in colon cancer are ones that lead to activation of Wnt/beta-catenin signaling, expression of Wnt-target genes, and tumorigenesis. Given its central role in tumorigenesis, there is much interest in identifying safe, effective inhibitors of Wnt/beta-catenin signaling. See, e.g., Wang, et al., *Science* (2010) 327:1650-1653. Polakis, *EMBO J.* (2012) 31: 2737-2746.

Thus, in another aspect, provided is a method of treating a β-catenin pathway-associated condition comprising administering to a subject in need thereof a compound of Formula (A), (B), (C), (D), or (E) or a pharmaceutically acceptable salt, quaternary amine, or N-oxide thereof. In another aspect, provided is a method of modulating the β-catenin pathway (e.g., by inhibiting the expression of beta-catenin target genes) in a cell comprising contacting a compound of Formula (A), (B), (C), (D), or (E) or a pharmaceutically acceptable salt, quaternary amine, or N-oxide thereof, with the cell. In certain embodiments, the method is an in vitro method. In certain embodiments, the method is an in vivo method.

Figure 15E:
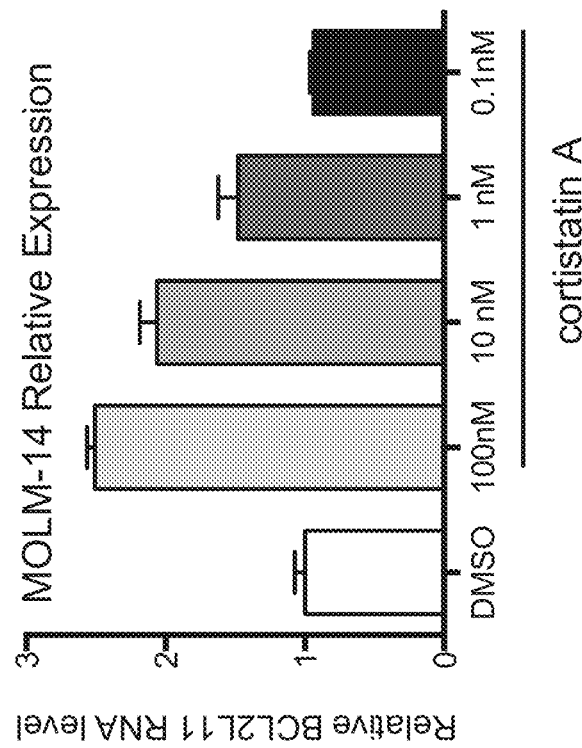
Figure 15D:
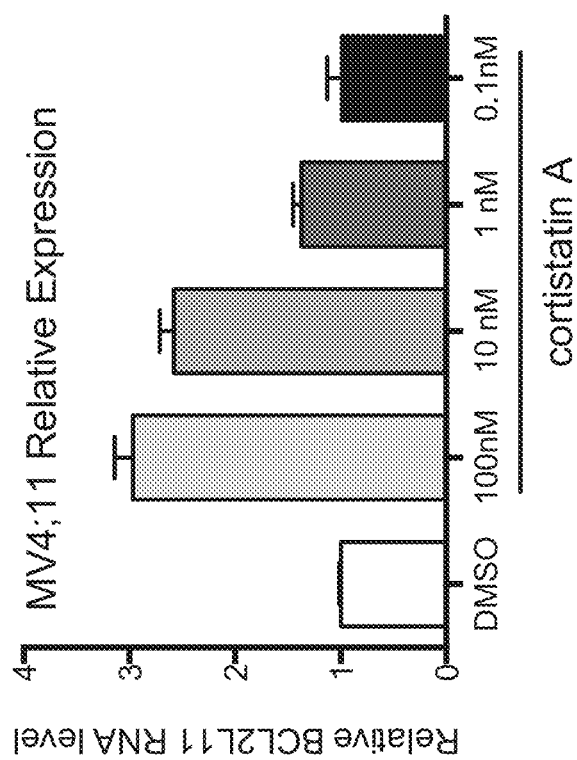

As shown in FIG. 15, cortistatin A inhibits beta-catenin activitated transcription in a reporter gene assay and expression of putative Wnt/beta-catenin target genes in AML cells. Numerous studies have linked beta-catenin pathway activation to tumor initiation, maintenance, and growth. Wnt/beta-catenin pathway alterations have been observed in breast cancer, colorectal cancer, hepatocellular carcinoma, medulloblastoma, pancreatic cancer, lymphoma/leukemia, lung cancer, kidney cancer, and Wilms' tumor. See, e.g., Saito-Diaz, et al., *Growth Factors* (2013) 31:1-31. In addition to cancer, other diseases with overactivation of the Wnt/beta-catenin pathway include high bone mass diseases and hypertrophic obesity. Furthermore, variants of the Wnt-beta catenin pathway transcription factor TCF7L2 have been associated with diabetes. See, e.g., MacDonald et al., *Developmental Cell* (2009) 17, 9-26.

In another aspect, provided is a method of treating a JAK-STAT pathway-associated condition comprising administering to a subject in need thereof a compound of Formula (A), (B), (C), (D), or (E) or a pharmaceutically acceptable salt, quaternary amine, or N-oxide thereof. In another aspect, provided is a method of modulating the STAT1 activity in a cell (e.g., by inhibiting phosphorylation of STAT1 S727 in the JAK-STAT pathway, leading to up- or down-reglulation of specific STAT1-associated genes) comprising contacting a compound of Formula (A), (B), (C), (D), or (E) or a pharmaceutically acceptable salt, quaternary amine, or N-oxide thereof, with the cell. In certain embodiments, the method is an in vitro method. In certain embodiments, the method is an in vivo method.

Figure 7:
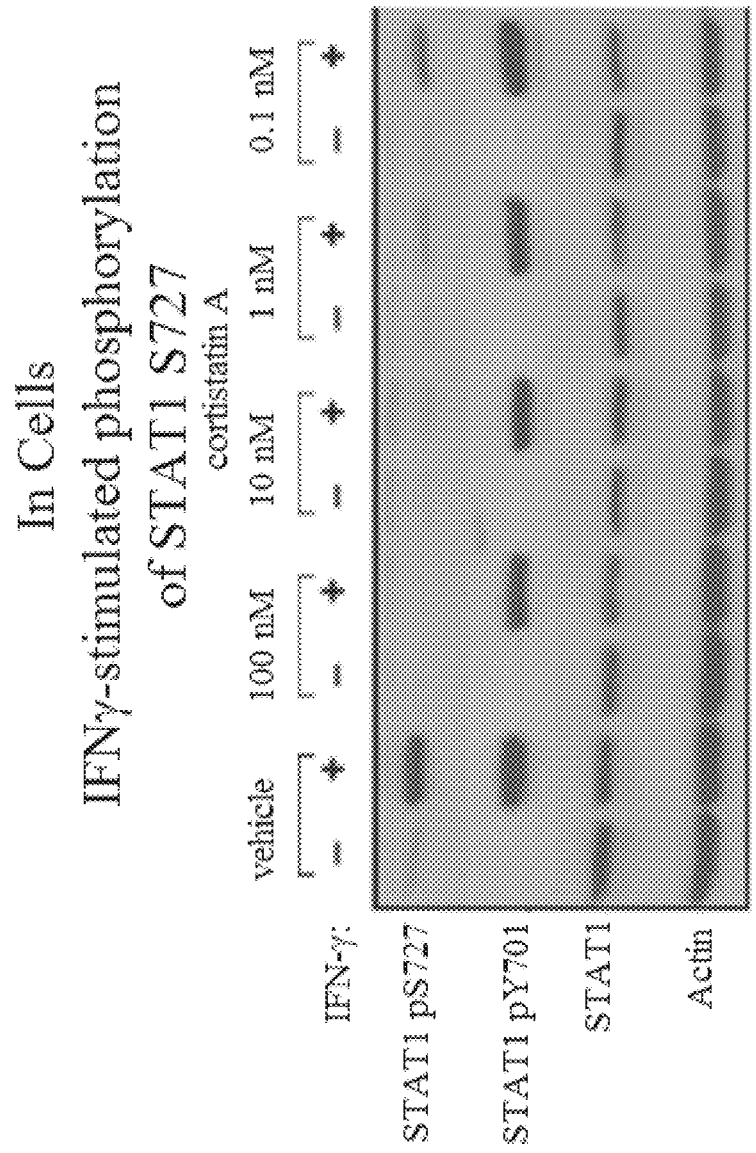
FIG. 7 demonstrates cortistatin A potently and selectively inhibits CDK8 module kinase activity in cells. CDK8 has been reported to inhibit interferon gamma-stimulated phosphorylation of STAT1 S727. See, e.g., Bancerek et al., Immunity (2013) 38:250-262. HepG2 cells were incubated with cortistatin A for 1 hour followed by the addition of human recombinant interferon-gamma (IFN-γ) for 1 hour. The cells were lysed and probed by western blot. As shown, cortistatin A potently inhibited the IFN-γ-stimulated increase in STAT1 pS727 without altering levels of STAT1 pY701 or total STAT1 and Actin.

As shown in FIG. 7, cortistatin A inhibits interferon-gamma-stimulated STAT1 phosphorylation. Inhibition of STAT1 phosphorylation may be a therapeutic strategy to treat aberrant inflammation, including in atherosclerosis, to treat cancers, including MPNs and leukemias, and to treat diabetes, through prevention of STAT1-mediated beta-cell apoptosis. IFN-gamma is expressed at high levels in atherosclerotic lesions leading to increased inflammation through STAT1 activation and IFN-gamma activates STAT1 to induce beta-cell apoptosis. See, e.g., Gysemans et al., *Biochem. Soc. Trans* (2008) 36:328. Phosphorylation of STAT1 by CDK8 has also been shown to restrain NK activation and tumor survellience. Therefore, inhibition of CDK8 kinase activity may beneficially enable an NK-mediated tumor cell killing in addition to directly inhibiting the proliferation of tumor cells. See, e.g., Putz et al., *CellReports* (2013) 4:437-444.

It has been reported that nuclear CDKs, such as CDK8, drive SMAD transcriptional activation and turnover in BMP and TGF-beta. See, e.g., Alarcon et al., *Cell* (2009) 139: 757-769. Thus, in yet another aspect, provided is a method of treating a TGF-beta/BMP pathway-associated condition comprising administering to a subject in need thereof a compound of Formula (A), (B), (C), (D), or (E) or a pharmaceutically acceptable salt, quaternary amine, or N-oxide thereof. In another aspect, provided is a method of modulating the TGF-beta/BMP pathway (e.g., by inhibiting CDK8/CDK19 phosphorylation SMAD proteins in the TGF-beta/BMP pathway leading to up- or down-regulation of specific SMAD protein-associated genes) in a cell comprising contacting a compound of Formula (A), (B), (C), (D), or (E) or a pharmaceutically acceptable salt, quaternary amine, or N-oxide thereof, with the cell. In certain embodiments, the method is an in vitro method. In certain embodiments, the method is an in vivo method.

TGF-beta and BMP pathways are critical for tissue homeostasis, modulation of TGF-beta and BMP pathway activity may be a treatment strategy for conditions including but not limited to muscle dystrophy (see, e.g., Ceco, *FEBS J.* (2013) 280:4198-4209), immune response to transplants, cancer, fibrosis, and Marfan syndrome (see, e.g., Akhurst and Hata, Nat Rev Drug Discov (2012) 11:790-811).

Hypoxia is a condition in which the body or region of the body is deprived of adequate oxygen supply, and may result from altitude sickness, ischaemia, stroke, heart attack, anemia, cancer, and carbon monoxide poisoning. CDK8 has been linked to regulation of hypoxic response, playing a role in induction of HIF-1-A (HIF-1-alpha) target genes. These genes are involved in angiogenesis, glycolysis, metabolic adaption, and cell survival, processes critical to tumor maintenance and growth. See, e.g., Galbraith, et al., *Cell* 153:1327-1339.

Thus, in one aspect, provided is a method of treating a condition associated with hypoxia comprising administering to a subject in need thereof a compound of Formula (A), (B), (C), (D), or (E) or a pharmaceutically acceptable salt, quaternary amine, or N-oxide thereof. In another aspect, provided is a method of reducing hypoxia injury comprising administering to a subject in need thereof a compound of Formula (A), (B), (C), (D), or (E) or a pharmaceutically acceptable salt, quaternary amine, or N-oxide thereof. In yet another aspect, provided is a method of modulating HIF-1-A (HIF-1-alpha) activity (e.g., by inhibiting the expression HIF-1-alpha associated genes) in a cell comprising contacting a compound of Formula (A), (B), (C), (D), or (E) or a pharmaceutically acceptable salt, quaternary amine, or N-oxide thereof, with the cell. In certain embodiments, the method is an in vitro method. In certain embodiments, the method is an in vivo method.

In another aspect, provided is a method of increasing BIM expression (e.g., BCLC2L11 expression) to induce apoptosis in a cell comprising contacting a compound of Formula (A), (B), (C), (D), or (E) or a pharmaceutically acceptable salt, quaternary amine, or N-oxide thereof, with the cell. In certain embodiments, the method is an in vitro method. In certain embodiments, the method is an in vivo method. BCL2L11 expression is tightly regulated in a cell. BCL2L11 encodes for BIM, a proapoptotic protein. BCL2L11 is down-regulated in many cancers and BIM is inhibited in many cancers, including chronic myelocytic leukemia (CML) and non-small cell lung cancer (NSCLC) and that suppression of BCL2L11 expression can confer resistance to tyrosine kinase inhibitors. See, e.g., Ng et al., *Nat. Med.* (2012) 18:521-528.

Furthermore, the cortistatins as a class of compounds have been found to have anti-antiogenic activity. See, e.g., Aoki, et al., *JACS* (2006) 128: 3148-9. Angiogenesis is the process of generating new capillary blood vessels from the pre-existing vasculature. After birth, angiogenesis contributes to organ growth, but in adulthood it is strictly regulated and occurs only during wound healing and in the female reproductive cycle. See, e.g., Klagsbrun et al., Molecular angiogenesis. *Chemistry & Biology* 1999, 6 (8), R217-R224. Under normal physiological conditions, angiogenesis is tightly controlled by a series of pro-angiogenic and anti-angiogenic factors, which allow vascular growth for controlled periods of time. See, e.g., Ferrara, Vascular Endothelial Growth Factor as a Target for Anticancer Therapy. *The Oncologist* 2004, 9:2-10. Persistent, unregulated angiogenesis has been implicated in a wide range of diseases, including rheumatoid arthritis, macular degeneration, atherosclerosis, obesity, benign neoplasms, and cancers. See, e.g., Moulton et al., Angiogenesis inhibitors endostatin or TNP-470 reduce intimal neovascularization and plaque growth in apolipoprotein E-deficient mice. *Circulation* 1999, 99, (13), 1726-1732; and Hanahan et al., The hallmarks of cancer. *Cell* 2000, 100, (1), 57-70. That these pathological states are unified by their status as "angiogenesis-dependent diseases" but are otherwise unrelated has led Folkman to propose the concept of angiogenesis as an "organizing principle" in biology, by which many types of seemingly dissimilar phenomena may be connected. See Folkman, Opinion-Angiogenesis: an organizing principle for drug discovery? *Nature Reviews Drug Discovery* 2007, 6(4):273-286.

Thus, in yet another aspect, provided is a method of treating a condition associated with angiogenesis, such as, for example, a diabetic condition (e.g., diabetic retinopathy), an inflammatory condition (e.g., rheumatoid arthritis), macular degeneration, obesity, atherosclerosis, or a proliferative disorder, comprising administering to a subject in need thereof a compound of Formula (A), (B), (C), (D), or (E) or a pharmaceutically acceptable salt, quaternary amine salt, or N-oxide thereof.

In certain embodiments, the condition associated with angiogenesis is a diabetic condition or associated complication. In certain embodiments, provided is a method of treating a diabetic condition or associated complication comprising administering to a subject in need thereof a compound of Formula (A), (B), (C), (D), or (E) or a pharmaceutically acceptable salt, quaternary amine salt, or N-oxide thereof.

As used herein, a "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type 2 diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes.

All forms of diabetes increase the risk of long-term complications (referred to herein as the "associated complication" of the diabetic condition). These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

As will be appreciated by those of ordinary skill in this art, in treating a diabetic condition or complication, an effective amount of a compound administered may, for example, reduce, prevent, or delay the onset, of any one of the following symptoms: reduce fasting plasma glucose level [typical diabetic level is ≥7.0 mmol/l (126 mg/dl); typical prediabetic range is 6.1 to 6.9 mmol/1]; reduce plasma glucose [typical diabetic level is ≥11.1 mmol/l (200 mg/dL) two hours after a 75 g oral glucose load as in a glucose tolerance test]; reduce symptoms of hyperglycemia and casual plasma glucose [typical diabetic level is ≥11.1 mmol/l (200 mg/dl)]; reduce levels of glycated hemoglobin (Hb A1C) [typical diabetic level is ≥6.5%]. Subjects with fasting glucose levels from 110 to 125 mg/dl (6.1 to 6.9 mmol/1) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

In certain embodiments, the associated complication is diabetic retinopathy. For example, in certain embodiments, provided is a method of treating diabetic retinopathy comprising administering to a subject in need thereof a compound of Formula (A), (B), (C), (D), or (E), or a pharmaceutically acceptable salt, quaternary amine, or N-oxide thereof.

In certain embodiments, the condition associated with angiogenesis is macular degeneration. In certain embodiments, provided is a method of treating macular degeneration comprising administering to a subject in need thereof a compound of Formula (A), (B), (C), (D), or (E) or a pharmaceutically acceptable salt, quaternary amine salt, or N-oxide thereof.

In certain embodiments, the condition associated with angiogenesis is obesity. As used herein, "obesity" and "obese" as used herein, refers to class I obesity, class II obesity, class III obesity and pre-obesity (e.g., being "overweight") as defined by the World Health Organization. In certain embodiments, provided is a method of treating obesity comprising administering to a subject in need thereof a compound of Formula (A), (B), (C), (D), or (E) or a pharmaceutically acceptable salt, quaternary amine salt, or N-oxide thereof. Evidence suggests that adipose tissue expansion is dependent on vasculature development. Therefore, inhibition of angiogenesis may be therapeutic strategy for restricting the expansion of adipose tissue to prevent and treat obesity. See, e.g., Christiaens and Lijnen, *Molecular and Cellular Endocrinology* (2010) 318:2-9.

In certain embodiments, the condition associated with angiogenesis is atherosclerosis. In certain embodiments, provided is a method of treating atherosclerosis comprising administering to a subject in need thereof a compound of Formula (A), (B), (C), (D), or (E) or a pharmaceutically acceptable salt, quaternary amine salt, or N-oxide thereof. Evidence suggests that new angiogenesis occurs in atherosclerotic lesions, contributing to their growth and rupture. Therefore, inhibition of angiogenesis may be a therapeutic strategy for restricting the expansion, growth, and ultimate rupture of atherosclerotic plaques to prevent and treat atherosclerosis. See, e.g., Ho-Tin-Noé et al., *Trends Cariovasc. Med.* (2011) 21:183-187.

In certain embodiments, the condition associated with angiogenesis is a proliferative disorder. In certain embodiments, provided is a method of treating a proliferative disorder comprising administering to a subject in need thereof a compound of Formula (A), (B), (C), (D), or (E) or a pharmaceutically acceptable salt, quaternary amine, or N-oxide thereof.

Exemplary proliferative disorders include, but are not limited to, tumors (e.g., solid tumors), begnin neoplasms, pre-malignant neoplasms (carcinoma in situ), and malignanat neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In certain embodiments, the cancer is associated with CDK8 and/or CDK19 kinase activity.

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML). As shown in FIGS. 4, 5, 6, and 8, cortistatin A or cortistatin A analogs inhibit proliferation of AML cell lines in vitro and as shown in FIG. 12, cortistatin A inhibits AML progression in vivo.

Figure 8A:
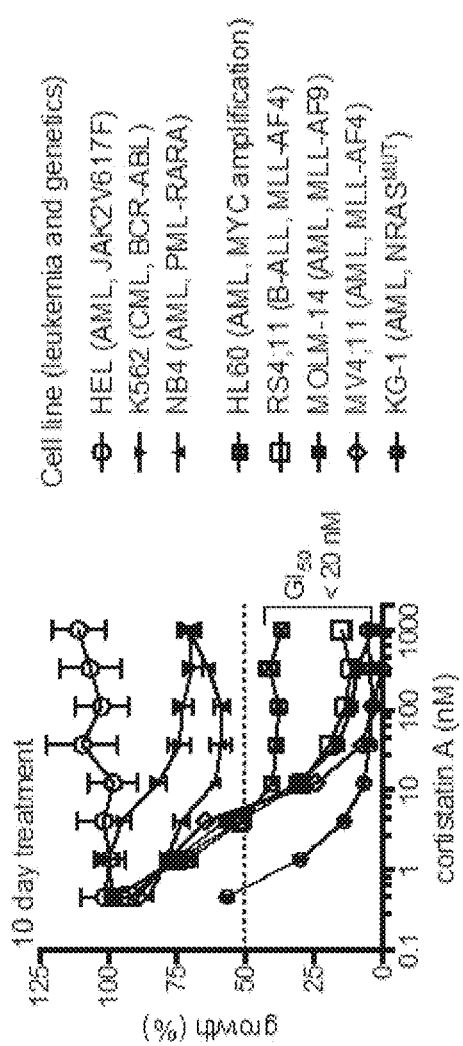
FIG. 8A, FIG. 8B, and FIG. 8C demonstrate cortistatin A inhibits proliferation of human cell lines derived from patients with a variety of hematologic malignancies and bearing diverse oncogenic drivers. The hematologic malignancies represented by these cell lines are: AML, including those derived from patients with myeloproliferative neoplasms (MPNs, UKE-1 and SET-2), T-ALL, B-ALL, CML, and Oncogenic drivers include MLL-fusions with FLT3-internal tandem duplications (FLT3-ITD) (MOLM-14, and MV4; 11) and without FLT3-ITD (RS4;11), JAK2V617F, and BCR-ABL. Also shown are JAK2V617F-expressing cell lines that have been subjected to prolonged treatment with JAK1/2 inhibitor ruxolitinib (SET-2per, UKE-1per) as previously described. See, e.g., Koppikar et al., Nature (2012) 489:155-159. As shown, cortistatin A also inhibited the proliferation of these cells that persist in presence of ruxolitinib. Cells were passaged and fresh cortistatin A was added on days 3 and 7 (mean+/−standard error, n=3).
Figure 8B:
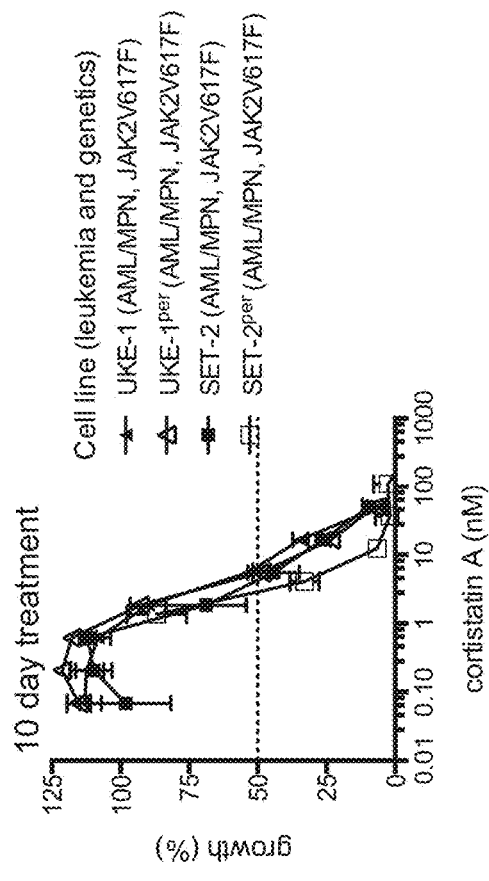
Figure 8C:
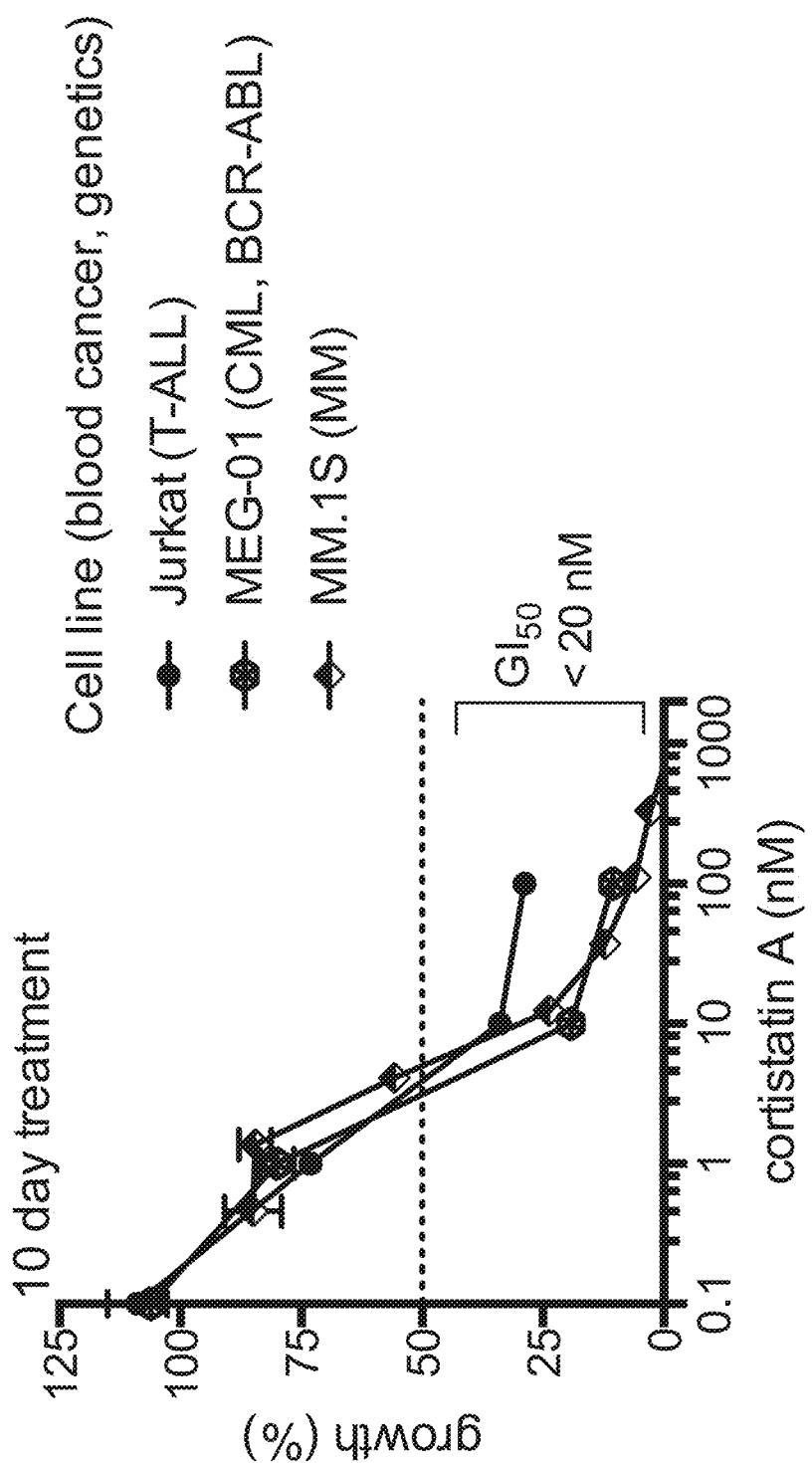
Figure 9:
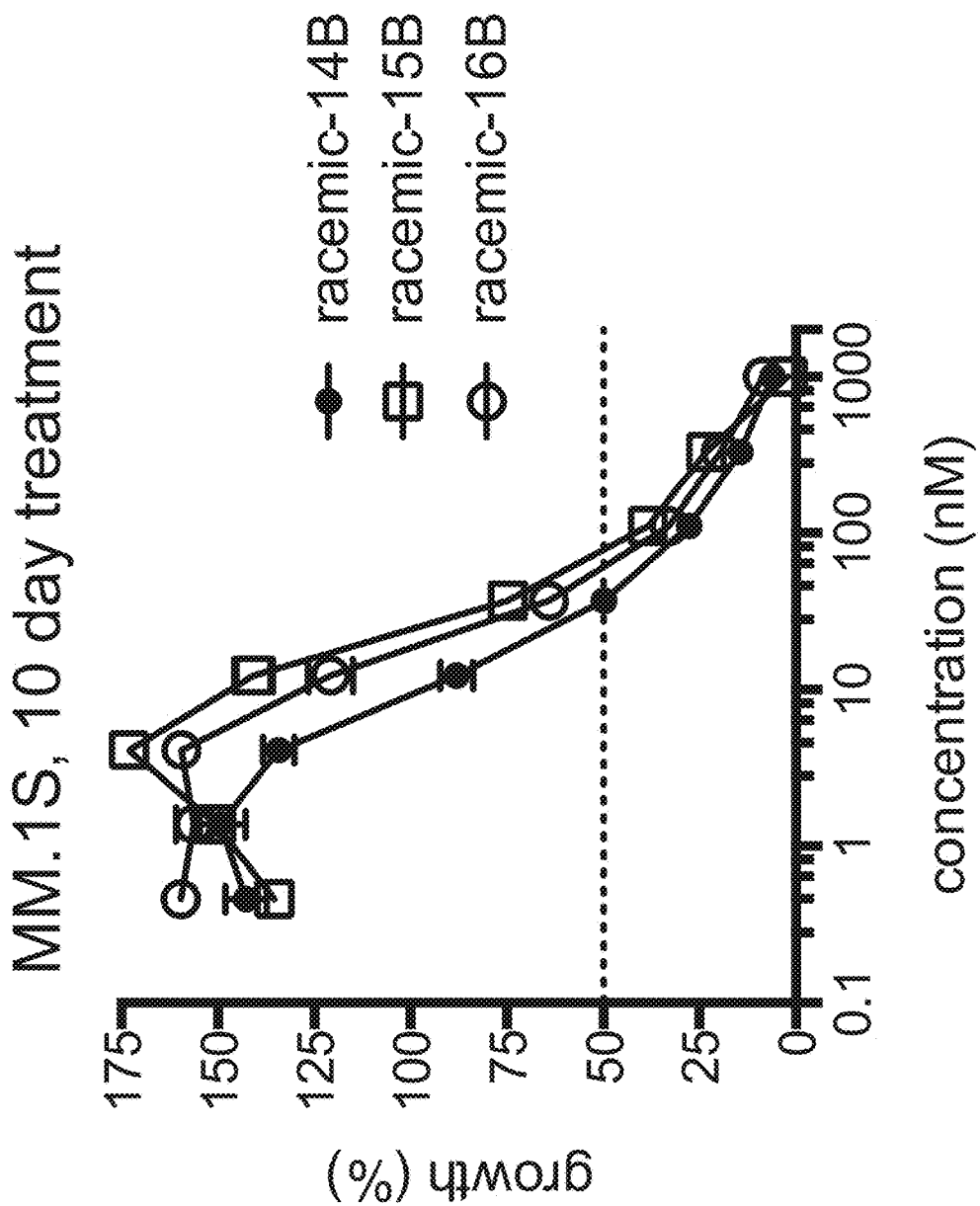
FIG. 9 depicts the dose-dependent inhibition of proliferation of multiple myeloma cell line MM.1S upon 10-day treatment with the indicated cortistatin analogs. Cells were passaged and fresh compounds were added on days 3 and 7 (mean+/−standard error, n=3).

In certain embodiments, the proliferative disorder is a myeloproliferative neoplasm. In certain embodiments, the myeloproliferative neoplasm (MPN) is primary myelofibrosis (PMF). As shown in FIG. 8, cortistatin A inhibits the proliferation of cell lines derived from patients with MPNs and as shown in FIG. 14, cortistatin A is efficacious in an in vivo model of PMF.

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

Compounds of Formula (A), (B), (C), (D), or (E) and pharmaceutically acceptable salts, quaternary amines, and N-oxides thereof, may be formulated in dosage unit form for ease of administration and uniformity of dosage. It will be understood, however, that the total daily usage of the compositions comprising a compound as described herein will be decided by the attending physician within the scope of sound medical judgment. The specific therapeutically effective dose level for any particular subject or organism will depend upon a variety of factors including the disease, disorder, or condition being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 0.1 mg to about 10 mg, or about 0.1 mg to about 15 mg, of a compound per unit dosage form.

In certain embodiments, the compound may be administered orally or parenterally to an adult human at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 0.01 mg/kg to about 1 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-inflammatory agent, anti-cancer agent, etc.), and/or it may achieve different effects (e.g., control of adverse side-effects, e.g., emesis controlled by an anti-emetic).

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In certain embodiments, the additional therapeutically active agent is an anti-cancer agent, e.g., radiation therapy and/or one or more chemotherapeutic agents.

Methods of Preparation

Still further provided are methods of preparing compounds of Formula (A), (B), (C), (D), and (E). An exemplary synthesis of compounds contemplated herein is provided in Schemes 2 to 14.

The synthesis initially is contemplated using a compound of Formula (I) as starting material. Oxidation (e.g., DDQ, $MnO_2$) of estrone (wherein $R^3$ is —$CH_3$) or norestrone (wherein $R^3$ is H) (I) provides the compound of Formula (III). See, e.g., Stephan et al., *Steroid,* 1995, 60, 809-811. The compound of Formula (III) is protected as an acetal or ketal (e.g., via reaction with $HX^4R^4$, or $HX^4R^4$—$R^4X^4H$, wherein the two $R^4$ groups are joined, wherein $R^{B1}$ and $R^{B2}$ are each independently —$X^4R^4$) to give a mixture (e.g., 1:1 mixture) of (IV)-A and (IV)-B. Exemplary conditions contemplated for protection include PTSA and ethylene glycol, PTSA and $CH(OMe)_3$, PTSA and $CH(OEt)_3$, PTSA and 2,2-dimethyl-1,3-propandiol). The protected compounds are then alkylated (e.g., methylated) using an alkylating agent (e.g., $Me_2SO_4$ and $K_2CO_3$, EtN(i-Pr)$_2$ and TMS-diazomethane) to afford (V)-A and (V)-B, wherein E is optionally substituted alkyl. See Scheme 2.

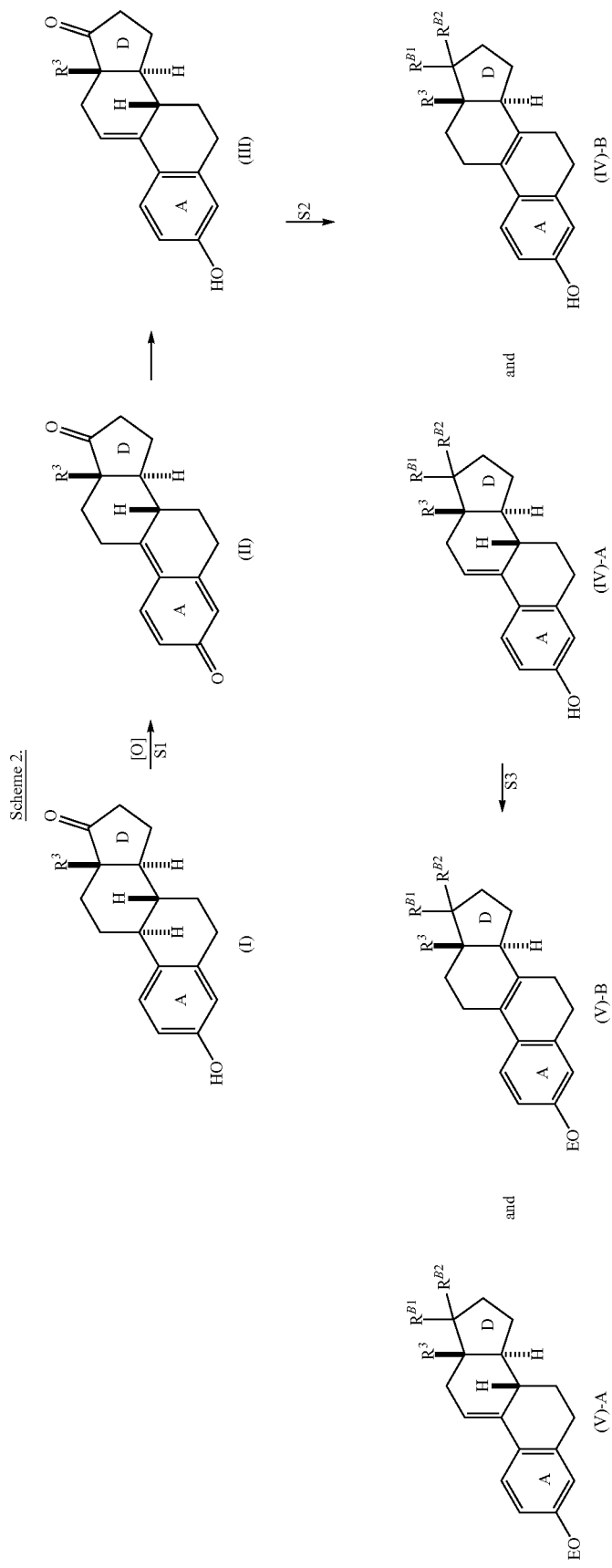

Scheme 3 provides other exemplary routes to provide a compound of Formula (IV-B), e.g., wherein $R^3$ is —$CH_3$. For example, the compound of Formula (V)-B is achieved as racemic mixtures from 6-methoxy-1-tetralone in four steps as described in Scheme 3(A). For the Grignard reaction, see, e.g., Saraber et al., *Tetrahedron,* 2006, 62, 1726-1742. For hydrogenation, see, e.g., Sugahara et al., *Tetrahedron Lett,* 1996, 37, 7403-7406. Scheme 3(B) shows method to obtain enantiopure Torgov's intermediate by chiral resolution. See, e.g., Bucourt et al., *J. Bull. Soc. Chim. Fr.* (1967) 561-563. Scheme 3(C) provides another method of preparing enantiopure Torgov's intermediate aided by enzymatic reduction. See, e.g., Gibian et al., *Tetrahedron Lett.* (1966) 7:2321-2330.

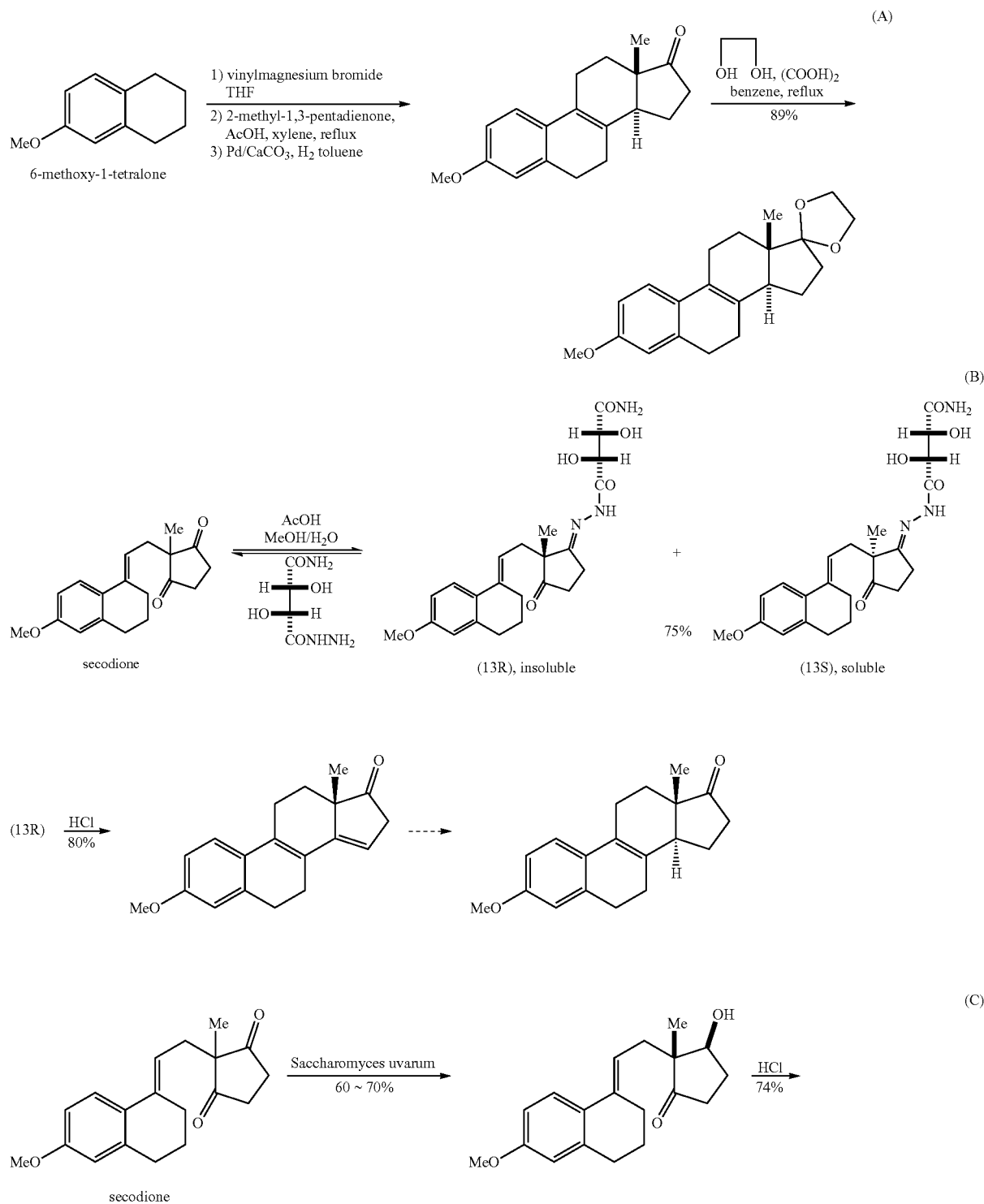

119
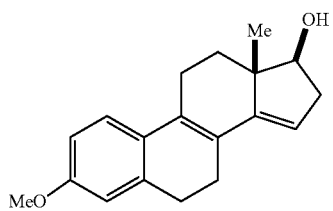
-continued
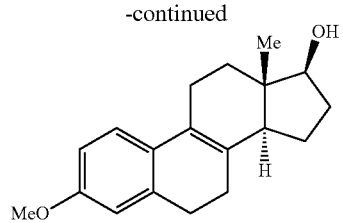
120
With compounds of Formula (IV-A) and (IV-B) in hand, epoxidation/epoxide opening/epoxidation reactions are conducted (e.g., MMPP, mCPBA) in one-pot to provide the compound of Formula (IX-A) and (IX-B), which are under equilibrium with (IX-A) as a major compound. See Schemes 4A and 4B.
Scheme 4.
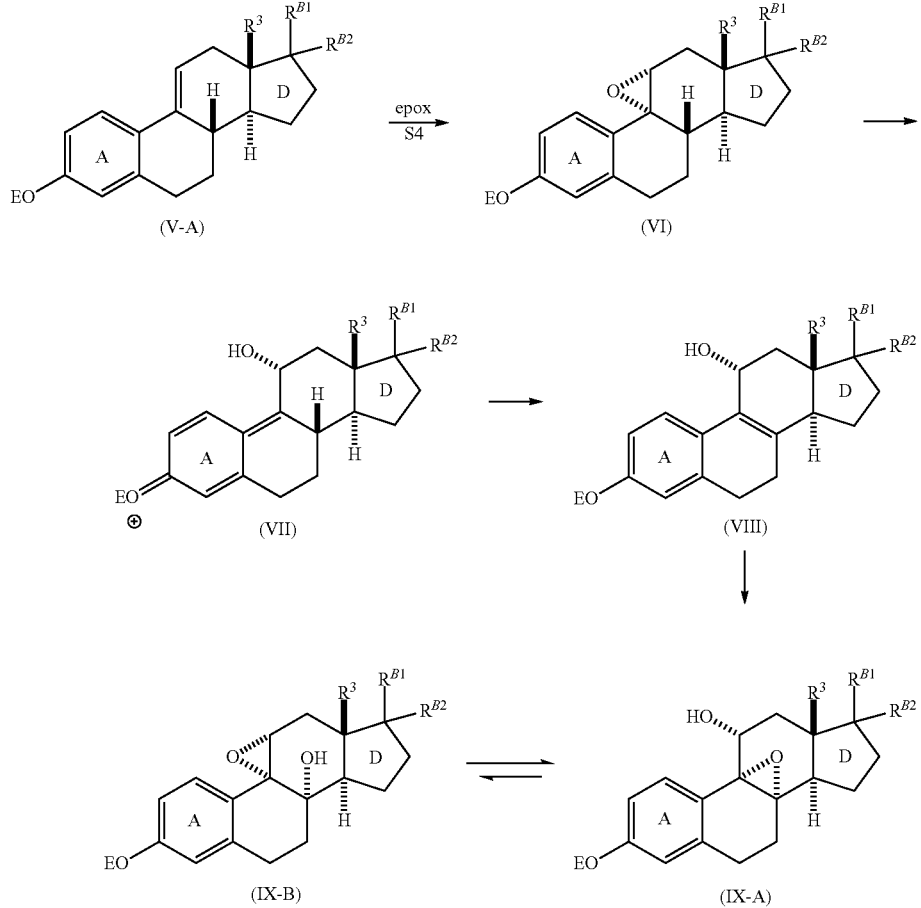
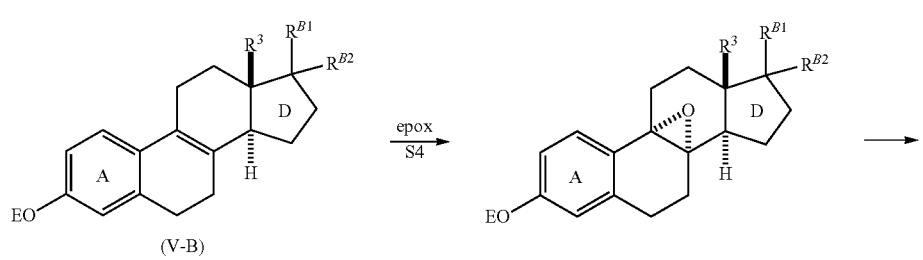

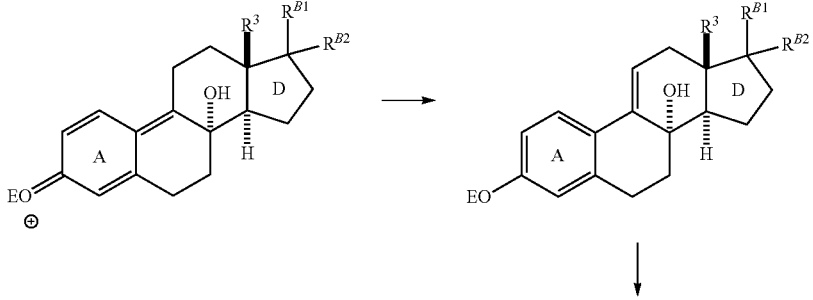

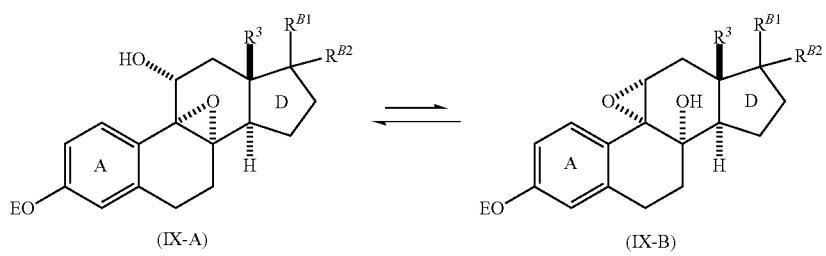

The compound of Formula (IX-A) and (IX-B) are exposed to Birch reduction condition (e.g., Li/NH$_3$ and t-BuOH, Na/NH$_3$ and t-BuOH) to give dearomatized compound (X). C$_3$ of A-ring is then protected as an acetal or ketal (e.g., via reaction with HX$^A$R$^4$, or HX$^A$R$^4$, —R$^A$X$^A$H, wherein the two R$^A$ groups are joined, and wherein R$^{B1}$ and R$^{B2}$ are each independently —X$^A$R$^A$) to afford the compound (XI). Exemplary protection conditions include PTSA and ethylene glycol, PTSA and CH(OMe)$_3$, PTSA and CH(OEt)$_3$, and PTSA and 2,2-dimethyl-1,3-propandiol. See Scheme 5.

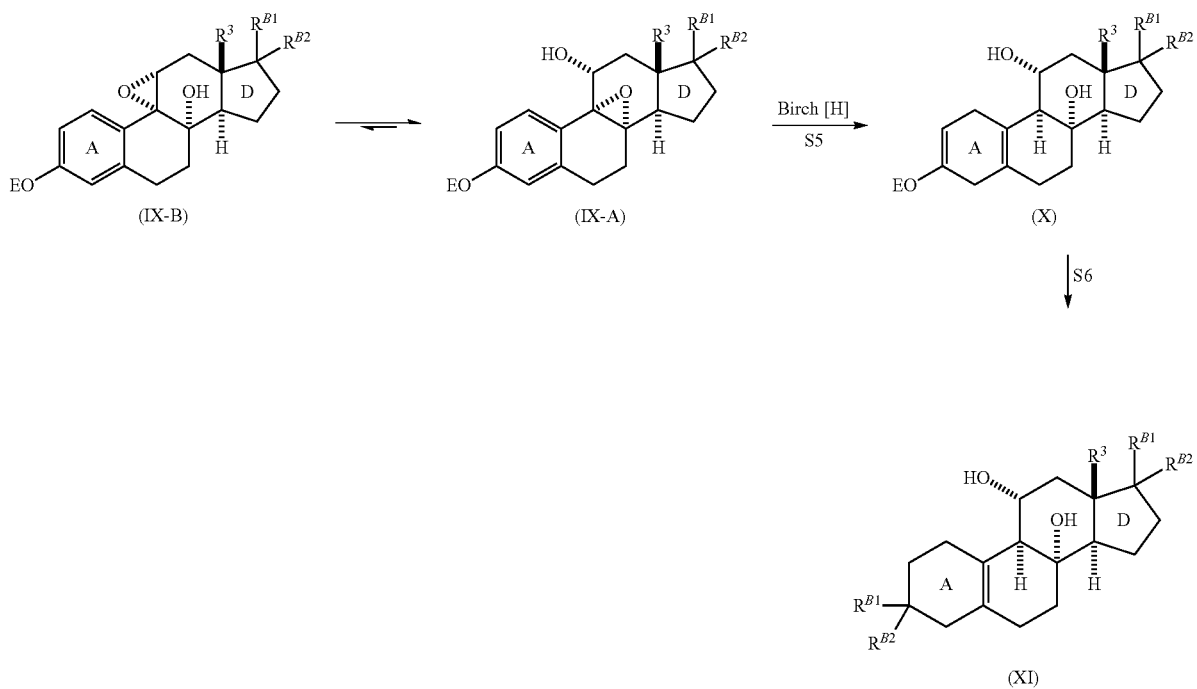

The compound (XI) is converted to a compound of Formula (XIII) through etherification (e.g., NBS, NIS, e.g., wherein X is Br or I). This compound is then oxidized (e.g., SO$_3$.Py/DMSO and triethylamine, IBX, (COCl)$_2$/DMSO and triethylamine) to provide the compound of Formula (XIV). This compound is then treated with base (e.g., DBU, triethylamine) to provide the compound of Formula (XV). This compound is then reduced (e.g., NaBH$_4$ and CeCl$_3$, L-selectride) to provide the compound of Formula (XVI).

The compound of Formula (XVI) is then treated with cyclopropanation reagents (e.g., ZnEt$_2$ and ClCH$_2$I, ZnEt$_2$ and CH$_2$I$_2$, Zn—Cu and CH$_2$I$_2$) to provide a compound of Formula (XVII). The alcohol of the cyclopropanated product is activated, wherein LG$^1$ is a sulfonyl (e.g., the alcohol is treated with Tf$_2$O, MsCl, to provide an activated alcohol wherein LG$^1$ is Tf or Ms) and treated with base (e.g., 2,6-di-t-butyl-4-methylpyridine, 2,6-lutidine, triethylamine) to provide the compound of Formula (XX). See, e.g., Magnus et al., *Org. Lett.* 2009, 11, 3938-3941. See Scheme 7.

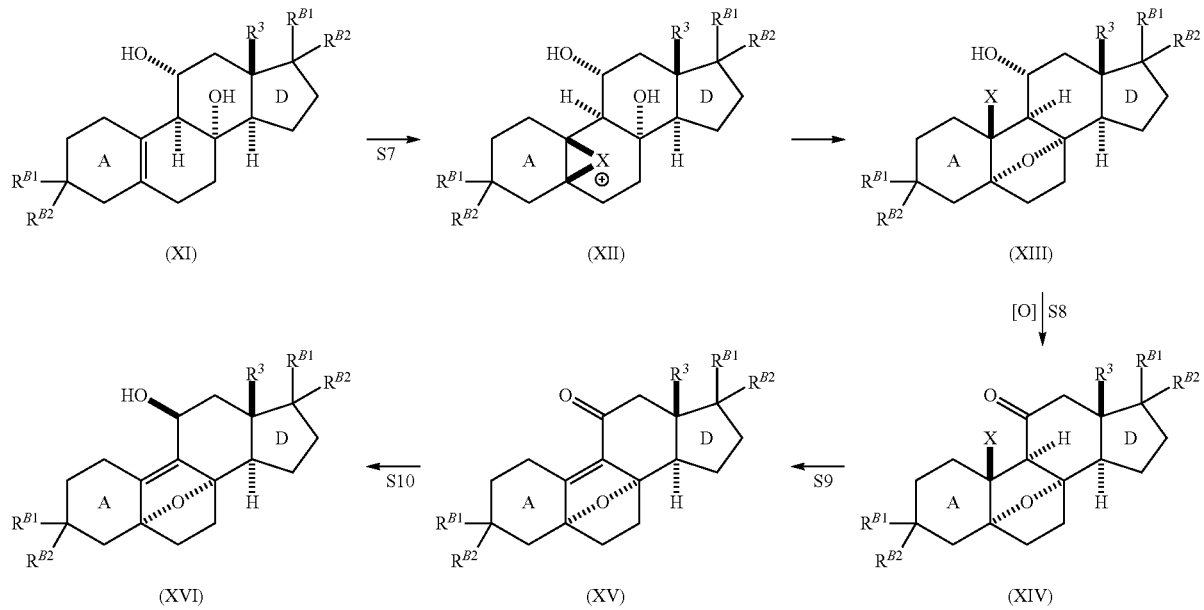

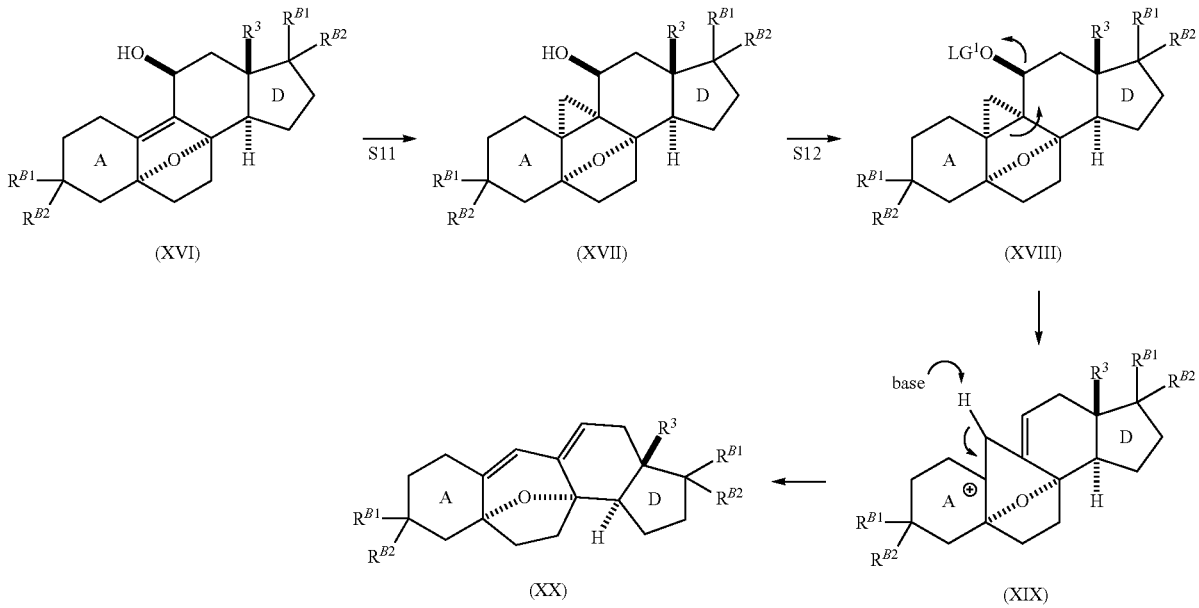

Protecting group on D-ring of the compound of Formula (XX) is then deprotected under acidic conditions (e.g., PTSA and acetone/water, TFA/water) to provide the ketone intermediate of Formula (XXI). This product is treated with a compound of Formula $R^{B1}$-M (e.g., $R^{B1}$—$CeCl_2$, $R^{B1}$—Mg) which is prepared from $R^{B1}$—X (e.g., $R^{B1}$—Br, $R^{B1}$—I) to provide a compound of Formula (XXII), wherein $R^{B1}$ is a non-hydrogen group as defined herein. The compound of Formula (XXII) is activated (e.g., TFAA and pyridine, PhNCS and KH) to provide a compound of Formula (XXIII). Reduction of the compound of Formula (XXIII) (e.g., AIBN and $Bu_3SnH$) provides the compound of Formula (XXIV). For steps S14, S15 and S16, see, e.g., Flyer et al., *Nature. Chem.* 2010, 2, 886-892, and Yamashita et al., *J. Org. Chem.* 2011, 76, 2408-2425. See Scheme 8A.

triflation, e.g., KHMDS and $PhNTf_2$, LiHMDS and $PhNTf_2$, $Tf_2O$ and 2,6-di-t-butyl-4-methylpyridine) followed by palladium-catalyzed cross coupling with $R^{B1}$-M, wherein M is a substituted boron (e.g., such as —B(R')$_2$, wherein each R' is —OR" or alkyl wherein the alkyl and R" is alkyl or may be joined to form a ring) to provide the compound of Formula (XXVI). Exemplary palladium-catalyzed cross coupling conditions include, but are not limited to, $R^{B1}$—B(pin), $R^{B1}$-(9-BBN—H), $R^{B1}$—OBBD, or $R^{B1}$—B(cat), and $Pd(PPh_3)_4$ and $Na_2CO_3$, or $Pd(dppf)Cl_2$ and $K_3PO_4$) (pin=pinacol; cat=catechol; OBBD=9-oxa-10-brabicyclo [3.3.2]decane; 9-BBN—H=9-broabicyclo[3.3.1]nonane). See, e.g., Nicolaou et al., *J. Am. Chem. Soc.* 2009, 131, 10587-10597. Hydrogenation of C16-C17 double bond (e.g., Pd/C and $H_2$, Raney Ni and $H_2$) gives the compound of Formula (XXIV). See Scheme 8B.

Scheme 8.

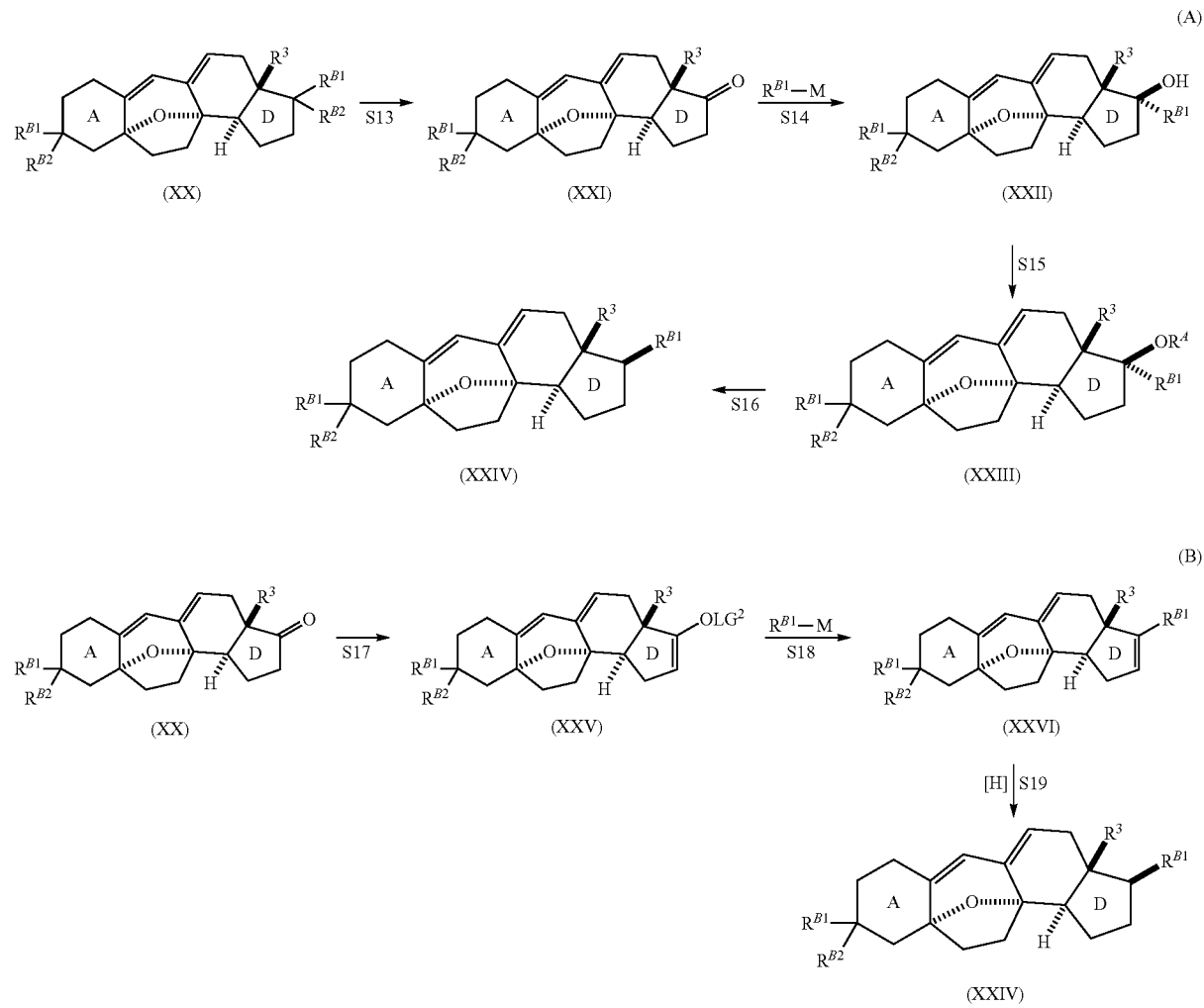

Compound (XXIV) may also be prepared from (XX) through conversion to an activated alcohol, wherein $LG^2$ is a sulfonyl (e.g., the alcohol is treated with $Tf_2O$, MsCl, to provide an activated alcohol wherein $LG^2$ is Tf or Ms; by Any one of the compounds of Formula (XXVI) or (XXIV) may then be deprotected (e.g., PTSA and acetone/water, TFA/water, HCl) and the resulting alpha carbon may be alkylated with an electrophile (e.g., $R^5$-LG, wherein LG is a leaving group, e.g., —OSO$_2$R$^{aa}$) to provide the corresponding alkylated products, wherein R$^5$ is a non-hydrogen group. See Scheme 9A and 9B.

Scheme 9.

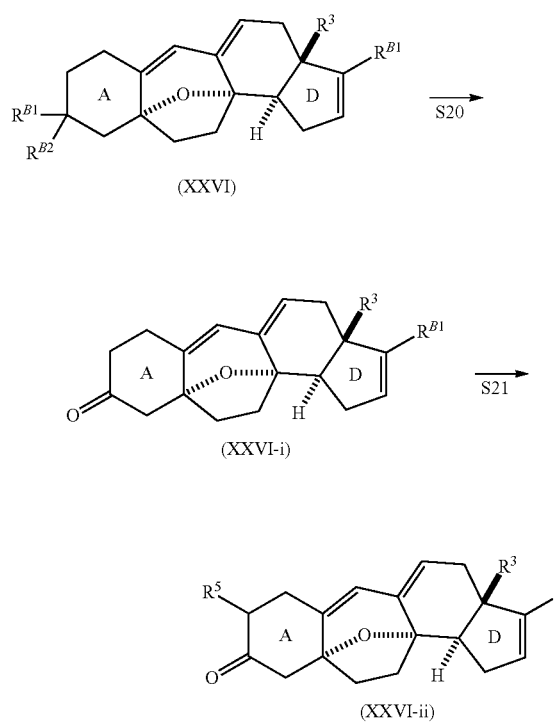

(XXVI)

(XXVI-i)

(XXVI-ii)

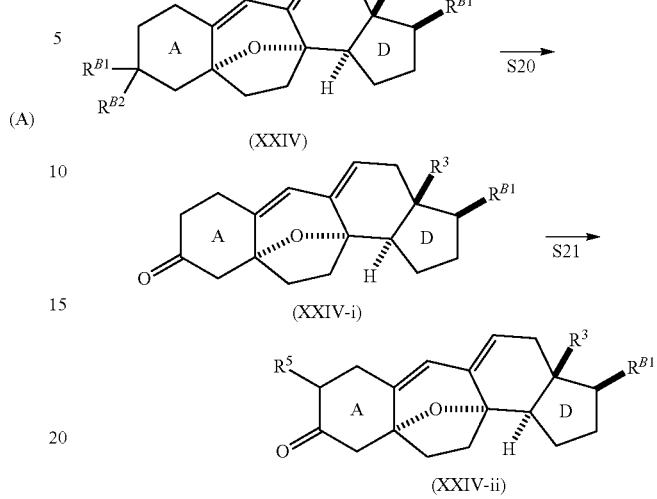

(XXIV)

(XXIV-i)

(XXIV-ii)

The ketone compounds as provided in Scheme 9(A) and 9(B) can then be treated with an amine of formula H$_2$NR$^1$ to form the condensation products, imines, as depicted in Step S22. The ketone compounds can also be treated with an amine of formula HNR$^1$R$_2$, or salt thereof, under reductive amination conditions to provide the aminated products, as depicted in Step S23. Exemplary reductive amination conditions include, but are not limited to, NaCNBH$_3$, NaCN (9BBN)H, or NaBH(OAc)$_3$ under acidic pH (e.g., pH of 3). The aminated products can further be oxidized to the corresponding N-oxide, as depicted in Step S25. Exemplary oxidizing conditions include, but are not limited to, H$_2$O$_2$, mCPBA, or DMDO. See Schemes 10A to 10D.

Scheme 10.

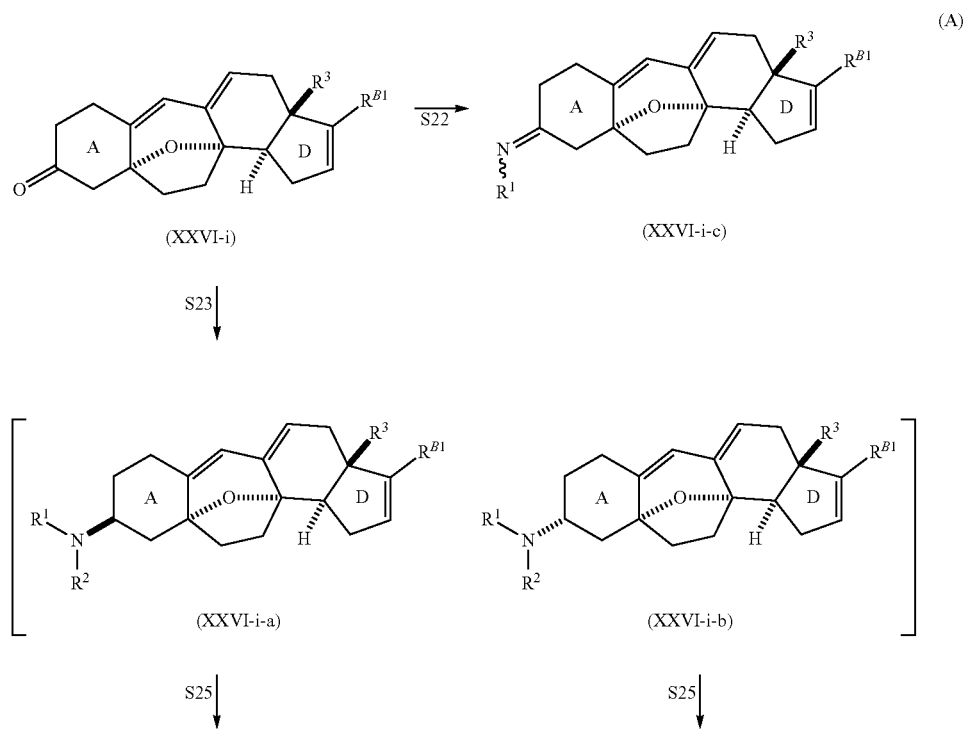

(XXVI-i)

(XXVI-i-c)

(XXVI-i-a)

(XXVI-i-b)

-continued
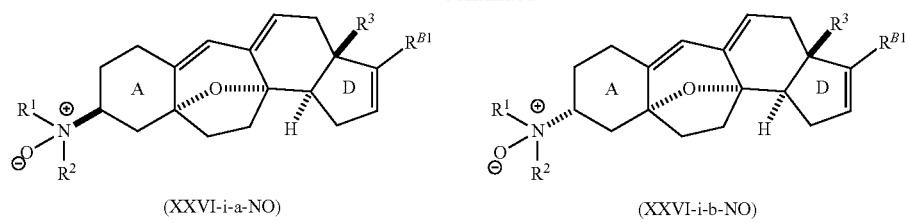
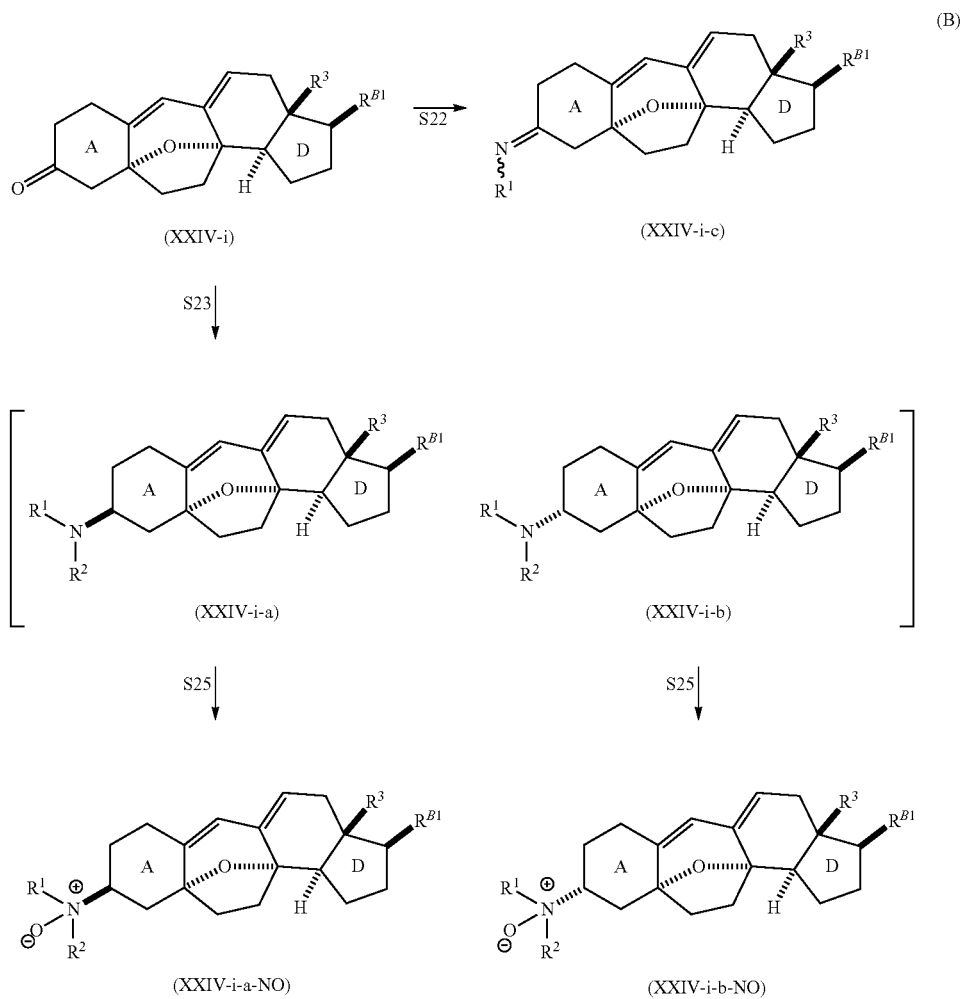
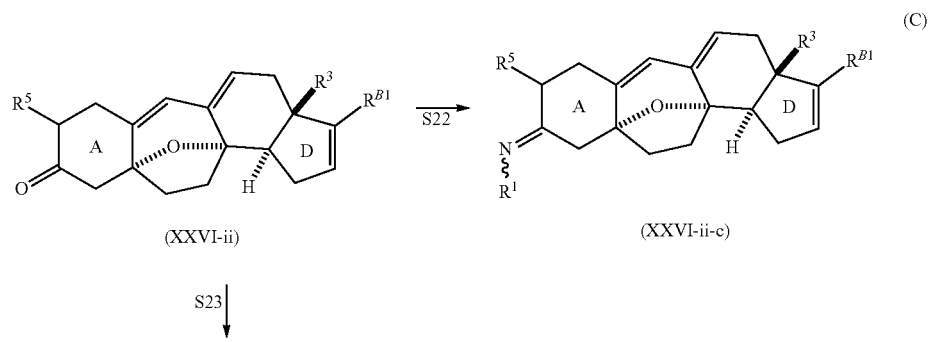

-continued
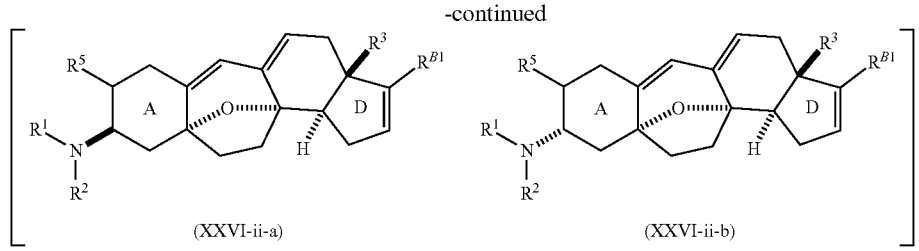
(XXVI-ii-a)            (XXVI-ii-b)
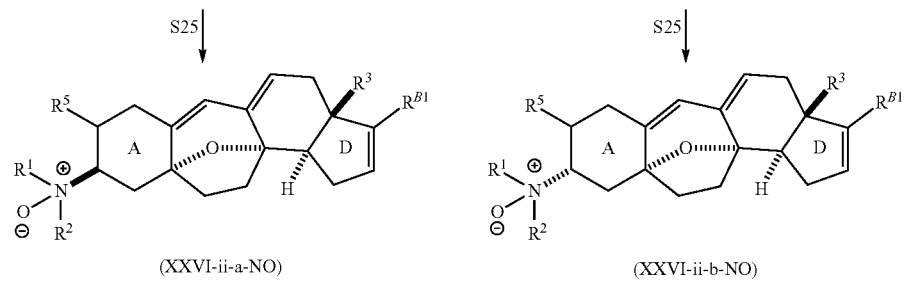
(XXVI-ii-a-NO)            (XXVI-ii-b-NO)
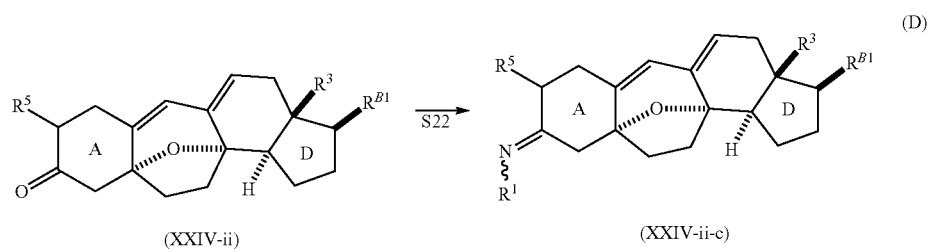
(XXIV-ii)            (XXIV-ii-c)
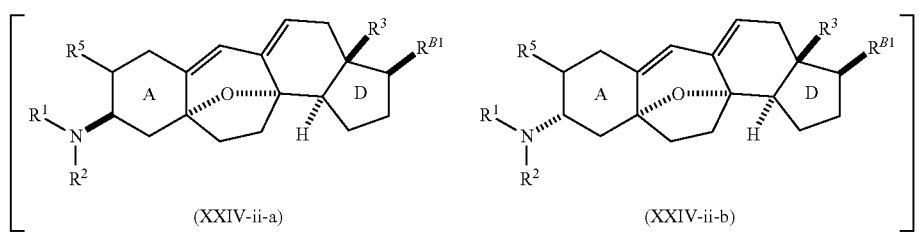
(XXIV-ii-a)            (XXIV-ii-b)
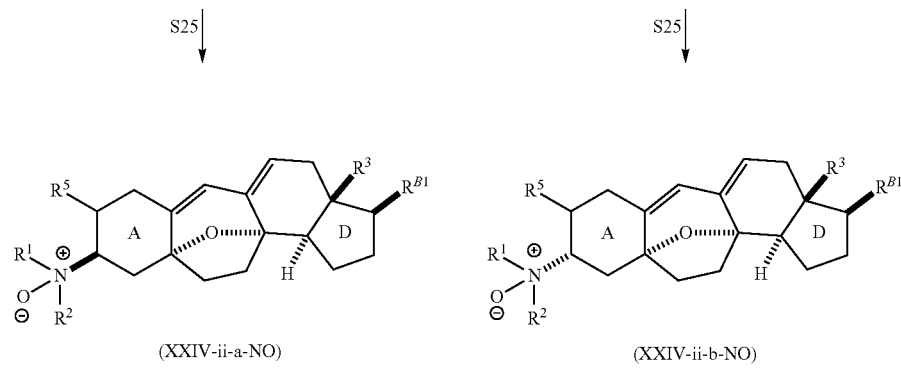
(XXIV-ii-a-NO)            (XXIV-ii-b-NO)

The compound of Formula (XXV) can be converted to the compound of Formula (XXV-i) through palladium-catalyzed carbonylative amination with CO and HN($R^L$)$R^{B3}$ (e.g., Pd(PPh$_3$)$_4$ and triethylamine, Pd(dppf)Cl$_2$ and triethylamine). Conditions for the following steps to get to the compound of Formula (XXV-i), (XXV-iii), (XXV-iv), and (XXV-v) are the same as described previously. See Scheme 11.

Scheme 11.

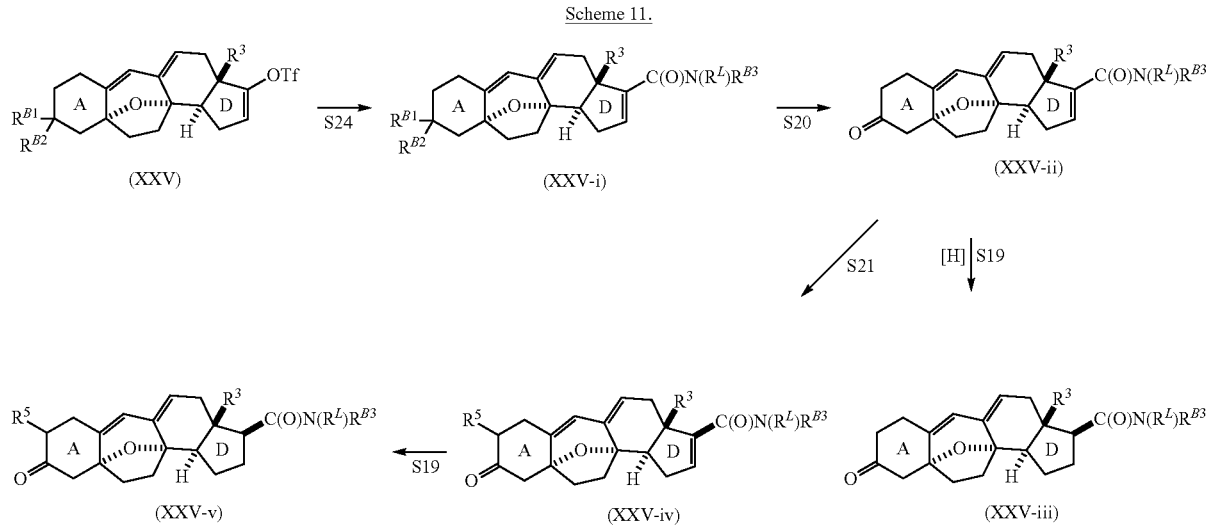

The ketone compounds as provided in Scheme 11 can then be converted to the corresponding imines, amines, and N-oxides, as described previously. See Scheme 12A and 12B.

Scheme 12.

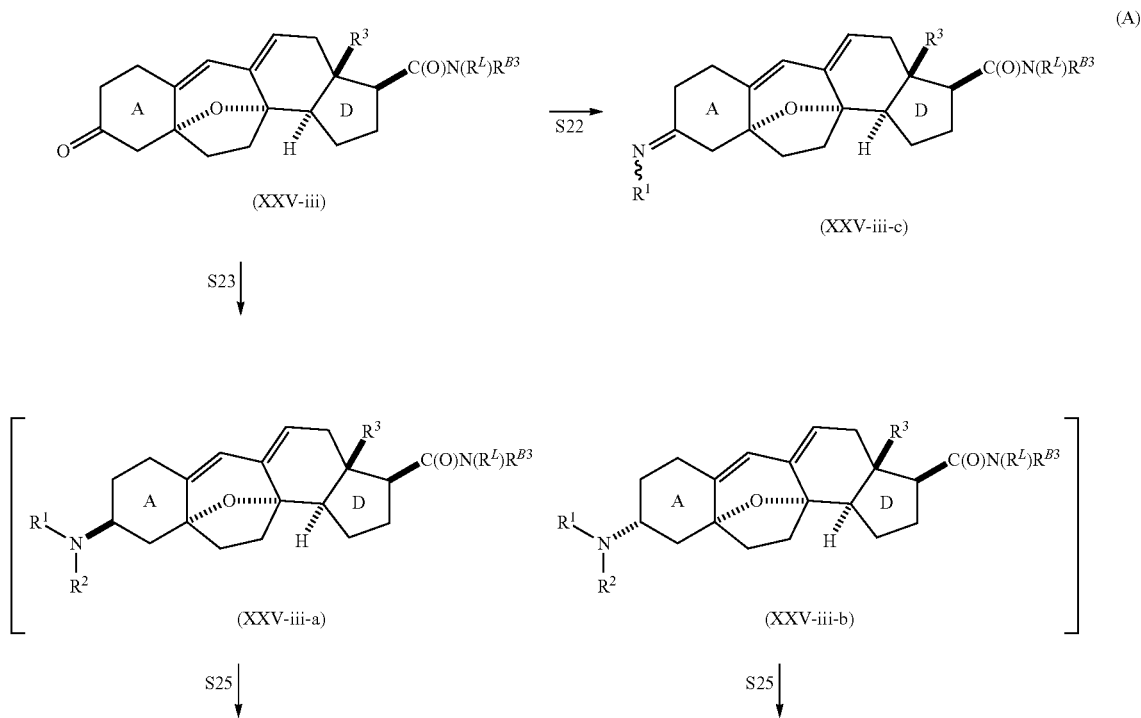

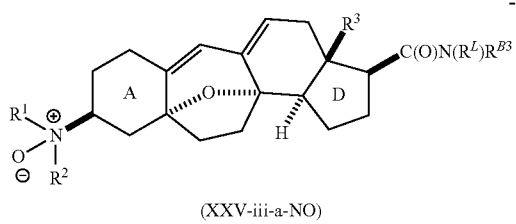
(XXV-iii-a-NO)

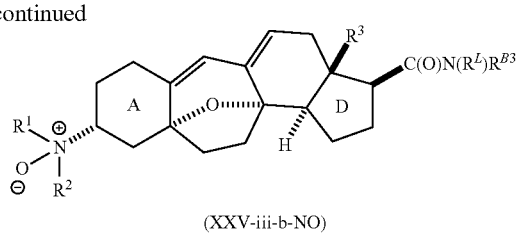
(XXV-iii-b-NO)

(B)

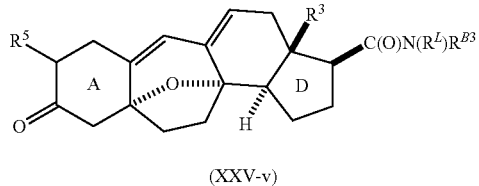
(XXV-v)

S22 →

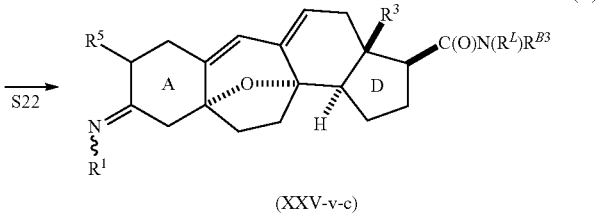
(XXV-v-c)

S23 ↓

[
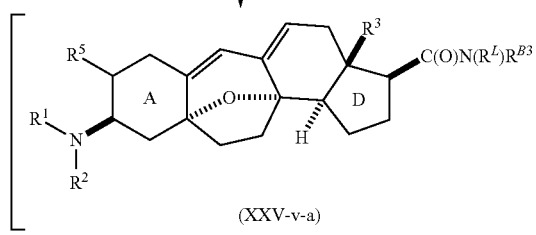
(XXV-v-a)

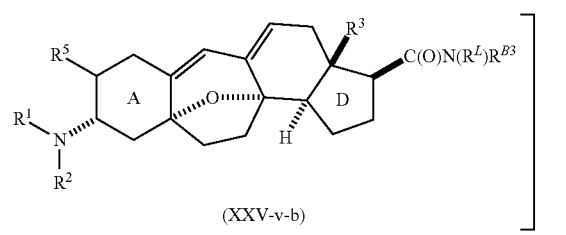
(XXV-v-b)
]

S25 ↓     S25 ↓

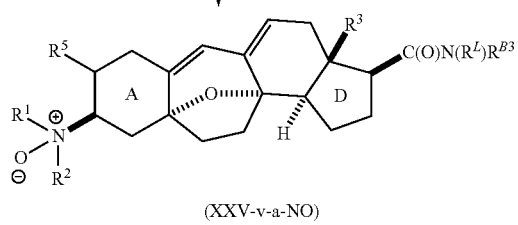
(XXV-v-a-NO)

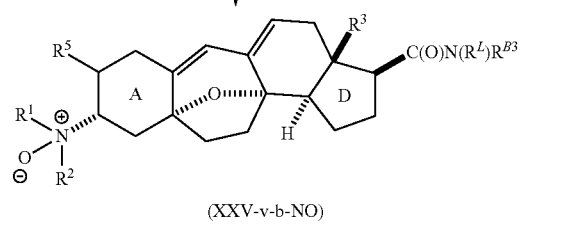
(XXV-v-b-NO)

The monoketone compound (XXI) can be reductively aminated with $HNR^{B4}R^{B5}$ (e.g., 1,2,3,4-tetrahydro-[2,7] naphthyridine) under conditions previously described to provide the compound of Formular (XXVII). Compound (XXVII) can be converted to the corresponding imines, amines, and N-oxides, as described previously. See Scheme 13.

Scheme 13.

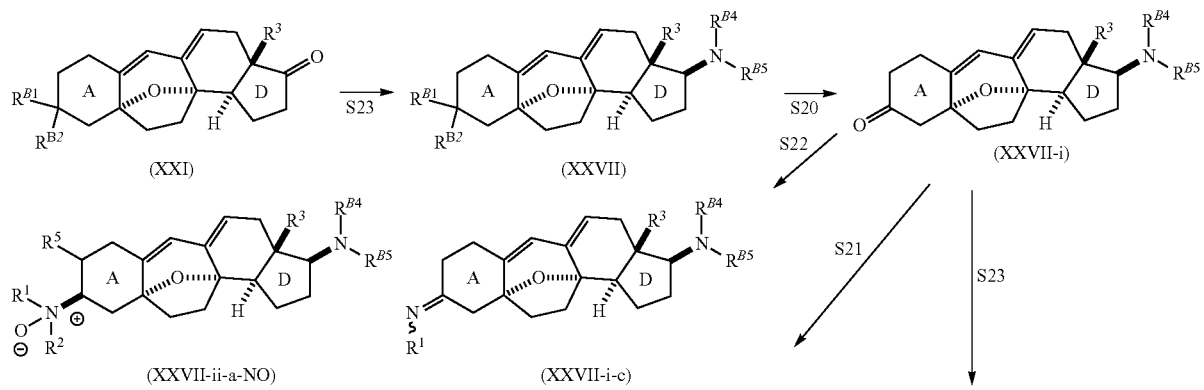

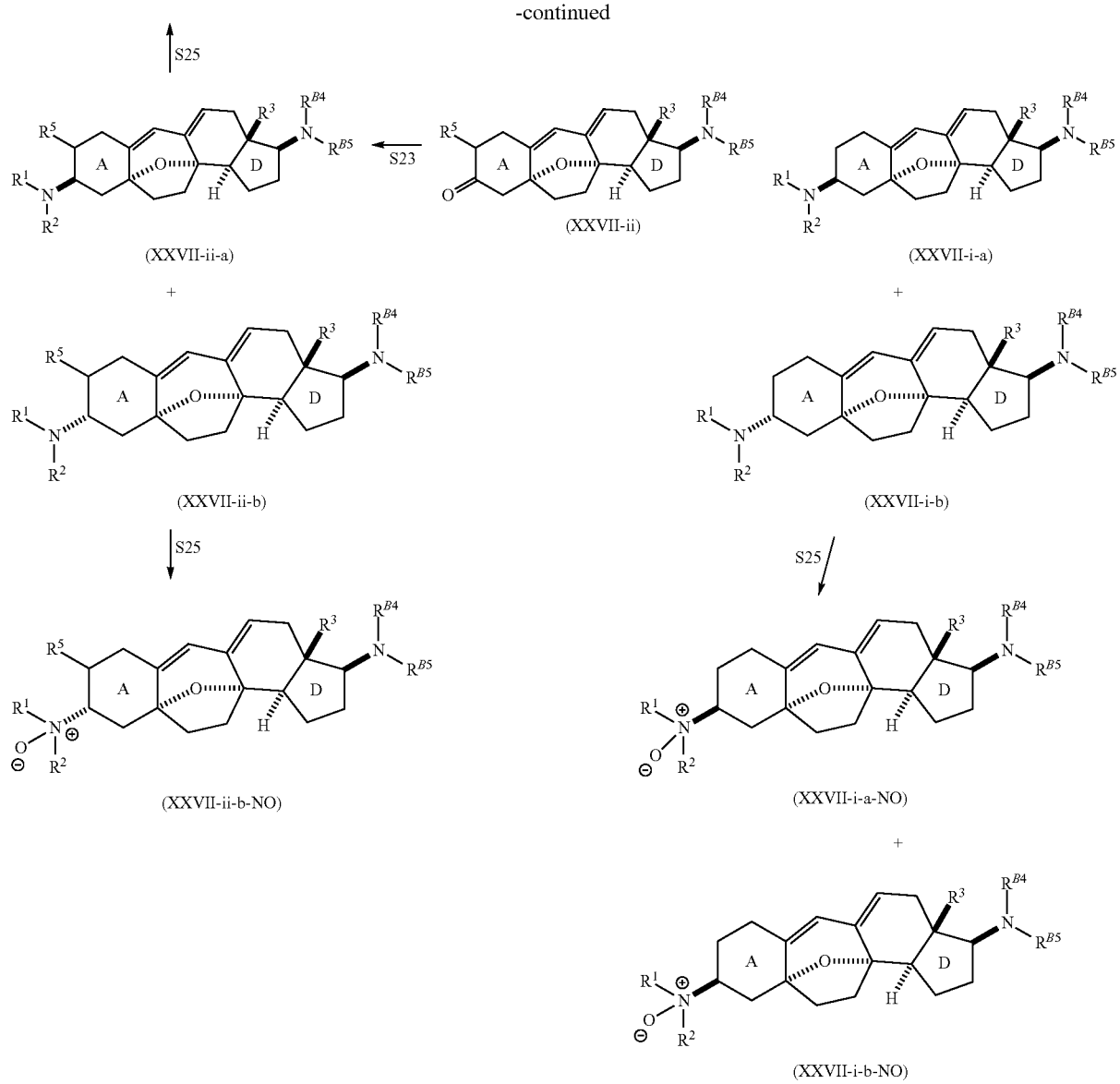

The ketone may be further synthetically manipulated to provide other compounds of interest. Taking the ketone of formula (XXIV-i) as an example, the ketone may be reduced (as depicted in step S26) in the presence of a reducing agent to provide the C-3 hydroxylated compound. See Scheme 14. Exemplary reducing agents include L-selectride, K-selectride, diisobutylaluminum hydride (DIBALH), and lithium aluminum hydride (LAH). Furthermore, various reducing agents will preferentially generate one C-3 hydroxylated compounds as the major isomer over the other, e.g., using L-selectride the beta isomer is preferably generated as the major isomer, while using lithium aluminum hydride (LAH) the alpha is preferably generated as the major isomer.

As used herein, a "major isomer" refers to the isomer that is produced in excess of the other isomer, i.e., greater than 50% of the sum of the two isomers produced from the reaction, e.g., greater than 60%, 70%, 80%, 90%, or 95% of the sum of the two isomers produced from the reaction.

The C-3 hydroxylated compound of Formula (D) may then be activated to a compound of Formula (E) (e.g., by reaction with a group LG-C(=O)$R^A$, wherein LG is a leaving group, either prior to commencing the reaction or in situ (during the reaction) via substitution with a group of formula —C(=O)$R^A$ under Mitsunobu reaction conditions (e.g., with HOC(=O)$R^A$, diethylazodicarboxylate (DEAD) or diisopropyl azodicarboxylate (DIAD), and $PPh_3$)) and then treated with an amine of formula $NHR^1R^2$ to provide a compound of Formula (A) with inverted C3 stereochemistry as the major isomer (as depicted in step S28). Alternatively, the C-3 hydroxlated compound of Formula (D) may be treated with base and a compound of formula $R^O$-LG, wherein LG is a leaving group, to provide a protected C3-hydroxyl compound with retention of C3-stereochemistry as the major isomer (as depicted in step S27).

Scheme 14.

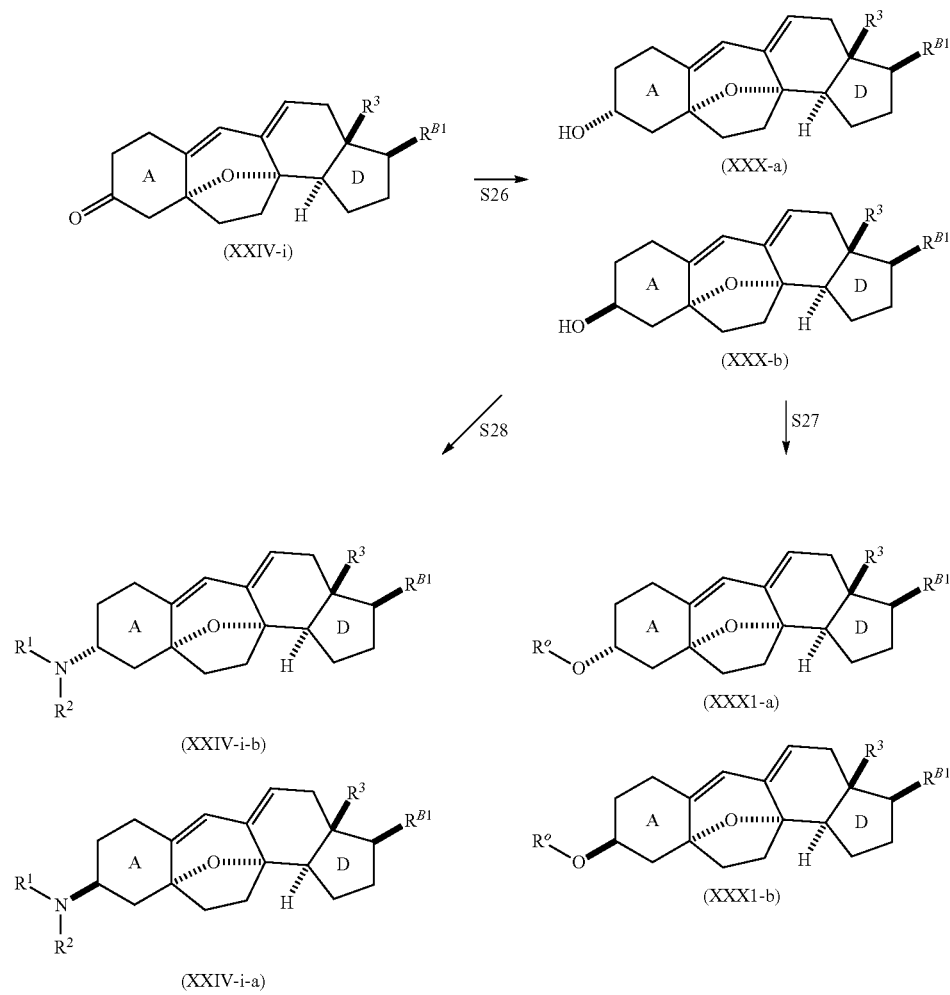

Thus, in one aspect, provided is a method of preparing a compound of Formula (A)

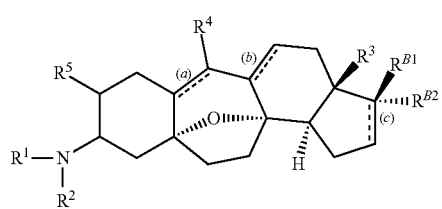

or a pharmaceutically acceptable salt, quaternary amine salt, or N-oxide thereof;

the method comprising contacting a compound of Formula (B):

(B)

or a pharmaceutically acceptable salt thereof, provided $R^{B1}$ and $R^{B2}$ are not joined to form an oxo group; with an amine of formula $HNR^1R^2$, or salt thereof, under reductive amination conditions. In certain embodiments, the method comprises preparing one C3 isomer as the major isomer over the other isomer. For example, in certain embodiments, the method comprises preparing the compound of Formula (A-1) as the major isomer. In other embodiments, the method comprises preparing the compound of Formula (A-2) as the major isomer.

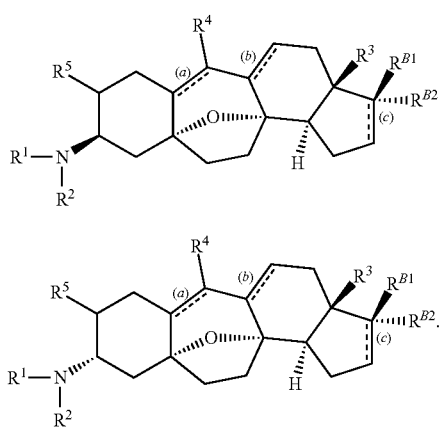
(A-1)

(A-2)

In certain embodiments, the method further comprises oxiding the compound of Formula (A) to provide an N-oxide of Formula (A-NO):

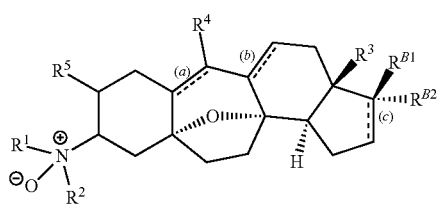
(A-NO)

or a pharmaceutically acceptable salt thereof.

In other embodiments, provided is a method of preparing a compound of Formula (D):

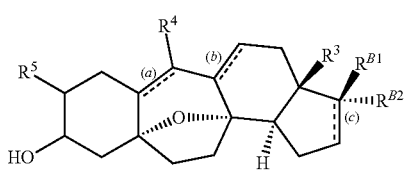
(D)

or a pharmaceutically acceptable salt, quaternary amine salt, or N-oxide thereof;
the method comprising contacting a compound of Formula (B):

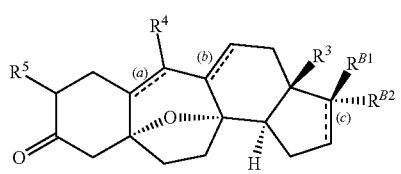
(B)

or a pharmaceutically acceptable salt thereof, with a reducing agent. In certain embodiments, the method comprises preparing one C3 isomer as the major isomer over the other isomer. For example, in certain embodiments, the method comprises preparing the compound of Formula (D-1) as the major isomer. In other embodiments, the method comprises preparing the compound of Formula (D-2) as the major isomer.

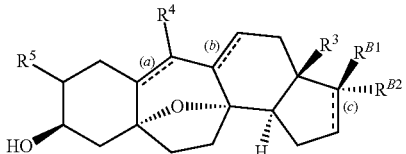
(D-1)

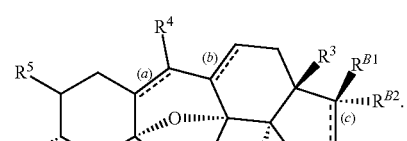
(D-2)

In another aspect, provided is a method of preparing a compound of Formula (E):

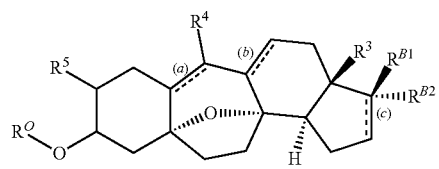

a pharmaceutically acceptable salt thereof; the method comprising contacting a compound of Formula (D):

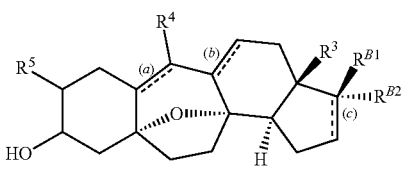

or a pharmaceutically acceptable salt thereof, with a compound of formula $R^O$-LG, wherein LG is a leaving group, to provide a compound of Formula (E).

In another aspect, provided is a method of preparing a compound of Formula (A):

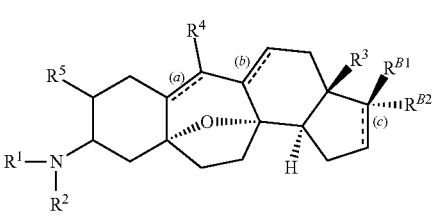
(A)

or a pharmaceutically acceptable salt, quaternary amine salt, or N-oxide thereof, the method comprising providing a compound of Formula (E):

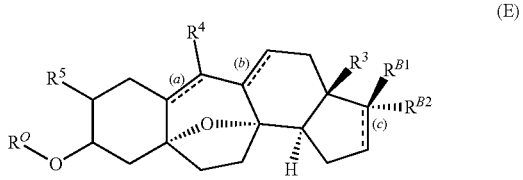

(E)

wherein $R^O$ is —C(=O)$R^A$, or a pharmaceutically acceptable salt thereof; and treating the compound of Formula (E) with a compound of formula NHR$^1$R$^2$, to provide a compound of Formula (A). In certain embodiments, the compound of Formula (E) wherein $R^O$ is —C(=O)$R^A$ is generated in situ from the activation of a compound of Formula (D) with a compound of formula $R^O$-LG. In certain embodiments, the compound of Formula (E) is a compound of Formula (E-1), and the method generates a compound of Formula (A-2) as the major isomer. In certain embodiments, the compound of Formula (E) is a compound of Formula (E-2), and the method generates a compound of Formula (A-1) as the major isomer.

Mutants and Assay Methods

As generally described herein, further provided novel CDK8 and CDK19 point mutants, and methods of their use.

CDK8 and CDK19 with point mutations at Trp105, such as Trp105Met, may retain cellular and in vitro activity but be insensitive to inhibition by cortistatins or cortistatin analogs. As shown in FIG. 10, FLAG-CDK8 W105M and FLAG-CDK19 W105M expression reduces the sensitivity of MOLM-14 cells to growth inhibition by cortistatin A and FLAG-CDK8W105M retains kinase activity in the presence of cortistatin A. CDK8 and/or CDK19 Trp105 point mutants may be used together with a cortistatin or cortistatin analog to validate CDK8 and CDK19 kinase activity in different contexts, including as drug targets for different diseases. In addition, CDK8 and/or CDK19 Trp105 point mutants may be used together with a cortistatin or cortistatin analog to elucidate CDK8 and/or CDK19 kinase substrates and signaling pathways. These point mutants may be expressed in cells by means of overexpression or knock-in and may be constitutively expressed or inducibly expressed. These point mutants may also be used in screening programs to discover new chemical structures that selectively target CDK8 and/or CDK19.

The wild-type amino acid sequence for CDK8 is provided below and in SEQ ID NO: 1. Trp105 is underlined. The CDK8 Trp105 point mutant useful herein comprises an amino acid substitution at position 105.

```
MDYDFKVKLSSERERVEDLFEYEGCKVGRGTYGHVYKAKRKDGKDDKDYA
LKQIEGTGISMSACREIALLRELKHPNVISLQKVFLSHADRKVWLLFDYA
EHDLWHIIKFHRASKANKKPVQLPRGMVKSLLYQILDGIHYLHANWVLHR
DLKPANILVMGEGPERGRVKIADMGFARLFNSPLKPLADLDPVVVTFWYR
APELLLGARHYTKAIDIWAIGCIFAELLTSEPIFHCRQEDIKTSNPYHHD
QLDRIFNVMGFPADKDWEDIKKMPEHSTLMKDFRRNTYTNCSLIKYMEKH
KVKPDSKAFHLLQKLLTMDPIKRITSEQAMQDPYFLEDPLPTSDVFAGCQ
IPYPKREFLTEEEPDDKGDKKNQQQQQGNNHTNGTGHPGNQDSSHTQGPP
LKKVRVVPPTTTSGGLIMTSDYQRSNPHAAYPNPGPSTSQPQSSMGYSAT
SQQPPQYSHQTHRY
```

The wild-type amino acid sequence for CDK19 is provided below and in SEQ ID NO: 2. Trp105 is underlined. The CDK19 Trp105 point mutant useful herein comprises an amino acid substitution at position 105.

```
MDYDFKAKLAAERERVEDLFEYEGCKVGRGTYGHVYKARRKDGKDEKEYA
LKQIEGTGISMSACREIALLRELKHPNVIALQKVFLSHSDRKVWLLFDYA
EHDLWHIIKFHRASKANKKPMQLPRSMVKSLLYQILDGIHYLHANWVLHR
DLKPANILVMGEGPERGRVKIADMGFARLFNSPLKPLADLDPVVVTFWYR
APELLLGARHYTKAIDIWAIGCIFAELLTSEPIFHCRQEDIKTSNPFHHD
QLDRIFSVMGFPADKDWEDIRKMPEYPTLQKDFRRTTYANSSLIKYMEKH
KVKPDSKVFLLLQKLLTMDPTKRITSEQALQDPYFQEDPLPTLDVFAGCQ
IPYPKREFLNEDDPEEKGDKNQQQQQNQHQQPTAPPQQAAAPPQAPPPQQ
NSTQTNGTAGGAGAGVGGTGAGLQHSQDSSLNQVPPNKKPRLGPSGANSG
GPVMPSDYQHSSSRLNYQSSVQGSSQSQSTLGYSSSSQQSSQYHPSHQAH
RY
```

Thus, in one aspect, provided is a method of validating CDK8 and/or CDK19 kinase activity in a cell by contacting a CDK8 or CDK19 Trp105 point mutant and a cortistatin or cortistatin analog, as described herein. In another aspect, provided is a method of validating CDK8 and/or CDK19 kinase activity in a cell by expressing CDK8 or CDK19 Trp105 point mutant in a cell to desensitize the cell to cortistatins or cortistatin analog, as described herein.

In another aspect, provided is a CDK8 Trp105 point mutant. In certain embodiments, the CDK8 Trp105 point mutant has an amino acid sequence that a degree of homology to the amino acid sequence of SEQ ID NO: 1 of at least about 80%, e.g., at least about 85%, at least about 90%, at least about 95%, or at least about 97%. Further provided is a protein that has a degree of homology to the amino acid sequence of SEQ ID NO: 1 of at least about 80%, e.g., at least about 85%, at least about 90%, at least about 95%, or at least about 97%.

In yet another aspect, provided is a CDK19 Trp105 point mutant. In certain embodiments, the CDK19 Trp105 point mutant has an amino acid sequence that a degree of homology to the amino acid sequence of SEQ ID NO: 2 of at least about 80%, e.g., at least about 85%, at least about 90%, at least about 95%, or at least about 97%. Further provided is a protein that has a degree of homology to the amino acid sequence of SEQ ID NO: 2 of at least about 80%, e.g., at least about 85%, at least about 90%, at least about 95%, or at least about 97%.

In yet another aspect, provided is a CDK19 Trp105 point mutant. In certain embodiments, the CDK19 Trp105 point mutant has an amino acid sequence as recited in SEQ ID NO. 2. Further provided is a protein that is 80% homologous to SEQ ID NO. 2. In one embodiment, the CDK8 Trp105 point mutant useful in the methods herein has a methionine substitution located at position 105 of the CDK8 polypeptide of SEQ ID NO: 1. In one embodiment, the CDK19 Trp105 point mutant useful in the methods herein has a methionine substitution located at position 105 of the CDK19 polypeptide of SEQ ID NO: 2. In any of the foregoing embodiments, another amino acid may be substituted in place of Trp105 such as other natural or non-natural amino acids. Non-limiting examples of natural amino acids include isoleucine, leucine, valine, alanine, lysine, arginine, threonine, glutamic acid, methionine, and cysteine. Non-limiting examples of non-natural amino acids include ethionine or norleucine.

In one embodiment, the CDK8 Trp105 point mutant useful herein have an amino acid sequence which has a degree of homology to the amino acid sequence of SEQ ID NO: 1 of at least about 80%, at least about 85%, at least about 90%, at least about 95%, or at least about 97%. In an embodiment, the CDK8 Trp105 point mutant of SEQ ID NO: 1 comprises additional one or more substitutions, deletions, and/or insertions of one or more amino acids. In another embodiment, the CDK8 Trp105 point mutant is an allelic variant of SEQ ID NO: 1. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In one embodiment, the CDK8 Trp105 point mutant is a fragment of SEQ ID NO: 1, or an allelic variant thereof, having CDK8 activity. A fragment of SEQ ID NO: 1 is a CDK8 Trp105 point mutant having one or more amino acids deleted from the amino and/or carboxyl terminus of SEQ ID NO: 1, or an allelic variant thereof.

The CDK8 Trp105 point mutant useful herein have at least about 20%, at least about 40%, at least about 60%, at least about 80%, at least about 90%, or at least about 95% of the CDK8 kinase activity of the CDK8 polypeptide of SEQ ID NO: 1.

In one embodiment, the CDK19 Trp105 point mutant useful herein have an amino acid sequence which has a degree of homology to the amino acid sequence of SEQ ID NO: 2 of at least about 80%, at least about 85%, at least about 90%, at least about 95%, or at least about 97%. In an embodiment, the CDK19 Trp105 point mutant of SEQ ID NO: 2 comprises additional one or more substitutions, deletions, and/or insertions of one or more amino acids. In another embodiment, the CDK19 Trp105 point mutant is an allelic variant of SEQ ID NO: 2.

In one embodiment, the CDK19 Trp105 point mutant is a fragment of SEQ ID NO:2, or an allelic variant thereof, having CDK19 activity. A fragment of SEQ ID NO:2 is a CDK19 Trp105 point mutant having one or more amino acids deleted from the amino and/or carboxyl terminus of SEQ ID NO:2, or an allelic variant thereof.

The CDK19 Trp105 point mutant useful herein have at least about 20%, at least about 40%, at least about 60%, at least about 80%, at least about 90%, or at least about 95% of the CDK19 kinase activity of the CDK19 polypeptide of SEQ ID NO:2.

In one embodiment, the CDK8 or CDK19 Trp105 point mutant useful herein comprises a tag such as a peptide tag (e.g., a FLAG® tag, GST tag, human influenza hemagglutinin (HA) tag, chitin binding protein (CBP) tag, maltose binding protein (MBP) tag, glutathione-S-transferase (GST) tag, poly(His) tag, V5-tag, Myc-tag) or fluorescent tags (e.g., eGFP tag, mCherry tag).

Also contemplated is a method of predicting or determining a subject's response to cortistatin or cortistatin analogs. For example, provided is a method of analyzing a sample from a subject to determine if a subject has a point mutation located at Trp105 of CDK8 and/or CDK19. In one embodiment the point mutation is a Trp105Met. The presence of one or more of Trp105 mutations is generally indicative of a decreased or ineffective response of a subject to the cortistatin or cortistatin analogs. In one embodiment, a different drug besides cortistatin or cortistatin analogs is administered to the subject if the subject has a point mutation located at Trp105 of CDK8 and/or CDK19.

EXAMPLES

In order that the invention described herein may be more fully understood, the following examples are set forth. It should be understood that these examples are for illustrative purposes only and are not to be construed as limiting this invention in any manner.

Synthetic Methods

Materials and Instrumentation

All reactions were performed in flame-dried glassware under a positive pressure of argon unless otherwise noted. Flash column chromatography was performed as described by Still et al., *J. Org. Chem.* 1978, 43, 2923-2925 employing silica gel 60 (40-63 µm, Whatman).

Commercial reagents and solvents were used as received with the following exceptions: tetrahydrofuran (THF), dichloromethane ($CH_2Cl_2$) were degassed with argon and passed through a solvent purification system (designed by J. C. Meyer of Glass Contour) utilizing alumina columns as described by Pangborn et al., *Organometallics* 1996, 15, 1518-1520. Pyridine and triethylamine were distilled over calcium hydride before use. The celite used was Celite® 545, purchased from J. T. Baker. The molarities of n-butyllithium solutions were determined by titration using 1,10-phenanthroline as an indicator (average of three determinations).

$^1$H NMR spectra were recorded with a Varian INOVA-600 or Varian INOVA-500 spectrometer. Proton chemical shifts are reported in parts per million (δ scale) and are calibrated using residual undeuterated solvent as an internal reference ($CDCl_3$: δ 7.26 ($CHCl_3$), $C_6D_6$: δ 7.15 ($C_6D_5H$)). Data for $^1$H NMR spectra are reported as follows: chemical shift (δ ppm) (multiplicity, coupling constant (Hz), integration). Multiplicities are reported as follows: s=singlet, d=doublet, t=triplet, q=quartet, m=multiplet, br=broad, app=apparent, or combinations thereof. $^{13}$C NMR spectra were recorded with a Varian INOVA-500 spectrometer. High-resolution mass spectra (HRMS) were obtained from the Harvard University Mass Spectrometry Laboratory where electrospray ionization (ESI) mass spectroscopy (MS) experiments were performed on an Agilent 6210 TOF LC/MS instrument.

Example 1. Synthesis of Isoquinoline-Containing Compounds

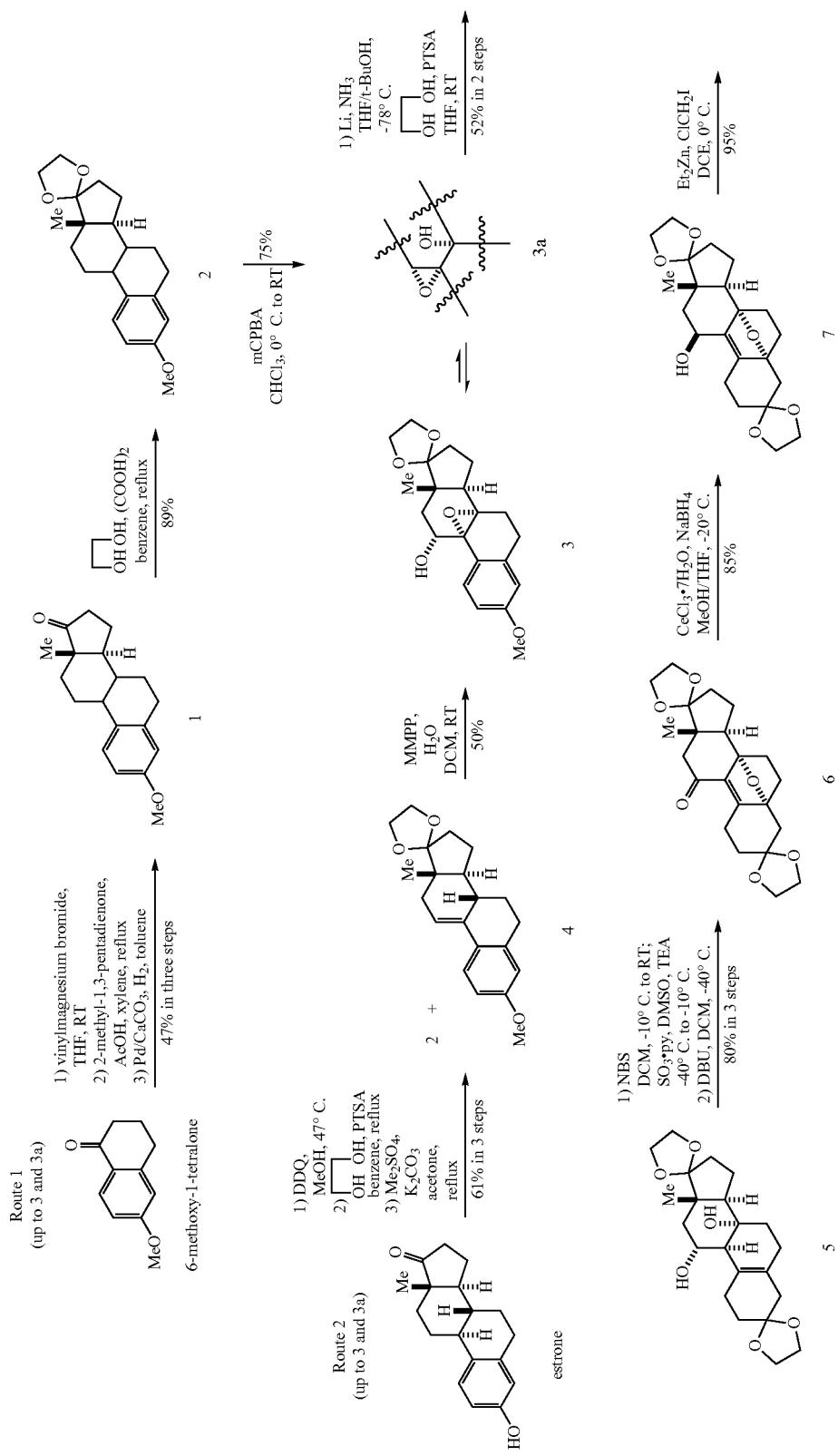

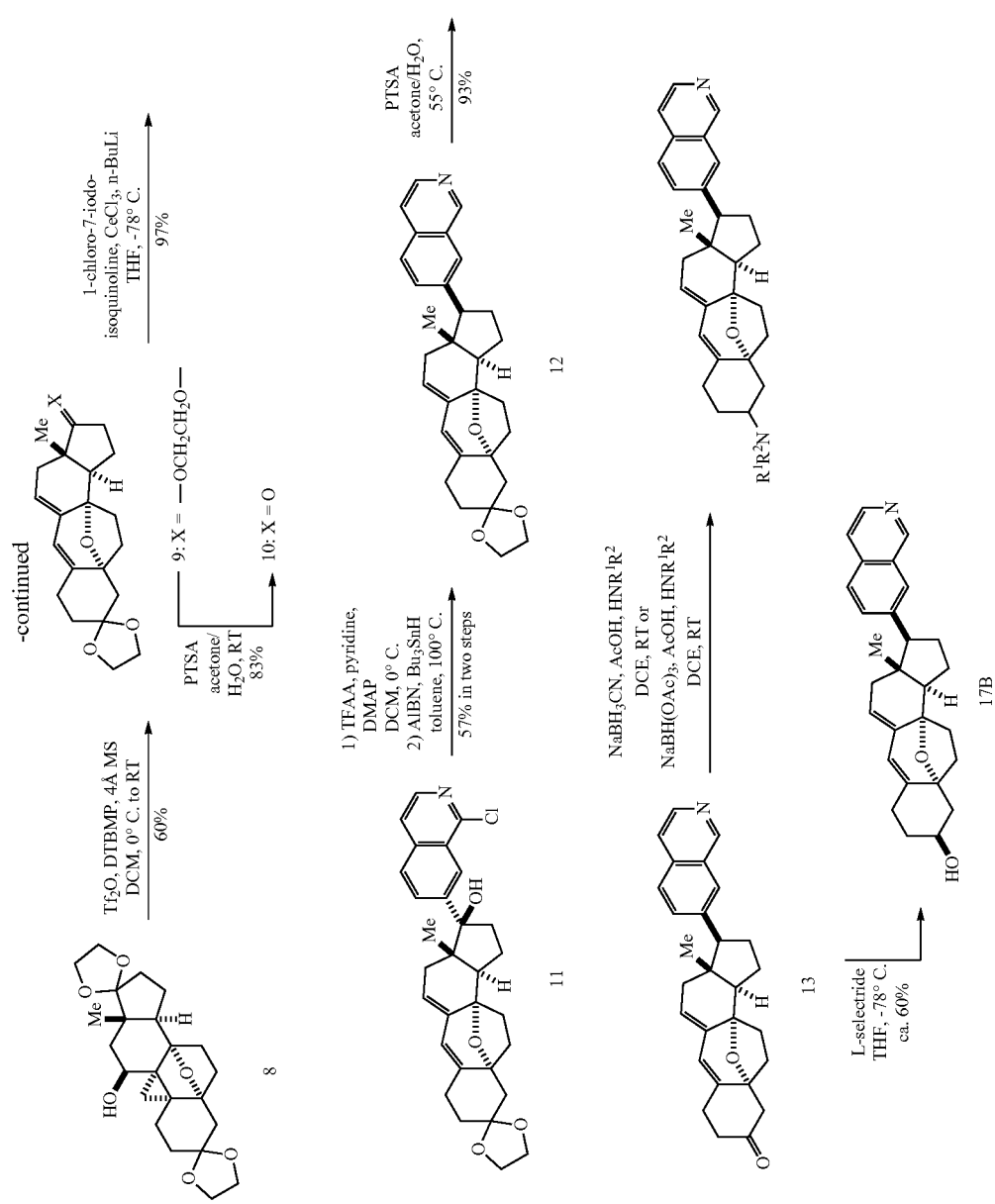

-continued
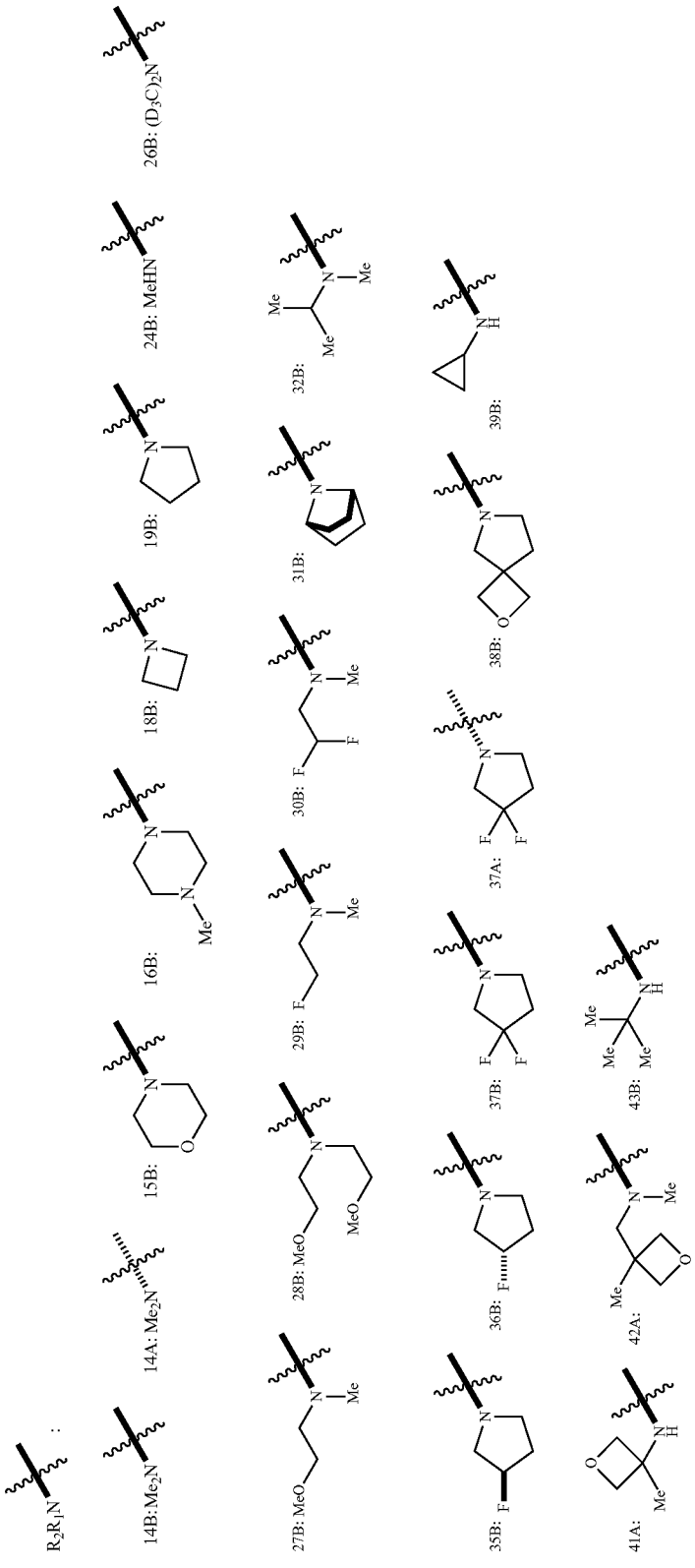

Scheme 1-2.

32B, 39B $\xrightarrow{\substack{\text{NaBH(OAc)}_3, \\ \text{formaldehyde or acetaldehyde} \\ \text{DCE, RT}}}$

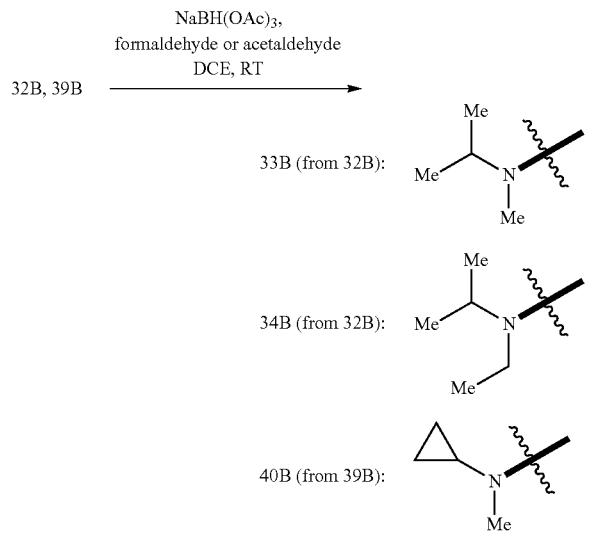

33B (from 32B):

34B (from 32B):

40B (from 39B):

Route 1: Synthesis of 8,9-unsaturated methoxyethyleneketone from 6-methoxy-1-tetralone (Compound 1)

The Grignard reaction was done with 20.0 g (113 mmol, 1.00 equiv) of 6-methoxy-1-tetralone and the product was used without purification by flash chromatography. See, e.g., Saraber et al., *Tetrahedron* 2006, 62, 1726-1742. To a solution of Grignard reaction product and 2-methyl-1,3-pentadienone (12.8 g, 114 mmol, 1.01 equiv) in xylene (140 mL) was added AcOH (64.6 mL, 1.13 mol, 10.0 equiv) and the reaction mixture was warmed to reflux. After 2 h, the reaction was allowed to cool to room temperature and the concentrated under reduced pressure. The mixture of 1:1 of toluene and ethyl ether was added to dissolve the solid residue and the mixture was filtered. The filtrate was washed sequentially with saturated NaHCO$_3$ solution (200 mL) and brine, dried over MgSO$_4$, and concentrated under reduced pressure. The residue was purified by flash chromatography (silica gel, eluent: 20:1:1 Hexanes:EtOAc:DCM) to afford the Torgov's diene. Spectral data was consistent with those previously reported. See, e.g., Soorukram, D.; Knochel, P. *Org. Lett.* 2007, 9, 1021-1023. The Torgov's diene was converted to 8,9-unsaturated methoxyethyleneketone compound 1 (15.0 g, 47% over 3 steps) based on the literature known procedure. See, e.g., Sugahara et al., *Tetrahedron Lett.* 1996, 37, 7403-7406.

Route 1: Synthesis of 8,9-unsaturated Methoxyethyleneketal (Compound 2)

To a solution of compound 1 (15.0 g, 53.1 mmol, 1.0 equiv) in benzene (215 mL) and ethylene glycol (72 mL) was added oxalic acid (2.30 g, 12.1 mmol, 0.22 equiv). The reaction mixture was allowed to warm to reflux and water was trapped by Dean-Stark apparatus. After 16 h, the reaction was cool to room temperature and saturated NaHCO$_3$ solution (150 mL) was added. The organic and aqueous layers were separated and the aqueous phase was extracted with ethyl acetate (2×200 mL). The combined organic phases were washed with brine (150 mL) and dried over Na$_2$SO$_4$. The solvent was evaporated under reduced pressure and the residue was purified by flash chromatography (silica gel, eluent: 15:1 Hexanes:EtOAc) to provide 8,9-unsaturated methoxyethyleneketal compound 2 (15.5 g, 89%). $^1$H NMR (500 MHz, CDCl$_3$) Shift=7.13 (d, J=8.3 Hz, 1H), 6.73-6.67 (m, 2H), 4.05-3.85 (m, 4H), 3.79 (s, 3H), 2.82-2.65 (m, 2H), 2.52-2.45 (m, 2H), 2.23-2.17 (m, 2H), 2.14 (ddd, J=2.2, 11.6, 14.0 Hz, 1H), 1.99-1.82 (m, 4H), 1.64 (td, J=4.2, 12.2 Hz, 1H), 1.49 (dq, J=6.8, 11.6 Hz, 1H), 0.86 (s, 3H). HRMS (ESI) (m/z) calc'd for C$_{21}$H$_{27}$O$_3$ [M+H]$^+$: 327.1955, found 327.1947.

Route 1: Synthesis of Epoxy Alcohols 3 and 3a

A solution of 8,9-unsaturated ethyleneketal 2 (1.63 g, 5.00 mmol, 1.0 equiv) in CHCl$_3$ (50 mL) was cooled to 0° C. and mCPBA (77% max, 2.46 g, 11.0 mmol, 2.2 equiv) was added. The reaction mixture was stirred for 10 min at 0° C. and warmed to room temperature. After additional 50 min, 10% Na$_2$S$_2$O$_3$ solution (40 mL) and saturated NaHCO$_3$ solution (40 mL) were sequentially added. The organic and aqueous layers were separated and the aqueous phase was extracted with dichloromethane (3×50 mL). The combined organic phases were washed with brine (50 mL), dried over Na$_2$SO$_4$, and concentrated under reduced pressure. The residue was purified by flash chromatography (silica gel, eluent: 3:1→1:1 Hexanes:EtOAc) to afford epoxy alcohol 3 and 3a (1.40 g, 75%). 3 and 3a were under equilibration in any solvent, with a major of 3. H NMR was analyzed for epoxy alcohol 3. Where indicted, cortistatin analogs (12, 13, 14A, 14B, 15B, 16B, and 17B) were applied to the biological experiments as racemic mixtures constructed from 6-methoxy-1-tetralone.

$^1$H NMR (500 MHz, CDCl$_3$) Shift=7.77 (d, J=8.3 Hz, 1H), 6.76 (dd, J=2.0, 8.3 Hz, 1H), 6.63 (d, J=2.0 Hz, 1H), 4.78 (dd, J=7.8, 9.8 Hz, 1H), 3.95-3.87 (m, 4H), 3.78 (s, 3H), 2.84 (dt, J=5.9, 14.4 Hz, 1H), 2.49 (dd, J=4.4, 15.1 Hz, 1H), 2.36-2.29 (m, 1H), 2.26 (dd, J=5.9, 14.2 Hz, 2H), 2.06 (t, J=11.7 Hz, 1H), 1.97 (dd, J=7.3, 12.2 Hz, 1H), 1.94-1.88 (m, 2H), 1.75 (dt, J=5.4, 14.2 Hz, 1H), 1.63-1.53 (m, 1H), 1.46 (t, J=11.0 Hz, 1H), 0.75 (s, 3H). HRMS (ESI) (m/z) calc'd for C$_{21}$H$_{27}$O$_5$ [M+H]$^+$: 359.1853, found 359.1852.

Route 2: Synthesis of 8,9 and 9,11-unsaturated Methoxyethyleneketal Compounds 2 and 4

The DDQ oxidation was done with 22.0 g (81.4 mmol, 1.0 equiv) of estrone and the $^{product}$ was used without purification by flash chromatography. See, e.g., Stephan et al., *Steroid.* 1995, 60, 809-811. To a solution of 9,11-unsaturated estrone in benzene (375 mL) was added ethylene glycol (110 mL, 1.99 mol, 24.4 equiv) and PTSA (3.00 g, 16.3 mmol, 0.20 equiv). The reaction mixture was warmed to reflux and water was trapped by Dean-Stark apparatus. After 18 h, the reaction was allowed to cool to room temperature and saturated NaHCO$_3$ solution (300 mL) was applied. The aqueous phase was extracted with ethyl acetate (2×300 mL) and the combined organic phases were washed with brine (200 mL). The organic phase was dried (Na$_2$SO$_4$) and the solvent was evaporated under reduced pressure. The product was used in the next step without further purification.

The ethyleneketal (mixture of the 8,9 and 9,11-unsaturated regioisomers) was dissolved in acetone (420 mL) and K$_2$CO$_3$ (22.5 g, 163 mmol, 2.00 equiv) was added. This was followed by the addition of Me$_2$SO$_4$ (9.30 mL, 97.6 mmol, 1.20 equiv) and the reaction mixture was warmed to reflux. After 18 h, the reaction was allowed to cool to room temperature and the acetone was evaporated. 2M NaOH solution was added (300 mL) and the aqueous phase was extracted with ethyl acetate (2×300 mL). The combined organic phases were dried ($Na_2SO_4$) and the solvent was evaporated under reduced pressure. The residue was purified by flash chromatography (silica gel, eluent: 15:1 Hexanes: EtOAc) to afford mixture of 8,9 and 9,11-unsaturated methoxyethyleneketal compounds 2 and 4 (16.3 g, 61% in three steps, ~4:5 mixture of 8,9-unsaturated:9,11-unsaturated regioisomers).

For 9,11-unsaturated isomer, only distinguishable peaks were assigned: 1H NMR (500 MHz, $CDCl_3$) Shift=7.53 (d, J=8.8 Hz, 1H), 6.60 (d, J=2.0 Hz, 1H), 6.13 (td, J=2.6, 5.0 Hz, 1H), 3.79 (s, 3H), 2.59 (td, J=3.2, 17.6 Hz, 1H), 2.09-2.00 (m, 3H), 1.45-1.33 (m, 2H), 0.90 (s, 3H). HRMS (ESI) (m/z) calc'd for $C_{21}H_{27}O_3$ [M+H]$^+$: 327.1955, found 327.1951.

Route 2: Epoxy Alcohol Compounds 3 and 3a

To a solution of mixture of 8,9 and 9,11-unsaturated ethyleneketal compounds 2 and 4 (15.7 g, 48.1 mmol, 1.00 equiv) in dichloromethane (700 mL) was added magnesium monoperoxyphthalate hexahydrate (68.4 g, 111 mmol, 2.30 equiv) and water (4.8 mL). The reaction mixture was stirred for 20 h at room temperature and then quenched with the mixture of 10% aqueous $Na_2S_2O_3$ (300 mL) and saturated $NaHCO_3$ solution (300 mL). The organic and aqueous layers were separated and the aqueous phase was extracted with dichloromethane (2×500 mL). The combined organic phases were washed with brine (300 mL) and dried ($Na_2SO_4$). The solvent was evaporated under reduced pressure and the residue was purified by flash chromatography (silica gel, eluent: 3:1→2:1 Hexanes:EtOAc) to provide epoxy alcohol 3 and 3a (8.60 g, 50%). Spectral data was consistent with epoxy alcohol 3 and 3a constructed from 8,9-unsaturated methoxyethyleneketal 2.

Synthesis of Diol Compound 5

Ammonia gas was condensed (240 mL) and to the liquid ammonia was added Li (3.90 g, 565 mmol, 25.0 equiv) at −78° C. After stirring for 30 min, epoxy alcohol 3 and 3a (8.10 g, 22.6 mmol, 1.0 equiv) in THF (110 mL) was cannulated and stirred additional 1.5 h at that temperature. To the reaction mixture was added the mixture of t-BuOH (32 mL) and THF (16 mL) at −78° C. and stirred additional 20 min at that temperature. The mixture of t-BuOH (92 mL) and THE (38 mL) was added followed by benzene (50 mL) and water (50 mL) at −78° C., and the flask was opened to gently evaporate liquid ammonia by removing the cooling bath. Water (200 mL) was added and the aqueous phase was extracted with ethyl acetate (2×250 mL). The combined organic phases were washed with brine (150 mL), dried ($Na_2SO_4$), and concentrated under reduced pressure. The product was used in the next step without further purification.

To a solution of Birch reduction product in THF (300 mL) and ethylene glycol (75 mL) was added PTSA (430 mg, 2.26 mmol, 0.10 equiv). The reaction mixture was stirred for 30 min at room temperature and saturated $NaHCO_3$ solution (200 mL) was added. The organic and aqueous layers were separated and the aqueous phase was extracted with ethyl acetate (4×250 mL). The combined organic phases were washed with brine (200 mL) and dried ($Na_2SO_4$). The solvent was evaporated under reduced pressure and the residue was purified by flash chromatography (silica gel, eluent: 4:1 Hexanes:EtOAc→100% EtOAc→10:1 EtOAc: MeOH) to provide diol 5 (4.60 g, 52%).

$^1$H NMR (500 MHz, $C_6D_6$) Shift=3.67-3.42 (m, 9H), 3.25-3.14 (m, 1H), 2.40 (dd, J=5.9, 13.2 Hz, 1H), 2.31 (br. s, 2H), 2.23-2.09 (m, 2H), 2.03 (t, J=10.7 Hz, 1H), 1.97-1.90 (m, 2H), 1.89 (dd, J=8.3, 14.2 Hz, 1H), 1.85-1.75 (m, 4H), 1.66-1.50 (m, 4H), 1.00 (s, 3H). HRMS (ESI) (m/z) calc'd for $C_{22}H_{32}NaO_6$ [M+Na]$^+$: 415.2091, found 415.2076.

Synthesis of Enone Compound 6

To a solution of diol 5 (4.05 g, 10.3 mmol, 1.00 equiv) in dichloromethane (230 mL) was added NBS (2.00 g, 11.4 mmol, 1.10 equiv) at one portion at −10° C. and the reaction mixture was warmed to room temperature. The reaction was monitored by TLC (about 30 min for the completion). Once the reaction is done, the reaction mixture was cooled to −40° C. and triethylamine (17.3 mL, 124 mmol, 12.0 equiv) was added. Pre-stirred S03-Py (16.4 g, 103 mmol, 10.0 equiv) in DMSO (115 mL) for 20 min at room temperature was added to the reaction mixture at −40° C., which was subsequently allowed to warm slowly to −10° C. After 4 h, saturated $NH_4Cl$ solution (130 mL) was added and the reaction was allowed to warm to room temperature. The organic and aqueous layers were separated and the aqueous phase was extracted with dichloromethane (2×200 mL). The combined organic phases were washed with brine (150 mL), dried over $Na_2SO_4$, and concentrated under reduced pressure. The product was used without further purification.

The oxidation product was dissolved in dichloromethane (300 mL) and the reaction mixture was cooled to −40° C. followed by the slow addition of DBU (3.90 mL, 25.6 mmol, 2.50 equiv). After 15 min, saturated $NH_4Cl$ solution (130 mL) was added and the reaction was allowed to warm to room temperature. The organic and aqueous layers were separated and the aqueous phase was extracted with dichloromethane (2×200 mL). The combined organic phases were washed with brine (150 mL), dried over $Na_2SO_4$, and concentrated under reduced pressure. The residue was purified by flash chromatography (silica gel, eluent: 3:1→1:1 Hexanes:EtOAc) to afford enone 6 (3.16 g, 80% in three steps).

$^1$H NMR (500 MHz, $C_6D_6$) Shift=3.58-3.51 (m, 1H), 3.49-3.34 (m, 6H), 3.28-3.23 (m, 2H), 3.19 (dt, J=4.2, 7.7 Hz, 1H), 2.80 (d, J=16.1 Hz, 1H), 2.60 (ddd, J=6.8, 12.7, 19.0 Hz, 1H), 2.55 (d, J=13.2 Hz, 1H), 2.43 (d, J=16.1 Hz, 1H), 2.31 (dd, J=1.5, 13.2 Hz, 1H), 1.98-1.88 (m, 2H), 1.88-1.80 (m, 3H), 1.71 (ddd, J=4.2, 9.6, 11.6 Hz, 1H), 1.68-1.59 (m, 3H), 1.20 (ddd, J=3.7, 8.4, 11.4 Hz, 1H), 0.90 (s, 3H). HRMS (ESI) (m/z) calc'd for $C_{22}H_{28}NaO_6$ [M+Na]$^+$: 411.1778, found 411.1786.

Synthesis of Allylic Alcohol Compound 7

To a solution of enone 6 (3.20 g, 8.32 mmol, 1.00 equiv) in MeOH (150 mL) and THF (20 mL) was added $CeCl_3 \cdot 7H_2O$ (9.20 g, 24.7 mmol, 3.00 equiv) at room temperature. After stirring 5 min, the reaction was cooled to −20° C. followed by the addition of $NaBH_4$ (623 mg, 16.5 mmol, 2.00 equiv). After 30 min, saturated $NH_4C_1$ solution (50 mL) and water (50 mL) was added, which was allowed to warm to room temperature. The aqueous phase was extracted with ethyl acetate (3×200 mL) and the combined organic phases were washed with brine (150 mL), dried over $Na_2SO_4$, and concentrated under reduced pressure. The residue was purified by flash chromatography (silica gel, eluent: 20:1 DCM:MeOH) to afford allylic alcohol 7 (2.72 g, 85%).

$^1$H NMR (500 MHz, C$_6$D$_6$) Shift=4.39-4.30 (m, 1H), 3.58-3.36 (m, 8H), 3.22 (dd, J=3.7, 16.4 Hz, 1H), 2.94 (dd, J=7.1, 12.5 Hz, 1H), 2.66 (d, J=13.2 Hz, 1H), 2.49-2.41 (m, 1H), 2.39 (dd, J=2.2, 12.9 Hz, 1H), 2.07-1.99 (m, 1H), 1.96-1.79 (m, 6H), 1.73 (br. s, 3H), 1.66-1.57 (m, 1H), 1.15-1.07 (m, 1H), 0.86 (s, 3H). HRMS (ESI) (m/z) calc'd for C$_{22}$H$_{30}$NaO$_6$ [M+Na]$^+$: 413.1935, found 413.1942.

Synthesis of Cyclopropane Compound 8

To a solution of ClCH$_2$I (1.98 mL, 27.1 mmol, 4.00 equiv) in 1,2-dichloroethane (140 mL) was added a solution of Et$_2$Zn in diethyl ether (1M, 13.6 mL, 13.6 mmol, 2.00 equiv) at 0° C. After stirring 5 min, allylic alcohol 7 (2.65 g, 6.79 mmol, 1.00 equiv) in 1,2-dichloroethane (70 mL) was added to the reaction flask at 0° C. After 30 min, the reaction was quenched by saturated NH$_4$Cl solution (100 mL) and allowed to warm to room temperature. The organic and aqueous layers were separated and the aqueous phase was extracted with dichloromethane (2×120 mL). The combined organic phases were washed with brine (100 mL), dried over Na$_2$SO$_4$, and concentrated under reduced pressure. The residue was purified by flash chromatography (silica gel, eluent: 2:1→1:1 Hexanes:EtOAc) to afford cyclopropane 8 (2.59 g, 93%).

$^1$H NMR (500 MHz, C$_6$D$_6$) Shift=3.92 (dd, J=3.7, 11.0 Hz, 1H), 3.51-3.40 (m, 8H), 2.72 (dd, J=7.1, 12.9 Hz, 1H), 2.39 (dd, J=5.4, 17.6 Hz, 1H), 2.38 (d, J=12.2 Hz, 1H), 2.15 (d, J=12.2 Hz, 1H), 2.12 (dt, J=4.9, 12.2 Hz, 1H), 2.02 (ddd, J=2.9, 11.2, 14.6 Hz, 1H), 1.92-1.82 (m, 3H), 1.82-1.73 (m, 2H), 1.69-1.54 (m, 5H), 1.52 (dd, J=6.1, 12.0 Hz, 1H), 1.49-1.44 (m, 1H), 0.98 (s, 3H), 0.86 (d, J=2.4 Hz, 1H), 0.15 (d, J=2.9 Hz, 1H). HRMS (ESI) (m/z) calc'd for C$_{23}$H$_{32}$NaO$_6$ [M+Na]$^+$: 427.2091, found 427.2088.

Synthesis of Oxabicyclo[3.2.1]octane Compound 9

Cyclopropane 8 (2.45 g, 6.06 mmol, 1.00 equiv) and 2,6-di-tert-butyl-4-methylpyridine (4.40 g, 21.2 mmol, 3.50 equiv) were azeotropically dried with benzene and dissolved in dichloromethane (120 mL). 4 Å molecular sieves (3.1 g) were added and the reaction flask was cooled to 0° C. A solution of triflic anhydride in dichloromethane (1 M, 12.1 mL, 12.1 mmol 2.00 equiv) was added dropwise and the ice bath was removed to warm the reaction flask to room temperature. After 2 h, the reaction was quenched with triethylamine (20 mL) and the filtered through a pad of celite. Saturated NaHCO$_3$ solution (100 mL) was added and the aqueous phase was extracted with dichloromethane (2×120 mL). The combined organic phases were washed with brine (100 mL), dried over Na$_2$SO$_4$, and concentrated under reduced pressure. The residue was purified by flash chromatography (silica gel, eluent: 3:1 Pentane:Diethyl ether) to afford oxabicyclo[3.2.1]octane compound 9 (1.42 g, 60%). See also Magnus et al., *Org. Lett.* 2009, 11, 3938-3941.

$^1$H NMR (500 MHz, CDCl$_3$) Shift=5.73 (s, 1H), 5.29-5.26 (m, 1H), 4.04-3.76 (m, 8H), 2.58-2.50 (m, 1H), 2.46 (t, J=15.1 Hz, 1H), 2.31-2.24 (m, 2H), 2.19 (t, J=11.2 Hz, 1H), 2.09 (d, J=13.2 Hz, 1H), 1.99 (dt, J=4.4, 13.2 Hz, 1H), 1.94 (dd, J=2.4, 13.2 Hz, 1H), 1.91-1.84 (m, 1H), 1.83-1.71 (m, 3H), 1.71-1.53 (m, 5H), 0.88 (s, 3H). HRMS (ESI) (m/z) calc'd for C$_{23}$H$_{30}$O$_5$ [M+H]$^+$: 387.2166, found 387.2180.

Synthesis of Monoketone Compound 10

To a solution of bisethyleneketal 9 (110 mg, 285 µmol, 1.0 equiv) in acetone (14.6 mL) and water (3.6 mL) was added PTSA (21.6 mg, 85.2 µmol, 0.30 equiv) and the reaction mixture was stirred for 3 d. Saturated NaHCO$_3$ solution (5 mL) and ethyl acetate (25 mL) were sequentially added to the reaction. The layers were separated and the aqueous layer was extracted with ethyl acetate (2×15 mL). The organic layers were combined, washed with brine (20 mL), dried over Na$_2$SO$_4$ and concentrated under reduced pressure. The resulting residue was then purified by flash chromatography (silica gel, eluent: 4:1 Hexanes:EtOAc) to afford monoketone 10 (79.0 mg, 81%).

$^1$H NMR (500 MHz, CDCl$_3$) Shift=5.73 (s, 1H), 5.29-5.25 (m, 1H), 3.98-3.90 (m, 4H), 2.48 (dd, J=8.8, 19.5 Hz, 1H), 2.46-2.40 (m, 1H), 2.36 (dd, J=5.9, 12.7 Hz, 1H), 2.34-2.25 (m, 2H), 2.24-2.08 (m, 5H), 2.09 (d, J=13.2 Hz, 1H), 1.95 (dd, J=2.4, 13.2 Hz, 1H), 1.90-1.81 (m, 1H), 1.79-1.70 (m, 2H), 1.70-1.61 (m, 2H), 0.89 (s, 3H). HRMS (ESI) (m/z) calc'd for C$_{21}$H$_{27}$O$_4$ [M+H]$^+$: 343.1909, found 343.1919.

Synthesis of 1-Chloroisoquinoline Adduct Compound 11

CeCl$_3$ (565 mg, 2.30 mmol, 10.0 equiv) in reaction flask was heated at 140° C. under vacuum for 2 h. The flask was charged with Ar and cooled to 0° C. After 30 min, THF (2.8 mL) was added and stirred at 0° C. for 2 h. The flask was then allowed to warm to room temperature and stirred for additional 16 h.

1-Chloro-7-iodoisoquinoline was synthesized following the procedure provided in Subasinghe et al., *Bioorg. Med. Chem. Lett.* 2013, 23, 1063-1069.

To a solution of CeCl$_3$/THF complex was added 1-chloro-7-iodoisoquinoline (396 mg, 1.40 mmol, 6.00 equiv) in THF (1.4 mL) followed by stirring for 10 min at room temperature, which was then allowed to cool to −78° C. A solution of n-butyllithium in hexanes (1.6 M, 716 µL, 1.10 mmol, 5.00 equiv) was then added dropwise. The reaction mixture was stirred additional 30 min at the same temperature and monoketone 10 (78.5 mg, 229 µmol, 1.00 equiv) was cannulated in THF (1.4 mL). After additional 30 min, saturated NH$_4$C$_1$ solution (5 mL) was added to the stirred reaction mixture, which was then allowed to warm to room temperature. The mixture was diluted with EtOAc (5 mL) and the layers were separated. The aqueous layer was extracted with EtOAc (3×5 mL) and the organic layers were combined, washed with brine (5 mL), and dried over Na$_2$SO$_4$ and concentrated under reduced pressure. The resulting residue was then purified by flash chromatography (silica gel, eluent: 2:1 Hexanes:EtOAc) to provide 1-chloroisoquinoline adduct 11 (115 mg, 97%).

$^1$H NMR (500 MHz, CDCl$_3$) Shift=8.34 (br. s, 1H), 8.24 (d, J=5.9 Hz, 1H), 7.89-7.83 (m, 1H), 7.76 (d, J=8.3 Hz, 1H), 7.56 (d, J=5.9 Hz, 1H), 5.63 (s, 1H), 5.16-4.99 (m, 1H), 4.02-3.87 (m, 4H), 2.62 (ddd, J=4.4, 9.8, 14.2 Hz, 1H), 2.48-2.38 (m, 2H), 2.36-2.26 (m, 3H), 2.26-2.19 (m, 1H), 2.18-2.08 (m, 2H), 1.96 (dd, J=2.4, 13.7 Hz, 1H), 1.88 (dd, J=5.1, 17.8 Hz, 1H), 1.82-1.70 (m, 2H), 1.67-1.57 (m, 3H), 1.49 (d, J=17.6 Hz, 1H), 1.20-1.08 (m, 3H). HRMS (ESI) (m/z) calc'd for C$_{30}$H$_{32}$NaO$_4$NCl [M+Na]$^+$: 528.1918, found 528.1929.

Synthesis of Isoquinoline Compound 12

A solution of 1-chloroisoquinoline adduct 11 (115 mg, 227 µmol, 1.00 equiv) in dichloromethane (20 mL) was cooled to 0° C. Pyridine (183 μL, 2.30 mmol, 10.0 equiv) and DMAP (13.9 mg, 114 μmol, 0.50 equiv) were then added sequentially to the solution. After 5 min, trifluoroacetic anhydride (158 μL, 1.14 mmol, 5.00 equiv) was added dropwise and stirred additional 30 min, at which point pH 7 phosphate buffer (15 mL) was added followed by warming the reaction flask to room temperature. The organic and aqueous layers were separated and the aqueous layer was extracted with dichloromethane (2×15 mL). The organic layers were combined, washed with brine (25 mL), dried over $Na_2SO_4$, and concentrated under reduced pressure. The resulting residue was then purified by short flash column chromatography (silica gel, eluent: 2:1 Hexanes:EtOAc) to afford trifluoroacetylated product which was quickly used for the next step.

Trifluoroacetylated product (130 mg, 216 mmol, 1.00 equiv) was azeotropically dried with benzene and dissolved in benzene (4.3 mL). AIBN (106 mg, 647 μmol, 3.00 equiv) was added and the reaction flask was degassed by the freeze-pump thaw process (3 cycles). $Bu_3SnH$ (1.16 mL, 4.31 mmol, 20.0 equiv) was added and the reaction mixture was allowed to warm to reflux. After 3 h, the reaction mixture was cooled to room temperature and concentrated under reduced pressure. The resulting residue was then purified by flash column chromatography (silica gel, eluent: 4:1→3:1→1:1 Hexanes:EtOAc) to provide isoquinoline 12 (67.0 mg, 65% in two steps). See also Yamashita et al., *J. Org. Chem.* 2011, 76, 2408-2425.

$^1$H NMR (500 MHz, $CDCl_3$) Shift=9.21 (s, 1H), 8.46 (d, J=5.9 Hz, 1H), 7.77 (s, 1H), 7.73 (d, J=8.3 Hz, 1H), 7.61 (d, J=5.9 Hz, 1H), 7.57 (d, J=8.3 Hz, 1H), 5.74 (s, 1H), 5.29-5.23 (m, 1H), 4.00-3.90 (m, 4H), 3.11 (t, J=10.0 Hz, 1H), 2.49 (dd, J=8.3, 11.2 Hz, 1H), 2.47-2.41 (m, 1H), 2.38-2.24 (m, 4H), 2.24-2.14 (m, 2H), 2.12 (d, J=13.2 Hz, 1H), 2.06-1.95 (m, 2H), 1.91 (dd, J=5.4, 17.6 Hz, 1H), 1.83 (dq, J=4.9, 11.7 Hz, 1H), 1.77 (td, J=2.3, 12.9 Hz, 1H), 1.72-1.59 (m, 3H), 0.52 (s, 3H). HRMS (ESI) (m/z) calc'd for $C_{30}H_{33}NaNO_3$ [M+Na]$^+$: 478.2353, found 478.2347.

Synthesis of Ketone 13

To a solution of isoquinoline 12 (19.0 mg, 41.7 μmol, 1.00 equiv) in acetone (1.4 mL) and water (350 μL) was added PTSA (20.9 mg, 83.4 μmol, 2.00 equiv) and the reaction mixture was warmed to 55° C. After 14.5 h, the reaction was cooled to room temperature and saturated $NaHCO_3$ solution (2 mL) and ethyl acetate (2.5 mL) were sequentially added to the reaction. The layers were separated and the aqueous layer was extracted with ethyl acetate (2×2.5 mL). The organic layers were combined, washed with brine (2 mL), dried over $Na_2SO_4$ and concentrated under reduced pressure. The resulting residue was then purified by flash chromatography (silica gel, eluent: 3:2→1:2 Hexanes:EtOAc) to afford ketone 13 (15.0 mg, 87%).

$^1$H NMR (500 MHz, $CDCl_3$) Shift=9.23 (s, 1H), 8.48 (d, J=5.9 Hz, 1H), 7.80 (s, 1H), 7.78 (d, J=8.3 Hz, 1H), 7.65 (d, J=5.9 Hz, 1H), 7.61 (d, J=8.3 Hz, 1H), 5.91 (s, 1H), 5.40-5.35 (m, 1H), 3.15 (t, J=10.0 Hz, 1H), 2.94 (d, J=15.1 Hz, 1H), 2.68 (d, J=15.1 Hz, 1H), 2.67-2.59 (m, 1H), 2.58-2.41 (m, 4H), 2.41-2.24 (m, 3H), 2.24-2.10 (m, 2H), 2.04 (tt, J=4.6, 13.2 Hz, 1H), 1.96 (dd, J=5.4, 17.6 Hz, 1H), 1.86 (dq, J=5.1, 12.1 Hz, 1H), 1.80-1.67 (m, 2H), 0.55 (s, 3H). HRMS (ESI) (m/z) calc'd for $C_{28}H_{30}NO_2$ [M+H]$^+$: 412.2271, found 412.2288.

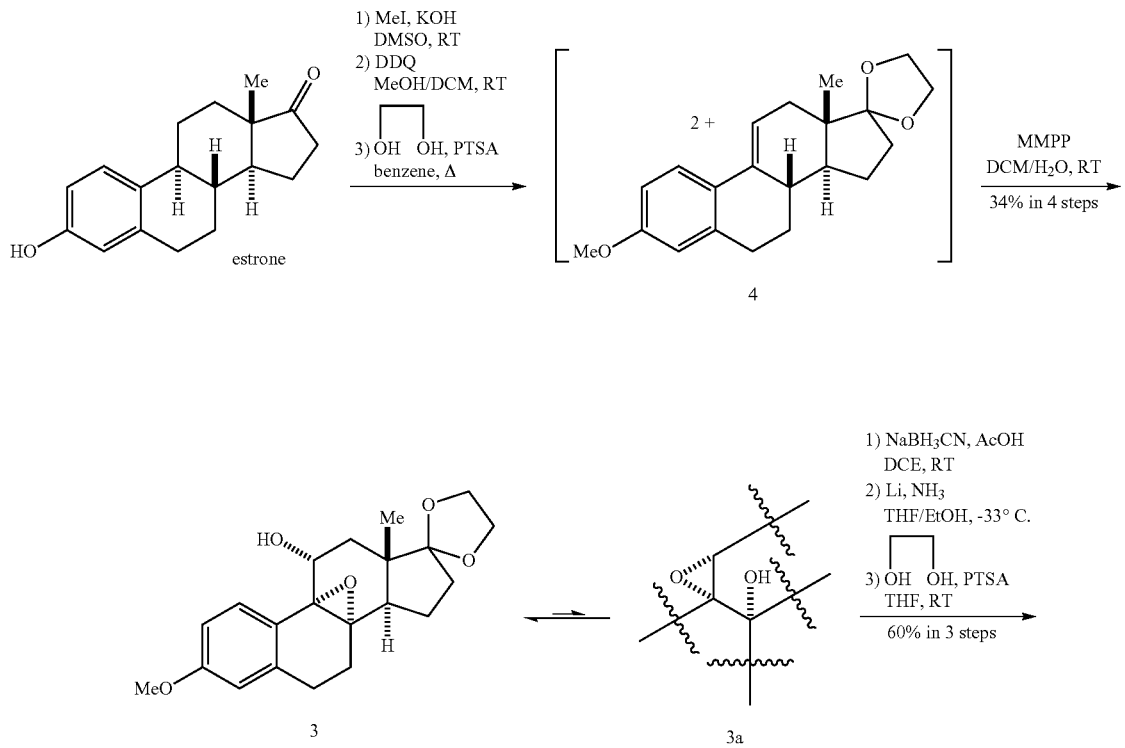

Scheme 1-3. Optimized Route 2

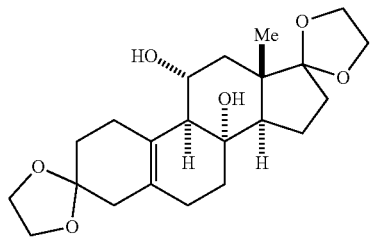

1) NBS
DCM, −10° C.
to RT;
SO₃py., DMSO,
TEA, −40° C. to RT
2) DBU
DCM, −40° C.

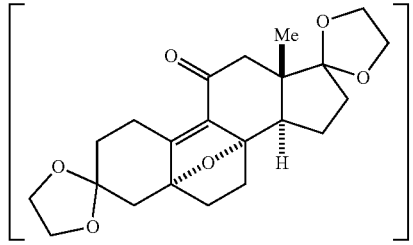

$CeCl_3·7H_2O$,
$NaBH_4$
MeOH/THF,
−20° C.

64%
in 3
steps

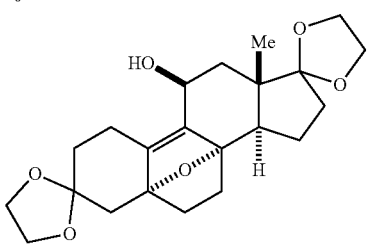

Epoxy Alcohol Compounds 3 and 3a

To a solution of estrone (180 g, 667 mmol, 1.00 equiv) in DMSO (2.8 L) was added KOH pellet (85% technical grade, 150 g, 2.26 mol, 3.40 equiv) and CH₃I (83.0 mL, 1.33 mol, 2.00 equiv). The reaction mixture was stirred for 3.5 hours at room temperature and distilled water (2 L) was slowly added at 0° C. The aqueous layer was extracted with dichloromethane (3×1.5 L) and the combined organic layer was washed with brine (1.5 L). The organic layer was concentrated under nitrogen flow to give white crystalline, which was washed with cold methanol. The 180 g of crude mixture was used in the next step without further purification. The rest of three steps were conducted in two batches.

To a solution of the crude mixture (100 g, 352 mmol, 1.00 equiv) in methanol (750 mL) and dichloromethane (750 mL) was added NaHCO₃ (93.8 g, 1.05 mmol, 3.00 equiv). DDQ (120 g, 527 mmol, 1.50 equiv) was added in four portions with 5 min interval and the reaction mixture was stirred for 2 hours and then quenched with the 10% aqueous Na₂S₂O₃ (500 mL). The reaction flask was stirred for additional 30 min and filtered through celite, washed with chloroform. The 2 M NaOH solution (500 mL) was added and the organic and aqueous layers were separated and the aqueous phase was extracted with chloroform (3×700 mL). The combined organic phases were washed with brine (700 mL) and dried (Na₂SO₄). The solvent was evaporated under reduced pressure and the 89 g of crude mixture was used in the next step without further purification.

To a solution of the crude mixture (81.4 g, 291 mmol, 1.00 equiv) in benzene (1.25 L) was added ethylene glycol (162 mL, 2.91 mol, 10 equiv) and PTSA (11.1 g, 58.3 mmol, 0.20 equiv). The reaction mixture was warmed to reflux and water was trapped by Dean-Stark apparatus. After 24 hours, the reaction was allowed to cool to room temperature and saturated NaHCO₃ solution (500 mL) was applied. The aqueous phase was extracted with ethyl acetate (3×300 mL) and the combined organic phases were washed with brine (500 mL). The organic phase was dried (Na₂SO₄) and the solvent was evaporated under reduced pressure. The 81.4 g of crude product was used in the next step without further purification.

To a solution of mixture of 8,9 and 9,11-unsaturated ethyleneketals (81.4 g, 249 mmol, 1.00 equiv) in dichloromethane (1.28 L) was added magnesium monoperoxyphthalate hexahydrate (354 g, 573 mmol, 2.30 equiv) and water (25 mL). The reaction mixture was stirred for 16 hours at room temperature and then filtered through celite pad. To the filtrate was added saturated NaHCO₃ solution (800 mL) and the organic and aqueous layers were separated and the aqueous phase was extracted with dichloromethane (3×700 mL). The combined organic phases were washed with brine (700 mL) and dried (Na₂SO₄). The solvent was evaporated under reduced pressure and the residue was purified by flash chromatography (silica gel, eluent: 3:1→2:1 Hexanes:EtOAc) to provide epoxy alcohol 3 and 3a (3:3a=8:1, 81.0 g from 180 g, 34% in 4 steps). ¹H NMR and ¹³C NMR were analyzed for epoxy alcohol 3.

$^1H$ NMR (500 MHz, $CDCl_3$) Shift=7.77 (d, J=8.3 Hz, 1H), 6.76 (dd, J=2.0, 8.3 Hz, 1H), 6.63 (d, J=2.0 Hz, 1H), 4.78 (dd, J=7.8, 9.8 Hz, 1H), 3.95-3.87 (m, 4H), 3.78 (s, 3H), 2.84 (dt, J=5.9, 14.4 Hz, 1H), 2.49 (dd, J=4.4, 15.1 Hz, 1H), 2.36-2.29 (m, 1H), 2.26 (dd, J=5.9, 14.2 Hz, 2H), 2.06 (t, J=11.7 Hz, 1H), 1.97 (dd, J=7.3, 12.2 Hz, 1H), 1.94-1.88 (m, 2H), 1.75 (dt, J=5.4, 14.2 Hz, 1H), 1.63-1.53 (m, 1H), 1.46 (t, J=11.0 Hz, 1H), 0.75 (s, 3H); $^{13}C$ NMR (500 MHz, $CDCl_3$) Shift=159.1, 139.5, 130.2, 125.9, 117.6, 114.3, 111.1, 69.0, 67.5, 65.4, 64.5, 61.8, 55.2, 47.4, 46.8, 37.0, 34.9, 26.2, 25.0, 21.3, 14.9; FTIR ($cm^{-1}$) 3464, 2944, 2885, 1610, 1503; HRMS (ESI) (m/z) calc'd for $C_{21}H_{27}O_5$ $[M+H]^+$: 359.1853, found 359.1852; $[\alpha]_D$=−147.4° (c=0.01 g/mL in $CHCl_3$).

Diol Compound 5

To a solution of 3 and 3a (10.0 g, 27.9 mmol, 1.00 equiv) in 1,2-dichloroethane (175 mL) was added NaBH₃CN (3.51 g, 55.8 mmol, 2.00 equiv) and AcOH (3.19 mL, 55.8 mmol, 2.00 equiv) sequentially at room temperature. After 2.5 hours, saturated NaHCO₃ solution (150 mL) was added and the organic and aqueous layers were separated. The aqueous phase was extracted with dichloromethane (3×150 mL). The combined organic phases were washed with brine (200 mL), dried over $Na_2SO_4$, and concentrated under reduced pressure. The crude mixture was used for the next step without further purification.

Ammonia gas was condensed (60 mL) and to the liquid ammonia was added Li (1.94 g, 279 mmol, 10.0 equiv) at −78° C. After stirring for 30 min, the crude mixture in THF (10 mL) and EtOH (6 mL) was cannulated and the reaction was warmed up to −40° C. After 1.5 hours, to the reaction mixture was added EtOH (20 mL) and EtOH:$H_2O$=1:1 (20 mL) sequentially, and the flask was opened to gently evaporate liquid ammonia by removing the cooling bath. Water (50 mL) was added and the aqueous phase was extracted with diethyl ether (3×90 mL). The combined organic phases were washed with brine (150 mL), dried ($Na_2SO_4$), and concentrated under reduced pressure. The product was used in the next step without further purification.

To a solution of Birch reduction product in THF (300 mL) and ethylene glycol (75 mL) was added PTSA (530 mg, 2.79 mmol, 0.100 equiv). The reaction mixture was stirred for 30 min at room temperature and saturated $NaHCO_3$ solution (200 mL) was added. The organic and aqueous layers were separated and the aqueous phase was extracted with chloroform (4×200 mL). The combined organic phases were washed with brine (200 mL) and dried ($Na_2SO_4$). The solvent was evaporated under reduced pressure and the residue was purified by flash chromatography (silica gel, eluent: 4:1 Hexanes:EtOAc→100% EtOAc→10:1 EtOAc:MeOH) to provide diol 5 (6.6 g, 60% in 3 steps).

$^1$H NMR (500 MHz, $C_6D_6$) Shift=3.67-3.42 (m, 9H), 3.25-3.14 (m, 1H), 2.40 (dd, J=5.9, 13.2 Hz, 1H), 2.31 (br. s, 2H), 2.23-2.09 (m, 2H), 2.03 (t, J=10.7 Hz, 1H), 1.97-1.90 (m, 2H), 1.89 (dd, J=8.3, 14.2 Hz, 1H), 1.85-1.75 (m, 4H), 1.66-1.50 (m, 4H), 1.00 (s, 3H); $^{13}$C NMR (500 MHz, $CDCl_3$) Shift=127.8, 126.9, 118.5, 108.5, 74.2, 72.0, 65.3, 64.7, 64.4, 64.3, 63.7, 58.9, 52.5, 45.9, 41.2, 40.5, 33.8, 31.6, 27.6, 25.8, 18.0, 16.6; FTIR (cm$^{-1}$) 3417, 2940, 2884; HRMS (ESI) (m/z) calc'd for $C_{22}H_{32}NaO_6$ [M+Na]$^+$: 415.2091, found 415.2076; $[\alpha]_D$=−13.4° (c=0.01 g/mL in $CHCl_3$).

Allylic Alcohol Compound 7

To a solution of diol 5 (4.05 g, 10.3 mmol, 1.00 equiv) in dichloromethane (230 mL) was added NBS (2.00 g, 11.4 mmol, 1.10 equiv) at one portion at −10° C. and the reaction mixture was warmed to room temperature. The reaction was monitored by TLC (about 30 min for the completion). Once the reaction is done, the reaction mixture was cooled to −40° C. and triethylamine (17.3 mL, 124 mmol, 12.0 equiv) was added. Pre-stirred $SO_3$ Py (16.4 g, 103 mmol, 10.0 equiv) in DMSO (115 mL) for 20 min at room temperature was added to the reaction mixture at −40° C., which was subsequently allowed to warm slowly to room temperature. After 3 hours, saturated $NH_4Cl$ solution (130 mL) was added and the reaction was allowed to warm to room temperature. The organic and aqueous layers were separated and the aqueous phase was extracted with dichloromethane (2×200 mL). The combined organic phases were washed with brine (150 mL), dried over $Na_2SO_4$, and concentrated under reduced pressure. The crude mixture was used without further purification.

The crude mixture was dissolved in dichloromethane (300 mL) and the reaction mixture was cooled to −40° C. followed by the slow addition of DBU (3.90 mL, 25.6 mmol, 2.50 equiv). After 15 min, saturated $NH_4Cl$ solution (130 mL) was added and the reaction was allowed to warm to room temperature. The organic and aqueous layers were separated and the aqueous phase was extracted with dichloromethane (2×200 mL). The combined organic phases were washed with brine (150 mL), dried over $Na_2SO_4$, and concentrated under reduced pressure.

To a solution of crude mixture (3.20 g, 8.32 mmol, 1.00 equiv) in MeOH (150 mL) and THF (20 mL) was added $CeCl_3.7H_2O$ (9.20 g, 24.7 mmol, 3.00 equiv) at room temperature. After stirring 5 min, the reaction was cooled to −20° C. followed by the addition of $NaBH_4$ (623 mg, 16.5 mmol, 2.00 equiv). After 30 min, saturated $NH_4Cl$ solution (50 mL) and water (50 mL) was added, which was allowed to warm to room temperature. The aqueous phase was extracted with ethyl acetate (3×200 mL) and the combined organic phases were washed with brine (150 mL), dried over $Na_2SO_4$, and concentrated under reduced pressure. The residue was purified by flash chromatography (silica gel, eluent: 20:1 DCM:MeOH) to afford allylic alcohol 7 (2.60 g, 64% in 4 steps).

$^1$H NMR (500 MHz, $C_6D_6$) Shift=4.39-4.30 (m, 1H), 3.58-3.36 (m, 8H), 3.22 (dd, J=3.7, 16.4 Hz, 1H), 2.94 (dd, J=7.1, 12.5 Hz, 1H), 2.66 (d, J=13.2 Hz, 1H), 2.49-2.41 (m, 1H), 2.39 (dd, J=2.2, 12.9 Hz, 1H), 2.07-1.99 (m, 1H), 1.96-1.79 (m, 6H), 1.73 (br. s, 3H), 1.66-1.57 (m, 1H), 1.15-1.07 (m, 1H), 0.86 (s, 3H); $^{13}$C NMR (500 MHz, $C_6D_6$) Shift=140.6, 139.1, 118.7, 109.5, 88.3, 86.2, 67.1, 65.4, 64.6, 64.2, 47.9, 46.5, 41.3, 40.9, 34.7, 34.2, 33.9, 30.0, 20.4, 19.8, 15.6; HRMS (ESI) (m/z) calc'd for $C_{22}H_{30}NaO_6$ [M+Na]$^+$: 413.1935, found 413.1942.

Reductive Amination

Method A

To a solution of ketone 13 (1.00 equiv) in 1,2-dichloroethane (0.02 M) was sequentially added amine (4.00 equiv), AcOH (1.50 equiv), and $NaBH_3CN$ (3.50 equiv) at room temperature. Triethylamine (4 equiv) was added if the reacting amine is a form of HCl salt (Method AA). Once the reaction is done, saturated $NaHCO_3$ solution was added and the layers were separated. The aqueous layer was extracted with dichloromethane. The organic layers were combined, washed with brine, dried over $Na_2SO_4$ and concentrated under reduced pressure. ($\alpha$-$NR_2$: $\beta$-$NR_2$=~1:1.2 to ~1:5).

Method B

To a solution of ketone 13 (1.00 equiv) in 1,2-dichloroethane (0.02 M) was sequentially added amine (2.00 equiv), AcOH (2.00 equiv), and $NaBH(OAc)_3$ (2.00 equiv) at room temperature. Triethylamine (2.00 equiv) was added if the reacting amine is a form of HCl salt (Method BB). Once the reaction is done, saturated $NaHCO_3$ solution was added and the layers were separated. The aqueous layer was extracted with dichloromethane. The organic layers were combined, washed with brine, dried over $Na_2SO_4$ and concentrated under reduced pressure. ($\alpha$-$NR_2$: $\beta$-$NR_2$=~1:1.2 to ~1:5).

Method C

To a solution of secondary amine (1.00 equiv) in dichloromethane (0.02 M) was added formaldehyde or acetaldehyde (5.00 equiv) and stirred 1 h at room temperature before the addition of $NaBH(OAc)_3$ (2.00 equiv). Once the reaction is done, saturated $NaHCO_3$ solution was added and the layers were separated. The aqueous layer was extracted with dichloromethane. The organic layers were combined, washed with brine, dried over $Na_2SO_4$ and concentrated under reduced pressure.

Method D: General Method for Favoring $\alpha$-Amine

To a solution of ketone 13 (1.00 equiv) in THF and t-BuOH (4:1, 0.02 M) was added amine (5.00 equiv) and $Ti(Oi-Pr)_4$ (3.00 equiv) sequentially, and stirred at room temperature for 15 hours (4 hours for $Me_2NH$, $MeNH_2$, and NH₃). The reaction mixture was cooled to −20° C. and NaBH₄ (1.50 equiv) was added. Once the reaction is done, saturated NaHCO₃ solution was added and the layers were separated. The aqueous layer was extracted with EtOAc. The organic layers were combined, washed with brine, dried over Na₂SO₄ and concentrated under reduced pressure. (α-NR₂: β-NR₂=~1.1:1 to ~3.7:1).

Method E: General Method for Methanesulfonamide Formation

To a solution of amine (1.00 equiv) in dichloromethane (0.013 M) was added trimethylamine (4.00 equiv) and the reaction mixture was cooled to −20° C. Methanesulfonic anhydride (2.50 equiv) was added as a solution in dichloromethane and stirred 30 min at the same temperature. 2 N NaOH solution was added and the layers were separated. The aqueous layer was extracted with dichloromethane. The organic layers were combined, washed with brine, dried over Na₂SO₄ and concentrated under reduced pressure.

β-Dimethylamine 14B and α-Dimethylamine 14A

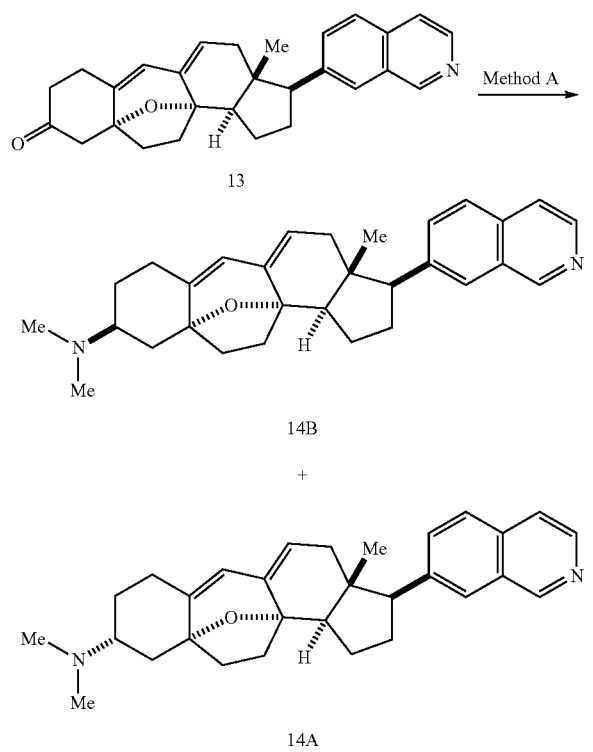

The crude mixture was purified sequentially by flash chromatography (silica gel, eluent: 20:1 EtOAc:2M NH₃ solution in MeOH) to afford β-dimethylamine 14B (21.5 mg, 65%). ca. 0.6 mg of α-dimethylamine 14A was prepared from 3 mg of 13 by HPLC (Eclipse XDB-C8 column, 9.4 mm×25 cm; gradient=0%→35% MeCN (0.1% formic acid): H₂O (0.1% formic acid) over 30 min)

β-dimethylamine 14B $^1$H NMR (500 MHz, C₆D₆) Shift=9.31 (s, 1H), 8.61 (d, J=5.4 Hz, 1H), 7.43 (s, 1H), 7.39 (d, J=8.8 Hz, 1H), 7.25 (d, J=5.4 Hz, 1H), 7.23 (d, J=8.8 Hz, 1H), 5.73 (br. s, 1H), 5.18 (s, 1H), 2.74 (t, J=10.0 Hz, 1H), 2.63 (dd, J=8.8, 11.2 Hz, 1H), 2.48-2.28 (m, 2H), 2.27-2.20 (m, 1H), 2.19-2.03 (m, 6H), 2.00 (br. s, 6H), 1.95-1.84 (m, 2H), 1.83-1.66 (m, 5H), 1.41 (tt, J=5.4, 13.2 Hz, 1H), 0.45 (s, 3H). HRMS (ESI) (m/z) calc'd for C₃₀H₃₇N₂O [M+H]⁺: 441.2900, found 441.2910.

α-dimethylamine 14A $^1$H NMR (600 MHz, C₆D₆) Shift=9.26 (s, 1H), 8.56 (d, J=5.9 Hz, 1H), 7.44-7.39 (m, 1H), 7.36 (d, J=8.2 Hz, 1H), 7.21-7.20 (m, 1H), 7.20 (d, J=5.9 Hz, 1H), 5.68-5.65 (m, 1H), 5.15-5.11 (m, 1H), 2.72-2.66 (m, J=10.0 Hz, 1H), 2.59 (dd, J=8.8, 11.2 Hz, 1H), 2.34 (tt, J=2.9, 12.1 Hz, 1H), 2.16 (td, J=3.2, 16.0 Hz, 1H), 2.09 (s, 6H), 2.13-1.92 (m, 8H), 1.85 (ddd, J=5.0, 9.0, 13.6 Hz, 1H), 1.73 (dt, J=5.3, 12.3 Hz, 1H), 1.72-1.66 (m, 2H), 1.60-1.57 (m, 1H), 1.57-1.49 (m, 1H), 1.20 (dq, J=4.1, 12.3 Hz, 1H), 0.40 (s, 3H). HRMS (ESI) (m/z) calc'd for C₃₀H₃₇N₂O [M+H]⁺: 441.2900, found 441.2909.

β-Morpholine 15B and α-Morpholine 15A

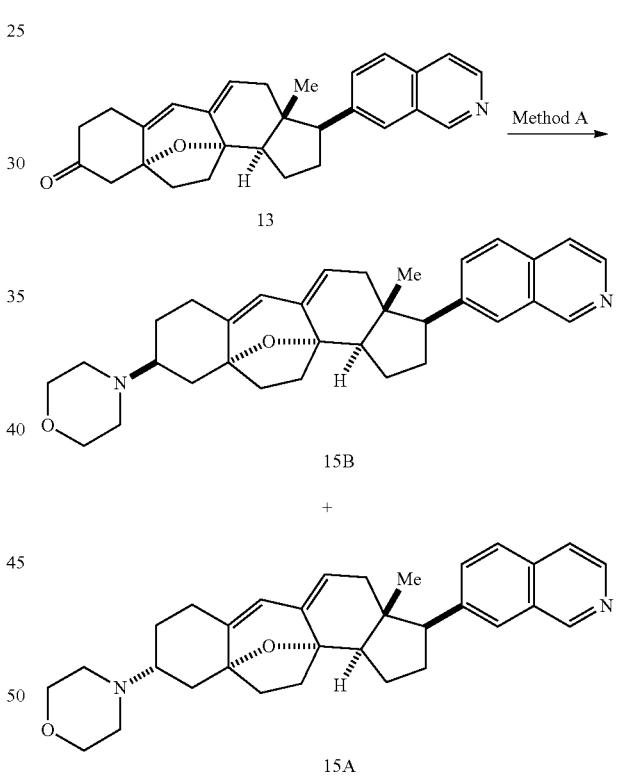

β-Morpholine 15B

The crude mixture was purified by flash chromatography (silica gel, eluent: 100% EtOAc→35:1→20:1→10:1 EtOAc:MeOH) to afford β-morpholine 15B (21 mg, 66%).
$^1$H NMR (500 MHz, CDCl₃) Shift=9.22 (s, 1H), 8.48 (d, J=5.9 Hz, 1H), 7.79 (s, 1H), 7.75 (d, J=8.3 Hz, 1H), 7.62 (d, J=5.9 Hz, 1H), 7.59 (dd, J=1.0, 8.8 Hz, 1H), 5.71 (s, 1H), 5.24 (d, J=2.9 Hz, 1H), 3.73 (br. s, 4H), 3.13 (t, J=10.0 Hz, 1H), 2.65-2.28 (m, 11H), 2.23-2.11 (m, 3H), 2.06 (d, J=13.2 Hz, 1H), 2.01 (dt, J=4.4, 9.0 Hz, 1H), 1.93 (dd, J=4.9, 17.1

Hz, 1H), 1.89-1.79 (m, 1H), 1.75-1.53 (m, 4H), 0.54 (s, 3H). HRMS (ESI) (m/z) calc'd for $C_{32}H_{39}N_2O_2$ [M+H]$^+$: 483.3006, found 483.3012.

β-N-Methylpiperazine 16B and α-N-Methylpiperazine 16A

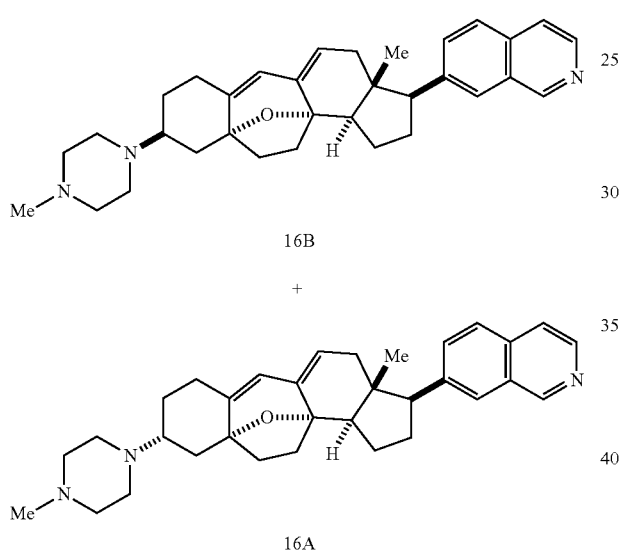

16B

+

16A

β-N-Methylpiperazine 16B

The crude mixture was purified sequentially by flash chromatography (silica gel, 1$^{st}$ column: eluent: 100% MeOH→10:1 EtOAc:2M NH$_3$ solution in MeOH/2$^{nd}$ column: eluent: 20:1 EtOAc:2M NH$_3$ solution in MeOH)) to afford β-N-methylpiperazine 16B (20 mg, 55%). $^1$H NMR (600 MHz, CDCl$_3$) Shift=9.22 (s, 1H), 8.48 (d, J=5.9 Hz, 1H), 7.79 (s, 1H), 7.75 (d, J=8.8 Hz, 1H), 7.62 (d, J=5.9 Hz, 1H), 7.59 (d, J=8.2 Hz, 1H), 5.70 (s, 1H), 5.25-5.22 (m, 1H), 3.13 (t, J=9.7 Hz, 1H), 2.53 (br. s., 1H), 2.50 (dd, J=8.8, 11.7 Hz, 1H), 2.41 (t, J=12.9 Hz, 1H), 2.38-2.33 (m, 3H), 2.32 (br. s, 3H), 2.22-2.11 (m, 3H), 2.10-1.95 (m, 3H), 1.95-1.89 (m, 2H), 1.84 (dq, J=5.3, 11.7 Hz, 1H), 1.79-1.50 (m, 11H), 0.62-0.43 (m, 3H). HRMS (ESI) (m/z) calc'd for $C_{33}H_{42}N_3O$ [M+H]$^+$: 496.3322, found 496.3337.

β-Azetidine 18B and α-Azetidine 18A

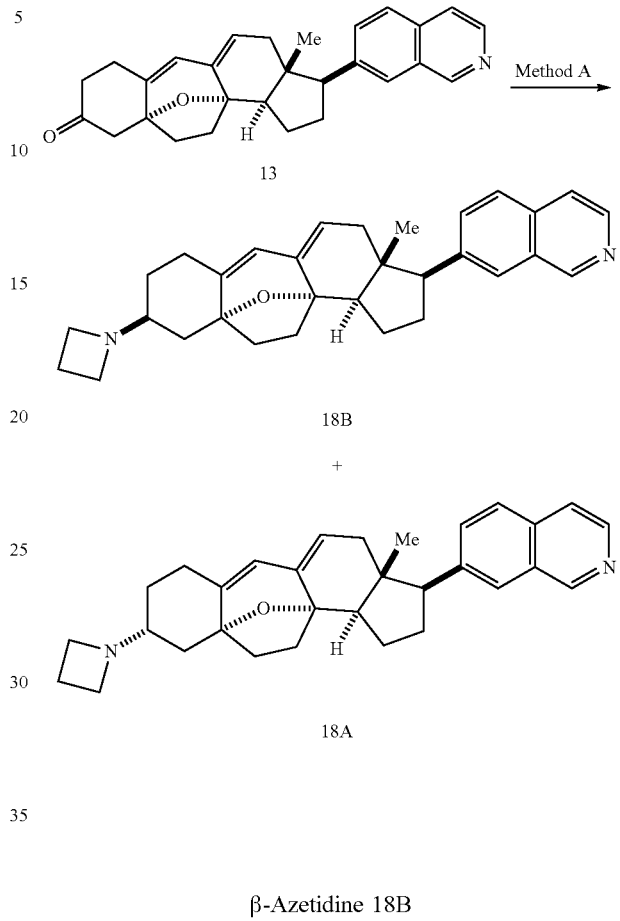

β-Azetidine 18B

The crude mixture was purified by preparative TLC (eluent: 1:1 EtOAc:MeOH) to afford β-azetidine 18B (2.7 mg, 50%). $^1$H NMR (500 MHz, CDCl$_3$) Shift=9.22 (s, 1H), 8.48 (d, J=5.9 Hz, 1H), 7.79 (s, 1H), 7.75 (d, J=8.8 Hz, 1H), 7.62 (d, J=5.4 Hz, 1H), 7.59 (d, J=8.3 Hz, 1H), 5.69 (s, 1H), 5.22 (d, J=2.4 Hz, 1H), 3.20-3.05 (m, 5H), 2.59-2.43 (m, 4H), 2.39-2.28 (m, 2H), 2.23-2.12 (m, 2H), 2.07-1.96 (m, 4H), 1.92 (dd, J=5.1, 17.3 Hz, 1H), 1.89-1.79 (m, 3H), 1.75-1.55 (m, 3H), 1.40 (t, J=13.2 Hz, 1H), 0.54 (s, 3H). HRMS (ESI) (m/z) calc'd for $C_{31}H_{37}N_2O$ [M+H]$^+$: 453.2906, found 453.2916.

β-Pyrrolidine 19B and α-Pyrrolidine 19A

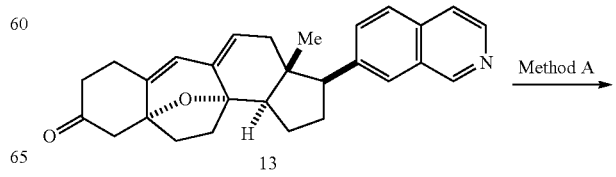

-continued

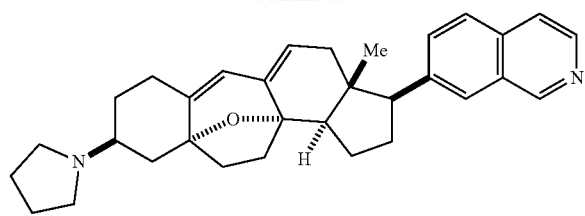

19B

+

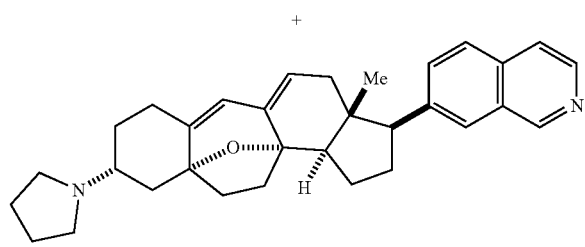

19A

β-Pyrrolidine 19B

The crude mixture was purified by preparative TLC (eluent: 20:10:3 EtOAc:Hexane: 2M NH$_3$ solution in MeOH) to afford β-pyrrolidine 19B (2.0 mg, 40%). $^1$H NMR (500 MHz, CDCl$_3$) Shift=9.22 (s, 1H), 8.48 (d, J=5.4 Hz, 1H), 7.79 (s, 1H), 7.75 (d, J=8.3 Hz, 1H), 7.62 (d, J=5.9 Hz, 1H), 7.59 (d, J=8.3 Hz, 1H), 5.70 (br. s., 1H), 5.22 (br. s., 1H), 3.13 (t, J=9.8 Hz, 1H), 2.59-2.46 (m, 6H), 2.44 (br. s., 1H), 2.41-2.28 (m, 3H), 2.23-2.12 (m, 2H), 2.11-2.00 (m, 2H), 2.00-1.82 (m, 4H), 1.79-1.65 (m, 6H), 1.64-1.51 (m, 2H), 0.54 (s, 3H). HRMS (ESI) (m/z) calc'd for C$_{32}$H$_{39}$N$_2$O [M+H]$^+$: 467.3057, found 467.3053.

β-Dimethylamine 17,18-unsaturated Isoquinoline 23B and α-Dimethylamine 17,18-unsaturated Isoquinoline 23A

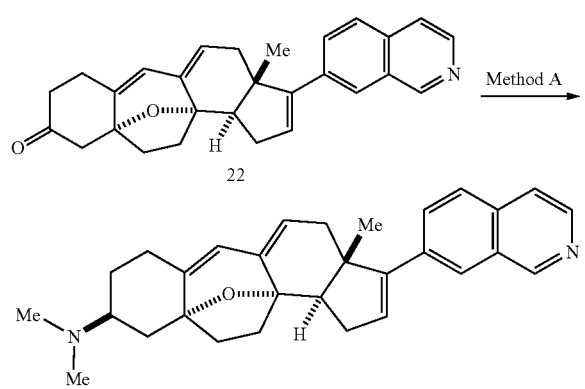

22

23B

+

-continued

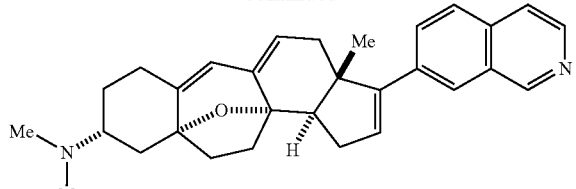

23A

β-Dimethylamine 17,18-unsaturated Isoquinoline 23B

The crude mixture was purified sequentially by flash chromatography (silica gel, eluent: 20:1 EtOAc:2M NH$_3$ solution in MeOH) to afford β-dimethylamine 17,18-unsaturated isoquinoline 23B (6.5 mg, 74%). $^1$H NMR (500 MHz, CDCl$_3$) Shift=9.24 (br. s., 1H), 8.51 (d, J=5.4 Hz, 1H), 7.94 (s, 1H), 7.84-7.76 (m, 2H), 7.63 (d, J=5.4 Hz, 1H), 6.27 (br. s., 1H), 5.97 (s, 1H), 5.50 (dd, J=2.4, 4.9 Hz, 1H), 2.98 (d, J=14.6 Hz, 1H), 2.78 (dd, J=6.8, 11.2 Hz, 1H), 2.71 (d, J=14.6 Hz, 1H), 2.72-2.63 (m, 1H), 2.61 (d, J=5.4 Hz, 1H), 2.59-2.54 (m, 2H), 2.54-2.50 (m, 2H), 2.50-2.42 (m, 2H), 2.39 (ddd, J=1.5, 11.0, 12.9 Hz, 1H), 2.20 (ddd, J=1.5, 9.5, 11.5 Hz, 1H), 2.01 (ddd, J=7.3, 8.8, 12.7 Hz, 1H), 1.79 (dt, J=7.3, 11.2 Hz, 1H), 1.18 (s, 3H). HRMS (ESI) (m/z) calc'd for C$_{30}$H$_{35}$N$_2$O [M+H]$^+$: 439.2744, found 439.2753.

β-Monomethylamine 24B and α-Monomethylamine 24A

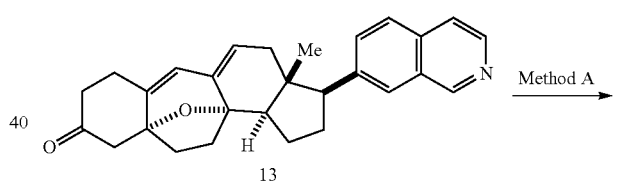

13

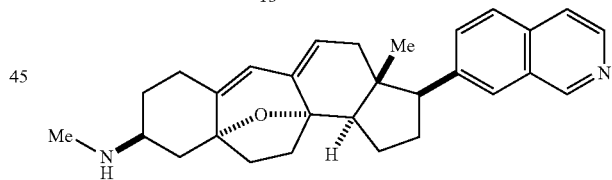

23B

+

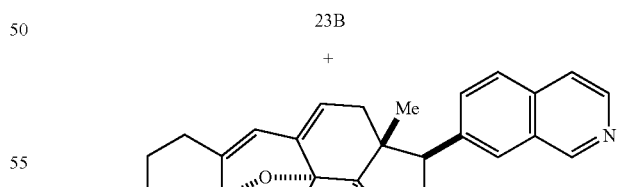

23A

β-Monomethylamine 24B

The crude mixture was purified by preparative TLC (eluent: 10:1 EtOAc:2M NH$_3$ solution in MeOH) to afford β-monomethylamine 24B (ca. 1.5 mg, 58%). $^1$H NMR (500 MHz, CDCl$_3$) Shift=9.22 (s, 1H), 8.48 (d, J=5.4 Hz, 1H), 7.79 (s, 1H), 7.75 (d, J=8.8 Hz, 1H), 7.62 (d, J=5.9 Hz, 1H), 7.59 (dd, J=1.0, 8.3 Hz, 1H), 5.72 (d, J=1.0 Hz, 1H), 5.24 (dd, J=2.2, 5.1 Hz, 1H), 3.13 (t, J=10.0 Hz, 1H), 3.03-2.98 (m, 1H), 2.57-2.50 (m, 1H), 2.51 (dd, J=8.3, 11.7 Hz, 1H), 2.44 (s, 3H), 2.36 (d, J=15.2 Hz, 1H), 2.36-2.28 (m, 2H), 2.26-2.13 (m, 2H), 2.09 (dd, J=3.7, 16.4 Hz, 1H), 2.07-1.99 (m, 2H), 1.98-1.92 (m, 1H), 1.93 (dd, J=5.9, 17.6 Hz, 1H), 1.85 (dq, J=4.9, 11.7 Hz, 1H), 1.82-1.76 (m, 1H), 1.76-1.58 (m, 3H), 0.54 (s, 3H). HRMS (ESI) (m/z) calc'd for $C_{29}H_{35}N_2O$ [M+H]$^+$: 427.2744, found 427.2740.

β-Deuterodimethylamine 26B and α-Deuterodimethylamine 26A

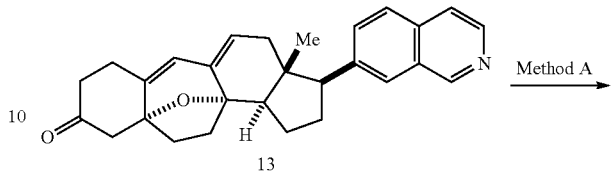

13

Method A

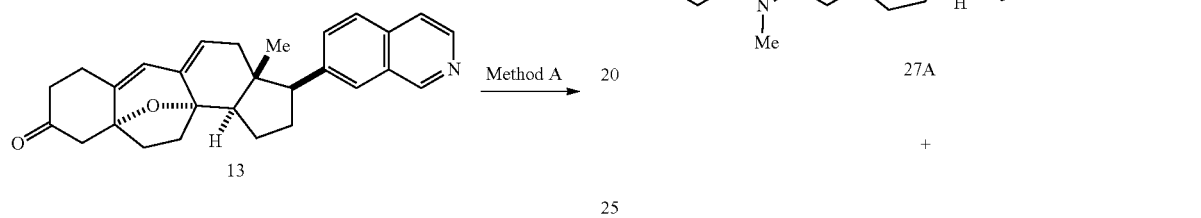

26B

+

26A

β-Deuterodimethylamine 26B

Triethylamine was added The crude mixture was purified sequentially by flash chromatography (silica gel, eluent: 20:1 EtOAc:2M NH$_3$ solution in MeOH) to afford β-deuterodimethylamine 26B (4 mg, 62%). $^1$H NMR (500 MHz, CDCl$_3$) Shift=9.24 (s, 1H), 8.50 (d, J=5.9 Hz, 1H), 7.80 (s, 1H), 7.77 (d, J=8.3 Hz, 1H), 7.64 (d, J=5.9 Hz, 1H), 7.60 (d, J=8.3 Hz, 1H), 5.74 (br. s., 1H), 5.26 (br. s., 1H), 3.15 (t, J=10.0 Hz, 1H), 2.51 (dd, J=8.8, 11.2 Hz, 1H), 2.50-2.42 (m, 1H), 2.37 (d, J=17.1 Hz, 1H), 2.38-2.26 (m, 2H), 2.26-2.09 (m, 4H), 2.08-1.98 (m, 2H), 1.95 (dd, J=5.1, 17.3 Hz, 1H), 1.87 (dq, J=5.4, 12.2 Hz, 1H), 1.80-1.68 (m, 3H), 1.62 (br. s., 2H), 0.63-0.50 (s, 3H). HRMS (ESI) (m z) calc'd for $C_{30}H_{31}D_6N_2O$ [M+H]$^+$: 447.3277, found 447.3281.

β-2-Methoxyethylmethylamine 27B and α-2-Methoxyethylmethylamine 27A

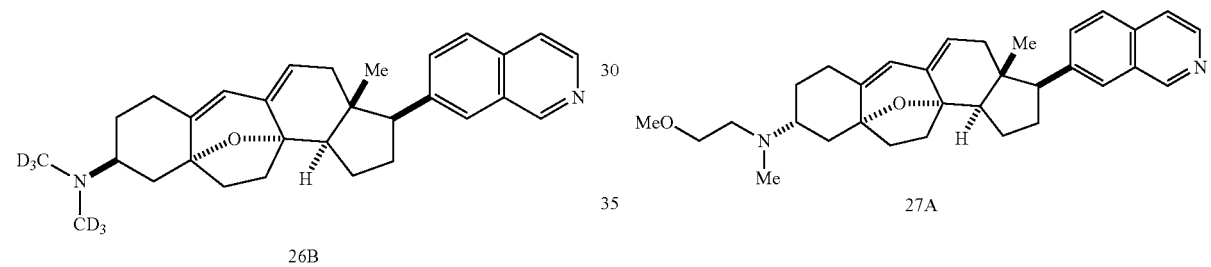

13

Method A

27A

+

27A

β-2-Methoxyethylmethylamine 27B

The crude mixture was purified by preparative TLC (eluent: 10:10:1 Hexanes:EtOAc:2M NH$_3$ solution in MeOH) to afford β-2-methoxyethylmethylamine 27B (ca. 1.2 mg, 20%). $^1$H NMR (500 MHz, CD$_3$OD) Shift=9.21 (s, 1H), 8.40 (d, J=5.4 Hz, 1H), 7.99 (s, 1H), 7.90 (d, J=8.8 Hz, 1H), 7.81 (d, J=5.9 Hz, 1H), 7.77 (s, 1H), 5.80 (s, 1H), 5.35-5.27 (m, 1H), 3.60 (t, J=5.4 Hz, 2H), 3.39 (s, 2H), 3.24 (t, J=10.0 Hz, 1H), 3.15-2.88 (m, 2H), 2.56 (br. s., 3H), 2.51 (dd, J=9.3, 10.7 Hz, 1H), 2.48-2.39 (m, 3H), 2.35-2.28 (m, 1H), 2.25-2.09 (m, 4H), 2.02-1.84 (m, 7H), 1.76 (s, 2H), 0.59 (s, 3H). HRMS (ESI) (m/z) calc'd for $C_{32}H_{41}N_2O_2$ [M+H]$^+$: 485.3163, found 485.3170.

β-Bis-2-methoxyethylamine 28B and α-Bis-2-methoxyethylamine 28A

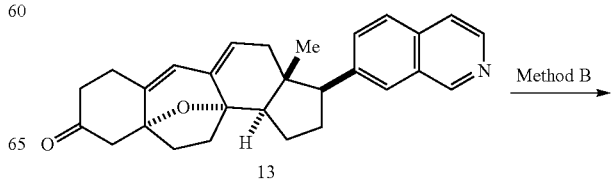

13

Method B

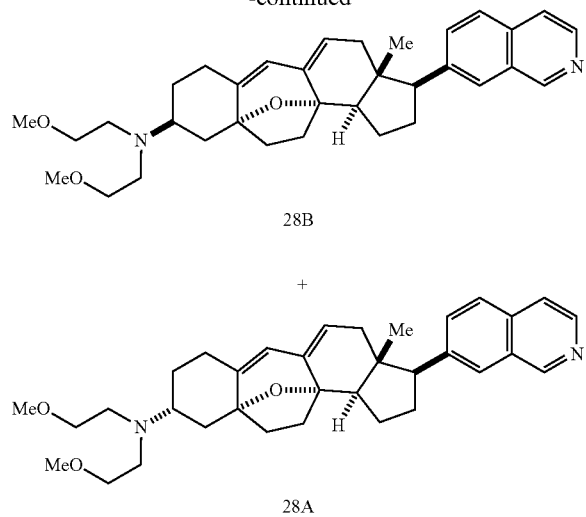

β-Bis-2-methoxyethylamine 28B

The crude mixture was purified by preparative TLC (eluent: 10:1 Dichloromethane:MeOH) to afford β-bis-2-methoxyethylamine 28B (ca. 1.1 mg, 19%). $^1$H NMR (500 MHz, CD$_3$OD) Shift=9.21 (s, 1H), 8.39 (d, J=5.9 Hz, 1H), 7.99 (s, 1H), 7.90 (d, J=8.8 Hz, 1H), 7.81 (d, J=5.9 Hz, 1H), 7.77 (s, 1H), 5.74 (s, 1H), 5.29-5.24 (m, 1H), 3.47 (t, J=6.1 Hz, 4H), 3.36 (s, 6H), 3.24 (t, J=10.5 Hz, 1H), 3.06-2.93 (m, 1H), 2.78 (d, J=5.9 Hz, 4H), 2.52 (dd, J=9.0, 11.5 Hz, 1H), 2.49-2.43 (m, 1H), 2.44 (d, J=17.6 Hz, 1H), 2.40-2.35 (m, 1H), 2.35-2.26 (m, 1H), 2.24-2.10 (m, 3H), 2.07-1.94 (m, 3H), 1.91 (dd, J=5.4, 17.6 Hz, 1H), 1.85 (d, J=14.6 Hz, 1H), 1.82-1.67 (m, 3H), 0.59 (s, 3H). HRMS (ESI) (m/z) calc'd for C$_{34}$H$_{45}$N$_2$O$_3$ [M+H]$^+$: 529.3425, found 529.3434.

β-2-Fluoroethylmethylamine 29B and α-2-Fluoroethylmethylamine 29A

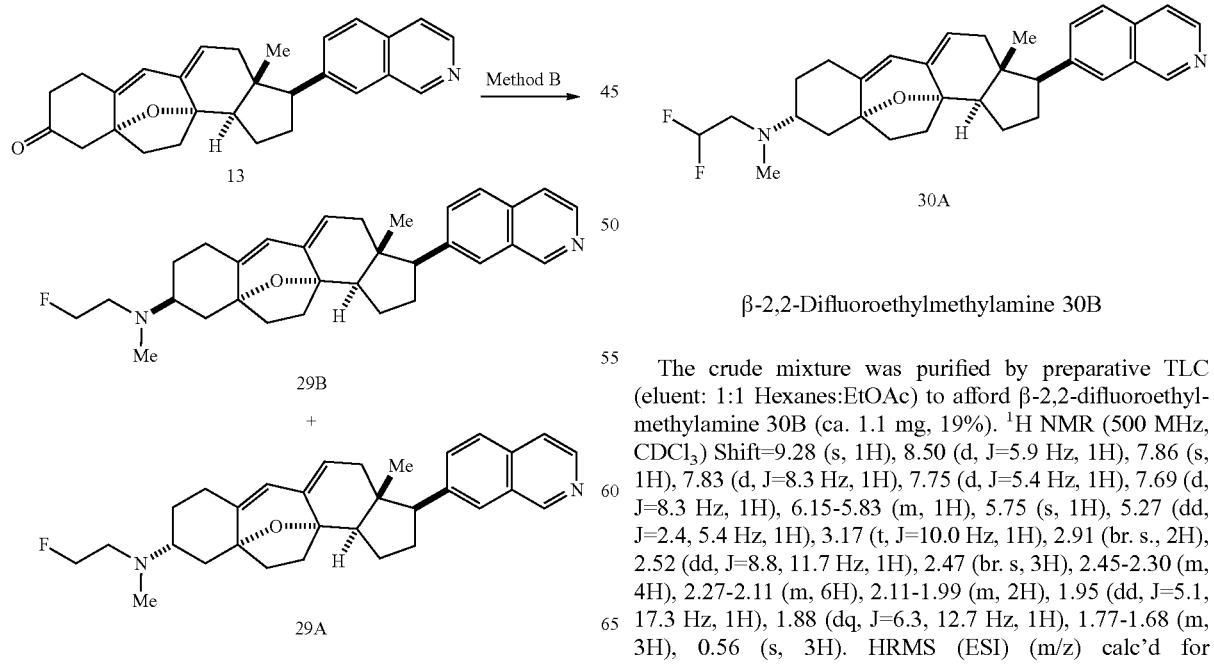

β-2-Fluoroethylmethylamine 29B

The crude mixture was purified by preparative TLC (eluent: 20:1 Dichloromethane:MeOH) to afford β-2-fluoroethylmethylamine 29B (2.7 mg, 51%). $^1$H NMR (500 MHz, CDCl$_3$) Shift=9.24 (s, 1H), 8.50 (d, J=5.9 Hz, 1H), 7.80 (s, 1H), 7.77 (d, J=8.8 Hz, 1H), 7.64 (d, J=5.9 Hz, 1H), 7.60 (dd, J=1.0, 8.3 Hz, 1H), 5.74 (br. s., 1H), 5.26 (br. s., 1H), 4.68-4.46 (m, 2H), 3.15 (t, J=9.8 Hz, 1H), 2.99-2.69 (m, 3H), 2.52 (dd, J=8.8, 11.2 Hz, 1H), 2.47-2.30 (m, 6H), 2.29-2.16 (m, 4H), 2.16-2.00 (m, 3H), 2.01-1.92 (m, 1H), 1.94 (dd, J=5.1, 17.3 Hz, 1H), 1.86 (dq, J=5.4, 12.2 Hz, 1H), 1.79-1.64 (m, 3H), 0.56 (s, 3H). HRMS (ESI) (m/z) calc'd for C$_{31}$H$_{38}$N$_2$OF [M+H]$^+$: 473.2963, found 473.2971.

β-2,2-Difluoroethylmethylamine 30B and α-2,2-Difluoroethylmethylamine 30A

β-2,2-Difluoroethylmethylamine 30B

The crude mixture was purified by preparative TLC (eluent: 1:1 Hexanes:EtOAc) to afford β-2,2-difluoroethylmethylamine 30B (ca. 1.1 mg, 19%). $^1$H NMR (500 MHz, CDCl$_3$) Shift=9.28 (s, 1H), 8.50 (d, J=5.9 Hz, 1H), 7.86 (s, 1H), 7.83 (d, J=8.3 Hz, 1H), 7.75 (d, J=5.4 Hz, 1H), 7.69 (d, J=8.3 Hz, 1H), 6.15-5.83 (m, 1H), 5.75 (s, 1H), 5.27 (dd, J=2.4, 5.4 Hz, 1H), 3.17 (t, J=10.0 Hz, 1H), 2.91 (br. s., 2H), 2.52 (dd, J=8.8, 11.7 Hz, 1H), 2.47 (br. s, 3H), 2.45-2.30 (m, 4H), 2.27-2.11 (m, 6H), 2.11-1.99 (m, 2H), 1.95 (dd, J=5.1, 17.3 Hz, 1H), 1.88 (dq, J=6.3, 12.7 Hz, 1H), 1.77-1.68 (m, 3H), 0.56 (s, 3H). HRMS (ESI) (m/z) calc'd for C$_{31}$H$_{37}$N$_2$OF$_2$ [M+H]$^+$: 491.2868, found 491.2879.

β-7-Azabicyclo[2.2.1]heptane 31B and
α-7-Azabicyclo[2.2.1]heptane 31A

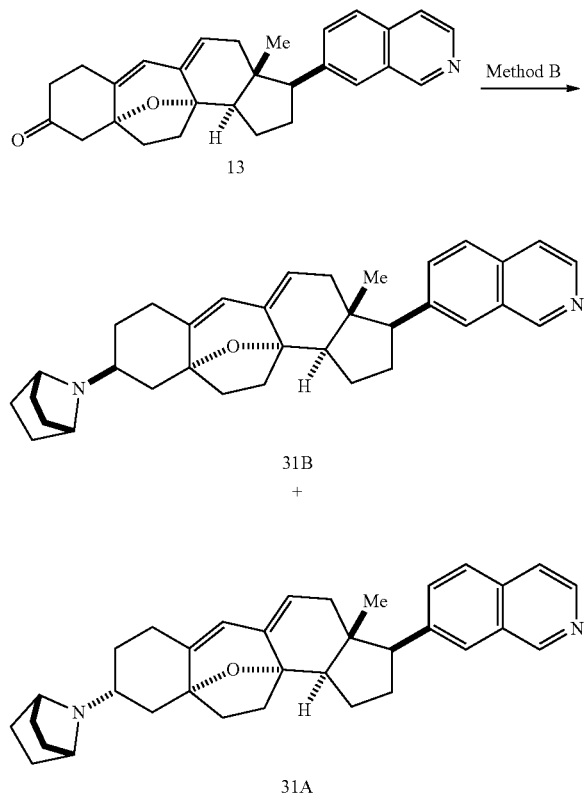

β-7-Azabicyclo[2.2.1]heptane 31B

The crude mixture was purified by flash chromatography (silica gel, eluent: 10:10:1→10:10:2 Hexanes:EtOAc:2M NH₃ solution in MeOH) to afford β-7-azabicyclo[2.2.1]heptane 31B (3 mg, 50%). ¹H NMR (500 MHz, CDCl₃) Shift=9.24 (s, 1H), 8.50 (d, J=5.9 Hz, 1H), 7.81 (s, 1H), 7.77 (d, J=8.3 Hz, 1H), 7.64 (d, J=5.9 Hz, 1H), 7.61 (d, J=8.3 Hz, 1H), 5.71 (br. s., 1H), 5.24 (br. s., 1H), 3.43 (br. s., 2H), 3.15 (t, J=9.8 Hz, 1H), 2.69 (br. s., 2H), 2.52 (t, J=9.8 Hz, 1H), 2.46 (br. s., 1H), 2.37 (d, J=17.6 Hz, 1H), 2.38-2.29 (m, 1H), 2.27-2.13 (m, 3H), 2.11-1.92 (m, 6H), 1.87 (dq, J=5.9, 12.7 Hz, 1H), 1.86-1.79 (m, 1H), 1.78-1.60 (m, 8H), 1.55 (t, J=13.2 Hz, 1H), 0.56 (s, 3H). HRMS (ESI) (m/z) calc'd for $C_{34}H_{41}N_2O$ [M+H]⁺: 493.3213, found 493.3224.

β-Isopropylamine 32B and α-Isopropylamine 32A

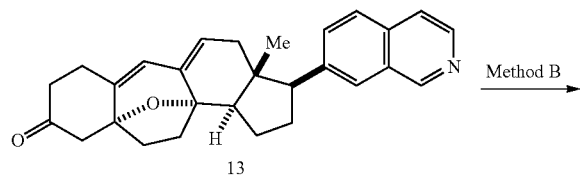

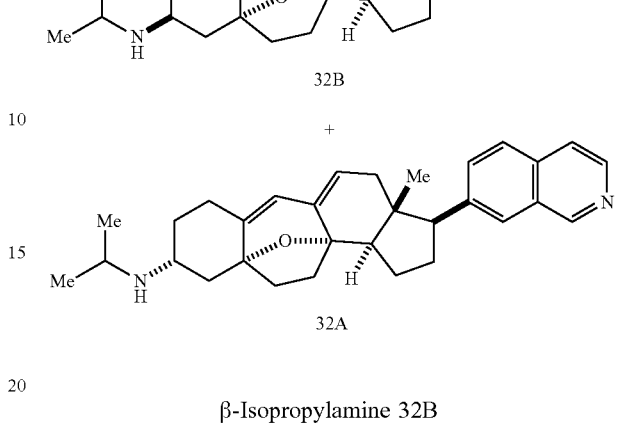

β-Isopropylamine 32B

The crude mixture was purified by flash chromatography (silica gel, eluent: 10:1 EtOAc:2M NH₃ solution in MeOH) to afford β-isopropylamine 32B (5 mg, 70%). ¹H NMR (600 MHz, CDCl₃) Shift=9.22 (s, 1H), 8.48 (d, J=5.9 Hz, 1H), 7.79 (s, 1H), 7.75 (d, J=8.8 Hz, 1H), 7.62 (d, J=5.9 Hz, 1H), 7.59 (d, J=8.2 Hz, 1H), 5.71 (s, 1H), 5.24 (d, J=2.9 Hz, 1H), 3.24 (br. s., 1H), 3.13 (t, J=9.7 Hz, 1H), 2.90 (br. s., 1H), 2.50 (dd, J=8.5, 11.4 Hz, 2H), 2.41-2.26 (m, 3H), 2.24-2.13 (m, 3H), 2.09 (dd, J=2.9, 15.3 Hz, 1H), 2.06-1.98 (m, 2H), 1.93 (dd, J=5.3, 17.6 Hz, 1H), 1.85 (dq, J=5.3, 12.3 Hz, 1H), 1.75-1.62 (m, 4H), 1.07 (br. s., 6H), 0.54 (s, 3H). HRMS (ESI) (m/z) calc'd for $C_{31}H_{39}N_2O$ [M+H]⁺: 455.3057, found 493.3049.

β-Isopropylmethylamine 33B

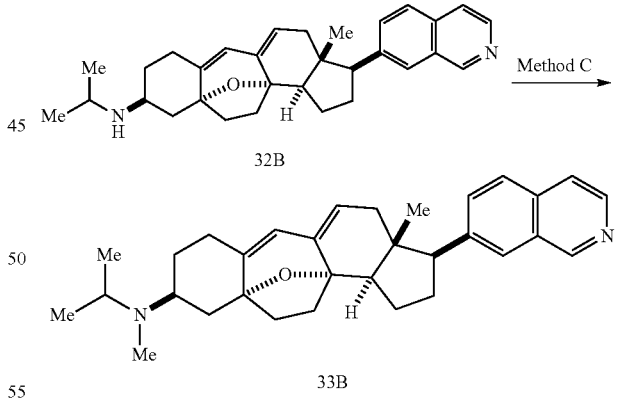

The crude mixture was purified by preparative TLC (eluent: 20:10:3 Hexanes:EtOAc:2M NH₃ solution in MeOH) to afford β-isopropylmethylamine 33B (4 mg, 78%). ¹H NMR (600 MHz, CDCl₃) Shift=9.22 (br. s., 1H), 8.49 (d, J=4.7 Hz, 1H), 7.79 (s, 1H), 7.75 (d, J=8.8 Hz, 1H), 7.62 (d, J=5.3 Hz, 1H), 7.59 (d, J=8.2 Hz, 1H), 5.70 (br. s., 1 H), 5.22 (br. s., 1H), 3.22 (br. s., 1H), 3.13 (t, J=10.0 Hz, 1H), 2.77 (br. s., 1H), 2.50 (t, J=8.2 Hz, 1H), 2.43 (t, J=12.9 Hz, 1H), 2.36 (d, J=17.6 Hz, 1H), 2.35-2.28 (m, 2H), 2.22-2.14 (m, 2H), 2.17 (dt, J=4.4, 9.0 Hz, 1H), 2.11 (br. s., 3H), 2.08-1.99 (m, 2H), 1.98-1.91 (m, 1H), 1.93 (dd, J=4.1, 17.0 Hz, 1H), 1.85 (dq, J=5.3, 12.3 Hz, 1H), 1.69 (br. s., 2H), 1.59 (br. s., 1H), 1.56 (br. s., 1H), 0.96 (br. s., 6H), 0.54 (s, 3H). HRMS (ESI) (m/z) calc'd for $C_{32}H_{41}N_2O$ [M+H]$^+$: 455.3057, found 493.3049.

β-Isopropylethylamine 34B

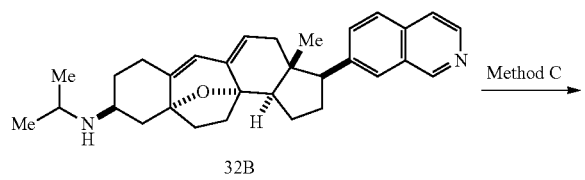

32B

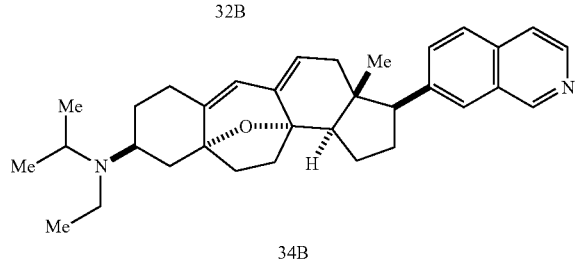

34B

The crude mixture was purified by preparative TLC (eluent: 100% MeOH) to afford β-isopropylethylamine 34B (ca. 1.5 mg, 20%). $^1$H NMR (600 MHz, CD$_3$OD) Shift=9.19 (s, 1H), 8.38 (d, J=5.9 Hz, 1H), 7.97 (s, 1H), 7.88 (d, J=8.8 Hz, 1H), 7.79 (d, J=5.9 Hz, 1H), 7.74 (d, J=8.2 Hz, 1H), 5.76 (br. s., 1H), 5.27 (br. s., 1H), 3.26-3.19 (m, 1H), 2.91-2.66 (m, 3H), 2.50 (dd, J=9.4, 11.2 Hz, 1H), 2.48-2.36 (m, 3H), 2.29 (t, J=10.6 Hz, 1H), 2.23-2.06 (m, 4H), 2.00-1.86 (m, 5H), 1.86-1.79 (m, 1H), 1.79-1.66 (m, 2H), 1.21-1.08 (m, 9H), 0.57 (s, 3H). HRMS (ESI) (m/z) calc'd for $C_{33}H_{43}N_2O$ [M+H]$^+$: 483.3370, found 483.3382.

β-(R)-3-Fluoropyrrolidine 35B and
α-(R)-3-Fluoropyrrolidine 35A

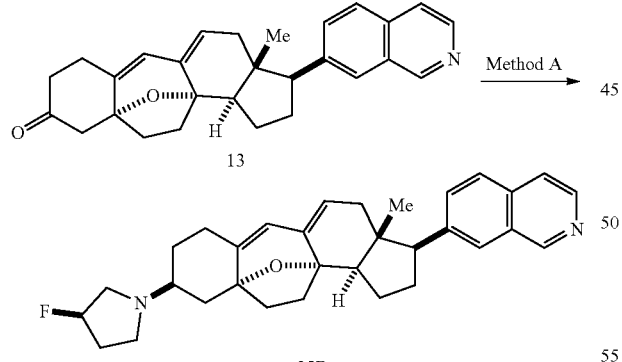

35B

+

35A

β-(R)-3-Fluoropyrrolidine 35B

The crude mixture was purified by preparative TLC (eluent: 47.5:47.5:5 EtOAc:Hexanes:2M NH$_3$ solution in MeOH) to afford β-(R)-3-fluoropyrrolidine 35B (2.2 mg, 38%). $^1$H NMR (500 MHz, CDCl$_3$) Shift=δ 9.22 (s, 1H), 8.49 (d, J=5.4 Hz, 1H), 7.79 (s, 1H), 7.75 (d, J=8.8 Hz, 1H), 7.62 (d, J=5.4 Hz, 1H), 7.59 (d, J=8.8 Hz, 1H), 5.71 (d, J=2.0 Hz, 1H), 5.23 (m, 1H), 5.11 (m, 1H), 3.40 (m, 1H), 3.13 (dd, J=9.3, 9.3 Hz, 1H), 2.88-2.96 (m, 2H), 2.66-2.77 (m, 1H), 2.48-2.58 (m, 3H), 2.29-2.45 (m, 3H), 2.12-2.23 (m, 3H), 1.99-2.09 (m, 5H), 1.83-1.97 (m, 2H), 1.67-1.74 (m, 2H), 1.59 (m, 1H), 0.55 (s, 3H). HRMS (ESI) (m/z) calc'd for $C_{32}H_{38}FN_2O$ [M+H]$^+$: 485.2968, found 485.2915.

β-(S)-3-Fluoropyrrolidine 36B and
α-(S)-3-Fluoropyrrolidine 36A

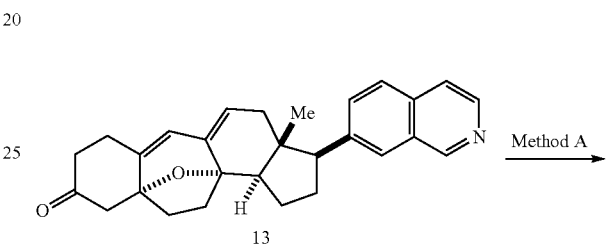

13

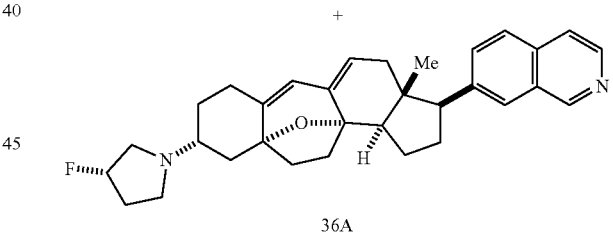

36B

+

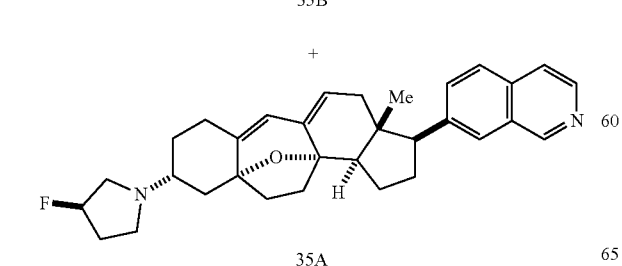

36A

β-(S)-3-Fluoropyrrolidine 36B

The crude mixture was purified by preparative TLC (eluent: 47.5:47.5:5 EtOAc:Hexanes:2M NH$_3$ solution in MeOH) to afford β-(S)-3-fluoropyrrolidine 36B (2.7 mg, 46%). $^1$H NMR (500 MHz, CD$_3$OD) Shift=9.21-9.18 (m, 1H), 8.37 (d, J=5.87 Hz, 1H), 7.98-7.96 (m, 1H), 7.88 (d, J=8.80 Hz, 1H), 7.80-7.77 (m, 1H), 7.74 (dd, J=8.56, 1.71 Hz, 1H), 5.71 (d, J=1.47 Hz, 1H), 5.23 (m, 1H), 5.22-5.07 (m, 2H), 3.22 (t, J=9.8 Hz, 1H), 3.08-2.97 (m, 1H), 2.90 (td, J=8.19, 5.62 Hz, 1H), 2.70-2.64 (m, 1H), 2.62-2.58 (m, 1H), 2.52-2.34 (m, 6H), 2.33-2.24 (m, 1H), 2.23-2.03 (m, 3H), 2.03-1.85 (m, 6H), 1.77-1.67 (m, 2H), 1.67-1.56 (m, 1H), 0.57 (s, 3H). HRMS (ESI) (m/z) calc'd for $C_{32}H_{38}FN_2O$ [M+H]$^+$: 485.6553, found 485.6551.

179

β-3,3-Difluoropyrrolidine 37B and α-3,3-Difluoropyrrolidine 37A

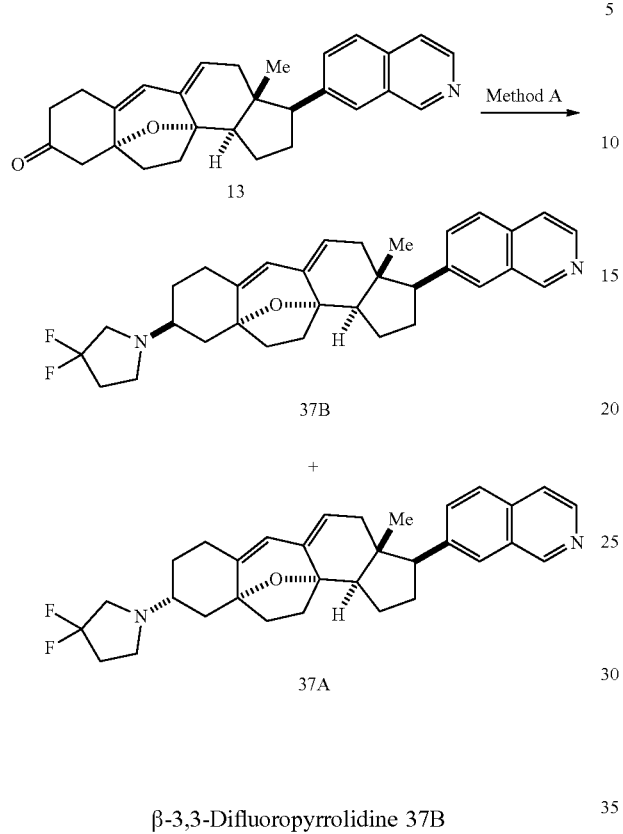

β-3,3-Difluoropyrrolidine 37B

The crude mixture was purified by preparative TLC (eluent: 80:15:5 EtOAc:Hexanes:2M $NH_3$ solution in MeOH) to afford β-3,3-difluoropyrrolidine 37B (2.9 mg, 40%). $^1$H NMR (500 MHz, $CDCl_3$) Shift=δ 9.22 (s, 1H), 8.49 (d, J=5.4 Hz, 1H), 7.79 (s, 1H), 7.75 (d, J=8.3 Hz, 1H), 7.62 (d, J=5.4 Hz, 1H), 7.59 (d, J=8.8 Hz, 1H), 5.72 (d, J=2.0 Hz, 1H), 5.25 (dd, J=5.4 Hz, 2.0 Hz, 1H), 3.13 (dd, J=9.3 Hz, 9.3 Hz, 1H), 2.86-3.03 (m, 2H), 2.14 (dd, J=6.9, 6.9 Hz, 2H), 2.58 (m, 1H), 2.50 (dd, J=11.7, 8.3 Hz, 2H), 2.13-2.44 (m, 6H), 1.98-2.10 (m, 2H), 1.90-1.96 (m, 1H), 1.83-1.89 (m, 2H), 1.66-1.74 (m, 2H), 1.53-1.61 (m, 1H), 0.55 (s, 3H). HRMS (ESI) (m/z) calc'd for $C_{32}H_{37}F_2N_2O$ $[M+H]^+$: 503.2874 found 503.2814.

α-3,3-Difluoropyrrolidine 37A

The crude mixture was purified by preparative TLC (eluent: 80:15:5 EtOAc:Hexanes:2M $NH_3$ solution in MeOH) to afford α-3,3-difluoropyrrolidine 37A (2.9 mg from 6.0 mg, 40%). $^1$H NMR (500 MHz, $CDCl_3$) Shift=δ 9.22 (s, 1H), 8.49 (d, J=5.4 Hz, 1H), 7.79 (s, 1H), 7.75 (d, J=8.8 Hz, 1H), 7.62 (d, J=5.4 Hz, 1H), 7.59 (d, J=8.8 Hz, 1H), 5.74 (s, 1H), 5.28 (d, J=2.4 Hz, 1H), 3.15 (dd, J=9.3 Hz, 9.3 Hz, 1H), 3.01 (dt, J=13.7, 2.4 Hz, 2H), 2.83 (dd, J=6.8, 6.8 Hz, 2H), 2.52 (dd, J=11.2, 8.3 Hz, 2H), 2.15-2.40 (m, 6H), 2.02-2.07 (m, 3H), 1.79-1.97 (m, 3H), 1.72 (m, 3H), 1.61 (m, 3H), 0.54 (s, 3H). HRMS (ESI) (m/z) calc'd for $C_{32}H_{37}F_2N_2O$ $[M+H]^+$: 503.2874 found 503.2807.

180

β-2-oxa-6-azaspiro[3.4]octane 38B and α-2-oxa-6-azaspiro[3.4]octane 38A

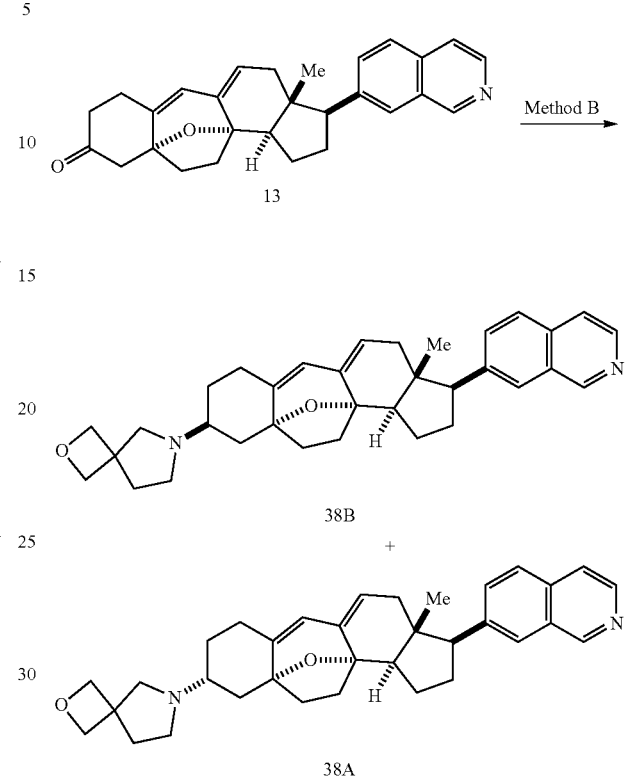

β-2-oxa-6-azaspiro[3.4]octane 38B

The crude mixture was purified by preparative TLC (eluent: 47.5:47.5:5 EtOAc:Hexanes:2M $NH_3$ solution in MeOH) to afford β-2-oxa-6-azaspiro[3.4]octane 38B (3.4 mg, 55%). $^1$H NMR (500 MHz, $CD_3OD$) Shift=9.21 (s, 1H), 8.39 (d, J=5.4 Hz, 1H), 7.99 (s, 1H), 7.90 (d, J=8.8 Hz, 1H), 7.81 (d, J=5.9 Hz, 1H), 7.76 (dd, J=1.7, 8.5 Hz, 1H), 5.73-5.70 (m, 1H), 5.28-5.23 (m, 1H), 4.63 (d, J=2.4 Hz, 4 H), 3.28-3.21 (m, 1H), 2.90 (dd, J=9.3, 49.8 Hz, 2H), 2.62 (t, J=7.3 Hz, 2H), 2.54-2.40 (m, 5H), 2.36-2.27 (m, 2H), 2.23-2.16 (m, 1H), 2.13 (s, 2H), 2.10-2.05 (m, 1H), 2.02-1.88 (m, 6H), 1.81-1.66 (m, 2H), 1.66-1.57 (m, 1H), 0.58 (s, 3H). HRMS (ESI) (m/z) calc'd for $C_{34}H_{41}N_2O_2$ $[M+H]^+$: 509.7015, found 509.7013. β-Cyclopropylamine 39B and α-Cyclopropylamine 39A

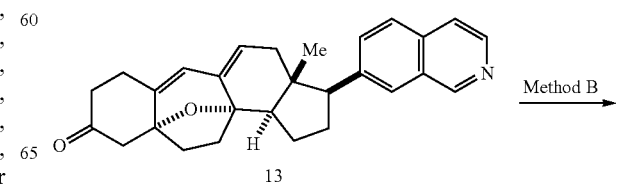

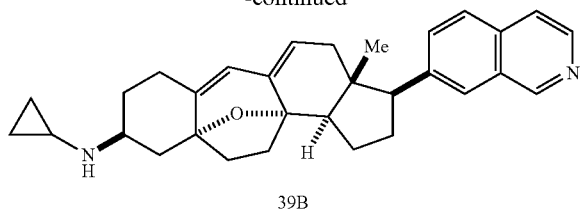

39B

+

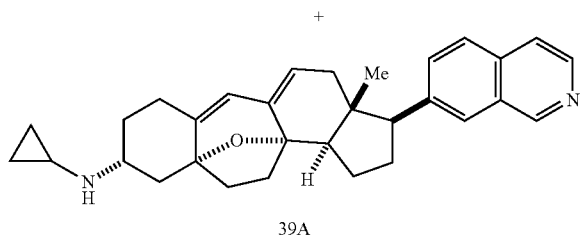

39A

β-cyclopropylamine 39B

The crude mixture was purified by preparative TLC (eluent: 47.5:47.5:5 EtOAc:Hexanes:2M NH$_3$ solution in MeOH) to afford β-cyclopropylamine 39B (3.7 mg, 55%). $^1$H NMR (500 MHz, CD$_3$OD) Shift=9.21 (s, 1H), 8.39 (d, J=5.9 Hz, 1H), 7.99 (s, 1H), 7.90 (d, J=8.8 Hz, 1H), 7.81 (d, J=5.4 Hz, 1H), 7.76 (dd, J=1.7, 8.5 Hz, 1H), 5.73 (d, J=2.0 Hz, 1H), 5.28-5.24 (m, 1H), 3.24 (t, J=20.0 Hz, 1H), 3.18-3.12 (m, 1H), 2.54-2.40 (m, 4H), 2.36-2.27 (m, 2H), 2.18 (s, 3H), 2.05-2.00 (m, 2H), 2.00-1.95 (m, 2H), 1.94-1.91 (m, 1H), 1.91-1.84 (m, 2H), 1.77-1.66 (m, 3H), 0.58 (s, 3H), 0.51 (d, J=4.4 Hz, 2H), 0.39 (dd, J=2.2, 3.7 Hz, 2H). HRMS (ESI) (m z) calc'd for C$_{31}$H$_{37}$N$_2$O [M+H]$^+$: 453.6383, found 453.6381.

β-Cyclopropylmethylamine 40B

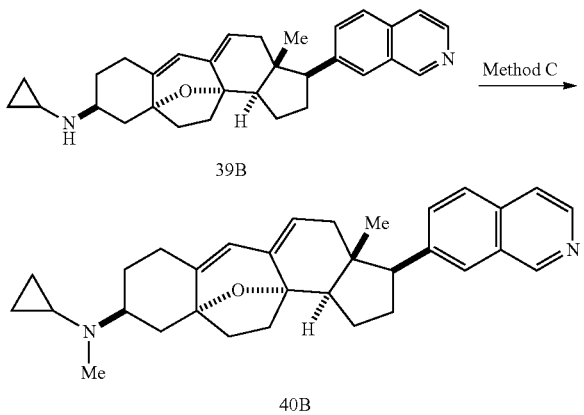

The crude mixture was purified by preparative TLC (eluent: 47.5:47.5:5 EtOAc:Hexanes:2M NH$_3$ solution in MeOH) to afford β-methylcyclopropylamine 40B (1.1 mg, 85%). $^1$H NMR (500 MHz, CD$_3$OD) Shift=9.21 (s, 1H), 8.39 (d, J=5.4 Hz, 1H), 8.00-7.98 (m, 1H), 7.90 (d, J=7.8 Hz, 1H), 7.81 (d, J=5.9 Hz, 1H), 7.76 (dd, J=1.5, 9.3 Hz, 1H), 5.78-5.74 (m, 1H), 5.29-5.25 (m, 1H), 3.26-3.24 (m, 1H), 3.23 (t, J=9.8 Hz, 1H), 3.27-3.21 (m, 1H), 2.88 (t, J=1.0 Hz, 1H), 2.56-2.49 (m, 1H), 2.48-2.41 (m, 2H), 2.37 (s, 3H), 2.33-2.26 (m, 1H), 2.23-2.10 (m, 3H), 2.03 (d, J=7.3 Hz, 2H), 2.01-1.96 (m, 1H), 1.96-1.88 (m, 2H), 1.88-1.82 (m, 1H), 1.79-1.68 (m, 2H), 0.59 (m, 5H), 0.50-0.46 (m, 2H). HRMS (ESI) (m/z) calc'd for C$_{32}$H$_{39}$N$_2$O [M+H]$^+$: 467.6649, found 467.6645.

β-3-Methyl-3-oxetanamine 41B and
α-3-Methyl-3-oxetanamine 41A

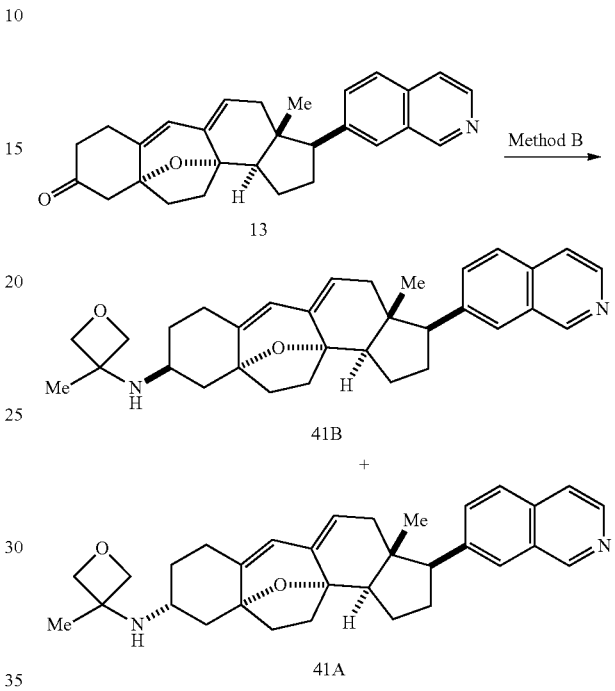

β-3-Methyl-3-oxetanamine 41B

The crude mixture was purified by preparative TLC (eluent: 47.5:47.5:5 EtOAc:Hexanes:2M NH$_3$ solution in MeOH) to afford β-3-methyl-3-oxetanamine 41B (4.7 mg, 81%). $^1$H NMR (500 MHz, CD$_3$OD) Shift=9.21 (s, 1H), 8.39 (d, J=5.4 Hz, 1H), 7.99 (s, 1H), 7.90 (d, J=8.8 Hz, 1H), 7.81 (d, J=5.9 Hz, 1H), 7.78-7.74 (m, 1H), 5.75 (d, J=1.5 Hz, 1H), 5.29-5.26 (m, 1H), 4.61 (dd, J=3.4, 5.9 Hz, 2H), 4.36 (dd, J=5.9, 8.3 Hz, 2H), 3.27-3.21 (m, 1H), 3.19-3.11 (m, 1H), 2.50 (d, J=8.3 Hz, 4H), 2.29 (s, 2H), 2.23-2.13 (m, 2H), 2.02-1.95 (m, 2H), 1.94-1.87 (m, 3H), 1.80-1.67 (m, 4H), 1.55 (br. s., 4H), 0.59 (s, 3H). HRMS (ESI) (m z) calc'd for C$_{32}$H$_{39}$N$_2$O$_2$ [M+H]$^+$: 483.6643, found 483.6640.

β-N-Methyl-1-(3-methyl-3-oxetanyl)methanamine
42B and α-N-Methyl-1-(3-methyl-3-oxetanyl)methanamine 42A

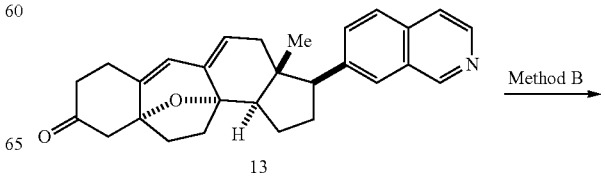

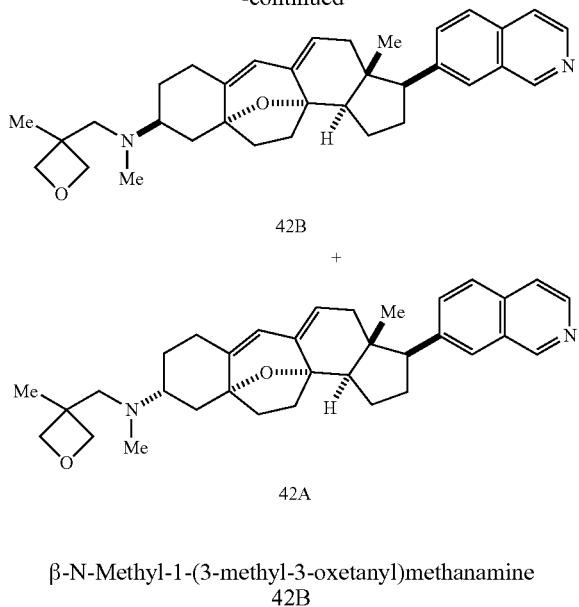

42B

+

42A

β-N-Methyl-1-(3-methyl-3-oxetanyl)methanamine 42B

The crude mixture was purified by preparative TLC (eluent: 47.5:47.5:5 EtOAc:Hexanes:2M $NH_3$ solution in MeOH) to afford β-N-methyl-1-(3-methyl-3-oxetanyl)methanamine 42B (1.5 mg, 24%). $^1$H NMR (500 MHz, $CD_3OD$) Shift=9.22 (s, 1H), 8.39 (d, J=5.9 Hz, 1H), 7.99 (s, 1H), 7.90 (d, J=8.3 Hz, 1H), 7.81 (d, J=5.9 Hz, 1H), 7.76 (dd, J=1.7, 8.5 Hz, 1H), 5.75-5.72 (m, 1H), 5.31-5.27 (m, 1H), 4.57-4.51 (m, 2H), 4.32 (dd, J=1.5, 5.9 Hz, 2H), 3.28-3.22 (m, 1H), 2.69 (s, 2H), 2.57-2.31 (m, 5H), 2.30-2.15 (m, 4H), 2.04-1.86 (m, 5H), 1.82 (t, J=24.9 Hz, 1H), 1.77-1.69 (m, 1H), 1.68-1.57 (m, 2H), 1.39 (d, J=2.9 Hz, 6H), 0.58 (s, 3H). HRMS (ESI) (m/z) calc'd for $C_{34}H_{43}N_2O_2$ $[M+H]^+$: 511.7174, found 511.7173.

β-t-Butylamine 43B and α-t-Butylamine 43A

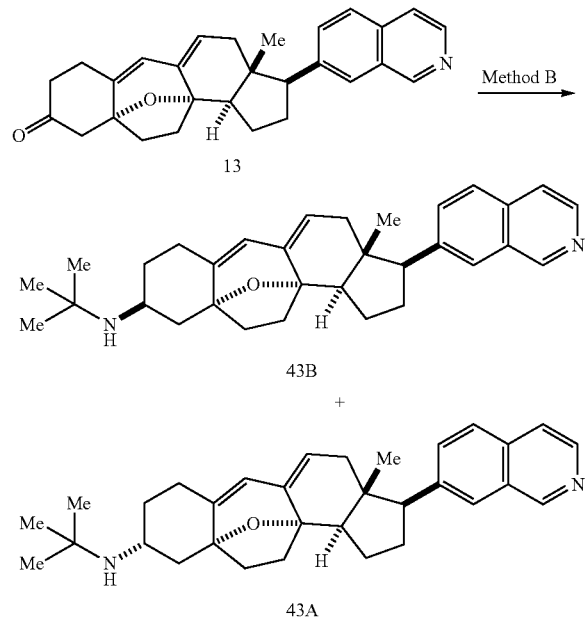

β-t-Butylamine 43B

The crude mixture was purified by flash chromatography (silica gel, eluent: 50:1 EtOAc:triethylamine) to afford β-t-butylamine 43B (3.4 mg, 60%). $^1$H NMR (500 MHz, $CDCl_3$) Shift=9.22 (s, 1H), 8.49 (d, J=5.9 Hz, 1H), 7.79 (s, 1H), 7.75 (d, J=8.3 Hz, 1H), 7.62 (d, J=5.9 Hz, 1H), 7.59 (d, J=8.3 Hz, 1H), 5.75 (d, J=2.0 Hz, 1H), 5.29 (m, 1H), 3.14 (dd, J=10.8, 10.8 Hz, 1H), 2.52 (dd, J=11.7, 8.8 Hz, 1H), 2.32-2.38 (m, 2H), 2.13-2.26 (m, 5H), 2.01-2.08 (m, 2H), 1.94 (dd, J=17.6, 5.4 Hz, 1H), 1.84-1.87 (m, 3H), 1.62-1.74 (m, 3H), 1.25 (br s, 9H). HRMS (ESI) (m/z) calc'd for $C_{32}H_{41}N_2O$ $[M+H]^+$: 469.3219, found 469.3265.

β-Aziridine 78B and α-Aziridine 78A

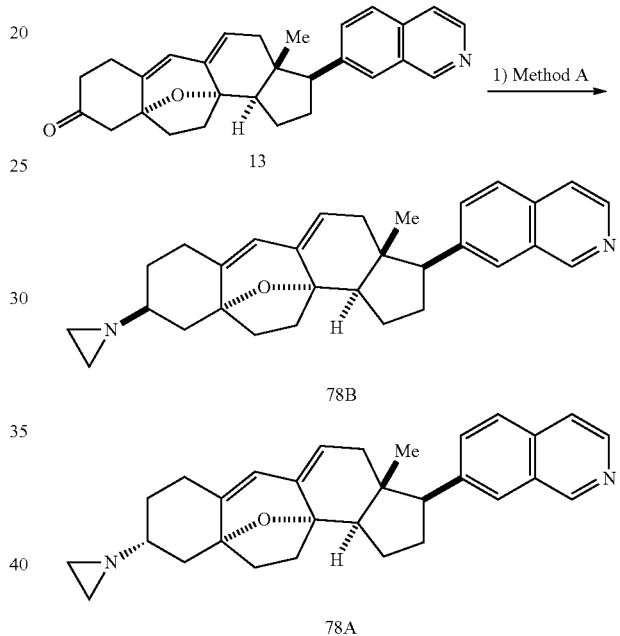

To a solution of ketone 13 (6 mg, 0.0146 mmol) in methanol (0.5 mL) was added 2-chloroethylamine hydrochloride (5.1 mg, 0.0437 mmol), followed by triethylamine (0.006 mL, 0.0437 mmol). This mixture was stirred at room temperature for 15 minutes. Glacial acetic acid (0.0025 mL, 0.0437 mmol) was added and this mixture was stirred at room temperature for 20 minutes. This mixture was cooled to 0° C. and sodium cyanoborohydride (3.2 mg, 0.0510 mml) was added. The reaction was allowed to warm to room temperature over 16 hours and then quenched with saturated solution of ammonium chloride (5 mL). This mixture was extracted with ethyl acetate (3×8 mL). The combined organic fractions were dried over anhydrous magnesium sulfate, filtered and concentrated. The crude was purified by silica gel chromatography (ethylacetate, 2% triethylamine as eluent) to afford the desired β-aziridine 78B (4.5 mg, 72% yield).

$^1$H NMR (500 MHz, $CDCl_3$) δ=9.22 (s, 1H), 8.48 (d, J=5.87 Hz, 1H), 7.79 (s, 1H), 7.75 (d, J=8.80 Hz, 1H), 7.63 (d, J=5.38 Hz, 1H), 7.59 (d, J=8.80 Hz, 1H), 5.74 (d, J=1.96 Hz, 1H), 5.25 (m, 1H), 3.34 (m, 2H), 3.14 (dd, J=10.27, 10.27 Hz, 1H), 2.75 (m, 3H), 2.51 (dd, J=11.25, 8.31 Hz, 1H), 2.44 (m, 1H), 2.29-2.37 (m, 3H), 2.12-2.27 (m, 3H), 1.81-

2.08 (m, 3H), 1.54-1.74 (m, 4H), 1.15 (m, 1H), 1.05 (m, 1H), 0.55 (s, 3H). HRMS (ESI) (m/z) calc'd for $C_{30}H_{35}N_2O$ [M+H]$^+$: 439.2749 found 439.2721.

β-Hydroxyproline 65B and α-Hydroxyproline 65A

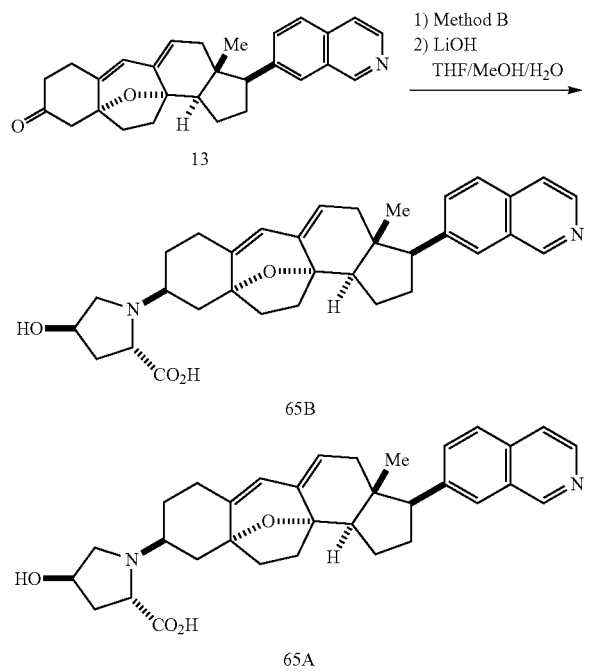 [SMILES: C[C@]12CC=C3C=C4CCC(=O)C[C@]45CC[C@]3(O5)[C@@H]1CC[C@@H]2c1ccc2ccncc2c1 ; C[C@]12CC=C3C=C4CC[C@H](N5C[C@H](O)C[C@H]5C(=O)O)C[C@]45CC[C@]3(O5)[C@@H]1CC[C@@H]2c1ccc2ccncc2c1 ; C[C@]12CC=C3C=C4CC[C@H](N5C[C@H](O)C[C@H]5C(=O)O)C[C@]45CC[C@]3(O5)[C@@H]1CC[C@@H]2c1ccc2ccncc2c1]

Ketone 13 was reacted with hydroxyproline methyl ester under condition 'Method B'. The crude mixture was dissolved in THF:MeOH:1 M LiOH in H$_2$O=3:3:1 and stirred at 55° C. for 1.5 hours. The crude mixture was roughly concentrated and pH 3.7 sodium acetate buffer was applied, followed by the extraction with chloroform three times. The crude mixture was purified by preparative TLC (eluent: 5:1 CHCl$_3$:MeOH) to afford β-hydroxyproline 65B (3.7 mg, 58% in 2 steps).

$^1$H NMR (500 MHz, CDCl$_3$) Shift=9.22 (br. s., 1H), 8.47 (br. s., 1H), 7.77 (br. s., 1H), 7.75 (d, J=8.2 Hz, 1H), 7.63 (br. s., 1H), 7.57 (d, J=8.2 Hz, 1H), 5.77 (s, 1H), 5.30 (br. s., 1H), 4.47 (br. s., 1H), 4.21-4.08 (m, 1H), 4.01-3.90 (m, 0H), 3.55 (br. s., 1H), 3.19-3.11 (m, 1H), 3.12 (t, J=8.8 Hz, 1H), 2.51-2.44 (m, J=10.6, 10.6 Hz, 1H), 2.44-2.37 (m, 2H), 2.35 (d, J=17.6 Hz, 2H), 2.31-2.14 (m, 6H), 2.11 (dd, J=6.2, 13.2 Hz, 1H), 2.06-1.96 (m, 2H), 1.92 (dd, J=4.7, 17.6 Hz, 1H), 1.87-1.68 (m, 3H), 0.53 (s, 3H). HRMS (ESI) (m/z) calc'd for $C_{33}H_{39}N_2O_4$ [M+H]$^+$: 527.2904, found 527.2921.

α-Dimethylamine 14A and β-Dimethylamine 14B

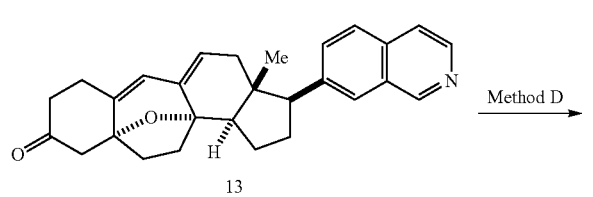

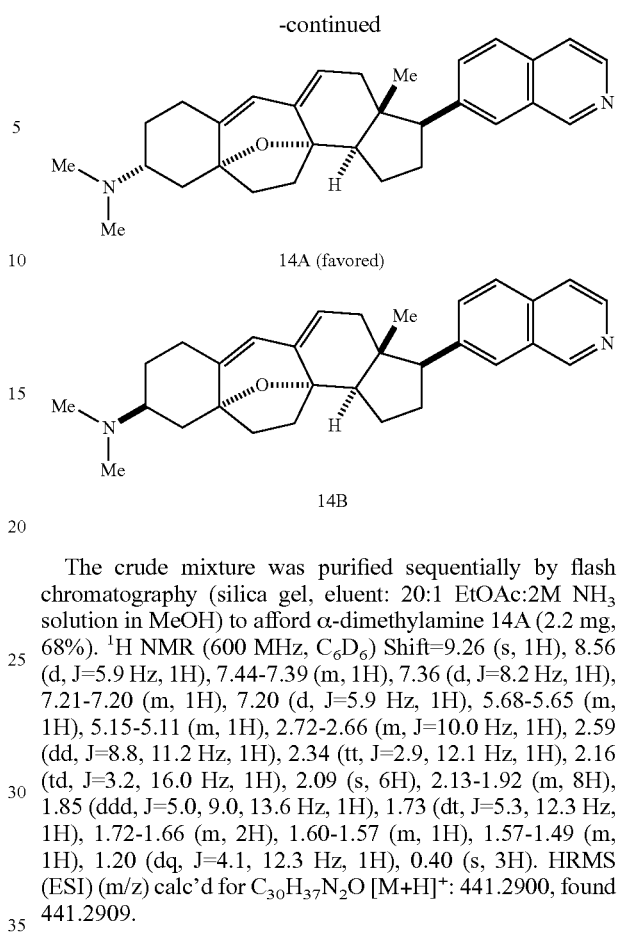

The crude mixture was purified sequentially by flash chromatography (silica gel, eluent: 20:1 EtOAc:2M NH$_3$ solution in MeOH) to afford α-dimethylamine 14A (2.2 mg, 68%). $^1$H NMR (600 MHz, C$_6$D$_6$) Shift=9.26 (s, 1H), 8.56 (d, J=5.9 Hz, 1H), 7.44-7.39 (m, 1H), 7.36 (d, J=8.2 Hz, 1H), 7.21-7.20 (m, 1H), 7.20 (d, J=5.9 Hz, 1H), 5.68-5.65 (m, 1H), 5.15-5.11 (m, 1H), 2.72-2.66 (m, J=10.0 Hz, 1H), 2.59 (dd, J=8.8, 11.2 Hz, 1H), 2.34 (tt, J=2.9, 12.1 Hz, 1H), 2.16 (td, J=3.2, 16.0 Hz, 1H), 2.09 (s, 6H), 2.13-1.92 (m, 8H), 1.85 (ddd, J=5.0, 9.0, 13.6 Hz, 1H), 1.73 (dt, J=5.3, 12.3 Hz, 1H), 1.72-1.66 (m, 2H), 1.60-1.57 (m, 1H), 1.57-1.49 (m, 1H), 1.20 (dq, J=4.1, 12.3 Hz, 1H), 0.40 (s, 3H). HRMS (ESI) (m/z) calc'd for $C_{30}H_{37}N_2O$ [M+H]$^+$: 441.2900, found 441.2909.

α-Monomethylamine 24A and β-Monomethylamine 24B

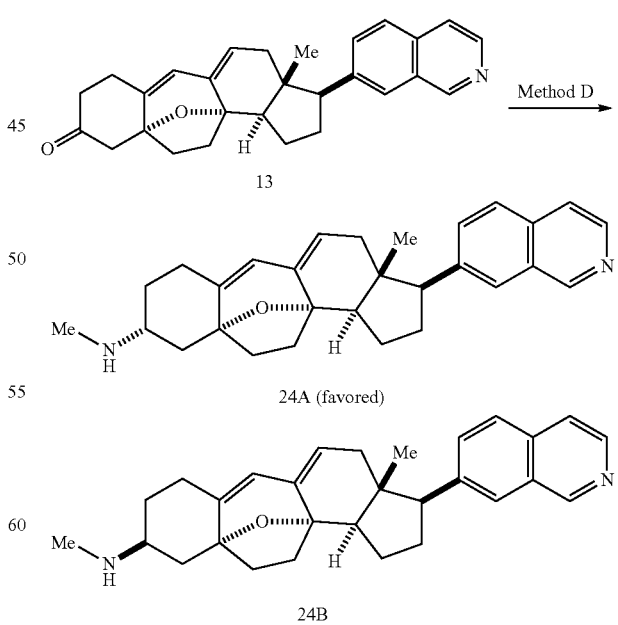

The crude mixture was purified by preparative TLC (silica gel, eluent: 10:1 EtOAc:2M NH$_3$ solution in MeOH) to afford α-monomethylamine 24A (ca. 1.2 mg, 37%). 1H NMR (500 MHz, CDCl3) Shift=9.24 (s, 1H), 8.50 (d, J=5.9 Hz, 1H), 7.81 (s, 1H), 7.77 (d, J=8.8 Hz, 1H), 7.64 (d, J=5.4 Hz, 1H), 7.61 (dd, J=1.0, 8.8 Hz, 1H), 5.76 (s, 1H), 5.29 (d, J=2.4 Hz, 1H), 3.16 (t, J=10.0 Hz, 1H), 2.61-2.50 (m, 3H), 2.49 (s, 3H), 2.43-2.30 (m, 3H), 2.30-2.15 (m, 4H), 2.13-1.99 (m, 2H), 1.95 (dd, J=5.4, 17.6 Hz, 1H), 1.88 (dq, J=4.9, 11.7 Hz, 1H), 1.79-1.60 (m, 3H), 1.19 (dq, J=4.4, 12.7 Hz, 1H), 0.56 (s, 3H). HRMS (ESI) (m/z) calc'd for $C_{29}H_{35}N_2O$ [M+H]+: 427.2744, found 427.2759.

α-Primaryamine 62A and β-Primaryamine 62B

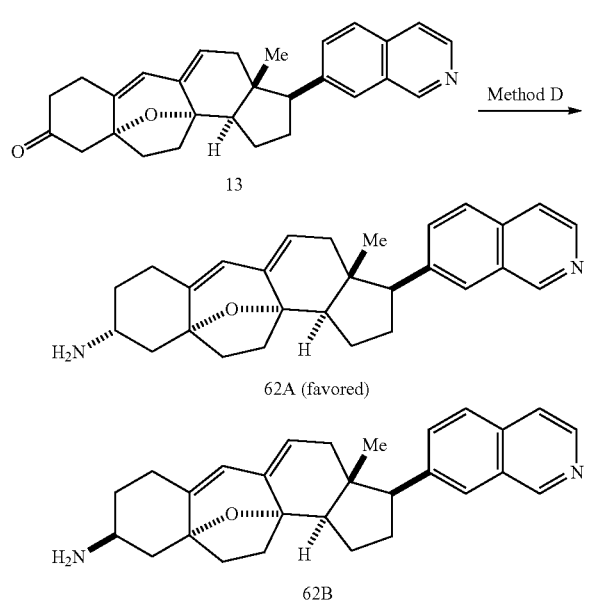

The crude mixture was purified by preparative TLC (silica gel, eluent: 25:1 EtOAc:2M NH3 solution in MeOH) to afford α-primaryamine 62A (3.7 mg, 38%) and β-primaryamine 62B (2.5 mg, 26%).

α-primaryamine 62A

1H NMR (500 MHz, CDCl3) Shift=9.22 (s, 1H), 8.48 (d, J=5.9 Hz, 1H), 7.79 (s, 1H), 7.75 (d, J=8.8 Hz, 1H), 7.62 (d, J=5.3 Hz, 1H), 7.59 (dd, J=1.2, 8.2 Hz, 1H), 5.74 (s, 1H), 5.27 (d, J=2.9 Hz, 1H), 3.14 (t, J=10.0 Hz, 1H), 2.85 (tt, J=3.2, 11.7 Hz, 1H), 2.51 (dd, J=8.5, 11.4 Hz, 1H), 2.40-2.28 (m, 3H), 2.27-2.12 (m, 4H), 2.10-1.96 (m, 3H), 1.93 (dd, J=5.3, 17.6 Hz, 1H), 1.92-1.81 (m, 2H), 1.76-1.62 (m, 2H), 1.22 (dtd, J=4.1, 11.7, 13.5 Hz, 1H), 0.53 (s, 3H). HRMS (ESI) (m/z) calc'd for $C_{28}H_{33}N_2O$ [M+H]+: 413.2587, found 413.2590.

β-primaryamine 62B

1H NMR (500 MHz, CDCl3) Shift=9.22 (s, 1H), 8.48 (d, J=5.9 Hz, 1H), 7.79 (s, 1H), 7.75 (d, J=8.2 Hz, 1H), 7.62 (d, J=5.3 Hz, 1H), 7.59 (dd, J=1.5, 8.5 Hz, 1H), 5.73 (d, J=1.2 Hz, 1H), 5.25 (d, J=2.9 Hz, 1H), 3.47 (td, J=3.7, 7.9 Hz, 1H), 3.13 (t, J=10.0 Hz, 1H), 2.58 (dt, J=5.3, 14.1 Hz, 1H), 2.51 (dd, J=8.5, 11.4 Hz, 1H), 2.39-2.21 (m, 5H), 2.17 (dq, J=5.3, 9.4 Hz, 1H), 2.13 (ddd, J=2.3, 4.7, 15.8 Hz, 1H), 2.10-1.99 (m, 2H), 1.93 (dd, J=5.3, 17.0 Hz, 1H), 1.86 (dq, J=5.3, 12.3 Hz, 1H), 1.82 (ddd, J=1.8, 4.1, 13.5 Hz, 1H), 1.78-1.66 (m, 3H), 0.54 (s, 3H). HRMS (ESI) (m/z) calc'd for $C_{28}H_{33}N_2O$ [M+H]+: 413.2587, found 413.2599.

α-Morpholine 15A and β-Morpholine 15B

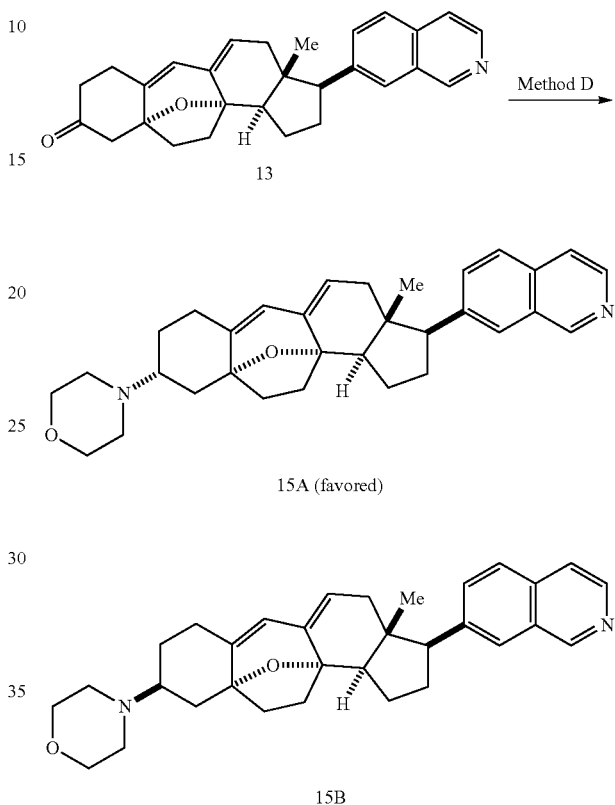

The crude mixture was purified by preparative TLC (silica gel, eluent: 40:1 EtOAc:MeOH) to afford α-morpholine 15A (ca. 1.5 mg, 38%). 1H NMR (600 MHz, CDCl3) Shift=9.23 (s, 1H), 8.49 (d, J=5.4 Hz, 1H), 7.80 (s, 1H), 7.76 (d, J=8.3 Hz, 1H), 7.63 (d, J=5.4 Hz, 1H), 7.60 (d, J=8.3 Hz, 1H), 5.74 (s, 1H), 5.29 (d, J=2.9 Hz, 1H), 3.73 (br. s., 4H), 3.15 (t, J=10.0 Hz, 1H), 2.60 (br. s., 4H), 2.52 (dd, J=8.5, 11.5 Hz, 2H), 2.46-2.29 (m, 3H), 2.29-2.13 (m, 4H), 2.12-1.99 (m, 2H), 1.94 (dd, J=5.1, 17.3 Hz, 1H), 1.94-1.81 (m, 3H), 1.73 (td, J=8.2, 12.3 Hz, 1H), 1.70-1.63 (m, 1H), 1.38 (dq, J=4.4, 12.2 Hz, 1H), 0.54 (s, 3H). HRMS (ESI) (m/z) calc'd for $C_{32}H_{39}N_2O_2$ [M+H]+: 483.3006, found 483.3000.

α-Pyrrolidine 19A and β-Pyrrolidine 19B

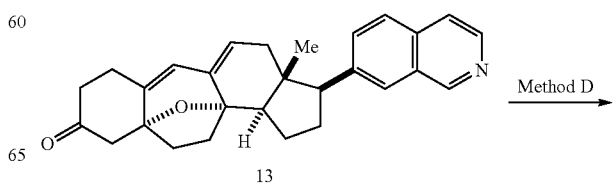

-continued

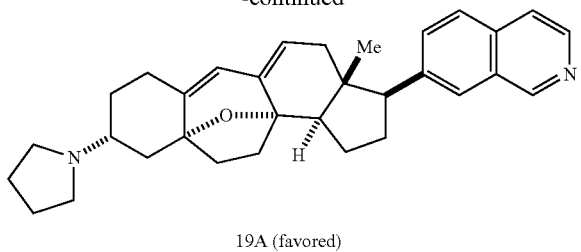

19A (favored)

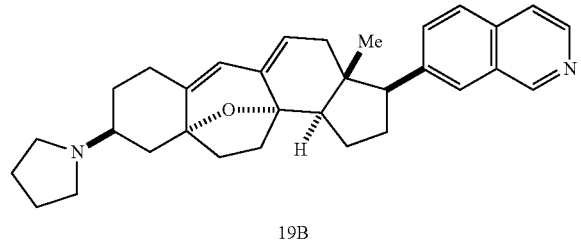

19B

The crude mixture was purified by preparative TLC (silica gel, eluent: 20:10:3 EtOAc:Hexanes:2M NH₃ solution in MeOH) to afford α-pyrrolidine 19A (2.5 mg, 55%). ¹H NMR (500 MHz, CDCl₃) Shift=9.22 (s, 1H), 8.48 (d, J=5.9 Hz, 1H), 7.79 (s, 1H), 7.75 (d, J=8.2 Hz, 1H), 7.62 (d, J=5.3 Hz, 1H), 7.59 (d, J=8.8 Hz, 1H), 5.72 (s, 1H), 5.27 (d, J=2.9 Hz, 1H), 3.14 (t, J=10.0 Hz, 1H), 2.63 (br. s., 4H), 2.52 (dd, J=8.8, 11.2 Hz, 1H), 2.42-2.29 (m, 3H), 2.28-2.15 (m, 5H), 2.12 (d, J=12.3 Hz, 1H), 2.10-2.00 (m, 2H), 1.93 (dd, J=5.3, 17.0 Hz, 1H), 1.90-1.83 (m, 2H), 1.80 (br. s., 4H), 1.72 (td, J=8.8, 12.9 Hz, 1H), 1.63 (br. s., 1H), 1.37 (dq, J=3.5, 11.7 Hz, 1H), 0.53 (s, 3H). HRMS (ESI) (m/z) calc'd for C₃₂H₃₉N₂O [M+H]⁺: 467.3057, found 467.3064.

α-Azetidine 18A and β-Azetidine 18B

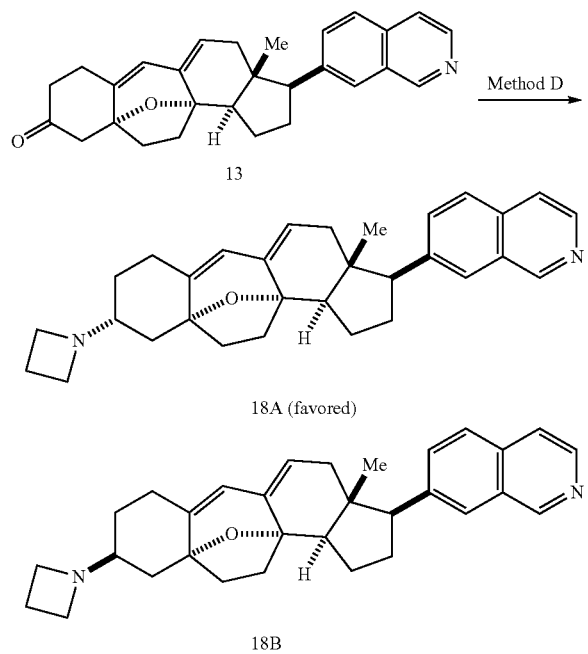 [SMILES: C[C@]12CC=C3C=C4CCC(=O)C[C@]45CC[C@]3(O5)[C@@H]1CC[C@@H]2c1ccc2ccncc2c1 ; C[C@]12CC=C3C=C4CC[C@@H](N5CCC5)C[C@]45CC[C@]3(O5)[C@@H]1CC[C@@H]2c1ccc2ccncc2c1 ; C[C@]12CC=C3C=C4CC[C@H](N5CCC5)C[C@]45CC[C@]3(O5)[C@@H]1CC[C@@H]2c1ccc2ccncc2c1]

The crude mixture was purified by preparative TLC (silica gel, eluent: 1:1 EtOAc:MeOH) to afford α-azetidine 18A (ca. 1.5 mg, 38%). ¹H NMR (500 MHz, CDCl₃) Shift=9.24 (s, 1H), 8.50 (d, J=5.4 Hz, 1H), 7.80 (s, 1H), 7.77 (d, J=8.8 Hz, 1H), 7.64 (d, J=5.9 Hz, 1H), 7.60 (d, J=8.8 Hz, 1H), 5.74 (s, 1H), 5.28 (br. s., 1H), 3.24 (br. s., 4H), 3.16 (t, J=9.8 Hz, 1H), 2.54 (dd, J=8.8, 11.2 Hz, 1H), 2.42-2.30 (m, 3H), 2.30-2.13 (m, 5H), 2.12-2.00 (m, 2H), 1.95 (dd, J=5.4, 18.1 Hz, 1H), 1.93-1.78 (m, 3H), 1.74 (td, J=8.3, 12.2 Hz, 1H), 1.67-1.54 (m, 3H), 1.11 (q, J=12.2 Hz, 1H), 0.55 (s, 3H). HRMS (ESI) (m/z) calc'd for C₃₁H₃₇N₂O [M+H]⁺: 453.2906, found 453.2900.

α-t-Butylamine 43A and β-t-Butylamine 43B

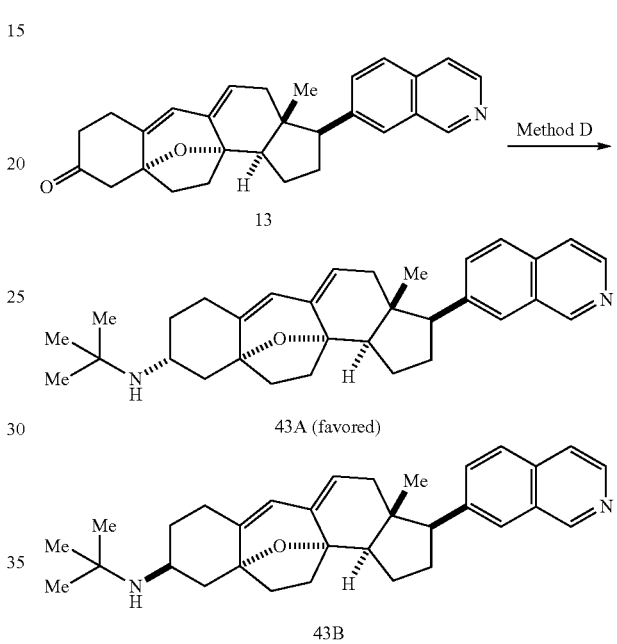

The crude mixture was purified by flash chromatography (silica gel, eluent: 10:1 CHCl3:i-PrOH) to afford α-t-butylamine 43A (2.4 mg, 42%) and β-t-butylamine 43B (1.6 mg, 28%).

α-t-Butylamine 43A

¹H NMR (500 MHz, CDCl₃) Shift=9.22 (br. s., 1H), 8.48 (d, J=5.9 Hz, 1H), 7.78 (s, 1H), 7.75 (d, J=8.8 Hz, 1H), 7.62 (d, J=5.3 Hz, 1H), 7.58 (dd, J=1.2, 8.2 Hz, 1H), 5.73 (s, 1H), 5.28 (d, J=2.3 Hz, 1H), 3.14 (t, J=9.7 Hz, 1H), 2.49 (dd, J=8.8, 11.2 Hz, 1H), 2.46-2.40 (m, 1H), 2.39-2.29 (m, 3H), 2.28-2.12 (m, 5H), 2.08-1.99 (m, 1H), 1.93 (dd, J=5.3, 17.0 Hz, 1H), 1.83 (dq, J=5.0, 12.2 Hz, 2H), 1.76-1.60 (m, 3H), 1.55 (br. s., 9H), 1.26-1.18 (m, 1H), 0.54 (s, 3H). HRMS (ESI) (m/z) calc'd for C₃₂H₄₁N₂O [M+H]⁺: 469.3213, found 469.3223.

β-t-Butylamine 43B

¹H NMR (500 MHz, CDCl₃) Shift=9.22 (s, 1H), 8.48 (d, J=5.3 Hz, 1H), 7.78 (s, 1H), 7.75 (d, J=8.8 Hz, 1H), 7.62 (d, J=5.9 Hz, 1H), 7.59 (d, J=9.4 Hz, 1H), 5.73 (br. s., 1H), 5.25 (br. s., 1H), 3.38-3.23 (m, 1H), 3.13 (t, J=10.0 Hz, 1H), 2.57-2.48 (m, 1H), 2.49 (dd, J=8.5, 10.9 Hz, 1H), 2.40-2.27 (m, 2H), 2.25-2.08 (m, 4H), 2.07-1.98 (m, 2H), 1.93 (dd, J=5.3, 17.6 Hz, 2H), 1.84 (dq, J=5.3, 12.3 Hz, 1H), 1.76-

1.66 (m, 2H), 1.65-1.47 (m, 3H), 1.42-0.94 (br. s., 9H), 0.54 (s, 3H). HRMS (ESI) (m/z) calc'd for $C_{32}H_{41}N_2O$ [M+H]$^+$: 469.3213, found 469.3225.

α-Hydroxyazetidine 70A and β-Hydroxyazetidine 70B

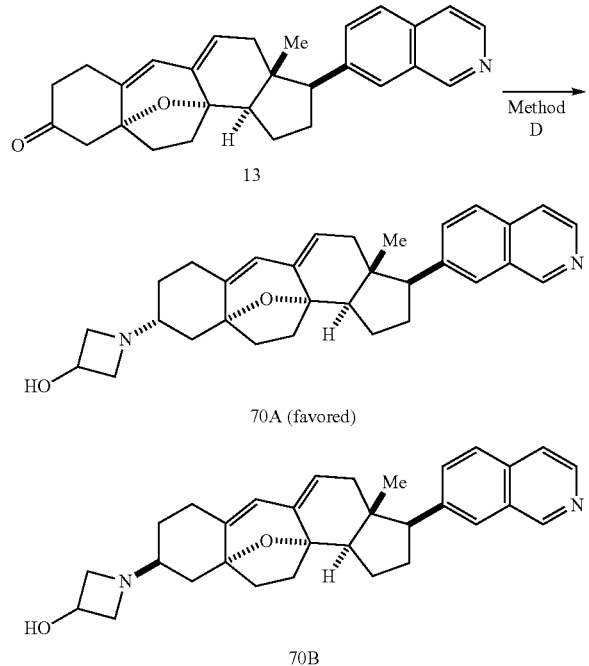

The crude mixture was purified by preparative TLC (silica gel, eluent: 2:3 EtOAc:MeOH) to afford α-hydroxyazetidine 70A (1.2 mg, 30%). $^1$H NMR (500 MHz, CDCl$_3$) Shift=9.24 (s, 1H), 8.50 (d, J=5.4 Hz, 1H), 7.80 (s, 1H), 7.77 (d, J=8.3 Hz, 1H), 7.64 (d, J=5.9 Hz, 1H), 7.60 (d, J=8.3 Hz, 1H), 5.77 (s, 1H), 5.32 (d, J=2.4 Hz, 1H), 4.66-4.55 (m, 1H), 3.94 (br. s., 2H), 3.34 (br. s., 2H), 3.16 (t, J=9.8 Hz, 1H), 2.53 (dd, J=8.5, 11.5 Hz, 1H), 2.41 (dd, J=15.6, 28.3 Hz, 2H), 2.34 (dt, J=4.9, 11.2 Hz, 1H), 2.28 (t, J=11.2 Hz, 1H), 2.25-2.14 (m, 3H), 2.10-1.98 (m, 2H), 1.95 (dd, J=5.4, 17.6 Hz, 1H), 1.96-1.89 (m, 1H), 1.86 (dd, J=5.4, 12.2 Hz, 1H), 1.84-1.76 (m, 2H), 1.74 (td, J=8.4, 12.4 Hz, 1H), 1.65 (dt, J=7.8, 10.5 Hz, 1H), 1.40-1.27 (m, 1H), 0.55 (s, 3H). HRMS (ESI) (m/z) calc'd for $C_{31}H_{37}N_2O_2$ [M+H]$^+$: 469.2850, found 469.2872.

α-Hydroxymethylazetidine 69A and β-Hydroxymethylazetidine 69B

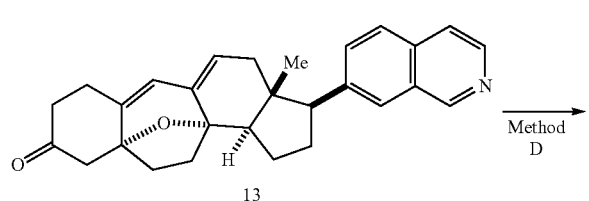

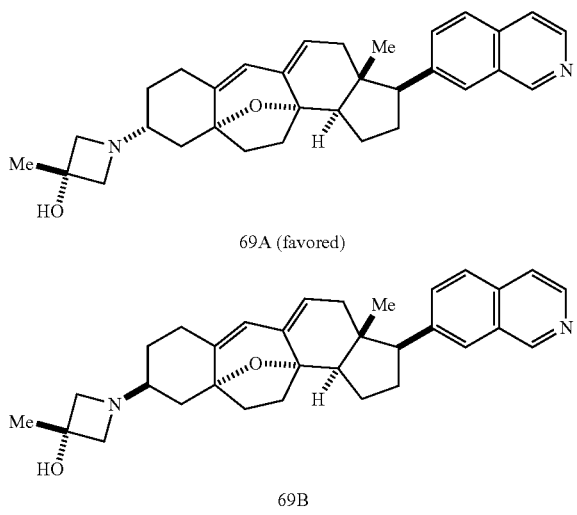

The crude mixture was purified by preparative TLC (silica gel, eluent: 1:1 EtOAc:MeOH) to afford α-hydroxymethylazetidine 69A (2.3 mg, 53%). $^1$H NMR (600 MHz, CDCl$_3$) Shift=9.23 (s, 1H), 8.49 (d, J=5.9 Hz, 1H), 7.80 (s, 1H), 7.76 (d, J=8.2 Hz, 1H), 7.63 (d, J=5.9 Hz, 1H), 7.59 (d, J=8.8 Hz, 1H), 5.76 (s, 1H), 5.30 (d, J=2.9 Hz, 1H), 3.65-3.35 (m, 4H), 3.15 (t, J=10.0 Hz, 1H), 2.52 (dd, J=8.5, 11.4 Hz, 1H), 2.40 (dd, J=16.4, 25.8 Hz, 2H), 2.33 (dt, J=4.1, 11.7 Hz, 1H), 2.26 (t, J=11.4 Hz, 1H), 2.24 (m, 3H), 2.09-2.00 (m, 1H), 1.98 (br. s., 1H), 1.94 (dd, J=5.0, 17.3 Hz, 1H), 1.92-1.77 (m, 4H), 1.73 (td, J=8.2, 12.9 Hz, 1H), 1.67-1.59 (m, 1H), 1.58-1.50 (br. s., 3H), 1.39-1.28 (m, 1H), 0.58-0.51 (s, 3H). HRMS (ESI) (m/z) calc'd for $C_{32}H_{39}N_2O_2$ [M+H]$^+$: 483.3006, found 483.3000.

α-Aminoethylsulfonamide 71A and β-Aminoethylsulfonamide 71B

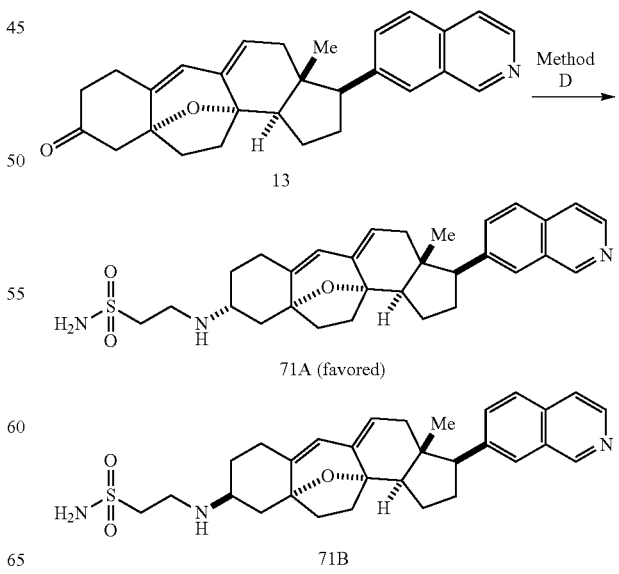

The crude mixture was purified by preparative TLC (silica gel, eluent: 100% EtOAc) to afford β-aminoethylsulfonamide 71B (0.7 mg, 15%) and α-aminoethylsulfonamide 71A (1.1 mg, 24%).

β-Aminoethylsulfonamide 71B $^1$H NMR (500 MHz, CD$_3$OD) Shift=9.21-9.17 (m, 1H), 8.37 (d, J=5.9 Hz, 1H), 7.97 (s, 1H), 7.88 (d, J=8.3 Hz, 1H), 7.79 (d, J=5.4 Hz, 1H), 7.74 (dd, J=1.5, 8.8 Hz, 1H), 5.74-5.69 (m, 1H), 5.28-5.22 (m, 1H), 3.26-3.18 (m, J=9.8 Hz, 1H), 3.14-3.00 (m, 4H), 2.59-2.38 (m, 4H), 2.37-2.26 (m, 2H), 2.23-2.06 (m, 3H), 2.03-1.86 (m, 5H), 1.85-1.76 (m, 1H), 1.76-1.59 (m, 3H), 0.57 (s, 3H). HRMS (ESI) (m/z) calc'd for C$_{30}$H$_{38}$N$_3$O$_3$S [M+H]$^+$: 520.2628, found 520.2640.

α-Aminoethylsulfonamide 71A $^1$H NMR (500 MHz, CD$_3$OD) Shift=9.19 (s, 1H), 8.37 (d, J=5.9 Hz, 1H), 7.97 (s, 1H), 7.88 (d, J=8.8 Hz, 1H), 7.79 (d, J=5.9 Hz, 1H), 7.74 (dd, J=1.7, 8.6 Hz, 1H), 5.77-5.71 (m, 1H), 5.30-5.24 (m, 1H), 3.29-3.24 (m, 2H), 3.23 (dd, J=9.0, 11.0 Hz, 1H), 3.13 (dt, J=2.7, 6.7 Hz, 2H), 2.73 (tt, J=3.1, 12.0 Hz, 1H), 2.50 (dd, J=8.6, 11.5 Hz, 1H), 2.47-2.38 (m, 2H), 2.39-2.34 (m, 1H), 2.32 (d, J=11.2 Hz, 1H), 2.30-2.22 (m, 2H), 2.17 (dtd, J=5.9, 9.3, 14.7 Hz, 2H), 2.10-2.03 (m, 1H), 2.01 (s, 1 H), 2.00-1.92 (m, 1H), 1.90 (dd, J=6.4, 17.1 Hz, 1H), 1.72 (td, J=8.3, 12.3 Hz, 1H), 1.68-1.60 (m, 2H), 1.18 (dq, J=4.4, 12.2 Hz, 1H), 0.56 (s, 3H). HRMS (ESI) (m/z) calc'd for C$_{30}$H$_{38}$N$_3$O$_3$S [M+H]$^+$: 520.2628, found 520.2643.

α-Hydroxyaminomethyloxetane 72A and β-Hydroxyaminomethyloxetane 72B

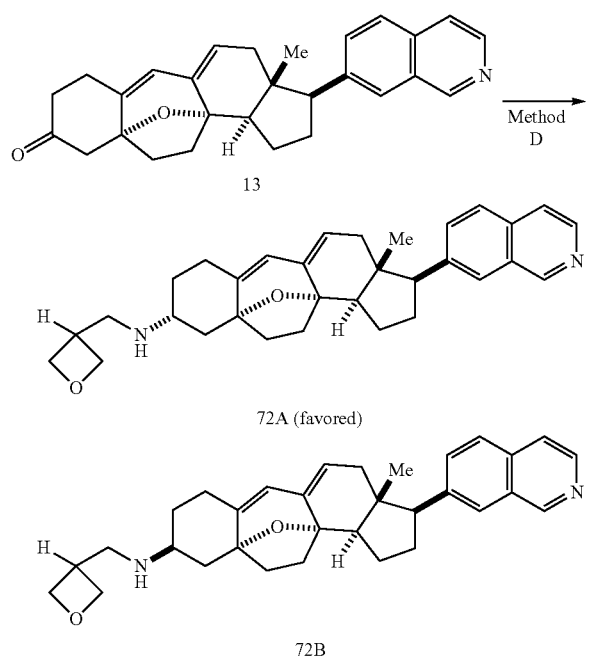

The crude mixture was purified by preparative TLC (silica gel, eluent: 100% EtOAc) to afford α-hydroxyaminomethyloxetane 72A (1.5 mg, 34%). $^1$H NMR (500 MHz, CD$_3$OD) Shift=9.19 (s, 1H), 8.38 (d, J=5.4 Hz, 1H), 7.97 (s, 1H), 7.88 (d, J=8.3 Hz, 1H), 7.79 (d, J=5.9 Hz, 1H), 7.74 (dd, J=1.5, 8.8 Hz, 1H), 5.84-5.78 (m, 1H), 5.35-5.30 (m, 1H), 4.64 (d, J=7.3 Hz, 2H), 4.57 (dd, J=3.7, 7.1 Hz, 2H), 3.48-3.40 (m, 2H), 3.24 (dd, J=9.0, 11.0 Hz, 2H), 2.54-2.48 (m, J=8.8 Hz, 1H), 2.48-2.40 (m, 3H), 2.40-2.24 (m, 4H), 2.24-2.13 (m, 3H), 2.01-1.85 (m, 4H), 1.80-1.64 (m, 2H), 1.46 (dq, J=4.9, 12.2 Hz, 1H), 0.57 (s, 3H). HRMS (ESI) (m/z) calc'd for C$_{32}$H$_{39}$N$_2$O$_3$ [M+H]$^+$: 499.2955, found 499.2933.

β-PEGamine 75B and α-PEGamine 75A

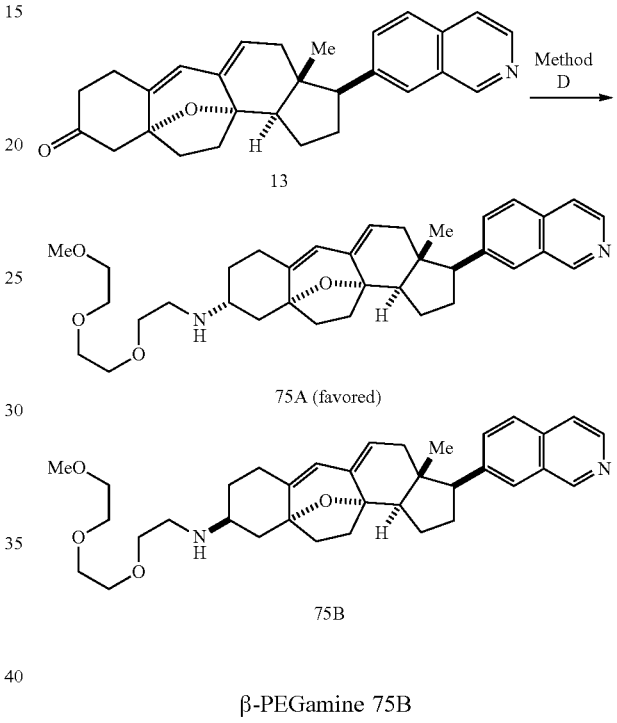

β-PEGamine 75B

The crude mixture was purified by preparative TLC (silica gel, eluent: 5:5:1 EtOAc:Dichloromethane:2M NH$_3$ solution in MeOH) to afford 13-PEGamine 75B (1.0 mg, 18%). $^1$H NMR (500 MHz, CDCl$_3$) Shift=9.24 (s, 1H), 8.50 (d, J=5.9 Hz, 1H), 7.81 (s, 1H), 7.77 (d, J=8.3 Hz, 1H), 7.64 (d, J=5.9 Hz, 1H), 7.61 (dd, J=1.7, 8.5 Hz, 1H), 5.72 (d, J=1.5 Hz, 2H), 5.25 (dd, J=2.2, 5.1 Hz, 1H), 3.71-3.64 (m, 6H), 3.62 (t, J=5.4 Hz, 2H), 3.58 (dd, J=3.7, 5.6 Hz, 2H), 3.41 (s, 3H), 3.19-3.12 (m, J=10.7 Hz, 1H), 3.11 (t, J=3.9 Hz, 1H), 2.79 (t, J=5.4 Hz, 2H), 2.56 (t, J=16.1 Hz, 1H), 2.52 (dd, J=8.3, 11.2 Hz, 1H), 2.42-2.29 (m, 3H), 2.27-2.13 (m, 2H), 2.12-2.01 (m, 2H), 2.02 (dd, J=3.7, 13.9 Hz, 1H), 1.95 (br. s., 2H), 1.86 (dq, J=5.4, 12.2 Hz, 1H), 1.80-1.73 (m, 1H), 1.71 (dd, J=3.2, 11.5 Hz, 1H), 1.68-1.58 (m, 2H), 0.56 (s, 3H). HRMS (ESI) (m/z) calc'd for C$_{35}$H$_{47}$N$_2$O$_4$ [M+H]$^+$: 559.3530, found 559.3545.

α-PEGamine 75A

The crude mixture was purified by preparative TLC (silica gel, eluent: 100:5:1 EtOAc:MeOH:Triethylamine) to afford α-PEGamine 75A (1.1 mg, 20%). $^1$H NMR (500 MHz, CDCl$_3$) Shift=9.24 (s, 1H), 8.50 (d, J=5.9 Hz, 1H), 7.81 (s, 1H), 7.77 (d, J=8.8 Hz, 1H), 7.64 (d, J=5.9 Hz, 1H), 7.61 (dd, J=1.5, 8.8 Hz, 1H), 5.75 (d, J=2.0 Hz, 1H), 5.28 (dd, J=2.2, 5.1 Hz, 1H), 3.70-3.65 (m, 7H), 3.64 (t, J=5.4 Hz, 2H), 3.61-3.55 (m, 2H), 3.41 (s, 3H), 3.16 (dd, J=9.0, 10.5 Hz, 1H), 2.87 (t, J=5.1 Hz, 2H), 2.67 (t, J=11.5 Hz, 1H), 2.54 (dd, J=8.3, 11.7 Hz, 1H), 2.38 (d, J=16.1 Hz, 3H), 2.24 (d, J=12.2 Hz, 2H), 2.22-2.14 (m, 2H), 2.11-2.02 (m, 2H), 1.95 (dd, J=5.4, 16.6 Hz, 1H), 1.88 (dq, J=5.4, 12.2 Hz, 1H), 1.78-1.69 (m, 2H), 1.68-1.62 (m, 1H), 1.27-1.19 (m, 1H), 0.55 (s, 3H). HRMS (ESI) (m/z) calc'd for $C_{35}H_{47}N_2O_4$ $[M+H]^+$: 559.3530, found 559.3542.

α-methylsulfonamide 73A

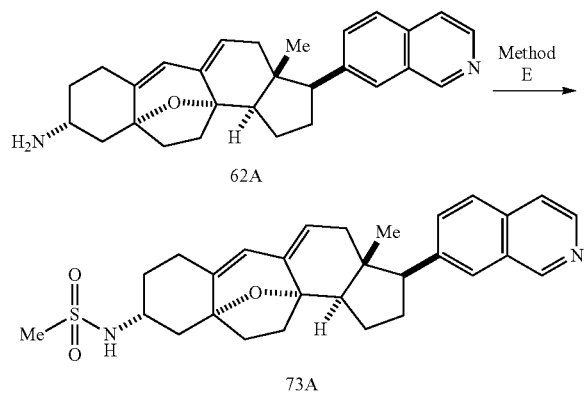

The crude mixture was purified by preparative TLC (silica gel, eluent: 40:1 MeOH:Dichloromethane) to afford α-methylsulfonamide 73A (2.0 mg, 82%). $^1$H NMR (500 MHz, CDCl$_3$) Shift=9.24 (br. s., 1H), 8.51 (d, J=4.9 Hz, 1H), 7.80 (s, 1H), 7.77 (d, J=8.3 Hz, 1H), 7.64 (d, J=5.9 Hz, 1H), 7.60 (dd, J=1.5, 8.3 Hz, 1H), 5.78 (d, J=1.5 Hz, 1H), 5.36-5.29 (m, 1H), 4.24 (d, J=7.8 Hz, 1H), 3.53 (tdt, J=3.9, 7.7, 11.7 Hz, 1H), 3.20-3.11 (m, J=10.7 Hz, 1H), 3.04 (s, 3H), 2.51 (dd, J=8.3, 11.7 Hz, 1H), 2.37 (d, J=16.6 Hz, 3H), 2.28 (br. s., 2H), 2.25-2.10 (m, 4H), 2.10-2.00 (m, 1H), 1.96 (dd, J=5.4, 17.6 Hz, 1H), 1.88 (dt, J=5.4, 11.7 Hz, 1H), 1.85 (t, J=12.2 Hz, 1H), 1.80-1.66 (m, 2H), 1.47-1.35 (m, J=4.4 Hz, 1H), 0.55 (s, 3H); HRMS (ESI) (m/z) calc'd for $C_{29}H_{35}N_2O_3S$ $[M+H]^+$: 491.2363, found 491.2387.

β-methylsulfonamide 73B

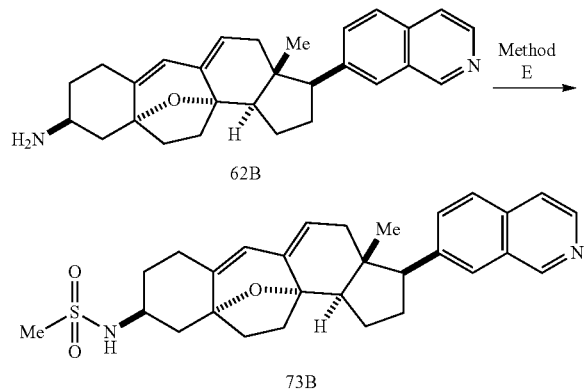

The crude mixture was purified by preparative TLC (silica gel, eluent: 40:1 MeOH:Dichloromethane) to afford β-methylsulfonamide 73B (1.7 mg, 90%). $^1$H NMR (500 MHz, CDCl$_3$) Shift=9.24 (s, 1H), 8.50 (d, J=5.9 Hz, 1H), 7.80 (s, 1H), 7.78 (d, J=8.8 Hz, 1H), 7.64 (d, J=5.9 Hz, 1H), 7.60 (dd, J=1.5, 8.3 Hz, 1H), 5.79 (d, J=1.5 Hz, 1H), 5.35-5.30 (m, 1H), 4.31 (d, J=6.3 Hz, 1H), 4.00 (quind, J=3.6, 6.7 Hz, 1H), 3.16 (dd, J=9.0, 10.5 Hz, 1H), 3.03 (s, 3H), 2.52 (dd, J=8.5, 11.5 Hz, 1H), 2.41 (t, J=16.1 Hz, 1H), 2.39 (br. s., 2H), 2.32-2.26 (m, 2H), 2.26-2.14 (m, 3H), 2.12-1.99 (m, 2H), 1.96 (dd, J=5.1, 17.3 Hz, 2H), 1.86 (dq, J=5.4, 12.2 Hz, 1H), 1.83-1.72 (m, 3H), 0.56 (s, 3H); HRMS (ESI) (m/z) calc'd for $C_{29}H_{35}N_2O_3S$ $[M+H]^+$: 491.2363, found 491.2376.

α-methyl-methylsulfonamide 76A

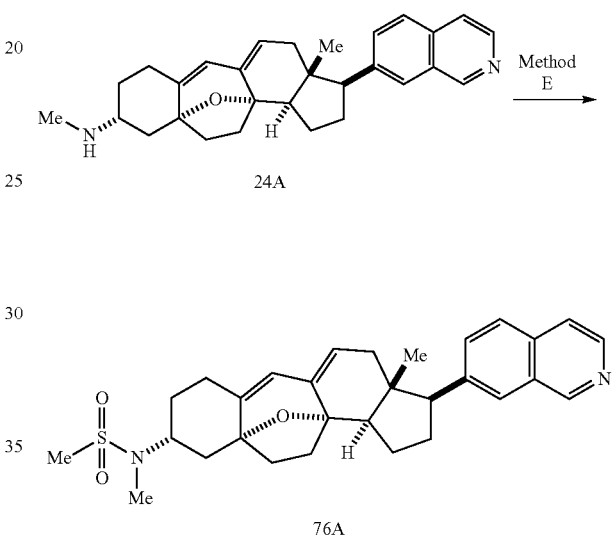

The crude mixture was purified by preparative TLC (silica gel, eluent: 40:1 MeOH:Dichloromethane) to afford α-methyl-methylsulfonamide 76A (0.7 mg, 57%). $^1$H NMR (500 MHz, CDCl$_3$) Shift=9.24 (s, 1H), 8.51 (d, J=5.9 Hz, 1H), 7.81 (s, 1H), 7.78 (d, J=8.3 Hz, 1H), 7.64 (d, J=5.9 Hz, 1H), 7.60 (dd, J=1.5, 8.3 Hz, 1H), 5.79 (s, 1H), 5.33 (dd, J=2.2, 5.6 Hz, 1H), 3.98 (tt, J=3.4, 12.4 Hz, 1H), 3.16 (dd, J=9.0, 10.5 Hz, 1H), 2.89 (s, 3H), 2.80 (s, 3H), 2.52 (dd, J=8.5, 11.5 Hz, 1H), 2.44 (ddd, J=2.7, 4.1, 16.6 Hz, 1H), 2.36 (br. s., 3H), 2.28 (d, J=10.7 Hz, 2H), 2.21 (dq, J=4.9, 9.1 Hz, 1H), 2.14 (t, J=12.7 Hz, 1H), 2.10-2.00 (m, 0H), 1.97 (dd, J=5.4, 17.6 Hz, 1H), 1.93 (dd, J=2.9, 12.2 Hz, 1H), 1.88 (dd, J=5.4, 12.2 Hz, 1H), 1.87-1.81 (m, 1H), 1.80-1.60 (m, 3H), 0.56 (s, 3H). HRMS (ESI) (m/z) calc'd for $C_{30}H_{37}N_2O_3S$ $[M+H]^+$: 505.2519, found 505.2537.

Example 2. Another Possible Route from Isoquinoline Compound 10 to 12

A new route to isoquinoline 12 was designed. See Scheme 2-1 below. Triflation/Suzuki cross-coupling reaction was achieved on a similar substrate with the designated reagents shown in the figure. See, e.g., Nicolaou et al. *J. Am. Chem. Soc.* 2009, 131, 10587-10597.

197

Scheme 2-1.

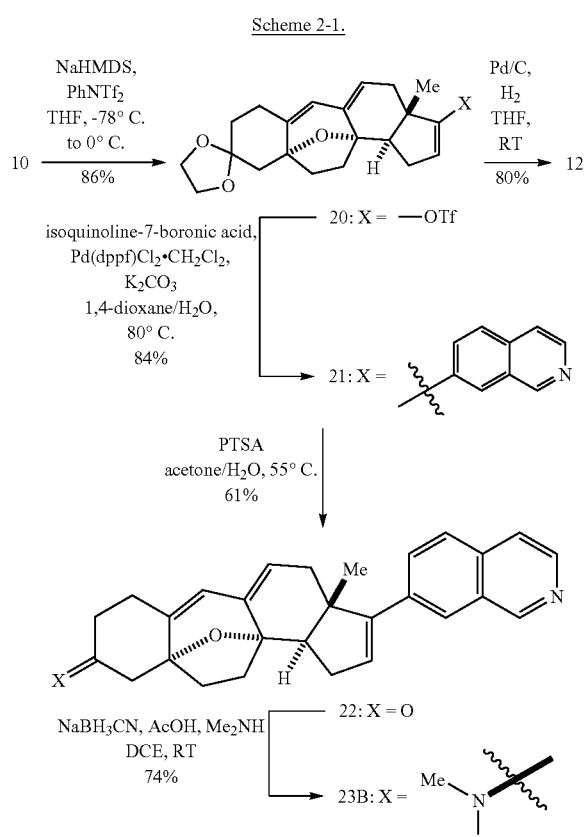

Synthesis of Triflate 20

To a solution of monoketone 10 (200 mg, 584 µmol, 1.00 equiv) in THF (4 mL) was added NaHMDS (1 M, 701 µL, 701 µmol, 1.20 equiv) at −78° C. dropwise. After stirring 1.5 h, PhNTf$_2$ (313 mg, 876 µmol, 1.50 equiv) in THF (2.5 mL) was cannulated and the reaction mixture was warmed up to 0° C. After additional 30 min, saturated NH$_4$Cl solution (8 mL) was added to the stirred reaction mixture and diluted with EtOAc (10 mL). The layers were separated and the aqueous layer was extracted with EtOAc (2×6 mL) and the organic layers were combined, washed with brine (15 mL), dried over Na$_2$SO$_4$, and concentrated under reduced pressure. The resulting residue was then purified by flash column chromatography (silica gel, eluent: 8:1→5:1 Hexanes:EtOAc) to provide triflate 20 (237 mg, 86%). $^1$H NMR (500 MHz, CDCl$_3$) Shift=5.76 (s, 1H), 5.67 (br. s., 1H), 5.32 (dd, J=2.0, 4.9 Hz, 1H), 4.02-3.94 (m, 4H), 2.67 (dd, J=6.8, 10.7 Hz, 1H), 2.49 (t, J=14.6 Hz, 1H), 2.45 (ddd, J=3.7, 6.5, 15.2 Hz, 1H), 2.38-2.28 (m, 4H), 2.17 (ddd, J=1.5, 10.7, 12.7 Hz, 1H), 2.12 (d, J=13.2 Hz, 1H), 2.10 (dd, J=5.9, 17.6 Hz, 1H), 1.98 (dd, J=2.7, 13.4 Hz, 1H), 1.88 (ddd, J=7.6, 8.9, 12.8 Hz, 1H), 1.80 (tdd, J=2.4, 4.8, 12.7 Hz, 1H), 1.74-1.63 (m, 2H), 1.03 (s, 3H). HRMS (ESI) (m/z) calc'd for C$_{22}$H$_{26}$O$_6$F$_3$S [M+H]$^+$: 475.1397, found 475.1411.

Synthesis of Suzuki Cross-Coupling for 17,18-Unsaturated Isoquinoline 21 from Triflate 20

To a solution of triflate 20 (1.00 equiv) and isoquinoline-7-boronic acid (3.00 equiv) in 1,4-dioxane and H$_2$O (10:1, 0.02M) was added K$_2$CO$_3$ (3.00 equiv) and the solution was

198 bubbled through inert Ar for 5 min. Pd(dppf)Cl$_2$.CH$_2$Cl$_2$ (0.05 equiv) was added and the reaction mixture was stirred at 80° C. for 1 h. The mixture was allowed to cool to room temperature and saturated NaHCO$_3$ solution was applied. The mixture was diluted with EtOAc and the layers were separated. The aqueous layer was extracted with EtOAc and the combined organic layers were washed with brine dried over Na$_2$SO$_4$, and concentrated under reduced pressure.

The crude mixture was purified by flash column chromatography (silica gel, eluent: 2:1→1:1→1:2 Hexanes:EtOAc) to provide 17,18-unsaturated isoquinoline 21 (490 mg, 84%). $^1$H NMR (500 MHz, CDCl$_3$) Shift=9.23 (s, 1H), 8.49 (d, J=5.4 Hz, 1H), 7.94 (s, 1H), 7.85-7.81 (m, 1H), 7.80-7.75 (m, 1H), 7.63 (d, J=5.4 Hz, 1H), 6.26 (br. s., 1H), 5.82 (s, 1H), 5.40 (d, J=3.4 Hz, 1H), 4.08-3.90 (m, 4H), 2.76 (dd, J=7.1, 11.0 Hz, 1H), 2.58 (dt, J=5.4, 17.6 Hz, 1H), 2.56-2.40 (m, 3H), 2.40-2.28 (m, 4H), 2.16 (d, J=13.2 Hz, 1H), 2.02 (dd, J=2.0, 13.2 Hz, 1H), 1.94 (td, J=8.8, 13.2 Hz, 1H), 1.81 (td, J=2.0, 12.7 Hz, 1H), 1.76-1.67 (m, 2H), 1.18 (s, 3H). HRMS (ESI) (m/z) calc'd for C$_{30}$H$_{32}$NO$_3$ [M+H]$^+$: 454.2377, found 454.2366.

Synthesis of Isoquinoline 12 from 17,18-Unsaturated Isoquinoline 21

To a solution of 17,18-unsaturated isoquinoline 21 (400 mg, 877 µmol, 1.0 equiv) in THF (36 mL) was added 10 wt % Pd/C (280 mg, 263 µmol, 0.30 equiv) and H$_2$ balloon was installed. After 3 h, the reaction mixture was filtered through a pad of celite and washed with 0.2 M NH$_3$ solution in MeOH (40 mL), concentrated under reduced pressure. The residue was purified by flash column chromatography (silica gel, eluent: 1:1→1:2 Hexanes:EtOAc) to provide isoquinoline 12 (325 mg, 80%). Spectral data was consistent with isoquinoline 12 constructed from 1-chloroisoquinoline adduct 11.

Example 3. Synthesis of Isoquinoline Analogs

Scheme 3-1.

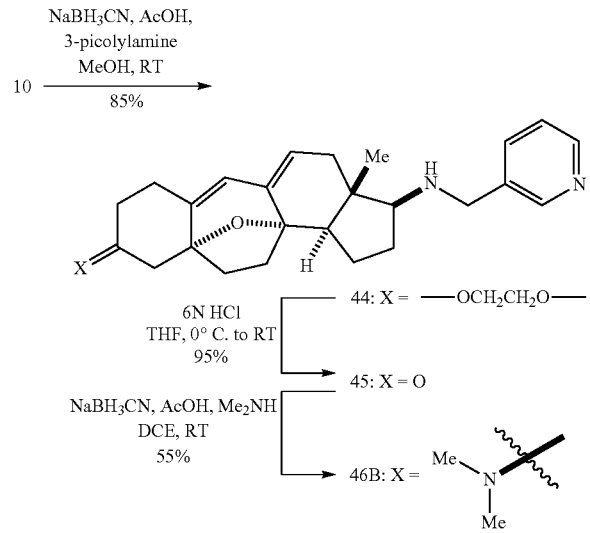

Scheme 3-2.
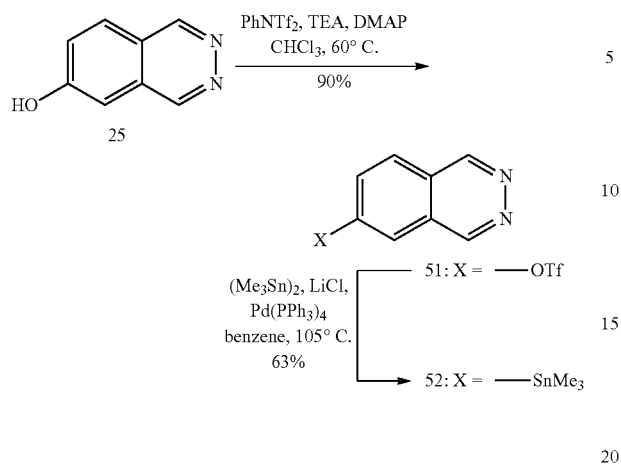
Scheme 3-3.
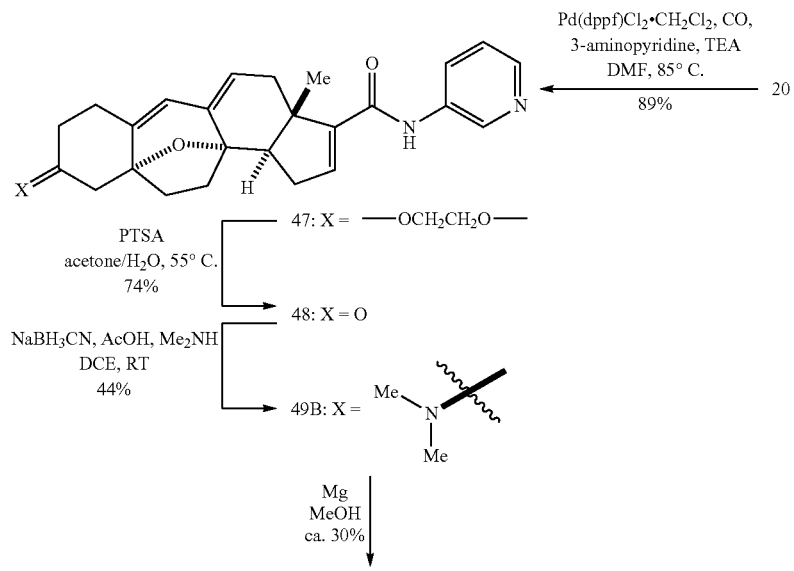
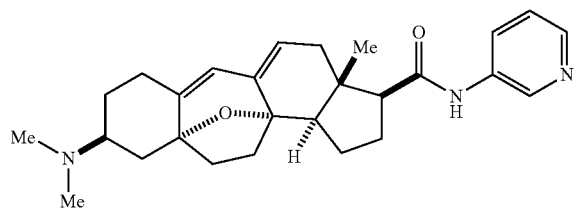
50B

Scheme 3-4.

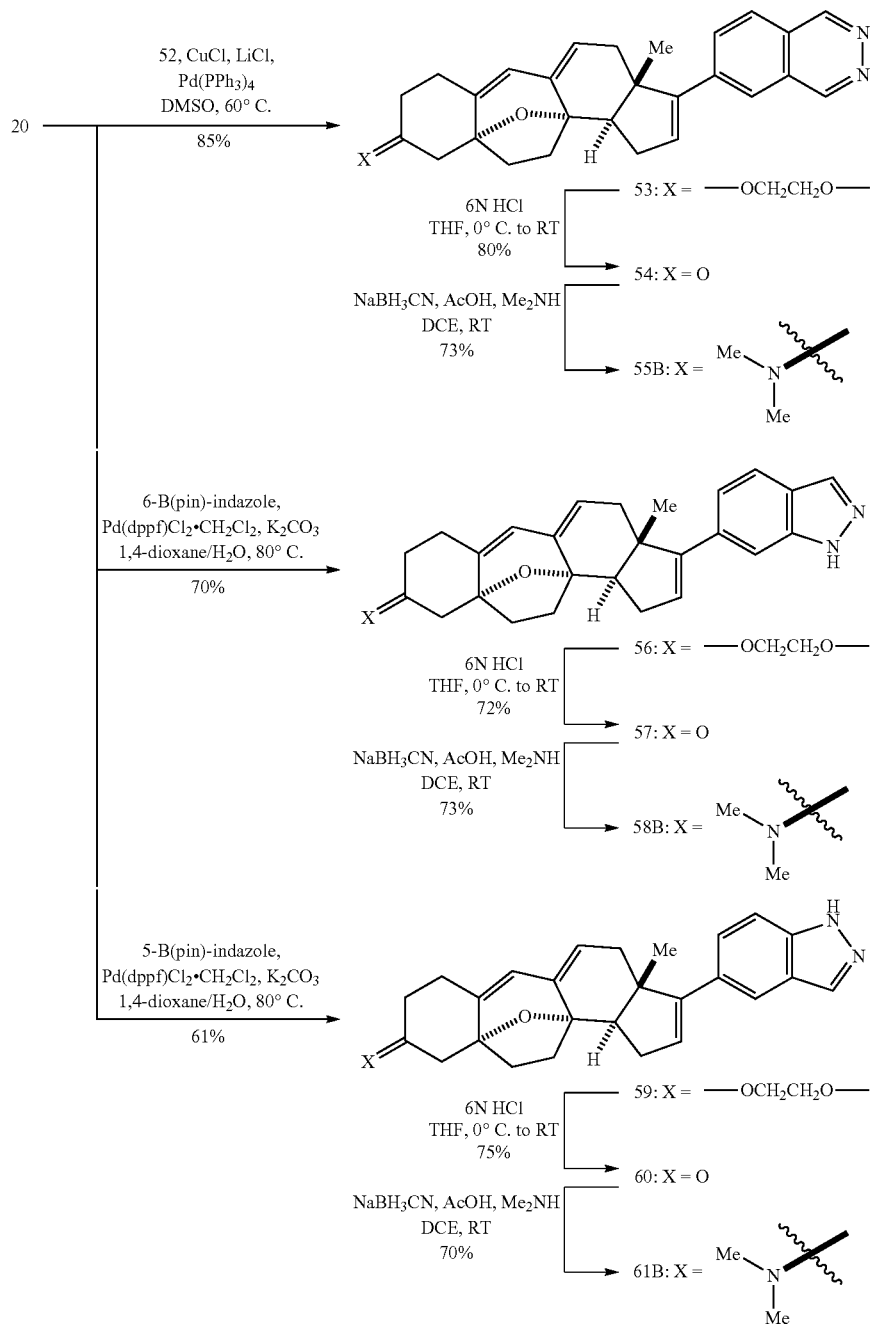

Suzuki Cross-Coupling for 17,18-Unsaturated 5-Indazole 56 from Triflate 20

To a solution of triflate 20 (1.00 equiv) and indazole-5-boronic ester (3.00 equiv) in 1,4-dioxane and H$_2$O (10:1, 0.02M) was added K$_2$CO$_3$ (3.00 equiv) and the solution was bubbled through inert Ar for 5 min. Pd(dppf)Cl$_2$.CH$_2$Cl$_2$ (0.05 equiv) was added and the reaction mixture was stirred at 80° C. for 1 h. The mixture was allowed to cool to room temperature and saturated NaHCO$_3$ solution was applied. The mixture was diluted with EtOAc and the layers were separated. The aqueous layer was extracted with EtOAc and the combined organic layers were washed with brine dried over Na$_2$SO$_4$, and concentrated under reduced pressure.

The crude mixture was purified by flash column chromatography (silica gel, eluent: 1:3→1:1 EtOAc:Hexanes) to afford 17,18-unsaturated 6-indazole 56 (13 mg, 70%). $^1$H NMR (500 MHz, CDCl$_3$) Shift=8.04 (s, 1H), 7.67 (d, J=10.0 Hz, 1H), 7.49 (s, 1H), 7.27 (d, J=10.0 Hz, 1H), 6.12 (br. s., 1H), 5.78 (br. s., 1H), 5.36 (t, J=5.0 Hz, 1H), 3.99 (m, 4H), 2.72 (m, 1H), 2.53-2.44 (m, 3H), 2.40 (br. d., J=10.0 Hz, 1H), 2.36-2.25 (m, 4H), 2.14 (d, J=10.0 Hz, 1H), 2.00 (dd, J=10.0, 5.0 Hz, 1H), 1.93-1.87 (m, 1H), 1.79 (m, 1H), 1.72-1.66 (m, 2H), 1.10 (s, 3H). HRMS (ESI) (m/z) calc'd for $C_{28}H_{31}N_2O_3$ [M+H]$^+$: 443.5573, found 443.5571.

Suzuki Cross-Coupling for 17,18-Unsaturated 6-Indazole 59 from Triflate 20

To a solution of triflate 20 (1.00 equiv) and indazole-6-boronic ester (3.00 equiv) in 1,4-dioxane and $H_2O$ (10:1, 0.02M) was added $K_2CO_3$ (3.00 equiv) and the solution was bubbled through inert Ar for 5 min. Pd(dppf)Cl$_2$—CH$_2$Cl$_2$ (0.05 equiv) was added and the reaction mixture was stirred at 80° C. for 1 h. The mixture was allowed to cool to room temperature and saturated NaHCO$_3$ solution was applied. The mixture was diluted with EtOAc and the layers were separated. The aqueous layer was extracted with EtOAc and the combined organic layers were washed with brine dried over Na$_2$SO$_4$, and concentrated under reduced pressure.

The crude mixture was purified by flash column chromatography (silica gel, eluent: 1:4→3:1 EtOAc:Hexanes) to afford 17,18-unsaturated 5-indazole 59 (5.9 mg, 65%). $^1$H NMR (500 MHz, CDCl$_3$) Shift=10.04 (br s, 1H), 8.05 (s, 1H), 7.75 (s, 1H), 7.46 (ABq, J$_{AB}$=8.8 Hz, Δv=33.5 Hz, 2H), 6.02 (s, 1H), 5.79 (s, 1H), 5.38 (dd, J=3.4, 3.4 Hz, 1H), 3.94-4.01 (m, 4H), 2.73 (dd, J=10.7, 6.8 Hz, 1H), 2.44-2.53 (m, 3H), 2.40 (d, 12.2 Hz, 1H), 2.28-2.36 (m, 3H), 2.15 (d, J=13.2 Hz, 1H), 2.03 (par obs d, J=11.2 Hz, 1H), 2.01 (par obs dd, J=13.2, 2.4 Hz, 1H), 1.91 (dt, J=12.21, 9.3 Hz, 1H), 1.77-1.82 (m, 1H), 1.66-1.73 (m, 2H), 1.10 (s, 3H). HRMS (ESI) (m/z) calc'd for $C_{28}H_{31}N_2O_3$ [M+H]$^+$: 443.2335, found 443.4956.

β-Dimethylamine Aminomethylpyridine 46B and α-Dimethylamine Aminomethylpyridine 46A

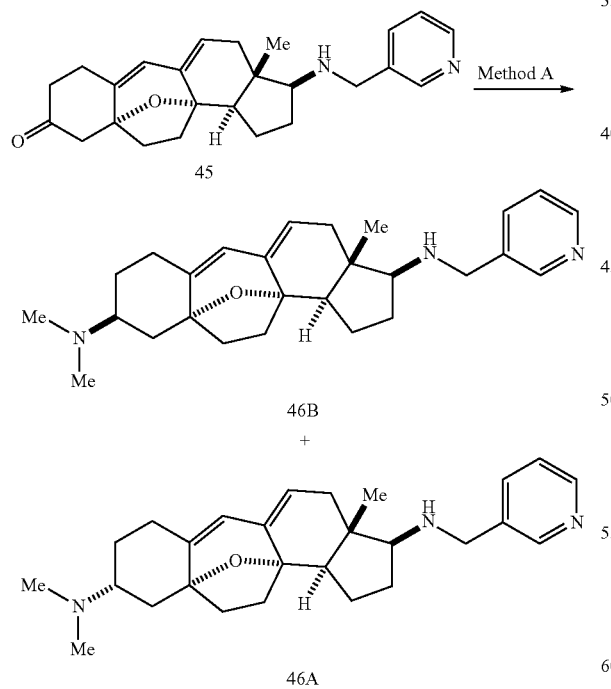

β-Dimethylamine Aminomethylpyridine 46B

The crude mixture was purified by flash chromatography (silica gel, eluent: 10:1 EtOAc:2M NH$_3$ solution in MeOH) to afford β-dimethylamine aminomethylpyridine 46B (5 mg, 55%). $^1$H NMR (500 MHz, CDCl$_3$) Shift=8.58 (s, 1H), 8.51 (dd, J=1.5, 4.9 Hz, 1H), 7.71 (td, J=2.0, 7.8 Hz, 1H), 7.26 (dd, J=4.9, 7.8 Hz, 1H), 5.71 (s, 1H), 5.24 (dd, J=2.4, 4.4 Hz, 1H), 3.88-3.80 (m, 2H), 2.81 (t, J=9.0 Hz, 1H), 2.45 (dt, J=6.3, 13.7 Hz, 1H), 2.46-2.37 (m, 1H), 2.30 (br. s., 6H), 2.26-2.19 (m, 3H), 2.17-2.07 (m, 5H), 1.92 (dd, J=2.9, 13.7 Hz, 2H), 1.79 (dddd, J=4.9, 8.3, 10.3, 13.2 Hz, 1H), 1.74-1.59 (m, 4H), 1.39 (ddt, J=4.4, 9.8, 12.7 Hz, 1H), 0.80 (s, 3H). HRMS (ESI) (m/z) calc'd for $C_{27}H_{38}N_3O$ [M+H]$^+$: 420.3009, found 420.2999.

β-Dimethylamine 17,18-unsaturated Amidepyridine 49B and α-Dimethylamine 17,18-unsaturated Amidepyridine 49A

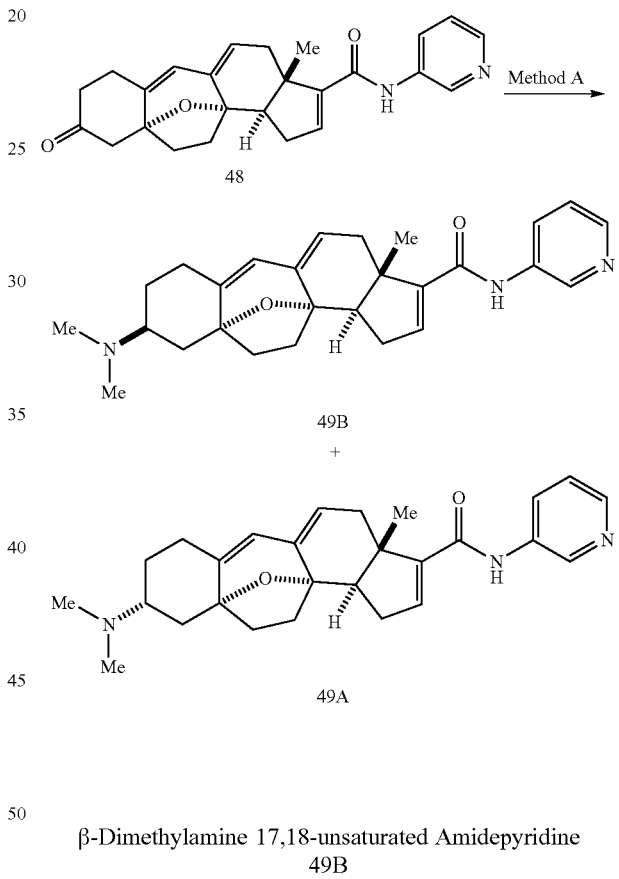

β-Dimethylamine 17,18-unsaturated Amidepyridine 49B

The crude mixture was purified by flash chromatography (silica gel, eluent: 8:1 EtOAc:2M NH$_3$ solution in MeOH) to afford β-dimethylamine 17,18-unsaturated amidepyridine 49B (2.1 mg, 44%). $^1$H NMR (500 MHz, CDCl$_3$) Shift=8.58 (d, J=2.4 Hz, 1H), 8.36 (dd, J=1.0, 4.9 Hz, 1H), 8.23 (td, J=2.0, 8.3 Hz, 1H), 7.49 (s, 1H), 7.29 (dd, J=4.9, 8.8 Hz, 1H), 6.57 (br. s., 1H), 5.73 (s, 1H), 5.33 (dd, J=2.0, 5.4 Hz, 1H), 2.66-2.56 (m, 2H), 2.54 (dd, J=3.2, 6.6 Hz, 1H), 2.51-2.32 (m, 5H), 2.28 (br. s., 6H), 2.20 (ddd, J=1.2, 11.0, 12.7 Hz, 1H), 2.10 (td, J=6.4, 13.1 Hz, 2H), 1.97-1.89 (m, 3H), 1.76 (dt, J=7.8, 11.2 Hz, 1H), 1.66-1.55 (m, 1H), 1.14 (s, 3H). HRMS (ESI) (m/z) calc'd for $C_{27}H_{34}N_3O_2$ [M+H]$^+$: 432.2646, found 432.2649.

β-Dimethylamine 17,18-unsaturated Phthalazine 55B and α-Dimethylamine 17,18-unsaturated Phthalazine 55A

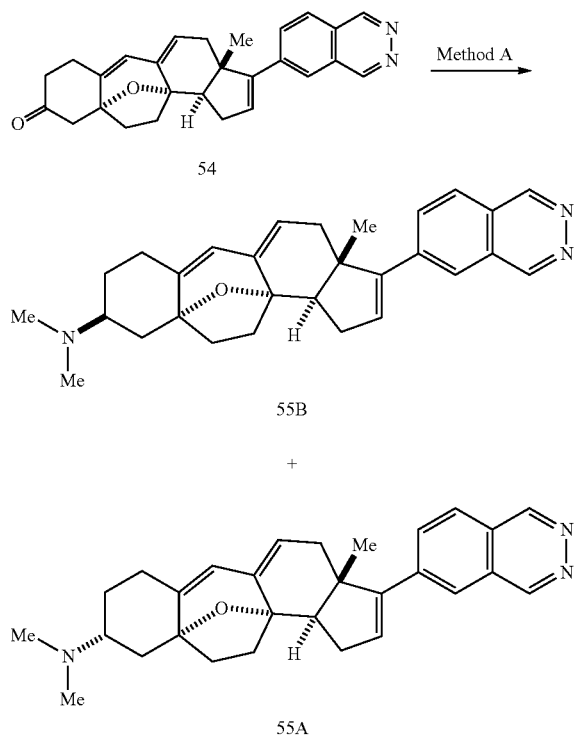

β-Dimethylamine 17,18-unsaturated Phthalazine 55B

The crude mixture was purified by flash chromatography (silica gel, eluent: 9:1 EtOAc:2M NH₃ solution in MeOH) to afford β-dimethylamine 17,18-unsaturated phthalazine 55B (5.5 mg, 73%). H NMR (500 MHz, CDCl₃) Shift=9.50 (s, 2H), 7.97-8.03 (m, 1H), 7.89 (d, J=4.39 Hz, 2H), 6.34-6.39 (m, 1H), 5.77-5.83 (m, 1H), 5.32-5.43 (m, 1H), 2.72 (dd, J=11.23, 6.84 Hz, 1H), 2.38-2.50 (m, 4H), 2.47 (br. m., 6H), 2.24-2.30 (m, 3H), 2.09-2.20 (m, 2H), 2.03 (d, J=10.25 Hz, 2H), 1.88-1.99 (m, 2H), 1.75-1.86 (m, 2H), 1.17 (s, 3H). HRMS (ESI) (m/z) calc'd for $C_{28}H_{33}N_3O$ [M+H]⁺: 440.5998, found 440.5995.

β-Dimethylamine 17,18-unsaturated 6-indazole 58B and α-Dimethylamine 17,18-unsaturated 6-indazole 58A

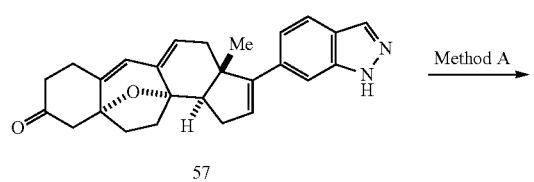

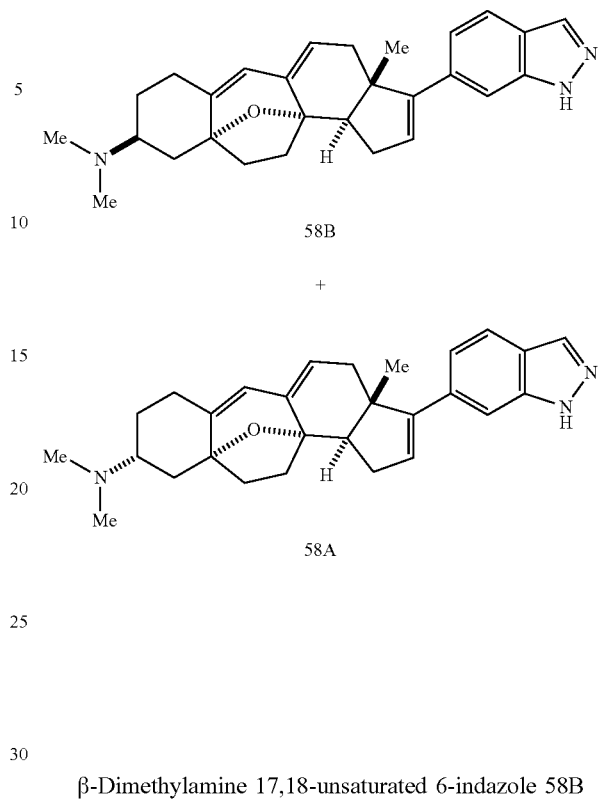

β-Dimethylamine 17,18-unsaturated 6-indazole 58B

The crude mixture was purified by flash chromatography (silica gel, eluent: 9:1 EtOAc: 2M NH₃ solution in MeOH) to afford β-dimethylamine 17,18-unsaturated 6-indazole 58B (3.9 mg, 73%). ¹H NMR (500 MHz, CDCl₃) Shift=8.03 (s, 1H), 7.67 (d, J=8.30 Hz, 1H), 7.49 (s, 1H), 7.25-7.28 (i, 1H), 6.12 (t, J=2.44 Hz, 1H), 5.75 (s, 1H), 5.33 (t, J=3.42 Hz, 1H), 3.22-3.38 (m, 1H), 2.71 (dd, J=11.23, 6.84 Hz, 1H), 2.44-2.50 (m, 4H), 2.41 (br. m., 6H), 2.22-2.31 (m, 3H), 2.09-2.20 (m, 2H), 2.04 (d, J=2.93 Hz, 2H), 1.78 (td, J=11.35, 7.08 Hz, 2H), 1.52-1.64 (m, 1H), 1.07-1.15 (s, 3H). HRMS (ESI) (m/z) calc'd for $C_{28}H_{33}N_3O$ [M+H]⁺: 428.5891, found 428.5889.

β-Dimethylamine 17,18-unsaturated 5-indazole 61B and α-Dimethylamine 17,18-unsaturated 5-indazole 61A

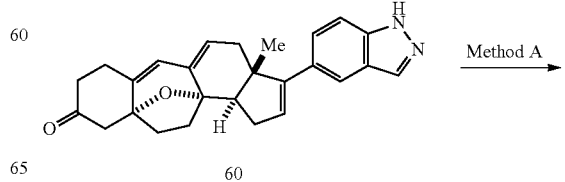

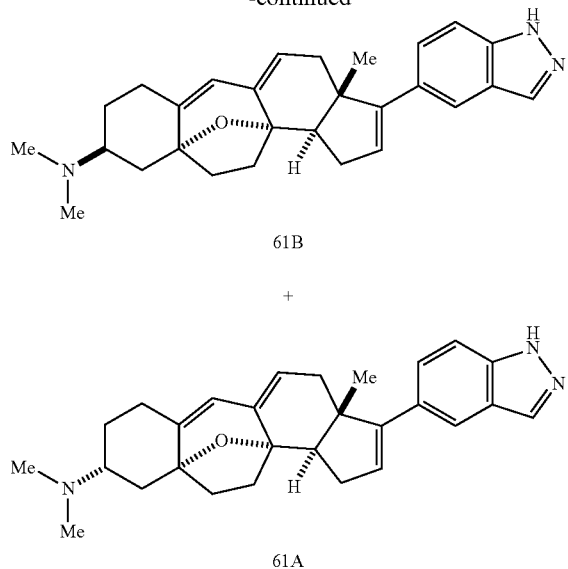

β-Dimethylamine 17,18-unsaturated 5-indazole 61B

The crude mixture was purified by flash column chromatography (silica gel, eluent: 9:1 EtOAc:2M NH₃ solution in MeOH) to afford β-dimethylamine 17,18-unsaturated 5-indazole 61B (2.5 mg, 70%). $^1$H NMR (500 MHz, CDCl₃) Shift=8.05 (s, 1H), 7.75 (s, 1H), 7.47 (ABq, $J_{AB}$=8.8 Hz, Δν=33.5 Hz, 2H), 6.02 (dd, J=2.0, 2.0 Hz, 1H), 5.74 (s, 1H), 5.33 (dd, J=3.4, 3.4 Hz, 1H), 2.72 (dd, J=11.2, 6.8 Hz, 1H), 2.43-2.48 (m, 5H), 2.37-2.41 (m, 2H), 2.26-2.35 (m, 8H), 2.11 (m, 2H), 2.04 (d, J=6.8 Hz, 1H), 1.88-1.98 (m, 3H), 1.77 (m, 1H), 1.10 (s, 3H). HRMS (ESI) (m/z) calc'd for C₂₈H₃₄N₃O [M+H]⁺: 428.2702, found 428.2653.

Synthesis of β-Dimethylamine Amidepyridine 50B

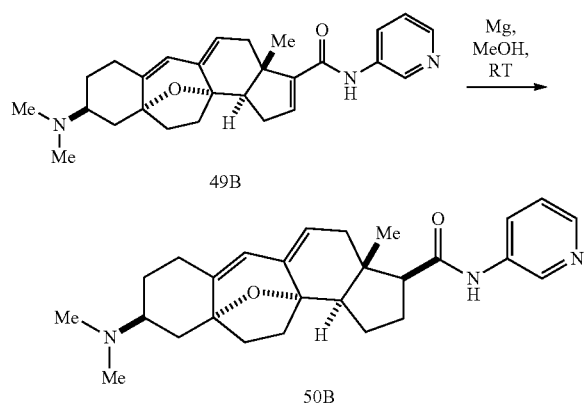

To a solution of β-dimethylamine 17,18-unsaturated amidepyridine 49B (ca. 1.2 mg) in MeOH (300 μL) was added Mg (ca. 1 mg) and stirred at room temperature for 48 h. The reaction mixture was added H₂O (700 μL) and diluted with EtOAc (700 μL). The aqueous phase was extracted with EtOAc (2×0.5 mL) and the combined organic phases were washed with brine (0.5 mL), dried over Na₂SO₄, and concentrated under reduced pressure. The residue was purified by HPLC (Eclipse XDB-C₈ column, 9.4 mm×25 cm; gradient=0%→35% MeCN (0.1% formic acid):H₂O (0.1% formic acid) over 30 min) to provide β-dimethylamine amidepyridine 50B (ca. 0.3 mg, 25%). Due too the small quantity, only diagnostic peaks were assigned. $^1$H NMR (500 MHz, CDCl₃) Shift=8.56 (br. s, 1H), 8.37 (d, J=3.4 Hz, 1H), 8.21 (d, J=8.3 Hz, 1H), 7.09 (br. s., 1H), 5.81 (s, 1H), 5.39-5.33 (m, 1H), 2.78 (br. s., 6H), 0.83 (s, 3H). HRMS (ESI) (m/z) calc'd for C₂₇H₃₅N₃O₂ [M+H]⁺: 434.2802, found 434.2815.

Synthesis of Phthalazine 6-triflate 51

To a solution of 6-phthalazinol (588.4 mg, 4.26 mmol, 1.0 equiv) in CHCl₃ was added N-Phenyl-bis(trifluoromethanesulfonimide) (1.73 g, 4.83 mmol, 1.2 equiv), Et₃N (0.9 mL, 6.04 mmol, 1.5 equiv) and DMAP (cat.). The mixture was warmed to 60° C. and stirred for 3 h. The reaction was cooled to room temperature and quenched with sat. NaHCO₃ and CH₂Cl₂ and the layers were separated. The aqueous layer was extracted with CH₂Cl₂. The organic layers were combined dried over Na₂SO₄ and concentrated under reduced pressure. The crude mixture was purified by flash column chromatography (silica gel, eluent: 9:1 Dichloromethane:MeOH) to afford phthalazine 6-triflate 51 (995 mg, 90%). $^1$H NMR (500 MHz, CDCl₃) Shift=9.68 (d, J=3.91 Hz, 2H) 8.19 (d, J=8.79 Hz, 1H) 7.96 (br. s., 1H) 7.84-7.89 (m, 1H). HRMS (ESI) (m/z) calc'd for C₉H₆F₃N₂O₃S [M+H]⁺: 279.2157, found 279.2152.

Synthesis of Phthalazine 6-trimethyltin 52

To a solution of phthalazine 6-triflate 52 (992 mg, 3.57 mmol, 1.0 equiv) in C₆H₆ was added LiCl (907 mg, 21.59 mmol, 6.0 equiv), Pd(PPh₃)₄ (412 mg, 0.3565 mmol, 0.1 equiv) and (Me₃Sn)₂ (0.78 mL, 3.743 mmol, 1.05 equiv). The solution was bubbled with argon in a sonicator for 10 mins and the mixture was warmed to 105° C. and stirred for 1 h. The reaction was cooled to rt, diluted with ethyl acetate and filtered over celite. The organic portion was washed with sat NaHCO₃ and dried over Na₂SO₄ and then concentrated under reduced pressure. The crude mixture was purified by flash column chromatography (silica gel, eluent: 1:1 EtOAc:Hexanes) to afford phthalazine 6-trimethyltin 52 (656 mg, 63%). $^1$H NMR (500 MHz, CDCl₃) Shift=9.54 (d, J=4.39 Hz, 2H) 8.12 (br. s., 1H) 8.08 (d, J=7.81 Hz, 1H) 7.92 (d, J=7.81 Hz, 1H) 0.43 (s, 9H). HRMS (ESI) (m/z) calc'd for C₁₁H₁₅N₂Sn [M+H]⁺: 293.9602, found 293.9601.

Synthesis of 17,18-Unsaturated phthalazine 53

To a solution of triflate 20 (20 mg, 42.15 μmol, 1.0 equiv) in DMSO was added (trimethylstannyl)phthalazine 52 (31 mg, 105.40 μmol, 2.0 equiv), CuCl (42 mg, 421.50 μmol, 10.0 equiv) and LiCl (18 mg, 421.50 μmol, 10.0 equiv). The mixture was deoxygenated by freeze-thaw method four times and Pd(PPh₃) (5 mg, 4.22 μmol, 0.1 equiv) was added. The mixture was heated to 60° C. and stir 1 h. The reaction was quenched with 5% NH₄OH and ethyl acetate and the layers were separated. The aqueous layer was extracted with ethyl acetate. The organic layers were combined, washed with brine, dried over Na₂SO₄ and concentrated under reduced pressure. The crude mixture was purified by flash chromatography (silica gel, eluent: 1:4→1:1→3:1 EtOAc:Hexanes) to afford 17,18-unsaturated phthalazine 53 (16.3 mg, 85%). $^1$H NMR (500 MHz, CDCl₃) Shift=9.51 (d, J=5.0

Hz, 2H) 8.02 (d, J=5.0 Hz, 1H), 7.91 (s, 1H), 7.90 (d, J=5.0 Hz, 1H), 6.37 (br. s., 1H), 5.80 (br. s., 1H), 5.37 (br. m., 1H), 3.98 (m, 4H), 2.75 (m, 1H), 2.59-2.52 (m, 2H), 2.50-2.42 (m, 3H), 2.37-2.26 (m, 3H), 2.14 (d, J=15.0 Hz, 1H), 2.00 (dd, J=15.0, 2.5 Hz, 1H), 1.93 (m, 1H), 1.79 (m, 1H), 1.72-1.66 (m, 2H), 1.16 (s, 3H). HRMS (ESI) (m/z) calc'd for $C_{29}H_{31}N_2O_3$ [M+H]$^+$: 455.5680, found 455.5679.

Synthesis of 17,18-Unsaturated Amidepyridine 47

To a solution of triflate 20 (20 mg, 42.1 µmol, 1.0 equiv) and 3-aminopyridine (19.8 mg, 210 µmol, 5.0 equiv) in DMF (1 mL) was added triethylamine (12 µL, 84.3 µmol, 2.0 equiv) and Pd(dppf)Cl$_2$.CH$_2$Cl$_2$ (1.72 mg, 2.10 µmol, 0.05 equiv). Reaction flask was installed with CO balloon and the solution was purged for 5 min at room temperature. Then, the reaction mixture was heated up to 85° C. and stirred for 4 h. The mixture was allowed to cool to room temperature and EtOAc (3 mL) and H$_2$O was added. The layers were separated and the aqueous layer was extracted with EtOAc (3×2 mL), and the combined organic layers were washed with brine (3 mL), dried over Na$_2$SO$_4$, and concentrated under reduced pressure. The crude mixture was purified by flash column chromatography (silica gel, eluent: 10:10:1→10:10:2 Hexanes:EtOAc:MeOH) to provide 17,18-unsaturated amidepyridine 47 (17 mg, 89%). $^1$H NMR (500 MHz, CDCl$_3$) Shift=8.57 (d, J=2.4 Hz, 1H), 8.33 (dd, J=1.2, 4.6 Hz, 1H), 8.20 (d, J=8.3 Hz, 1H), 7.70 (s, 1H), 7.26 (dd, J=4.9, 7.8 Hz, 1H), 6.55 (br. s., 1H), 5.77 (s, 1H), 5.36 (d, J=2.9 Hz, 1H), 4.03-3.89 (m, 4H), 2.63-2.56 (m, 2H), 2.52 (ddd, J=2.9, 7.3, 17.1 Hz, 1H), 2.52-2.37 (m, 3H), 2.36-2.27 (m, 2H), 2.20 (t, J=12.2 Hz, 1H), 2.12 (d, J=13.2 Hz, 1H), 1.97 (dd, J=2.2, 12.9 Hz, 1H), 1.89 (td, J=8.8, 13.2 Hz, 1H), 1.78 (tdd, J=2.4, 4.8, 12.8 Hz, 1H), 1.71-1.62 (m, 2H), 1.11 (s, 3H). HRMS (ESI) (m/z) calc'd for $C_{27}H_{31}N_2O_4$ [M+H]$^+$: 447.2278, found 447.2289.

Example 4. General Method for Synthesis of Ketones

To a solution of ketal in THF at 0° C. was added 6N HCl (THF:6N HCl=1:1, 0.05M). The mixture was warmed to room temperature and stirred for 1 h. The reaction was quenched with 6 N NaOH and ethyl acetate and the layers were separated. The aqueous layer was extracted with ethyl acetate. The organic layers were combined dried over Na$_2$SO$_4$ and concentrated under reduced pressure.

Synthesis of Ketone 45

The crude mixture was purified by flash column chromatography (silica gel, eluent: 15:1 Dichloromethane:MeOH) to afford ketone 45 (8.5 mg, 95%). $^1$H NMR (500 MHz, CDCl$_3$) Shift=8.60 (s, 1H), 8.52 (d, J=3.9 Hz, 1H), 7.74 (br. s., 1H), 7.28 (dd, J=4.4, 8.3 Hz, 1H), 5.91 (s, 1H), 5.37 (dd, J=2.7, 4.6 Hz, 1H), 3.88 (d, J=13.7 Hz, 1H), 3.84 (d, J=13.7 Hz, 1H), 2.91 (d, J=14.6 Hz, 1H), 2.82 (t, J=9.0 Hz, 1H), 2.65 (d, J=15.1 Hz, 1H), 2.64 (dd, J=10.3, 14.6 Hz, 1H), 2.59-2.41 (m, 3H), 2.32-2.20 (m, 3H), 2.19-2.07 (m, 3H), 1.85-1.72 (m, 2H), 1.72-1.61 (m, 2H), 1.44 (br. s., 1H), 0.82 (s, 3H). HRMS (ESI) (m/z) calc'd for $C_{25}H_{31}N_2O_2$ [M+H]$^+$: 391.2380, found 391.2366.

Synthesis of Ketone 54

The crude mixture was purified by flash column chromatography (silica gel, eluent: 1:1 EtOAc:Hexanes) to afford ketone 54 (8.7 mg, 80%). $^1$H NMR (500 MHz, CDCl$_3$) Shift=9.54 (d, J=10.0 Hz, 2H) 8.04 (d, J=10.0 Hz, 1H), 7.93 (br. s., 2H), 6.40 (br. s., 1H), 5.95 (br. s., 1H), 5.47 (br. m., 1H), 2.95 (d, J=10.0 Hz, 1H), 2.77 (m, 1H), 2.71-2.62 (m, 2H), 2.59-2.44 (m, 7H), 2.34 (t, J=10.0 Hz, 1H), 2.19 (t, J=10.0 Hz, 1H), 2.00 (m, 1H), 1.78 (m, 1H), 1.18 (s, 3H). HRMS (ESI) (m/z) calc'd for $C_{27}H_{27}N_2O_2$ [M+H]$^+$: 411.5155, found 411.5152.

Synthesis of Ketone 57

The crude mixture was purified by flash column chromatography (silica gel, eluent: 1:1 EtOAc:Hexanes) to afford ketone 57 (13.7 mg, 72%). $^1$H NMR (500 MHz, CDCl$_3$) Shift=8.04 (br. s., 1H), 7.68 (d, J=10.0 Hz, 1H), 7.48 (br. s., 1H), 7.27 (d, J=10.0 Hz, 1H), 6.13 (br. s., 1H), 5.93 (br. s., 1H), 5.45 (br. t., J=5 Hz, 1H), 2.97 (d, J=15.0 Hz, 1H), 2.76-2.64 (m, 3H), 2.53-2.43 (m, 6H), 2.40-2.34 (m, 2H), 2.17 (t, J=10.0 Hz, 1H), 1.98 (m, 1H), 1.77 (m, 1H), 1.11 (s, 3H). HRMS (ESI) (m/z) calc'd for $C_{26}H_{27}N_2O_2$ [M+H]$^+$: 399.5048, found 399.5047.

Synthesis of Ketone 60

The crude mixture was purified by flash column chromatography (silica gel, eluent: 1:1→3:1 EtOAc:Hexanes, buffered with 2% triethylamine) to afford ketone 60 (3.3 mg, 68%). $^1$H NMR (500 MHz, CDCl$_3$) Shift=9.93-10.27 (br s, 1H), 8.06 (s, 1H), 7.75 (s, 1H), 7.47 (ABq, J$_{AB}$=8.8 Hz, Δν=29.5 Hz, 2H), 6.03 (dd, J=2.0, 2.0 Hz, 1H), 5.94 (s, 1H), 5.47 (dd, J=3.9, 3.9 Hz, 1H), 2.97 (d, J=15.1 Hz, 1H), 2.63-2.76 (m, 3H), 2.53-2.59 (m, 1H), 2.44-2.50 (m, 5H), 2.35-2.42 (m, 2H), 2.17 (dd, J=9.3, 9.3 Hz, 1H), 1.95-2.01 (m, 1H), 1.74-1.80 (m, 1H), 1.11 (s, 3H). HRMS (ESI) (m/z) calc'd for $C_{26}H_{27}N_2O_2$ [M+H]$^+$: 399.2073, found 399.2043.

Synthesis of Ketone 22

For the method, see 'Synthesis of Ketone 13'. The resulting residue was then purified by flash chromatography (silica gel, eluent: 3:2→1:2 Hexanes:EtOAc) to afford ketone 22 (8.2 mg, 61%). $^1$H NMR (500 MHz, CDCl$_3$) Shift=9.24 (br. s., 1H), 8.51 (d, J=5.4 Hz, 1H), 7.94 (s, 1H), 7.84-7.76 (m, 2H), 7.63 (d, J=5.4 Hz, 1H), 6.27 (br. s., 1H), 5.97 (s, 1H), 5.50 (dd, J=2.4, 4.9 Hz, 1H), 2.98 (d, J=14.6 Hz, 1H), 2.78 (dd, J=6.8, 11.2 Hz, 1H), 2.71 (d, J=14.6 Hz, 1H), 2.72-2.63 (m, 1H), 2.61 (d, J=5.4 Hz, 1H), 2.59-2.54 (m, 2H), 2.54-2.50 (m, 2H), 2.50-2.42 (m, 2H), 2.39 (ddd, J=1.5, 11.0, 12.9 Hz, 1H), 2.20 (ddd, J=1.5, 9.5, 11.5 Hz, 1H), 2.01 (ddd, J=7.3, 8.8, 12.7 Hz, 1H), 1.79 (dt, J=7.3, 11.2 Hz, 1H), 1.18 (s, 3H). HRMS (ESI) (m/z) calc'd for $C_{28}H_{28}NO_2$ [M+H]$^+$: 410.2115, found 410.2111.

Synthesis of Ketone 48

For the method, see 'Synthesis of Ketone 13'. The resulting residue was then purified by flash chromatography (silica gel, eluent: 20:10:3 Hexanes:EtOAc:2M NH$_3$ solution in MeOH) to afford ketone 48 (5.0 mg, 74%). $^1$H NMR (500 MHz, CDCl$_3$) Shift=8.60 (d, J=2.0 Hz, 1H), 8.37 (dd, J=1.0, 4.9 Hz, 1H), 8.24-8.20 (m, 1H), 7.55 (s, 1H), 7.30 (dd, J=4.9, 8.3 Hz, 1H), 6.57 (br. s., 1H), 5.94 (s, 1H), 5.48 (dd, J=2.2, 5.1 Hz, 1H), 2.95 (d, J=15.1 Hz, 1H), 2.69 (d, J=14.6 Hz, 1H), 2.68 (d, J=12.7 Hz, 1H), 2.66-2.61 (m, 2H), 2.61-2.53 (m, 2H), 2.52-2.44 (m, 3H), 2.41 (d, J=18.1 Hz, 1H), 2.29 (ddd, J=1.5, 11.1, 12.8 Hz, 1H), 2.22-2.15 (m, J=1.5, 9.4, 11.1 Hz, 1H), 1.98 (ddd, J=7.6, 9.0, 12.7 Hz, 1H), 1.76 (dt, J=7.3, 11.2 Hz, 1H), 1.14 (s, 3H). HRMS (ESI) (m/z) calc'd for $C_{25}H_{27}N_2O_3$ [M+H]$^+$:403.2016, found 403.2023.

Example 5. General Method for Synthesis of N-Oxides

To a solution of amine (1.00 equiv) in methanol (0.028 M) was added $H_2O_2$ (32.0 equiv) at room temperature. After 25 h, saturated NaHCO$_3$ solution was added, diluted with dichloromethane, and the layers were separated. The aqueous layer was extracted with dichloromethane. The organic layers were combined, washed with brine, dried over Na$_2$SO$_4$ and concentrated under reduced pressure.

Synthesis of 14B-N-oxide (14BNO)

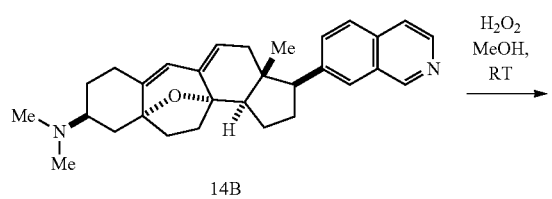

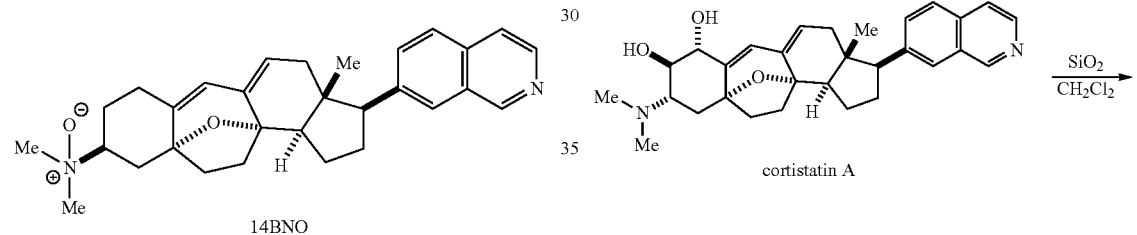

The crude mixture was purified by flash column chromatography (silica gel, eluent: 90:9:1→80:18:2 Chloroform:Methanol:5N NH$_4$OH solution in H$_2$O) to provide N-oxide 14BNO (23.5 mg, 95%). $^1$H NMR (500 MHz, CDCl$_3$) Shift=9.21 (s, 1H), 8.48 (d, J=5.9 Hz, 1H), 7.77 (s, 1H), 7.75 (d, J=8.3 Hz, 1H), 7.61 (d, J=5.9 Hz, 1H), 7.57 (dd, J=1.0, 8.8 Hz, 1H), 5.76 (s, 1H), 5.28 (d, J=2.9 Hz, 1H), 3.44-3.36 (m, 1H), 3.22 (s, 3H), 3.12 (t, J=10.8 Hz, 1H), 3.10 (d, J=1.0 Hz, 3H), 2.47 (dd, J=8.8, 11.2 Hz, 1H), 2.44-2.29 (m, 5H), 2.28-2.13 (m, 4H), 2.09 (ddd, J=1.5, 9.3, 11.2 Hz, 1H), 2.06-1.97 (m, 2H), 1.94 (dd, J=5.1, 17.4 Hz, 1H), 1.85 (dq, J=5.4, 12.2 Hz, 1H), 1.83-1.76 (m, 1H), 1.72 (td, J=9.3, 12.2 Hz, 1H), 0.54 (s, 3H). HRMS (ESI) (m z) calc'd for $C_{30}H_{37}N_2O_2$ [M+H]$^+$:457.2850, found 457.2842.

Synthesis of 14A-N-oxide (14ANO)

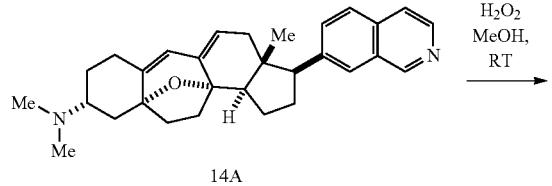

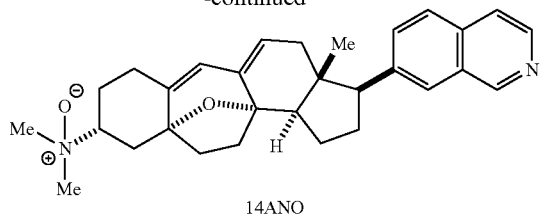

The crude mixture was purified by flash column chromatography (silica gel, eluent: 90:9:1→80:18:2 Chloroform:Methanol:5N NH$_4$OH solution in H$_2$O) to provide N-oxide 14ANO (3.6 mg, 77%). $^1$H NMR (500 MHz, CDCl$_3$) Shift=9.24 (s, 1H), 8.50 (d, J=5.9 Hz, 1H), 7.80 (s, 1H), 7.77 (d, J=8.8 Hz, 1H), 7.64 (d, J=5.9 Hz, 1H), 7.60 (d, J=8.8 Hz, 1H), 5.81 (s, 1H), 5.36 (d, J=2.9 Hz, 1H), 3.46 (t, J=12.4 Hz, 1H), 3.24 (s, 3H), 3.18 (s, 3H), 3.16 (t, J=9.8 Hz, 1H), 2.64 (dd, J=3.2, 7.1 Hz, 1H), 2.59-2.47 (m, 3H), 2.43-2.28 (m, 4H), 2.28-2.15 (m, 2H), 2.09-1.99 (m, 2H), 1.97 (dd, J=5.1, 12.4 Hz, 1H), 1.88 (dq, J=5.4, 12.2 Hz, 1H), 1.81-1.71 (m, 2H), 1.51 (dq, J=4.1, 12.3 Hz, 1H), 0.56 (s, 3H). HRMS (ESI) (m/z) calc'd for $C_{30}H_{37}N_2O_2$ [M+H]$^+$:457.2850, found 457.2846.

Cortistatin a N-Oxide Formation

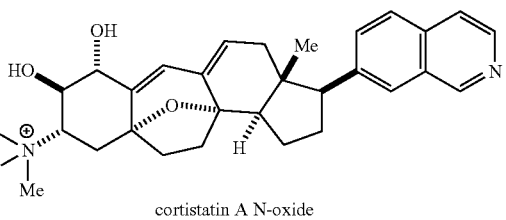

Cortistatin a N-Oxide:

To a solution of cortistatin A (2 mg) in ethyl acetate (1 mL) was added Aldrich silica gel Davisil™ (200 mesh) (200 mg) and this solution was stirred exposed to air for 1 hour. Silica gel was filtered and the filtrate was concentrated to give crude cortistatin A N-oxide that was further purified by SiO$_2$ chromatography (eluent: 50% methanol/ethyl acetate) to afford cortistatin A N-oxide (1.8 mg, 90% yield). $^1$H NMR (500 MHz, CDCl$_3$) δ 9.22 (s, 1H), 8.50 (d, J=5.8 Hz, 1H), 7.78 (s, 1H), 7.76 (d, J=8.8 Hz, 1H), 7.63 (d, J=5.9 Hz, 1H), 7.58 (d, J=8.8 Hz, 1H), 6.28 (s, 1H), 5.49 (m, 1H), 4.15 (d, J=9.3 Hz, 1H), 3.83 (t, J=9.8, 9.8 Hz, 1H), 3.31-3.36 (m, 1H), 3.26 (s, 3H), 3.19 (s, 3H), 3.16 (dd, J=9.3, 9.3 Hz, 1H), 2.50 (dd, J=11.7, 8.8 Hz, 1H), 2.14-2.40 (m, 5H), 1.97-2.07 (m, 3H), 1.81-1.90 (m, 2H), 1.68-1.75 (m, 1H), 1.49-1.65 (m, 1H), 0.55 (s, 3H). HRMS (ESI) (m/z) calc'd for $C_{30}H_{37}N_2O_4$ [M+H]$^+$: 489.2753, found 489.5928.

Example 6. Synthesis of C3-Alcohols and Substituted Analogs

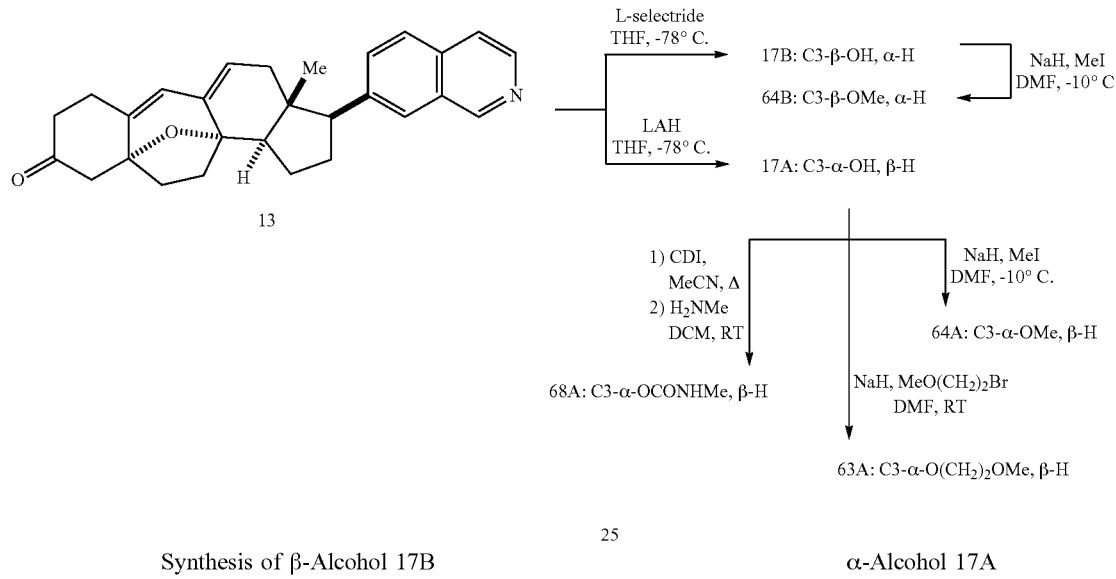

Synthesis of β-Alcohol 17B

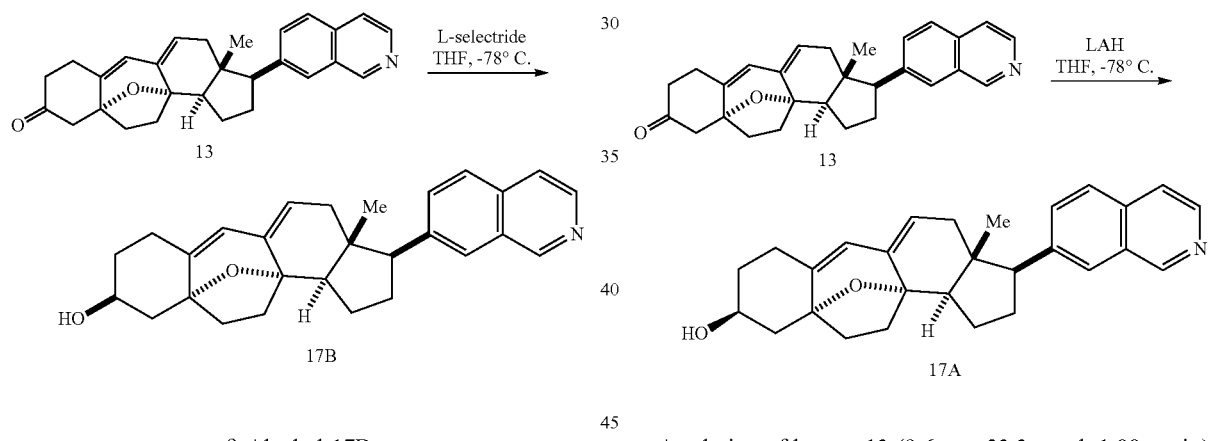

α-Alcohol 17A

β-Alcohol 17B

A solution of ketone 13 (2.00 mg, 4.85 μmol, 1.0 equiv) in THF (350 μL) was cooled to −78° C. and a solution of L-selectride in THF (1 M, 9.71 μL, 9.71 μmol, 2.0 equiv) was added. After 1 h, saturated NH$_4$Cl solution (400 μL) and ethyl acetate (300 μL) was added, which was allowed to warm to room temperature. The aqueous phase was extracted with ethyl acetate (3×1 mL) and the combined organic phases were washed with brine (1 mL), dried over Na$_2$SO$_4$, and concentrated under reduced pressure. The residue was purified by preparative TLC (eluent: 1:1 Hexanes:EtOAc) to afford β-alcohol 17B (ca. 1.2 mg, 60%).

$^1$H NMR (600 MHz, CDCl$_3$) Shift=9.26 (br. s, 1H), 8.49 (br. s, 1H), 7.82 (s, 1H), 7.78 (d, J=8.2 Hz, 1H), 7.69 (br. s, 1H), 7.63 (d, J=7.6 Hz, 1H), 5.75 (s, 1H), 5.26 (br. s, 1H), 4.36 (br. s, 1H), 3.15 (t, J=9.7 Hz, 1H), 2.63 (t, J=13.5 Hz, 1H), 2.51 (dd, J=9.1, 10.9 Hz, 1H), 2.42-2.28 (m, 2H), 2.24 (t, J=10.6 Hz, 1H), 2.21-2.12 (m, 2H), 2.12-1.97 (m, 3H), 1.93 (dd, J=5.0, 17.3 Hz, 2H), 1.90-1.80 (m, 2H), 1.79-1.58 (m, 3H), 0.54 (s, 2H). HRMS (ESI) (m/z) calc'd for C$_{28}$H$_{32}$NO$_2$ [M+H]$^+$: 414.2428, found 414.2436.

A solution of ketone 13 (9.6 mg, 23.3 μmol, 1.00 equiv) in THF (750 μL) was cooled to −78° C. and a solution of LAH in diethyl ether (1.0 M, 35.0 μL, 35.0 μmol, 1.50 equiv) was added. After 10 min, saturated NH$_4$Cl solution (500 μL) and ethyl acetate (500 μL) was added, which was allowed to warm to room temperature. The aqueous phase was extracted with ethyl acetate (3×1 mL) and the combined organic phases were washed with brine (1 mL), dried over Na$_2$SO$_4$, and concentrated under reduced pressure. The residue was purified by flash column chromatography (silica gel, eluent: 1:1→1:5 Hexanes:EtOAc→100% EtOAc) to provide α-alcohol 17A (8.5 mg, 88%). $^1$H NMR (500 MHz, CDCl$_3$) Shift=9.22 (s, 1H), 8.47 (d, J=5.3 Hz, 1H), 7.79 (s, 1H), 7.75 (d, J=8.2 Hz, 1H), 7.63 (d, J=5.9 Hz, 1H), 7.59 (dd, J=1.2, 8.8 Hz, 1H), 5.75 (s, 1H), 5.28 (d, J=2.3 Hz, 1H), 3.78 (tt, J=4.0, 11.3 Hz, 1H), 3.14 (t, J=10.0 Hz, 1H), 2.51 (dd, J=8.5, 11.4 Hz, 1H), 2.40-2.33 (m, 2H), 2.32 (dt, J=4.7, 12.3 Hz, 1H), 2.28-1.98 (m, 7H), 1.93 (dd, J=5.0, 17.3 Hz, 1H), 1.90-1.81 (m, 2H), 1.74-1.62 (m, 2H), 1.40 (dtd, J=5.9, 11.6, 13.8 Hz, 1H), 0.53 (s, 3H). HRMS (ESI) (m/z) calc'd for C$_{28}$H$_{32}$NO$_2$ [M+H]$^+$: 414.2428, found 414.2437.

α-Methylether 64A

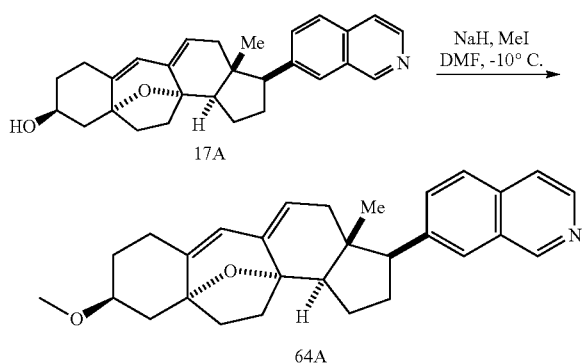

To a solution of α-alcohol 17A (2.0 mg, 4.83 μmol, 1.00 equiv) in DMF (300 μL) was added 60 wt % NaH (1.0 mg, 24.1 μmol, 5.00 equiv) at room temperature and pre-stirred 30 min. Temperature was lowered to −10° C. and MeI (2.0 μL, 29.0 μmol, 6.00 equiv) was added. After 2.5 hours, 2 M NaOH solution (200 μL) and ethyl acetate (500 μL) was added, which was allowed to warm to room temperature. The aqueous phase was extracted with ethyl acetate (3×1 mL) and the combined organic phases were washed with brine (1 mL), dried over $Na_2SO_4$, and concentrated under reduced pressure. The residue was purified by preparative TLC (eluent: 1:2 Hexanes:EtOAc) to afford α-methylether 64A (ca. 1.2 mg, 58%). $^1$H NMR (600 MHz, $CDCl_3$) Shift=9.22 (s, 1H), 8.48 (d, J=5.9 Hz, 1H), 7.79 (s, 1H), 7.75 (d, J=8.8 Hz, 1H), 7.63 (d, J=5.9 Hz, 1H), 7.59 (dd, J=1.5, 8.5 Hz, 1H), 5.74 (s, 1H), 5.28 (d, J=2.9 Hz, 1H), 3.39 (s, 3H), 3.29 (tt, J=3.5, 11.4 Hz, 1H), 3.14 (t, J=10.0 Hz, 1H), 2.52 (dd, J=8.5, 11.4 Hz, 1H), 2.42-2.29 (m, 3H), 2.25 (t, J=11.7 Hz, 1H), 2.24-2.08 (m, 5H), 2.06 (td, J=4.1, 12.9 Hz, 1H), 1.93 (dd, J=5.3, 17.0 Hz, 1H), 1.86 (dq, J=5.3, 12.3 Hz, 1H), 1.79 (t, J=12.0 Hz, 1H), 1.75-1.61 (m, 2H), 1.32 (dtd, J=4.7, 11.5, 14.0 Hz, 1H), 0.53 (s, 3H). HRMS (ESI) (m/z) calc'd for $C_{28}H_{32}NO_2$ $[M+H]^+$: 428.2584, found 428.2573.

β-Methylether 64B

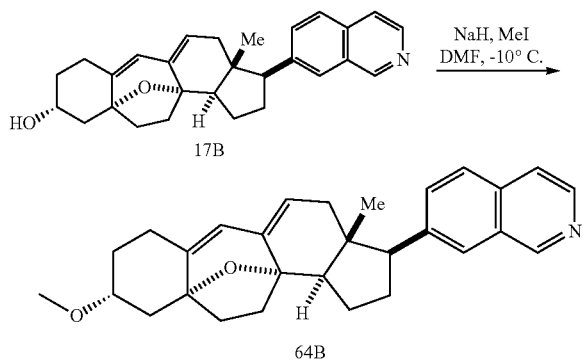

The reaction condition is same as the synthesis of α-methylether 64A. The residue was purified by preparative TLC (eluent: 1:2 Hexanes:EtOAc) to afford C3 β-methylether 64B (1.2 mg, 58%). $^1$H NMR (500 MHz, $CDCl_3$) Shift=9.22 (s, 1H), 8.48 (d, J=5.9 Hz, 1H), 7.79 (s, 1H), 7.76 (d, J=8.8 Hz, 1H), 7.63 (d, J=5.9 Hz, 1H), 7.60 (dd, J=1.5, 8.3 Hz, 1H), 5.74-5.70 (m, 1H), 5.25 (dd, J=2.2, 5.1 Hz, 1H), 3.75-3.69 (m, 1H), 3.35 (s, 3H), 3.18-3.10 (m, J=9.3 Hz, 1H), 2.51 (dd, J=8.5, 11.5 Hz, 1H), 2.52-2.44 (m, 1H), 2.40-2.26 (m, 4H), 2.17 (s, 3H), 2.14-2.08 (m, 1H), 2.07-1.96 (m, 2H), 1.96-1.90 (m, 2H), 1.86 (dq, J=4.9, 12.0 Hz, 1H), 1.76-1.61 (m, 1H), 1.55-1.45 (m, 1H), 0.54 (s, 3H). HRMS (ESI) (m/z) calc'd for $C_{28}H_{32}NO_2$ $[M+H]^+$: 428.2584, found 428.2599.

α-Monomethylcarbamate 68A

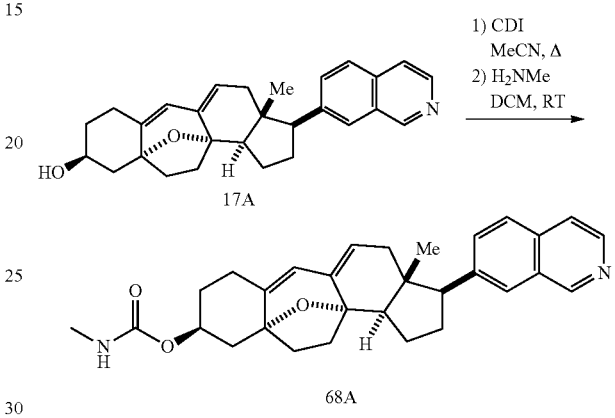

To a solution of α-alcohol 17A (3.5 mg, 8.5 μmol, 1.00 equiv) in $CH_3CN$ (350 μL) was added CDI (2.1 mg, 12.7 μmol, 1.50 equiv) and the reaction mixture was refluxed for 4 hours. The crude mixture was concentrated under reduced pressure and used for the next reaction without further purification.

To a solution of the crude mixture in DCM (300 μL) was added $MeNH_2$ in THF (2 M, 50 μL) at room temperature and stirred 14 hours. The crude mixture was concentrated under reduced pressure and purified by preparative TLC (eluent: 1:1 Hexanes:EtOAc) to afford C3 α-monomethylcarbamate 68A (2.4 mg, 60% in 2 steps). $^1$H NMR (500 MHz, $CDCl_3$) Shift=9.28 (s, 1H), 8.50 (d, J=5.9 Hz, 1H), 7.87 (s, 1H), 7.83 (d, J=8.8 Hz, 1H), 7.75 (d, J=5.9 Hz, 1H), 7.69 (d, J=8.8 Hz, 1H), 5.77 (s, 1H), 5.30 (dd, J=2.2, 4.6 Hz, 1H), 4.76 (t, J=11.7 Hz, 1H), 4.61 (br. s., 1H), 3.17 (t, J=10.0 Hz, 1H), 2.82 (d, J=4.4 Hz, 3H), 2.53 (dd, J=8.5, 11.5 Hz, 1H), 2.38 (d, J=17.1 Hz, 2H), 2.32 (dd, J=3.7, 11.5 Hz, 1H), 2.30-2.14 (m, 5H), 2.13-2.01 (m, 2H), 1.95 (dd, J=5.1, 17.3 Hz, 1H), 1.94-1.82 (m, 2H), 1.78-1.67 (m, 2H), 1.43 (dq, J=4.9, 12.7 Hz, 1H), 0.55 (s, 3H). HRMS (ESI) (m/z) calc'd for $C_{30}H_{35}N_2O_3$ $[M+H]^+$: 471.2642, found 471.2631.

α-Methoxyethylether 63A

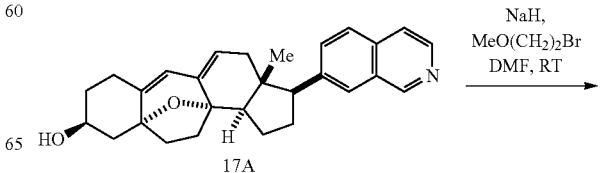

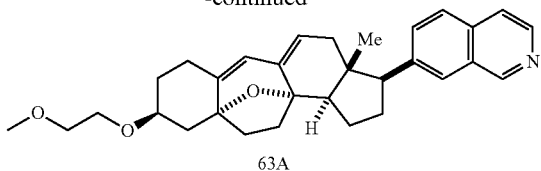

63A

To a solution of α-alcohol 17A (2.0 mg, 4.83 μmol, 1.00 equiv) in DMF (300 μL) was added 60 wt % NaH (1.0 mg, 24.1 μmol, 5.00 equiv) at room temperature and pre-stirred 30 min before the addition of MeO(CH$_2$)$_2$Br (1.6 μL, 16.6 μmol, 3.00 equiv). After 36 hours, 2 M NaOH solution (200 μL) and ethyl acetate (500 μL) was added. The aqueous phase was extracted with ethyl acetate (3×1 mL) and the combined organic phases were washed with brine (1 mL), dried over Na$_2$SO$_4$, and concentrated under reduced pressure. The residue was purified by preparative TLC (eluent: 2:5 Hexanes:EtOAc) to afford C$_3$ α-methoxyethylether 63A (ca. 0.7 mg, 27%). $^1$H NMR (600 MHz, CDCl$_3$) Shift=9.24 (s, 1H), 8.50 (d, J=5.9 Hz, 1H), 7.81 (s, 1H), 7.77 (d, J=8.3 Hz, 1H), 7.65 (d, J=5.9 Hz, 1H), 7.61 (d, J=8.8 Hz, 1H), 5.75 (s, 1H), 5.29 (d, J=2.4 Hz, 1H), 3.74-3.63 (m, 2H), 3.61-3.51 (m, 2H), 3.44 (tt, J=3.9, 11.7 Hz, 1H), 3.44-3.39 (s, 3H), 3.16 (t, J=9.8 Hz, 1H), 2.54 (dd, J=8.5, 11.5 Hz, 1H), 2.43-2.30 (m, 3H), 2.30-2.17 (m, 4H), 2.17-2.02 (m, 3H), 1.95 (dd, J=5.1, 17.3 Hz, 1H), 1.92-1.82 (m, 2H), 1.78-1.62 (m, J=8.3 Hz, 2H), 1.41 (dtd, J=4.1, 11.9, 13.5 Hz, 1H), 0.55 (s, 3H). HRMS (ESI) (m/z) calc'd for C$_{28}$H$_{32}$NO$_2$ [M+H]$^+$: 472.2846, found 472.2850.

Example 7. Synthesis of Amines from Alcohols

α-Dimethylhydantoin 74A

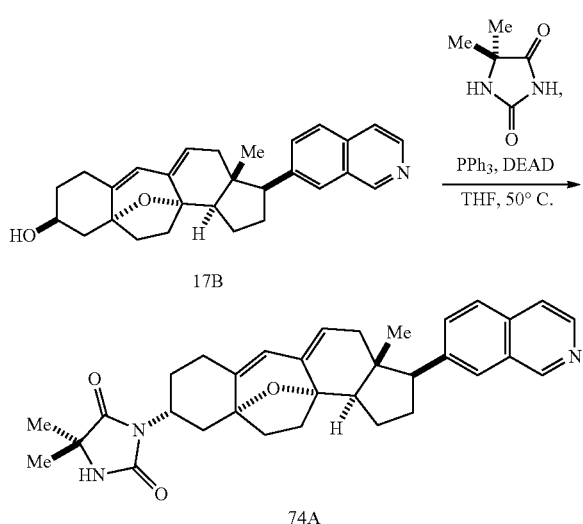

To a solution of β-alcohol 17B (5.0 mg, 12.3 μmol, 1.0 equiv) in THF (400 μL) was added dimethylhydantoin (7.8 mg, 61.6 μmol, 5.0 equiv) and PPh$_3$ (9.7 mg, 36.9 μmol, 3.0 equiv). Reaction mixture was cooled to 0° C. and DEAD (16.1 μL of 40 wt % solution in toluene, 36.9 μmol, 3.0 equiv). Reaction was warmed up to 50° C. and stirred 17 h. After cooling the reaction mixture to room temperature, 1N NaOH solution (300 μL) and was added and the aqueous phase was extracted with ethyl acetate (3×0.5 mL) and the combined organic phases were washed with brine (1 mL), dried over Na$_2$SO$_4$, and concentrated under reduced pressure. The crude mixture was purified by preparative TLC (silica gel, eluent: 40:1 MeOH:Dichloromethane) to afford α-dimethylhydantoin 74A (0.9 mg, 14%). $^1$H NMR (500 MHz, CDCl$_3$) Shift=9.24 (s, 1H), 8.50 (d, J=5.4 Hz, 1H), 7.81 (s, 1H), 7.77 (d, J=8.8 Hz, 1H), 7.64 (d, J=5.4 Hz, 1H), 7.61 (dd, J=1.5, 8.8 Hz, 1H), 5.79 (d, J=1.5 Hz, 1H), 5.32 (dd, J=2.7, 5.1 Hz, 1H), 5.18 (s, 1H), 4.10 (tdd, J=3.2, 11.3, 13.1 Hz, 1H), 3.16 (dd, J=9.3, 10.7 Hz, 1H), 2.86 (t, J=12.7 Hz, 1H), 2.54 (dd, J=8.3, 11.7 Hz, 1H), 2.45 (dd, J=2.9, 14.6 Hz, 1H), 2.30 (br. s., 6H), 2.19 (tq, J=4.4, 9.0 Hz, 1H), 2.09-2.00 (m, 1H), 1.96 (dd, J=5.4, 17.6 Hz, 1H), 1.92-1.80 (m, 2H), 1.80-1.64 (m, 3H), 1.42 (d, J=4.9 Hz, 6H), 0.56 (s, 3H). HRMS (ESI) (m/z) calc'd for C$_{33}$H$_{38}$N$_3$O$_3$ [M+H]$^+$: 524.2908, found 524.2892.

Biological Methods

Cell Culture and Cell Lines

MV4;11, RS4;11, HL-60, K562, L-Wnt3A and L cells were obtained from ATCC. HEL, NB4, KG1, UKE-1, UKE-1per, SET-2 and SET-2per cells were provided by Ross Levine (MSKCC). MOLM-14 was provided by Scott Armstrong (Boston Children's Hospital). MV4;11-mCLP cells were provided by Andrew Kung (Dana Farber Cancer Institute). HEK293 STF cells were provided by Jeremy Nathans (Johns Hopkins University School of Medicine). All cells were maintained in a humidified incubator set to 37° C., 5% CO$_2$. MV4; 11, RS4;11, K562, HEL, NB4, MOLM-14 and KG1 cells were grown in RPMI-1640 with 10% FBS, 100 U ml$^{-1}$ penicillin and 100 μg ml$^{-1}$ streptomycin. HaCaT and HEK293 STF cells were grown in DMEM with 10% FBS, 100 U ml$^{-1}$ penicillin, and 100 μg ml$^{-1}$ streptomycin, with 200 μg ml$^{-1}$ G418 for HEK293STF cells. L-Wnt3A and L cells were grown in DMEM with 10% FBS, 100 U ml$^{-1}$ penicillin, 100 μg ml$^{-1}$ streptomycin, and 400 μg ml$^{-1}$ G418 (for L-Wnt3A only). SET-2 cells were grown in RPMI-1640 with 20% FBS, 100 U ml$^{-1}$ penicillin and 100 μg ml$^{-1}$ streptomycin. HL-60 were grown in IMDM with 20% FBS, 100 U ml$^{-1}$ penicillin and 100 μg ml$^{-1}$ streptomycin. UKE-1 cells were grown in RPMI-1640 with 10% FBS, 10% horse serum, 100 U ml$^{-1}$ penicillin, 100 μg ml$^{-1}$ streptomycin and 1 μM hydrocortisone. SET-2per and UKE-1per cells were maintained in the presence of 0.7 μM and 1 μM ruxolitinib, respectively. Human Umbilical Vein Endothelial Cells (HU-VECs) were obtained from Life Technologies and cultured in M200 medium with low serum growth supplement (LSGS, Life Technologies).

Reagents

Compounds for testing were prepared as 100% DMSO stock solutions and stored under argon at −80° C. Doxorubicin HCl, anti-FLAG (F1804) and anti-Actin (A5060) antibodies were obtained from Sigma-Aldrich. Anti-Smad 2/3 (8565), anti-Stat1 (9172), Anti-phospho-Stat1 Tyr701 (9171), and anti-phospho-Stat Ser727 (9177) antibodies were obtained from Cell Signaling Technologies. Anti-phospho-Smad 2/3 T220/T179 was obtained from Rockland, IFNγ was obtained from Life Technologies and TGFβ1 was obtained from R&D Systems. Wnt3A conditioned media and L-cell conditioned media were obtained as described by ATCC.

Plasmids, Mutagenesis, Packaging and Transduction.

5'-FLAG-tagged CDK8 was PCR amplified from pBabe.puro.CDK8.flag (Addgene, original source Firestein et al., Nature (2008) 455, 547-551) with the addition of EcoRI (5') and XbaI (3') restriction sites and cloned into the lentiviral expression vector pLVX-EF1alpha-IRES-mCherry (Clonetech) by sticky-end ligation (EcoRI and XbaI) and transformed into *E. coli* (One Shot Stbl3, Invitrogen). 5'-FLAG-tagged CDK19 was PCR amplified from F-CDK8L (Addgene, original source Conaway et al., *FEBS Letters* (2005) 579, 904-908) with the addition of SpeI (5') and XbaI (3') restriction sites and cloned into the lentiviral expression vector pLVX-EF1alpha-IRES-ZsGreen1 (Clonetech) by sticky-end ligation and transformed into *E. coli* (One Shot Stbl3, Invitrogen). Point mutations were introduced by whole plasmid PCR (QuikChange II XL Site-Directed Mutagenesis Kit, Agilent). 5'-FLAG-tagged CDK8 or CDK19 mutant was subsequently PCR amplified, using EF1alpha forward and IRES reverse primers (see Table 1), and cloned into pLVX-EF1 alpha-IRES-mCherry or pLVX-EF1alpha-IRES-ZsGreen1, respectively, and transformed into *E. coli* (One Shot Stbl3, Invitrogen). Primers used to clone CDK8 and CDK19 and introduce the W105M point mutation into each protein are provided in Table 1.

TABLE 1

Primers used to clone CDK8 and CDK19 and introduce W105M point mutation

| Primer | Sequence |
| --- | --- |
| 1st round 5' EcoRI CDK8 (SEQ ID NO.: 3): | GAATTCGCCACCATGGACTA |
| 1st round 3' XbaI CDK8 (SEQ ID NO.: 4): | TCTAGATCAGTACCGATGTGTCT |
| 2nd round 5' EcoRI CDK8 (SEQ ID NO.: 5): | TAGCTAGAATTCGCCACCATG |
| 2nd round 3' XbaI CDK8 (SEQ ID NO.: 6): | GTCGAGTCTAGATCAGTACCG |
| 1st round 5' SpeI CDK19 (SEQ ID NO.: 7): | ACTAGTATGCCAGACTACAAGGA |
| 1st round 3' XbaI CDK19 (SEQ ID NO.: 8): | TCTAGATCAGTACCGGTGGG |
| 2nd round 5' SpeI CDK19 (SEQ ID NO.: 9): | GTCGAGACTAGTATGCCAGAC |
| 2nd round 3' XbaI CDK19 (SEQ ID NO.: 10): | TCGAGTCTAGATCAGTACCGG |
| EF1alpha forward (SEQ ID NO.: 11): | TCAAGCCTCAGACAGTGGTTC |
| IRES reverse (SEQ ID NO.: 12): | ACGTGTATAAGATACACCT |
| CDK8 W105M: Trp105 (TGG) → Met (ATG) (forward) (SEQ ID NO.: 13): | CTATGCTGAACATGACCTCATGCATATAATCAAGTTTCAC |
| CDK8 W105M: Trp105 (TGG) → Met (ATG) (reverse) (SEQ ID NO.: 14): | GTGAAACTTGATTATATGCATGAGGTCATGTTCAGCATAG |
| CDK19 W105M: Trp105 (TGG) → Met (ATG) (forward) (SEQ ID NO.: 15): | GCAGAGCATGACTTGATGCATATTATTAAGTTTCACC |

TABLE 1-continued

Primers used to clone CDK8 and CDK19 and introduce W105M point mutation

| Primer | Sequence |
|---|---|
| CDK19 W105M: Trp105 (TGG) → Met (ATG) (reverse) (SEQ ID NO.: 15): | GGTGAAACTTAATAATATGCATCAAGTCATGCTCTGC |

The lentiviral expression vectors were packaged by the University of Massachusetts RNAi Core Facility by cotransfection of 293T cells with packaging vector psPAX2 (Addgene) and envelope vector pMD2.G (Addgene). 48 h after transfection, viral supernatants were collected, passed through 0.45 µm filter (Millipore) and used for transduction (MOI 2 for 293T cells). Transductions were performed with RetroNectin (Clontech), according to the manufacturers instructions. Briefly, sterile 24-well plates were coated with 500 µL of 20 µg/ml RetroNectin in sterile PBS and stored at 4° C. overnight. The next day, the RetroNectin solution was aspirated and the plates were blocked with 2% BSA in sterile PBS for 30 min at room temperature. The plates were then washed 1× with PBS and 300 to 500 µL of viral supernatant was added. The plates were then centrifuged at 2000×g for 1.5 hr with a 1800 change in orientation after 45 min. The plates were then incubated for 2 h in a humidified incubator set to 37° C., 5% $CO_2$. The viral supernatant was then removed and 500 µL of 200,000 cells/ml was added to each well. After incubation of the plates for 1-3 days, the cells were expanded and the fluorescent protein-expressing cells were isolated by FACS.

Figure 10B:
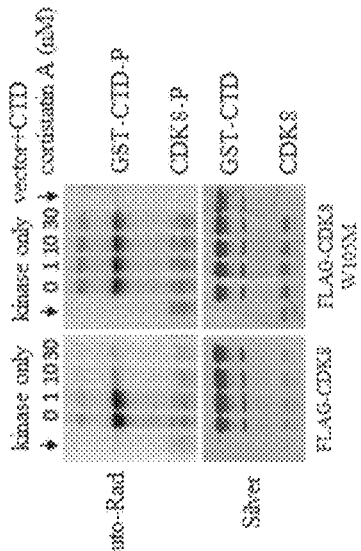
FIG. 10A, FIG. 10B, and FIG. 10C demonstrate that CDK8/CDK19 mediate the antiproliferative effects of cortistatin A by showing that alleles of CDK8 and CDK19 render cells resistant to growth inhibition by cortistatin A (FIG. 10A) and resistant to CDK8 kinase inhibition by cortistatin A in vitro (FIG. 10B) and in cells (FIG. 10C).
Figure 10A:
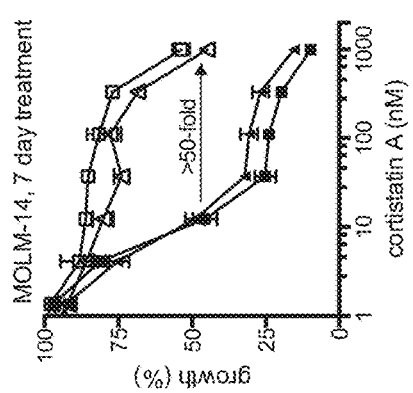
Figure 10C:
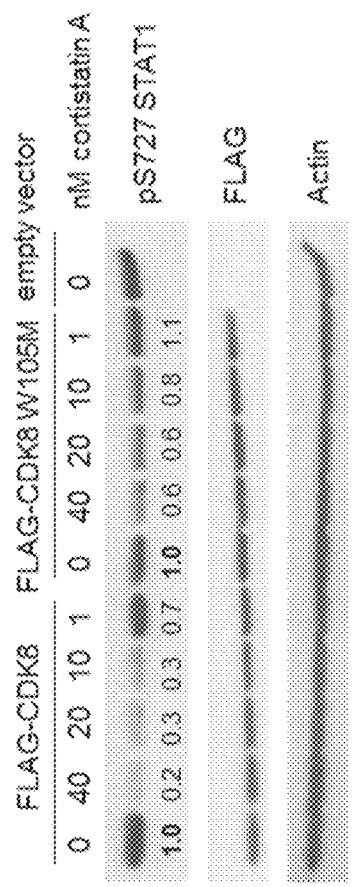
Figure 22B:
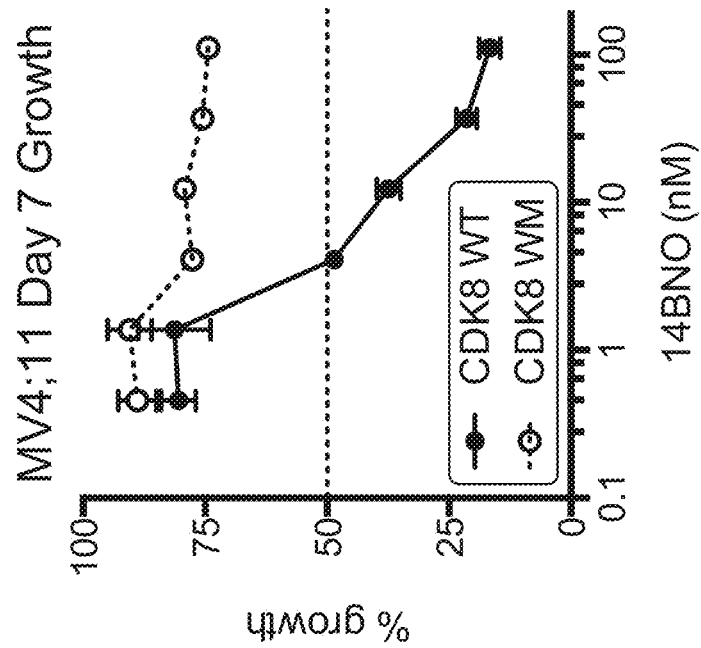
FIG. 22A and FIG. 22B, demonstrate alleles of CDK19 (FIG. 22A) and CDK8 (FIG. 22B) render MV4; 11 cells resistant to growth inhibition by the N-oxide of compound 14B (14BNO), indicating that CDK8/CDK19 mediate the antiproliferative effects of 14BNO.
Figure 22A:
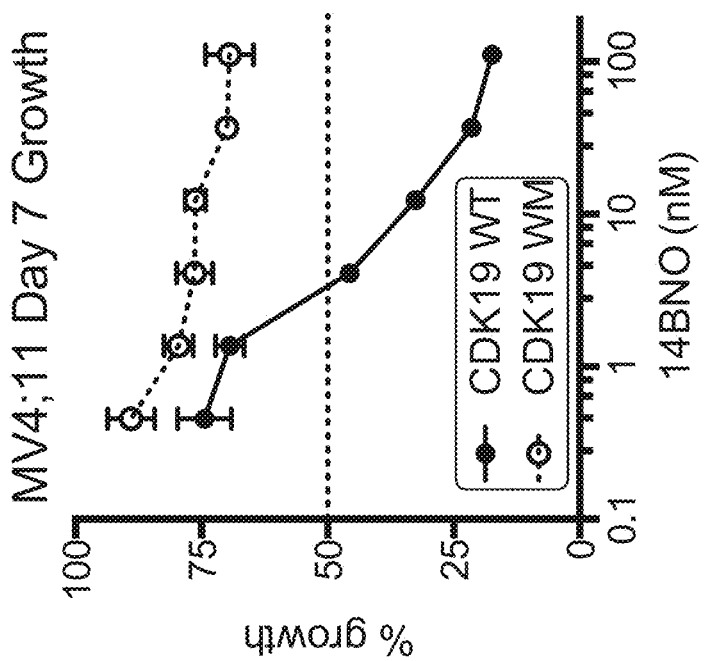

In order to determine whether CDK8 and CDK19 mediate the antiproliferative effects of cortistatin A or cortistatin A analogs, alleles of both mediator kinases were identified that would render cells resistant to growth inhibition by cortistatin A. With guidance from our crystal structure, CDK8 Trp105 was selected for mutation to Met since the molecular modelling suggested that it would disrupt CDK8 binding to cortistatin A but not ATP. It was found that MOLM-14 cells overexpressing either FLAG-CDK8 W105M or FLAG-CDK19 W105M were highly desensitized to growth inhibition of cortistatin A (>50-fold, FIG. 10A) and 14BNO (>50-fold, FIG. 22). Furthermore, CDK8 W105M was catalytically competent yet far less sensitive to kinase inhibition by cortistatin A in vitro (FIG. 10B) and in cells (FIG. 10C), thus proving that these mutations act by reducing affinity for cortistatin A, but not ATP (FIG. 10B). Collectively, these results provided unequivocal proof that CDK8 and CDK19 act redundantly to mediate the antiproliferative effects of cortistatin A. For FIGS. 10A and 22, cells were passaged and fresh compound was added on day 3 (mean+/−standard error, n=3). For FIG. 10B, FLAG-CDK8 and FLAG-CDK8 W105M were isolated from MOLM-14 cells overexpressing each protein and subjected to kinase reactions in presence of the indicated concentrations of cortistatin A. For FIG. 10C, MOLM-14 cells expressing equal levels of FLAG-CDK8 or FLAG-CDK8 W105M were treated with the indicated concentrations of cortistatin A for 1 hour followed by IFN-gamma for 1 hr. Cells were then collected, lysed, and analyzed by western blot.

Cell Growth Assays

HUVECs were plated in triplicate in 96-well plates at a density of 1,000 cells/well in 75 µL. After 24 h, compounds were serially diluted in medium and delivered to cells as 4× solutions in 25 µL (0.1% DMSO final for assay). 96 h after compound addition, CellTiter-Blue (Promega) was added to the wells, plates were incubated at 37° C. for 90 min, and fluorescence (555 nm excitation; 580 nm emission) was detected using a SPECTRAmax M3. $IC_{50}$ was determined by fitting the data to a four-parameter dose-response curve using GraphPad Prism 5.0.

For all other cell lines, compounds were serially diluted in medium and dispensed in triplicate in 96-well plates (0.1% DMSO final for assay) followed by the addition of exponentially growing cells at densities ranging from 5,000 to 30,000 cells/well. Cells were also seeded into 2 additional control wells containing vehicle (0.1% DMSO). After 3 days, the number of viable cells in one of the control wells was counted by hemocytometer or MOXI Z (Orflo) and an equal volume of cells for all wells were split-back with fresh vehicle/compounds such that the resulting seeding density for the control well was 5,000-30,000 cells/well, matching the initial seeding density in that well. This procedure was repeated on day 7 and day 10. % growth was calculated as % growth=100×(total estimated cell number in well −day 0 starting cell number)/(total average vehicle estimated cell number −day 0 starting cell number). To determine the estimated cell number in each well, cells that were counted in the control well were diluted 3-fold for an 8-point dilution series, and transferred to 384-well plates in duplicate, 20 µL per well. Cells in all other wells were diluted 4-fold and transferred to 384-well plates in duplicate, 20 µL per well. 20 µL of CellTiter-Glo (Promega) was subsequently added to all wells and luminescence was detected using a SPECTRAmax M3. The control well dilution series was fit to a linear regression and used as a standard for calculating the estimated cell number for each well. For days 7 and 10, total estimated cell number represents the split-adjusted theoretical cell number.

In Vitro CDK8 Kinase Assay

The in vitro kinase assay was performed as previously described (See, e.g., Knuesel et al., *Mol. Cell. Biol.* (2009) 29, 650-661). FLAG-CDK8 and FLAG-CDK8 W105M were overexpressed and purified from MOLM-14 cells.

X-Ray Crystal Structure

The X-ray crystal structure of cortistatin A (CA) bound to CDK8/Cyclin C was obtained by Proteros Biostructures GmbH. Expression and purification of CDK8/Cyclin C was performed as previously described (See, e.g., Schneider et al., *J. Mol. Biol.* (2011) 412, 251-266). Diffraction data were collected at the SWISS LIGHT SOURCE (SLS, Villigen, Switzerland). The structure was solved and refined to a final resolution of 2.40 Å. Data were processed using the programs XDS and XSCALE. The phase information necessary to determine and analyze the structure was obtained by molecular replacement with a previously solved structure of CDK8/CycC as a search model. Subsequent model building and refinement was performed with the software packages CCP4 and COOT. For the calculation of the free R-factor, a measure to crossvalidate the correctness of the final model, about 3.4% of measured reflections were excluded from the refinement procedure. TLS refinement (using REFMAC5, CCP4) has been carried out, which resulted in lower R-factors and higher quality of the electron density map. The ligand parameterization and generation of the corresponding library files were carried out with CORINA. The water model was built with the "Find waters"-algorithm of COOT by putting water molecules in peaks of the $F_o-F_c$ map contoured at 3.0 followed by refinement with REFMAC5 and checking all waters with the validation tool of COOT. The criteria for the list of suspicious waters were: B-factor greater 80 Å$^2$, $2F_o-F_c$ map less than 1.2 σ, distance to closest contact less than 2.3 Å or more than 3.5 Å. The suspicious water molecules and those in the active site (distance to inhibitor less than 10 Å) were checked manually. The occupancy of side chains, which were in negative peaks in the $F_o-F_c$ map (contoured at $-3.0\sigma$), were set to zero and subsequently to 0.5 if a positive peak occurred after the next refinement cycle. The Ramachandran Plot of the final model shows 93.2% of all residues in the most favoured region, 6.6% in the additionally allowed region, and 0.2% in the generously allowed region. No residues are found in the disallowed region. Data collection, processing and refinement tables follow. Values in parenthesis refer to the highest resolution bin.

TABLE 2

Data collection and processing statistics for Cortistatin A

| Ligand | Cortistatin A |
|---|---|
| X-ray source | PXI/XO6SA (Swiss Light Source, Villigen, Switzerland) |
| Wavelength [Å] | 1.00004 |
| Detector | PILATUS 6M |
| Temperature [K] | 100 |
| Space group | P 2$_1$ 2$_1$ 2$_1$ |
| Cell: a; b; c; [Å] | 70.49; 71.25; 171.25 |
| α; β; γ; [°] | 90.0; 90.0; 90.0 |
| Resolution [Å] | 2.40 (2.65-2.40) |
| Unique reflections | 32875 (8656) |
| Multiplicity | 2.8 (2.8) |
| Completeness [%] | 94.9 (98.6) |
| Rsym [%] | 7.4 (44.8) |
| Rmeas [%] | 9.0 (54.8) |
| Mean (I)/sd, calculated from independent reflections | 10.99 (2.66) |

TABLE 3

Refinement statistics for Cortistatin A

| Ligand | Cortistatin A |
|---|---|
| Resolution [Å] | 85.62-2.40 |
| Number of reflections (working/test) | 31676/1115 |
| R$_{crys}$ [%] | 21.7 |
| R$_{free}$ [%], test-set contains 3.4% of measured reflections | 26.6 |
| Total number of atoms: | |
| Protein | 5017 |
| Water | 104 |
| Ligand | 35 |
| Formic acid | 15 |
| Deviation from ideal geometry (root mean square deviations from geometric target values): | |
| Bond lengths [Å] | 0.009 |
| Bond angles [°] | 1.13 |
| Bonded B's [Å], calculated with MOLEMAN | 2.1 |
| Ramachandran plot (calculated with PROCHECK): | |
| Most favoured regions [%] | 93.2 |
| Additional allowed regions [%] | 6.6 |
| Generously allowed regions [%] | 0.2 |
| Disallowed regions [%] | 0.0 |

Figure 16B:
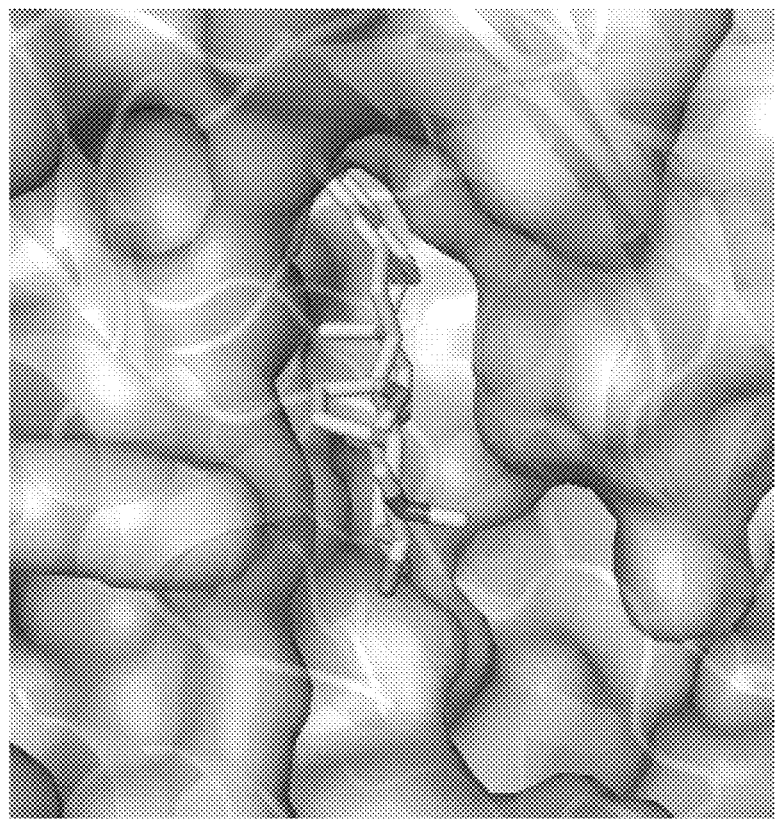
Figure 16A:
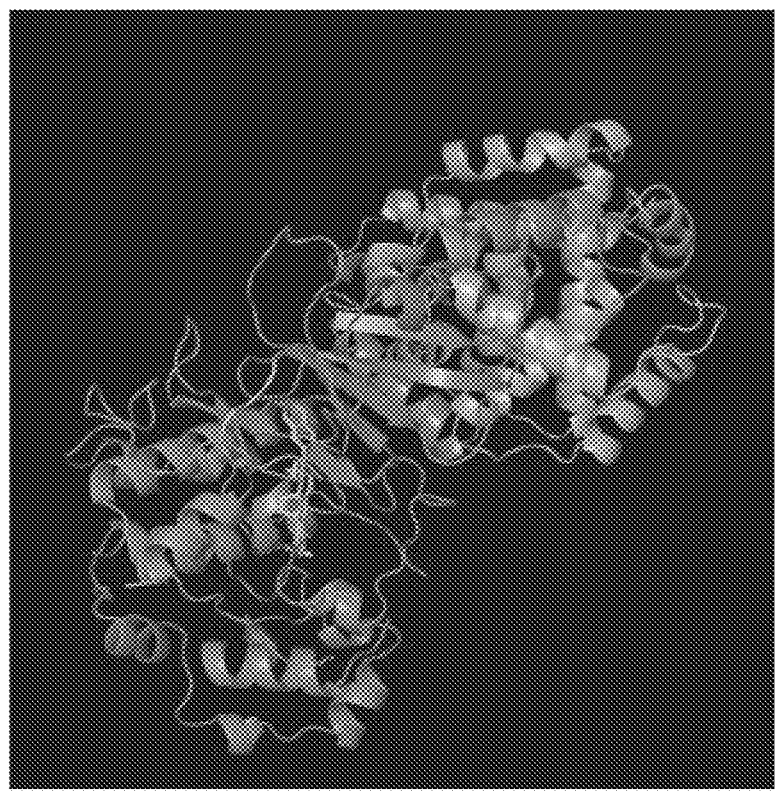
Figure 16C:
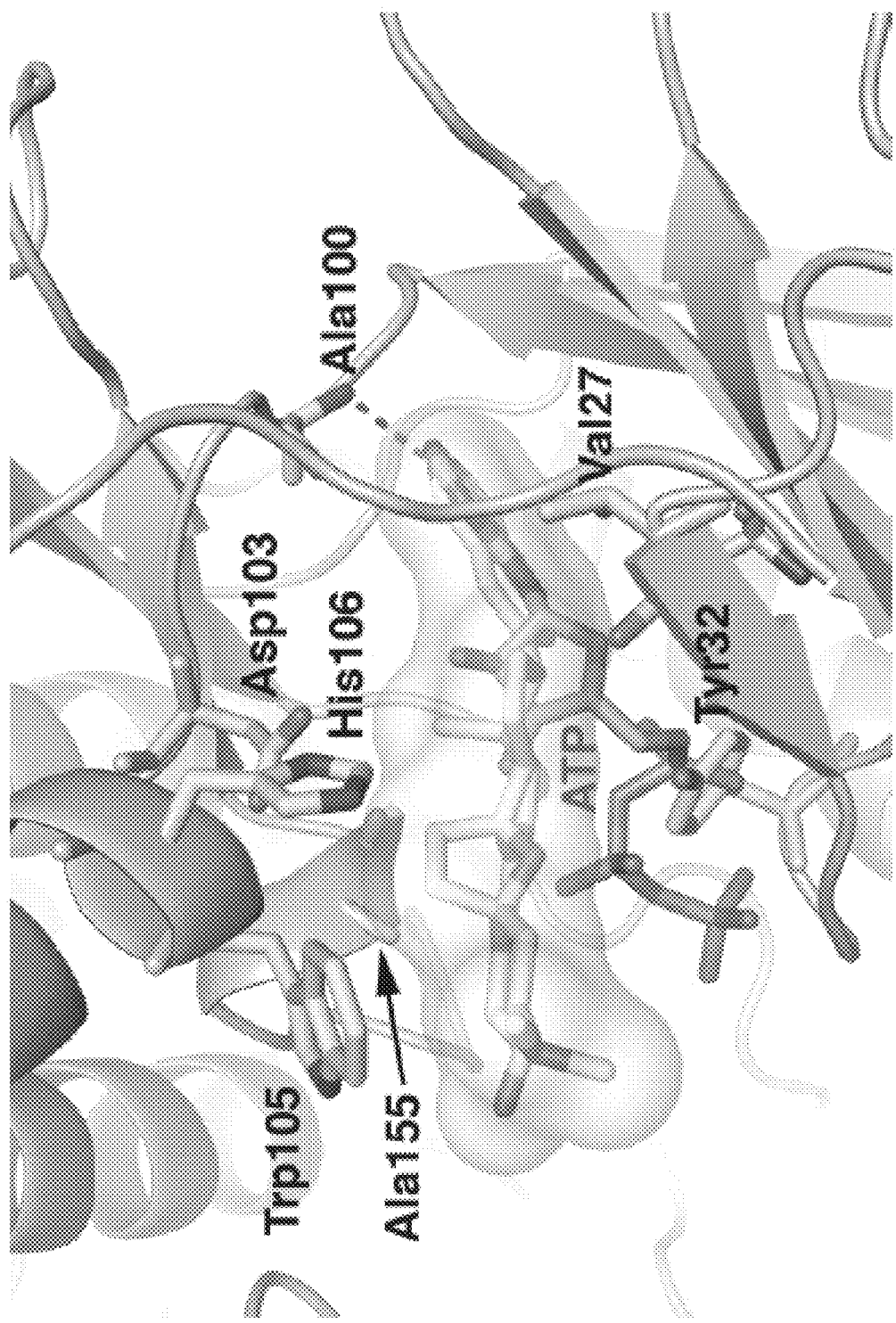

To understand how cortistatin A inhibits CDK8, we solved an X-ray crystal structure of the cortistatin A/CDK8/cyclin C ternary complex at 2.40 Å resolution (FIG. 16A). Cortistatin A binds in the ATP-binding site of CDK8 and forms a single H-bond with CDK8 (dashed line, FIG. 16C) between the isoquinoline nitrogen of cortistatin A and the main chain amide N—H of Ala100 located in the hinge region. The remaining contacts between cortistatin A and CDK8 are hydrophobic, with cortistatin A exhibiting remarkable shape complementarity with the ATP-binding site (FIG. 16B). In particular, the C13 angular methyl group and C5-C9 ethane bridge of cortistatin A perfectly fill hydrophobic cavities formed by the side-chains of His106, Ala155, Trp105, and Asp103 (FIG. 16C). Other CDKs do not have similar hydrophobic cavities to accommodate the C13-methyl and C5-C9 ethane bridge of cortistatin A, perhaps explaining the impressive selectivity of cortistatin A for CDK8/CDK19.

There is also an apparent cation-0 interaction between the charged C3-N,N-dimethylammonium ion of cortistatin A and Trp105 of CDK8, which are within close contact (3.4 Å). CDK8 and CDK19 are the only CDKs with Trp at amino acid 105, suggesting that the cation-☐ interaction as well as hydrophobic contacts between cortistatin A and Trp105 might be important for the high affinity and selectivity of cortistatin A for CDK8. A closer view of the contact between Trp105 and the N,N-dimethylammonium ion of cortistatin A is shown in FIG. 16D. There is a direct contact between one methyl group of the N,N-dimethylamine of cortistatin A and Trp105, which is perfect for a cation-☐ interaction.

It is very surprising that 14B was as potent or more potent (approximately 2-fold more potent) than cortistatin A in cell growth inhibition and in CDK8 kinase inhibition since the C3 amine is now axial and might have been expected to clash with Trp105.

Western Blotting

For STAT1 studies, MOLM-14 cells were treated with vehicle (0.1% DMSO) or compound for 1 h followed by the addition of IFNγ (Life Technologies, PHC4031) for 1 h. Cells were then collected, washed twice with cold PBS and snap frozen in liquid nitrogen. For all Western blotting, whole-cell lysates were prepared in RIPA buffer (Sigma- Aldrich, R0278) with phosphatase and protease inhibitor additives (Sigma-Aldrich, P8340, P0044, P5762) and protein concentration was determined by BCA assay (Thermo Scientific, 23225). RIPA extracts were resolved by denaturing polyacrylamide gel electrophoresis (Life Technologies, NuPAGE) and transferred to PVDF membrane (Millipore) using the Mini Trans-Blot system (BioRad). The membranes were probed as recommended by the antibody manufacturers and proteins detected by chemiluminescence using horseradish peroxidase-conjugated secondary antibodies. For SMAD2/3 studies, HaCaT cells were treated as described for STAT1 with the addition of TGFβ1 (R&D Systems) in place of IFNγ.

Reporter Assay

Exponentially growing HEK293 STF were plated in triplicate in 96-well plates at a density of 5,000 cells/well in 75 μL. For experiments with azakenpaullone, after 24 h, cortistatin A was serially diluted in medium containing 40 μM azakenpaullone and delivered to cells as 4× solutions in 25 μL (0.2% DMSO and 10 μM azakenpaullone final for assay). Additional triplicate control wells on each plate had media without cells or cells without azakenpaullone. For experiments with Wnt3A conditioned media, after 24 h, compounds were serially diluted in Wnt3A conditioned media as 1× solutions (0.1% DMSO final). Old media was removed from the cells and replaced with the compound/Wnt3A-media. Additional triplicate control wells on each plate had media without cells or cells that were treated with L-conditioned media (no Wnt3A). After 24 h, the CellTiter-Fluor and Steady-Glo assays (Promega) were subsequently performed in series to determine viability and luminescence, respectively, in each well (measurements made on a SPECTRAmax M3, Molecular Devices). Graphs were made in Prism 5 (GraphPad Software, Inc.) with nonlinear regression fit to a sigmoidal dose-response curve (variable slope).

Gene Expression

Exponentially growing MOLM-14, MV4; 11, and K562 cells were seeded in 12-well plates at a density of 500,000 to 800,000 cells/mL in 1 mL of media followed by the addition of vehicle (0.1% DMSO) or cortistatin A at 10 nM ("CA10") for MOLM-14 and MV4;11 cells and 25 nM for K562 cells in triplicate wells. After 24 h, cells were washed 2× with cold PBS, snap frozen, and RNA was isolated by RNeasy Plus Microkit (Qiagen) or TRIzol (Life Technologies). RNA was processed by the Dana Farber Cancer Institute Microarray Core Facility and hybridized to the Human U133 Plus 2.0 microarray (Affymetrix). Microarrays were quality controlled using the affyQCReport Bioconductor package (See, e.g., Gentleman et al., *Genome Biol* (2004) 5: R80; R Development Core Team, R: A Language and Environment for Statistical Computing. Vienna, Austria. ISBN 3-900051-07-0). Satisfactory arrays were corrected for background, normalized, and log 2-transformed using the rma function of the affy Bioconductor package (See, e.g., Rafael et al., *Nucleic Acids Research* (2003) 31:e15; Bolstad et al., *Bioinformatics* (2003) 19:185-193; Irizarry et al., *Biostatistics* (2003) 4: 249-264). Present/Absent calls were made using the mas5calls function of the affy package. Probe sets present in >20% of samples and for which the interquartile range was >log 2(1.2) were retained for further analysis. Batch-correction by cell type (MOLM-14 vs. MV4; 11) was performed with ComBat (See, e.g., Johnson et al., *Biostatistics* (2007) 8:118-127). We used GenePattern for unsupervised hierarchical clustering of the samples based on Euclidean distance. Probe sets that were significantly up- or down-regulated at least 1.5-fold in CA10-treated vs. DMSO control samples were identified using the limma Bioconductor package (See, e.g., Smyth, G. K. (2005). Limma: linear models for microarray data. In: 'Bioinformatics and Computational Biology Solutions using R and Bioconductor'. R. Gentleman, V. Carey, S. Dudoit, R. Irizarry, W. Huber (eds), Springer, New York, 2005). We set a p-value of <0.05, corrected for multiple hypothesis testing by the Benjamini-Hochberg method (See, e.g., Benjamini, Y. & Hochberg, Y. J. R. Stat. Soc., B (1995) 57:289-300) as our significance cut-off. Gene Set Enrichment Analysis (See, e.g., Subramanian et al., *Proc Natl Acad Sci USA*. (2005) 102:15545-50) was carried out using T-tests on log 2 values as the metric. Signatures included curated gene sets (C2) downloaded from the Broad's MSigDB as well as signatures curated in-house from literature.

In Vivo Studies

Figure 11A:
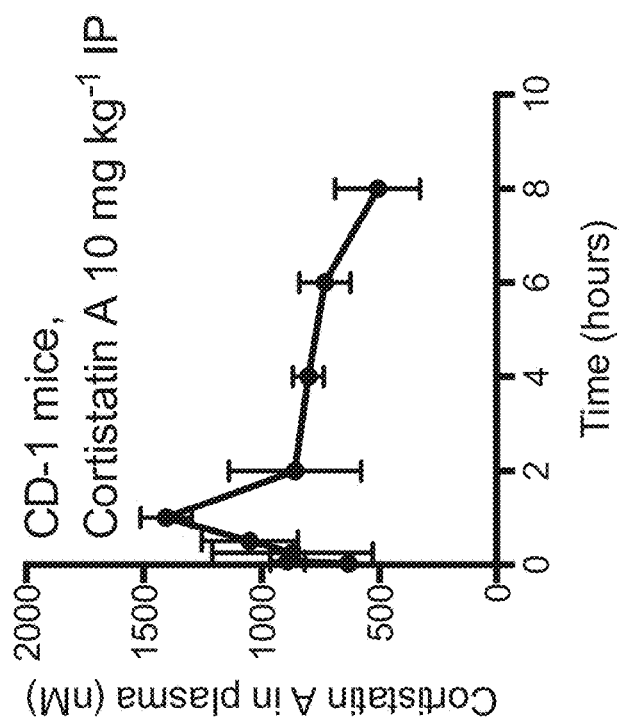
FIG. 11A and FIG. 11B depict pharmacokinetic results for cortistatin A.
Figure 11B:
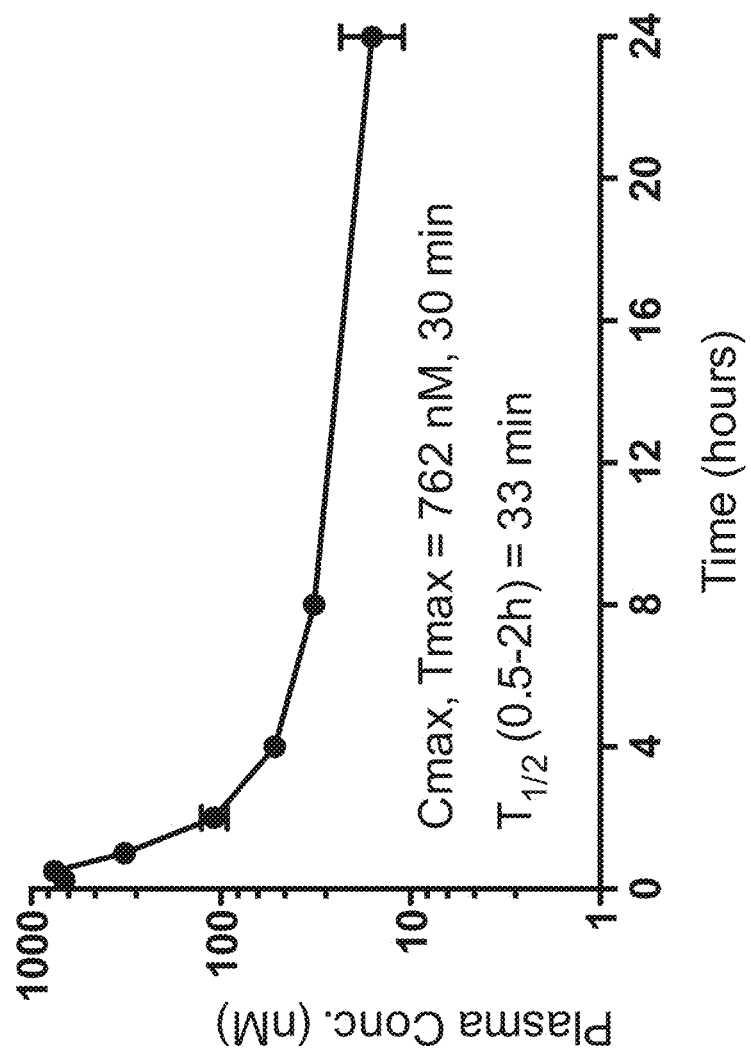
Figure 12A:
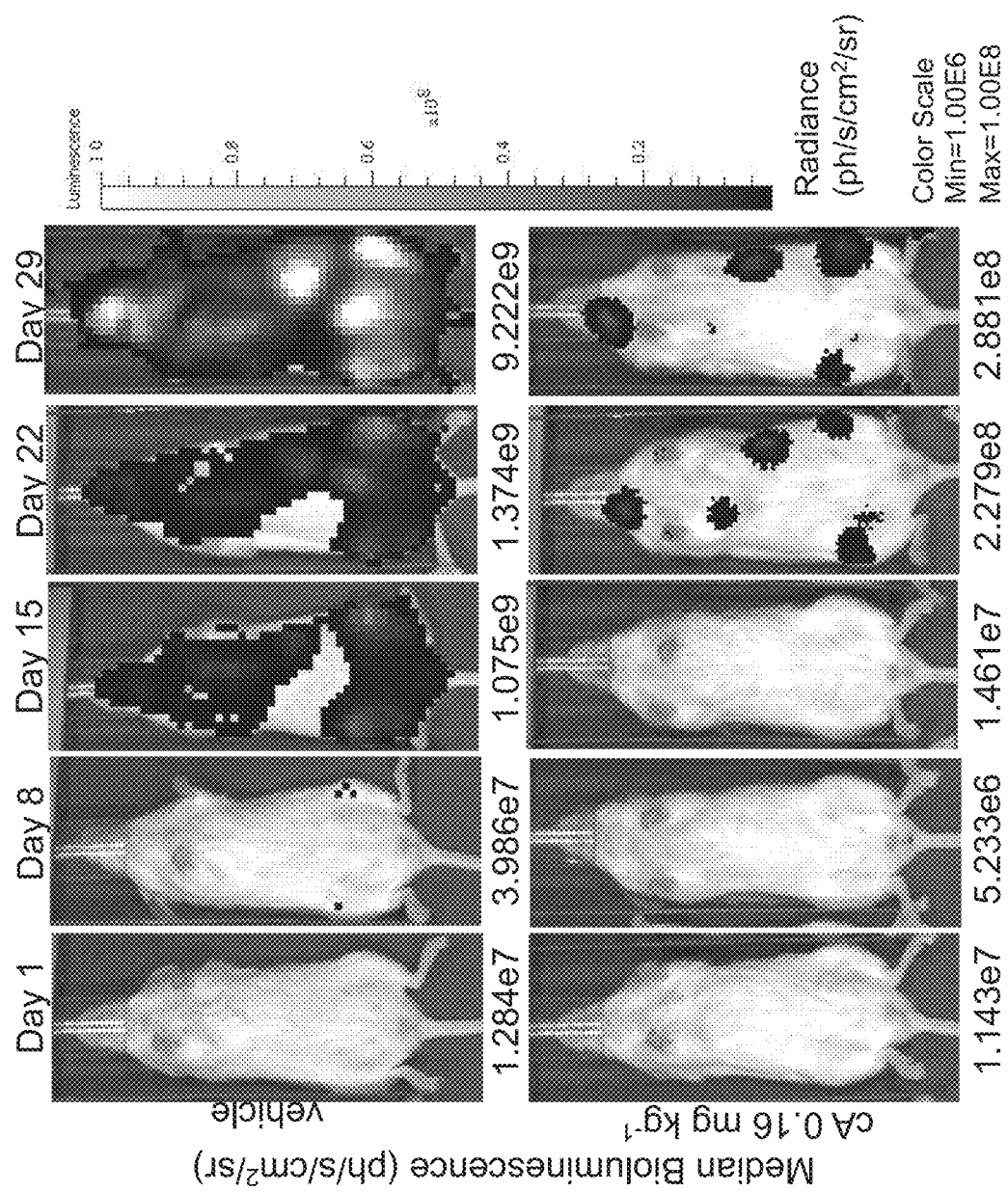
FIG. 12A, FIG. 12B, FIG. 12C, FIG. 12D, FIG. 12E, FIG. 12F, and FIG. 12G demonstrate cortistatin A is effective in MV4; 11 disseminated leukemia mouse model of AML. MV4;11 AML cells expressing mCherry, luciferase and puromycin resistance gene were injected into the tail-vein of immunocompromised NOD-SCID-IL2Rcγ$^{null}$ (NSG) mice. After 7 days, engraftment was documented by bioluminescence imaging and mice were treated with vehicle (20% 2-hydroxypropyl β-cyclodextrin), 0.05 and 0.16 mg/kg once daily for 15 days. Time after first treatment is indicated.
Figure 12B:
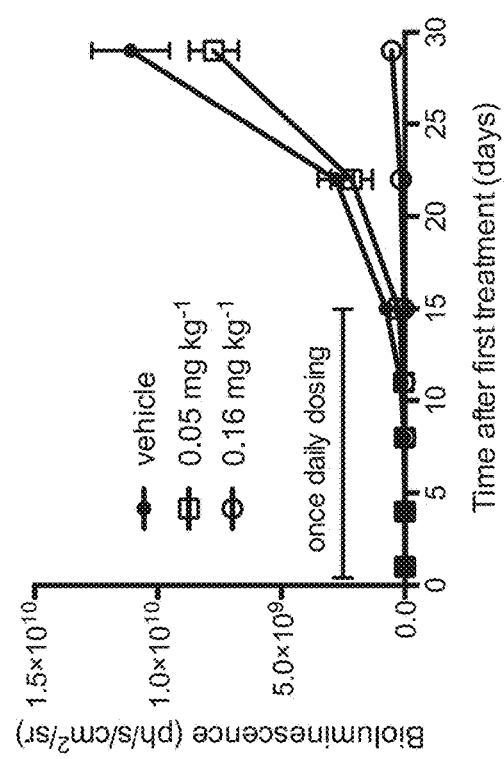
Figure 12C:
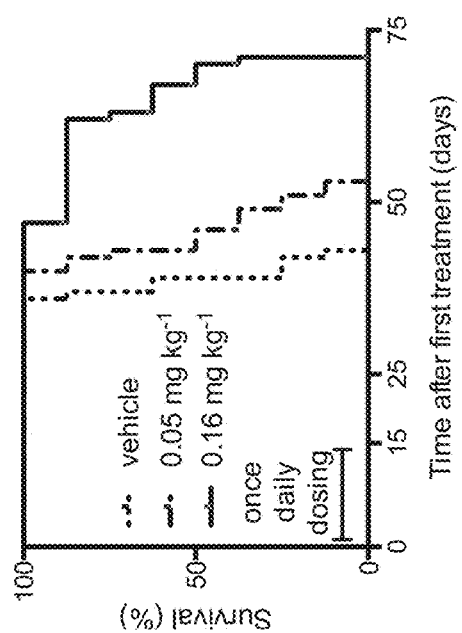
Figure 12F:
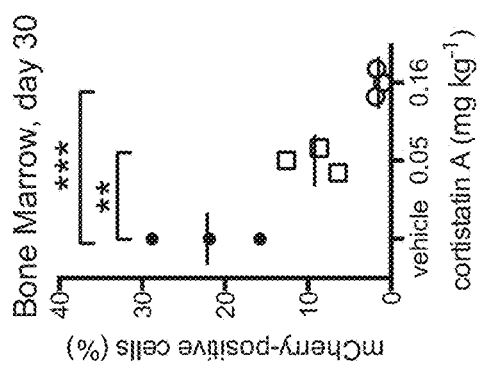
Figure 12E:
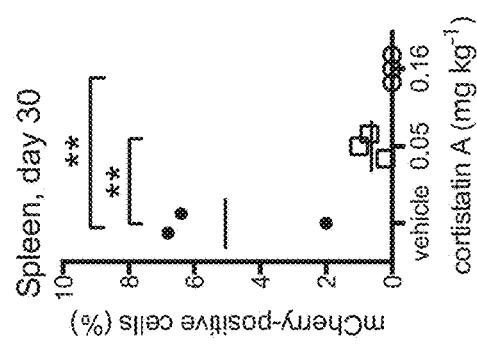
Figure 12D:
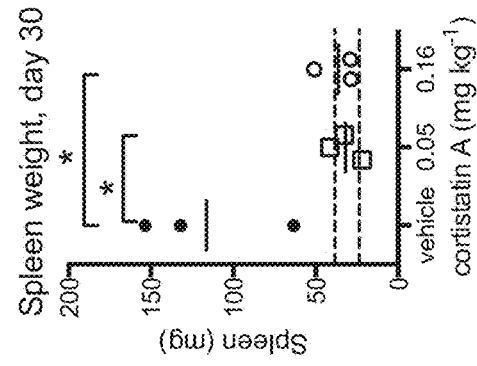
Figure 12G:
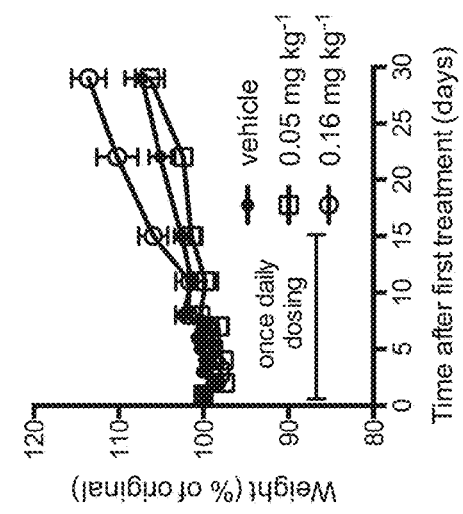

For pharmacokinetic studies with cortistatin A (CA), blood samples from CD-1 mice were collected at the indicated times following i.p. administration of cortistatin A at 10 mg kg$^{-1}$ (FIG. 11A) and 1 mg/kg (FIG. 11B) and analyzed by HPLC/MS/MS to evaluate the concentration of cortistatin A.

Figure 24A:
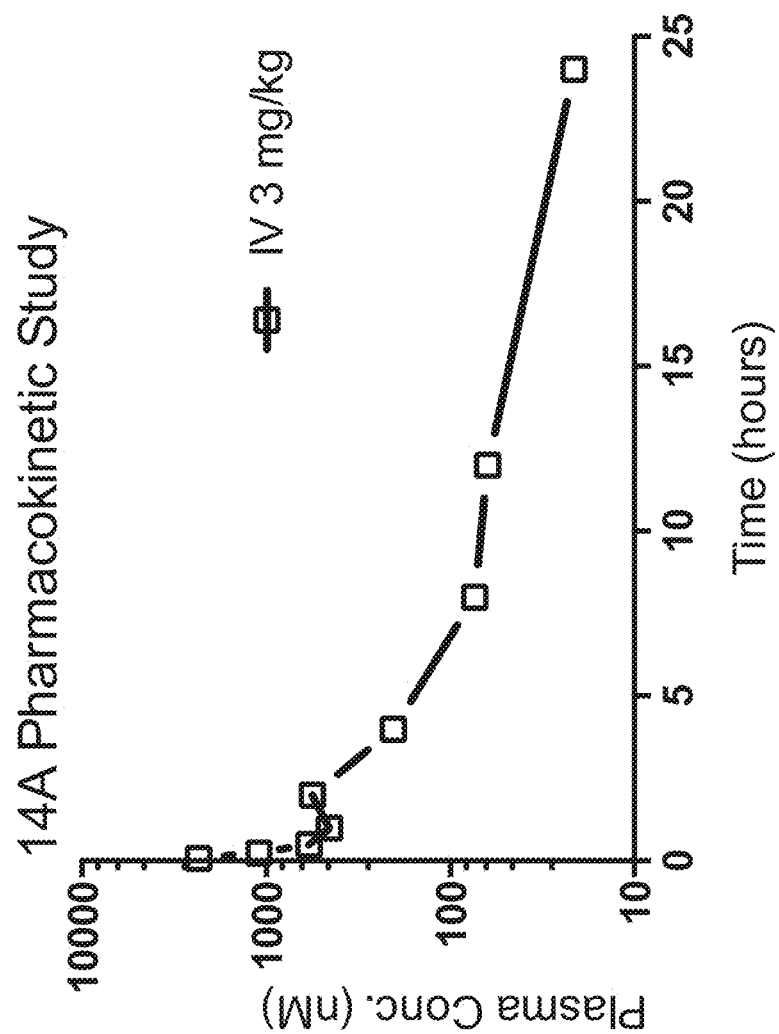
FIG. 24A, FIG. 24B, and FIG. 24C provides the results of a pharmacokinetic study with compound (14A) formulated in 20% hydroxypropyl-beta-cyclodextrin in male CD-1 mice given a single dose at 3 mg/kg IV (FIG. 24A), 3 mg/kg IP (FIG. 24B), or 10 mg/kg oral (PO) (FIG. 24C). Prior to dosing, mice were fasted overnight until 4 hours post-dosing. Blood samples were collected at the indicated timepoints and analyzed by HPLC/MS/MS to evaluate the concentration of (14A). The Cmax after oral dosing was 255 ng/mL after 2 hours, the calculated T ½ was approximately 5 hours, and the oral bioavailability was 44%. The IV clearance was 29/ml/min/kg, the Vss was 11.7 L/kg, and the IP bioavailability was 95%.
Figure 24B:
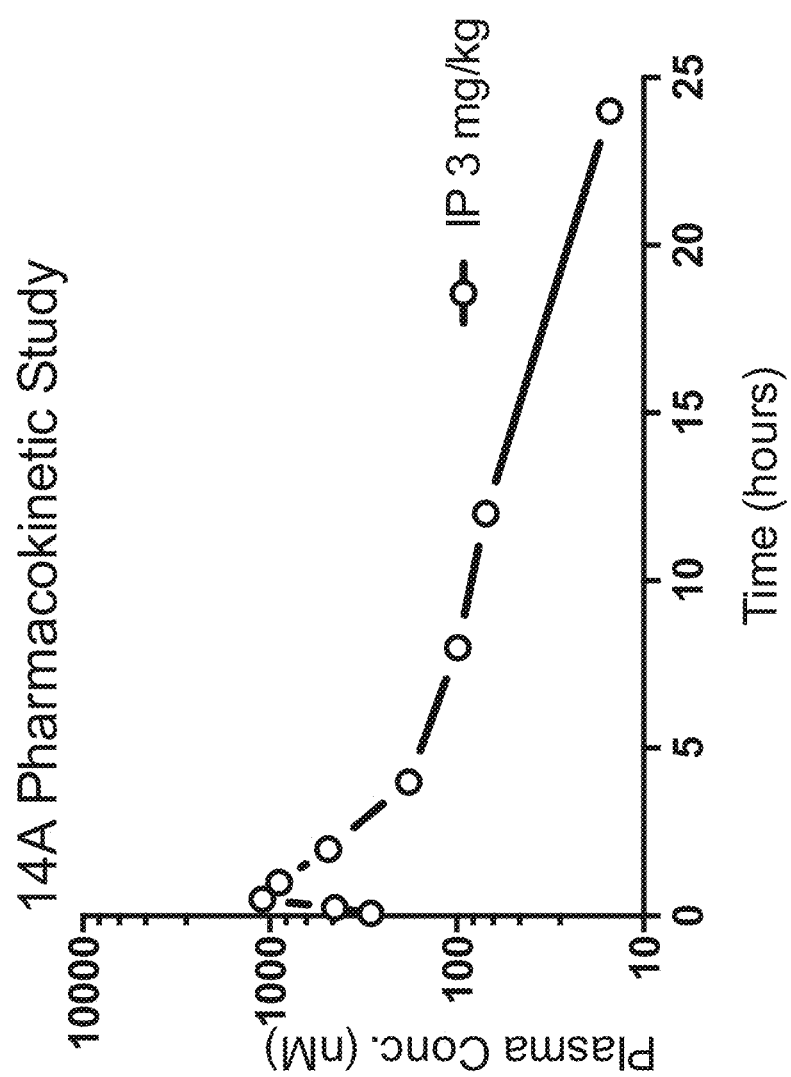
Figure 24C:
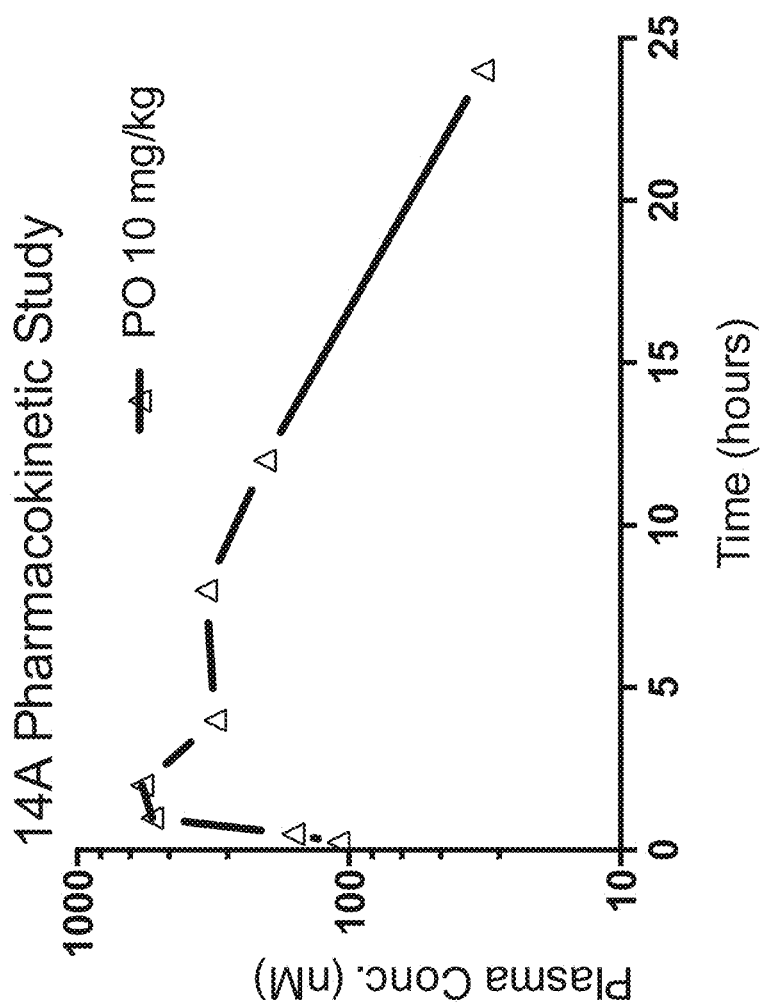

For pharmacokinetic studies with (14A), (14A) was formulated in 20% hydroxypropyl-beta-cyclodextrin (HPCD) and male CD-1 mice were given a single dose of 14A at 3 mg/kg i.p. and intravenous (i.v.) and 10 mg/kg oral (p.o.). Prior to dosing, mice were fasted overnight until 4 hours post-dosing. Blood samples were collected at the indicated timepoints and analyzed by HPLC/MS/MS to evaluate the concentration of (14A). See FIG. 24. From these studies, the following observations were made: (1) compound (14A) has an IV clearance in male CD-1 mice of 29 mL/min/kg, which is only $\frac{1}{3}^{rd}$ of hepatic blood flow in this species and indicates that (14A) has good stability; (2) the Vss is large (approximately 11.7 L/kg) so (14A) has good tissue distribution; (3) the oral bioavailability was found to be approximately 44%; (4) the Cmax after oral dosing was 255 ng/mL; (5) the t½ after oral dosing was approximately 5 hours (oral C24 trough concentrations were 14.2 ng/mL); and (5) IP bioavailability was 95%.

Figure 13A:
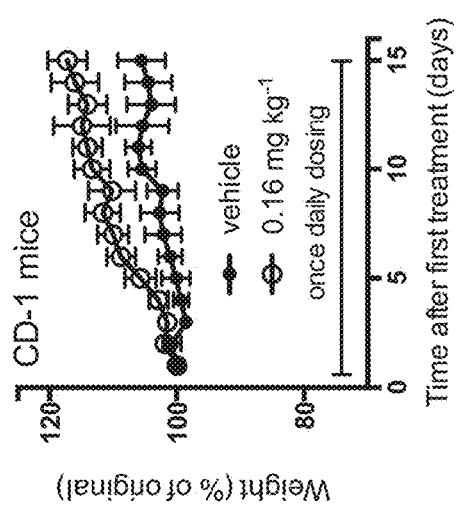
FIG. 13A and FIG. 13B, demonstrate cortistatin A is tolerated in healthy CD-1 mice. CD-1 mice were treated with the same dosing regimen as in FIG. 12 (once daily for 15 days) and body weight and complete blood count (CBC) were performed.
Figure 13B:
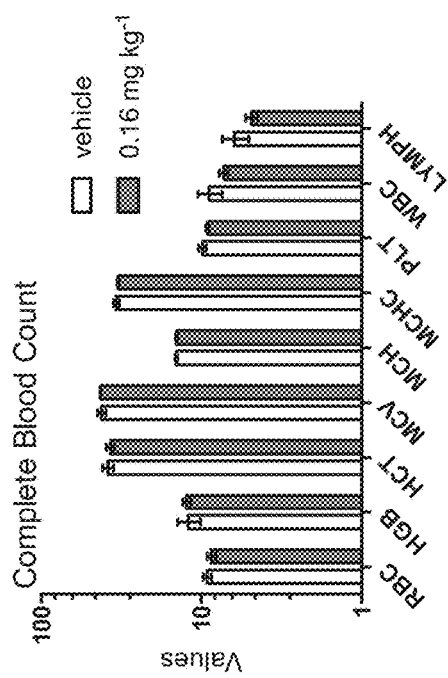

Efficacy studies using the MV4; 11 xenograft model were performed as previously described. See, e.g., Etchin et al., *Leukemia* (2013) 27, 66-74. Briefly, 2 million MV4;11 mCLP cells were introduced into 7-week-old female NOD-SCID-IL2Rcγ$^{null}$ (NSG) mice (The Jackson Laboratory) via tail vein injection. The tumor burden was assessed by bioluminescence imaging (BLI) using an IVIS Spectrum system (Caliper Life Sciences). 7 days-post injection, leukemia establishment was documented by BLI and the mice were split into treatment groups to receive either vehicle (20% hydroxypropyl-β-cyclodextrin) or cortistatin A (0.05 and 0.16 mg kg$^{-1}$) and treated once daily for 15 days. At 30 days post-treatment start date, 3 mice per group were sacrificed and blood counts were obtained using Hemavet 950 F instrument (Drew Scientific) and spleen, femur, and peripheral blood cells were collected and analyzed by flow cytometry (LSR Fortessa, BD Biosciences). The mice and a portion of the spleen were also preserved in bouins for histopathology. Mice were sectioned, paraffin-embedded and stained with hematoxylin and eosin. Survival of the drug-treated mice was measured as the time from initiation of therapy until moribund state. Survival benefit was assessed by Kaplan-Meier analysis. For safety testing with cortistatin A (FIG. 13), female CD-1 mice were treated with either vehicle (20% hydroxypropyl-β-cyclodextrin) or cortistatin A (0.16 mg kg$^{-1}$) once daily for 15 days and weighed daily. 2 h after the last dose, the mice were sacrificed, blood counts were obtained, blood chemistry was analyzed and the mice were fixed with bouins for histopathology. Efficacy studies using the murine model of primary myelofibrosis (MPLW515L mice) were performed as previously described (See, e.g., Marubayashi, et al., *J. Clin, Invest*. (2010) 120, 3578-3593) with once daily dosing with vehicle (20% hydroxypropyl-P3-cyclodextrin) or cortistatin A. For the efficacy studies using the SET-2 subcutaneous xenograft model, 1×10$^7$ SET-2 cells tumor cells in 50% matrigel were injected subcutaneously into the the flank of 8 to 12 week old female SCID Beige mice. Once tumors reached an average size of 80-120 mm$^3$, the mice were treated with vehicle or 0.16 mg kg$^1$ daily for the duration of the study.

Liver Microsome Metabolic Stability Assay

Test compounds were incubated at 37° C. with liver microsomes pooled from multiple donors at 1 micromolar in the presence of a NADPH regenerating system at 0.5 mg/ml microsomal protein. At 0, 5, 10, 20, 30, and 60 minutes, samples were removed, and mixed with cold acetonitrile containing an internal standard. After protein separation, samples were analyzed by LC/MS/MS for disappearance of the test compound using the ratio of peak area of analyte to internal standard. From the values, the microsome clearance was calculated. Species used were human, Sprague Dawley rat, beagle dog, and CD-1 mouse.

Human Hepatocyte Stability Assay

Test compounds were incubated in duplicate with cryo-preserved hepatocytes at 37° C. The cells were thawed; viable cells counted, and equilibrated according to the supplier's directions. After 30 min equilibration at 37° C. with gentle agitation, the test compounds were added into the cells to give the desired final concentration of 1 μM. The cell suspension was incubated at 37° C. as above. At the indicated times, samples were removed and mixed with an equal volume of ice-cold Stop Solution (acetonitrile containing internal standards). Stopped reactions were incubated at least ten minutes on ice, and an additional volume of water was added. The samples were centrifuged to remove precipitated protein, and the supernatants were analyzed by LC/MS/MS to quantitate the remaining parent. Data were converted to % remaining by dividing by the time zero concentration value. Data were fit to a first-order decay model to determine half-life. From a plot of log (ln) peak area against time, the slope of the line was determined. Subsequently, half-life and intrinsic clearance were calculated using the equations below: Elimination rate constant (k)=(−slope); Half-life (T½) min=0.693/k; Intrinsic Clearance (CLint) (ml/min/million cells)=(V×0.693)/T½; V=incubation volume ml/number of cells.

In Vitro Data

TABLE 4

| | MV4; 11 GI50 day 10 (nM) | MOL M14 GI50 day 10 (nM) | MV4; 11 GI50 day 7 (nM) | MOL M14 GI50 day 7 (nM) | MV 4; 11 GI50 day 3 (nM) | MOL M14 GI50 day 3 (nM) | MM. 1S GI50 day 10 (nM) | CDK8 Kinase inhibition (100 nM) | SET-2 GI50 day 10 (nM) | K562 GI50 day 10 (nM)* |
|---|---|---|---|---|---|---|---|---|---|---|
| CA | 4 | 5 | 9 | 9 | | | | + | | >1000 |
| racemic-12 | | | | | 600 | 1000 | | | | |
| racemic-17B | | | | | 600 | 600 | | | | |
| racemic-13 | | | | | 150 | 150 | | + | | |
| racemic-16B | | | | | 100 | 40 | 60 | + | | |
| racemic-14B | | | 10 | 20 | 60 | 20 | 40 | + | | |
| racemic-14A | | | 10 | 20 | | | | + | | |
| racemic-15B | | | | | 100 | 40 | 80 | + | | |
| 14ANO | 1.75 | 14 | | | | | | | | |
| 14B | 4 | 3 | 8 | 7 | | | | | | >1000 |
| 14BNO | 1 | 2 | | | | | | | | >1000 |
| 15A | 2.5 | 20 | | | | | | | 8 | |
| 15B | 12 | 12.5 | | | | | | | | >1000 |
| 16B | 8 | 9 | 15 | 17 | | | | | | >1000 |
| 17A | 1 | 6 | | | | | | | | |
| 18A | 1 | 3 | | | | | | | | |
| 18B | 13 | 13 | 20 | 25 | | | | | | >1000 |
| 19A | 1.5 | 5 | | | | | | | 0.4 | |
| 19B | 8 | 10 | 15 | 16 | | | | | | |
| 23B | 35 | 55 | | | | | | | | >1000 |
| 24A | 1 | 18 | | | | | | | 0.5 | |
| 24B | 20 | 50 | | | | | | | | |
| 26B | 4 | 6 | | | | | | | | |
| 27B | 7 | 10 | | | | | | | | |
| 28B | 9.5 | 15 | | | | | | | | |
| 29B | 7 | 14 | | | | | | | | |
| 30B | 20 | 55 | | | | | | | | |
| 31B | 75 | 100 | | | | | | | | |
| 32B | 27 | 55 | | | | | | | | |
| 33B | 22 | 60 | | | | | | | | |
| 34B | 8.5 | 15 | | | | | | | | |
| 35B | 80 | 160 | | | | | | | | |

TABLE 4-continued

Cell Growth Inhibition Data

| | MV 4;11 GI50 day 10 (nM) | MOL M14 GI50 day 10 (nM) | MV4;11 GI50 day 7 (nM) | MOL M14 GI50 day 7 (nM) | MV 4;11 GI50 day 3 (nM) | MOL M14 GI50 day 3 (nM) | MM.1S GI50 day 10 (nM) | CDK8 Kinase inhibition (100 nM) | SET-2 GI50 day 10 (nM) | K562 GI50 day 10 (nM)* |
|---|---|---|---|---|---|---|---|---|---|---|
| 36B | 19 | 95 | | | | | | | | |
| 37B | 65 | 200 | | | | | | | | |
| 38B | 10 | 10 | | | | | | | | |
| 39B | 17 | 30 | | | | | | | | |
| 40B | 16 | 25 | | | | | | | | |
| 41B | 8 | 16 | | | | | | | | |
| 42B | 7.5 | 20 | | | | | | | | |
| 43A | 175 | 200 | | | | | | | | |
| 43B | 95 | 150 | | | | | | | | |
| 46B | | | ** | ** | | | | | | |
| 49B | | | ** | ** | | | | | | |
| 50B | | | ** | ** | | | | | | |
| 55B | | | ** | ** | | | | | | |
| 58B | | | ** | ** | | | | | | |
| 61B | | | ** | ** | | | | | | |
| 62B | 20 | 70 | | | | | | | | |
| 62A | 0.4 | 5 | | | | | | | 0.45 | |
| 63A | 12 | 30 | | | | | | | | |
| 64A | 15 | 45 | | | | | | | | |
| 65B | 3 | 16 | | | | | | | | |
| 68A | 120 | 150 | | | | | | | | |
| 69A | 9.5 | 30 | | | | | | | | |
| 70A | 7 | 12 | | | | | | | | |
| 71B | 18 | 50 | | | | | | | | |
| 71A | 2 | 20 | | | | | | | | |
| 72A | 8 | 4 | | | | | | | | |
| 73A | 90 | 200 | | | | | | | | >1000 |
| 73B | 150 | 200 | | | | | | | | >1000 |
| 74A | 400 | 800 | | | | | | | | >1000 |

*lack of activity at inhibiting the proliferation of K562 is evidence that analogs are on-target and match the selective antiproliferative activity of CA.
** >1,000 nM, day 7.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a myeloproliferative disorder, comprising administering to a subject in need thereof a compound of formula

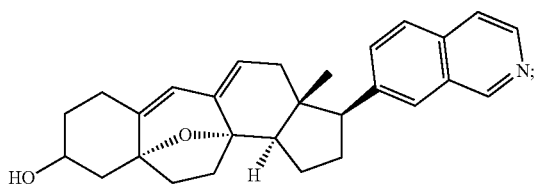 [SMILES: C[C@]12CC=C3C=C4CCC(O)C[C@]45CC[C@]3(O5)[C@@H]1CC[C@@H]2c1ccc2ccncc2c1]

or a pharmaceutically acceptable salt thereof, wherein the compound or pharmaceutically acceptable salt thereof is optionally in a pharmaceutical composition.

2. The method of claim 1, wherein the subject is a human.

3. The method of claim 2, wherein the myeloproliferative disorder is a hematopoietic cancer.

4. The method of claim 3, wherein the hematopoietic cancer is multiple myeloma.

5. The method of claim 3, wherein the hematopoietic cancer is lymphoma or leukemia.

6. The method of claim 5, wherein the leukemia is acute myelocytic leukemia (AML).

7. The method of claim 2, wherein the compound is

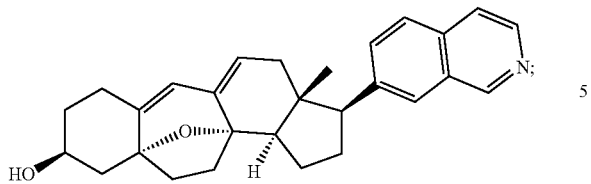

or a pharmaceutically acceptable salt thereof.

8. The method of claim 2, wherein the compound is

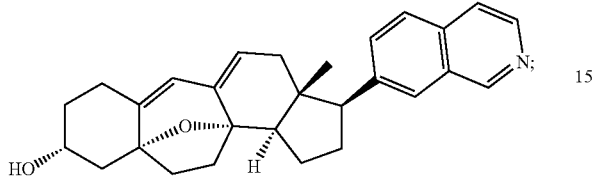

or a pharmaceutically acceptable salt thereof.

9. The method of claim 8, wherein the myeloproliferative disorder is a hematopoietic cancer.

10. The method of claim 9, wherein the hematopoietic cancer is multiple myeloma.

11. The method of claim 9, wherein the hematopoietic cancer is lymphoma or leukemia.

12. The method of claim 11, wherein the leukemia is acute myelocytic leukemia (AML).

* * * * *

SEQUENCE LISTING

<160> NUMBER OF SEQ ID NOS: 16

<210> SEQ ID NO 1
<211> LENGTH: 464
<212> TYPE: PRT
<213> ORGANISM: Homo sapiens

<400> SEQUENCE: 1

Met Asp Tyr Asp Phe Lys Val Lys Leu Ser Ser Glu Arg Glu Arg Val
1               5                   10                  15

Glu Asp Leu Phe Glu Tyr Glu Gly Cys Lys Val Gly Arg Gly Thr Tyr
            20                  25                  30

Gly His Val Tyr Lys Ala Lys Arg Lys Asp Gly Lys Asp Asp Lys Asp
        35                  40                  45

Tyr Ala Leu Lys Gln Ile Glu Gly Thr Gly Ile Ser Met Ser Ala Cys
    50                  55                  60

Arg Glu Ile Ala Leu Leu Arg Glu Leu Lys His Pro Asn Val Ile Ser
65                  70                  75                  80

Leu Gln Lys Val Phe Leu Ser His Ala Asp Arg Lys Val Trp Leu Leu
                85                  90                  95

Phe Asp Tyr Ala Glu His Asp Leu Trp His Ile Ile Lys Phe His Arg
            100                 105                 110

Ala Ser Lys Ala Asn Lys Lys Pro Val Gln Leu Pro Arg Gly Met Val
        115                 120                 125

Lys Ser Leu Leu Tyr Gln Ile Leu Asp Gly Ile His Tyr Leu His Ala
    130                 135                 140

Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
                165                 170                 175

Ala Arg Leu Phe Asn Ser Pro Leu Lys Pro Leu Ala Asp Leu Asp Pro
            180                 185                 190

Val Val Val Thr Phe Trp Tyr Arg Ala Pro Glu Leu Leu Leu Gly Ala
        195                 200                 205

Arg His Tyr Thr Lys Ala Ile Asp Ile Trp Ala Ile Gly Cys Ile Phe
    210                 215                 220

Ala Glu Leu Leu Thr Ser Glu Pro Ile Phe His Cys Arg Gln Glu Asp
225                 230                 235                 240

Ile Lys Thr Ser Asn Pro Tyr His His Asp Gln Leu Asp Arg Ile Phe
                245                 250                 255

Asn Val Met Gly Phe Pro Ala Asp Lys Asp Trp Glu Asp Ile Lys Lys
            260                 265                 270

Met Pro Glu His Ser Thr Leu Met Lys Asp Phe Arg Arg Asn Thr Tyr
        275                 280                 285

Thr Asn Cys Ser Leu Ile Lys Tyr Met Glu Lys His Lys Val Lys Pro
    290                 295                 300

Asp Ser Lys Ala Phe His Leu Leu Gln Lys Leu Leu Thr Met Asp Pro
305                 310                 315                 320

Ile Lys Arg Ile Thr Ser Glu Gln Ala Met Gln Asp Pro Tyr Phe Leu
                325                 330                 335

Glu Asp Pro Leu Pro Thr Ser Asp Val Phe Ala Gly Cys Gln Ile Pro
            340                 345                 350

Tyr Pro Lys Arg Glu Phe Leu Thr Glu Glu Pro Asp Asp Lys Gly
        355                 360                 365

```
Asp Lys Lys Asn Gln Gln Gln Gln Gly Asn Asn His Thr Asn Gly
    370             375                 380

Thr Gly His Pro Gly Asn Gln Asp Ser Ser His Thr Gln Gly Pro Pro
385             390                 395                 400

Leu Lys Lys Val Arg Val Val Pro Pro Thr Thr Thr Ser Gly Gly Leu
                405             410                 415

Ile Met Thr Ser Asp Tyr Gln Arg Ser Asn Pro His Ala Ala Tyr Pro
                420             425                 430

Asn Pro Gly Pro Ser Thr Ser Gln Pro Gln Ser Ser Met Gly Tyr Ser
                435             440                 445

Ala Thr Ser Gln Gln Pro Pro Gln Tyr Ser His Gln Thr His Arg Tyr
450             455                 460

<210> SEQ ID NO 2
<211> LENGTH: 502
<212> TYPE: PRT
<213> ORGANISM: Homo sapiens

<400> SEQUENCE: 2

Met Asp Tyr Asp Phe Lys Ala Lys Leu Ala Ala Glu Arg Glu Arg Val
1               5                   10                  15

Glu Asp Leu Phe Glu Tyr Glu Gly Cys Lys Val Gly Arg Gly Thr Tyr
                20                  25                  30

Gly His Val Tyr Lys Ala Arg Arg Lys Asp Gly Lys Asp Glu Lys Glu
            35                  40                  45

Tyr Ala Leu Lys Gln Ile Glu Gly Thr Gly Ile Ser Met Ser Ala Cys
    50                  55                  60

Arg Glu Ile Ala Leu Leu Arg Glu Leu Lys His Pro Asn Val Ile Ala
65                  70                  75                  80

Leu Gln Lys Val Phe Leu Ser His Ser Asp Arg Lys Val Trp Leu Leu
                85                  90                  95

Phe Asp Tyr Ala Glu His Asp Leu Trp His Ile Ile Lys Phe His Arg
                100                 105                 110

Ala Ser Lys Ala Asn Lys Lys Pro Met Gln Leu Pro Arg Ser Met Val
            115                 120                 125

Lys Ser Leu Leu Tyr Gln Ile Leu Asp Gly Ile His Tyr Leu His Ala
    130                 135                 140

Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
                165                 170                 175

Ala Arg Leu Phe Asn Ser Pro Leu Lys Pro Leu Ala Asp Leu Asp Pro
                180                 185                 190

Val Val Val Thr Phe Trp Tyr Arg Ala Pro Glu Leu Leu Leu Gly Ala
            195                 200                 205

Arg His Tyr Thr Lys Ala Ile Asp Ile Trp Ala Ile Gly Cys Ile Phe
    210                 215                 220

Ala Glu Leu Leu Thr Ser Glu Pro Ile Phe His Cys Arg Gln Glu Asp
225                 230                 235                 240

Ile Lys Thr Ser Asn Pro Phe His His Asp Gln Leu Asp Arg Ile Phe
                245                 250                 255

Ser Val Met Gly Phe Pro Ala Asp Lys Asp Trp Glu Asp Ile Arg Lys
                260                 265                 270

Met Pro Glu Tyr Pro Thr Leu Gln Lys Asp Phe Arg Arg Thr Thr Tyr
            275                 280                 285
```

```
Ala Asn Ser Ser Leu Ile Lys Tyr Met Glu Lys His Lys Val Lys Pro
    290                 295                 300
Asp Ser Lys Val Phe Leu Leu Gln Lys Leu Leu Thr Met Asp Pro
305                 310                 315                 320
Thr Lys Arg Ile Thr Ser Glu Gln Ala Leu Gln Asp Pro Tyr Phe Gln
                325                 330                 335
Glu Asp Pro Leu Pro Thr Leu Asp Val Phe Ala Gly Cys Gln Ile Pro
            340                 345                 350
Tyr Pro Lys Arg Glu Phe Leu Asn Glu Asp Pro Glu Glu Lys Gly
        355                 360                 365
Asp Lys Asn Gln Gln Gln Gln Asn Gln His Gln Gln Pro Thr Ala
    370                 375                 380
Pro Pro Gln Gln Ala Ala Ala Pro Pro Gln Ala Pro Pro Gln Gln
385                 390                 395                 400
Asn Ser Thr Gln Thr Asn Gly Thr Ala Gly Gly Ala Gly Val
                405                 410                 415
Gly Gly Thr Gly Ala Gly Leu Gln His Ser Gln Asp Ser Ser Leu Asn
                420                 425                 430
Gln Val Pro Pro Asn Lys Lys Pro Arg Leu Gly Pro Ser Gly Ala Asn
            435                 440                 445
Ser Gly Gly Pro Val Met Pro Ser Asp Tyr Gln His Ser Ser Ser Arg
    450                 455                 460
Leu Asn Tyr Gln Ser Ser Val Gln Gly Ser Ser Gln Ser Gln Ser Thr
465                 470                 475                 480
Leu Gly Tyr Ser Ser Ser Ser Gln Gln Ser Ser Gln Tyr His Pro Ser
                485                 490                 495
His Gln Ala His Arg Tyr
            500

<210> SEQ ID NO 3
<211> LENGTH: 20
<212> TYPE: DNA
<213> ORGANISM: Artificial Sequence
<220> FEATURE:
<223> OTHER INFORMATION: 1st round 5' EcoRI CDK8 Primer

<400> SEQUENCE: 3
gaattcgcca ccatggacta                                          20

<210> SEQ ID NO 4
<211> LENGTH: 23
<212> TYPE: DNA
<213> ORGANISM: Artificial Sequence
<220> FEATURE:
<223> OTHER INFORMATION: 1st round 3' XbaI CDK8 Primer

<400> SEQUENCE: 4
tctagatcag taccgatgtg tct                                      23

<210> SEQ ID NO 5
<211> LENGTH: 21
<212> TYPE: DNA
<213> ORGANISM: Artificial Sequence
<220> FEATURE:
<223> OTHER INFORMATION: 2nd round 5' EcoRI CDK8 Primer

<400> SEQUENCE: 5
tagctagaat tcgccaccat g                                        21
```

<210> SEQ ID NO 6
<211> LENGTH: 21
<212> TYPE: DNA
<213> ORGANISM: Artificial Sequence
<220> FEATURE:
<223> OTHER INFORMATION: 2nd round 3' XbaI CDK8 Primer

<400> SEQUENCE: 6
gtcgagtcta gatcagtacc g                                     21

<210> SEQ ID NO 7
<211> LENGTH: 23
<212> TYPE: DNA
<213> ORGANISM: Artificial Sequence
<220> FEATURE:
<223> OTHER INFORMATION: 1st round 5' SpeI CDK19 Primer

<400> SEQUENCE: 7
actagtatgc cagactacaa gga                                   23

<210> SEQ ID NO 8
<211> LENGTH: 20
<212> TYPE: DNA
<213> ORGANISM: Artificial Sequence
<220> FEATURE:
<223> OTHER INFORMATION: 1st round 3' XbaI CDK19 Primer

<400> SEQUENCE: 8
tctagatcag taccggtggg                                       20

<210> SEQ ID NO 9
<211> LENGTH: 21
<212> TYPE: DNA
<213> ORGANISM: Artificial Sequence
<220> FEATURE:
<223> OTHER INFORMATION: 2nd round 5' SpeI CDK19 Primer

<400> SEQUENCE: 9
gtcgagacta gtatgccaga c                                     21

<210> SEQ ID NO 10
<211> LENGTH: 21
<212> TYPE: DNA
<213> ORGANISM: Artificial Sequence
<220> FEATURE:
<223> OTHER INFORMATION: 2nd round 3' XbaI CDK19 Primer

<400> SEQUENCE: 10
tcgagtctag atcagtaccg g                                     21

<210> SEQ ID NO 11
<211> LENGTH: 21
<212> TYPE: DNA
<213> ORGANISM: Artificial Sequence
<220> FEATURE:
<223> OTHER INFORMATION: EF1alpha forward Primer

<400> SEQUENCE: 11
tcaagcctca gacagtggtt c                                     21

<210> SEQ ID NO 12
<211> LENGTH: 19
<212> TYPE: DNA
<213> ORGANISM: Artificial Sequence
<220> FEATURE:
<223> OTHER INFORMATION: IRES reverse Primer

```
<400> SEQUENCE: 12
acgtgtataa gatacacct                                               19

<210> SEQ ID NO 13
<211> LENGTH: 40
<212> TYPE: DNA
<213> ORGANISM: Artificial Sequence
<220> FEATURE:
<223> OTHER INFORMATION: CDK8 W105M: Trp105 (TGG)--->Met (ATG) (forward)
      Primer

<400> SEQUENCE: 13
ctatgctgaa catgacctca tgcatataat caagtttcac                        40

<210> SEQ ID NO 14
<211> LENGTH: 40
<212> TYPE: DNA
<213> ORGANISM: Artificial Sequence
<220> FEATURE:
<223> OTHER INFORMATION: CDK8 W105M: Trp105 (TGG)--->Met (ATG) (reverse)
      Primer

<400> SEQUENCE: 14
gtgaaacttg attatatgca tgaggtcatg ttcagcatag                        40

<210> SEQ ID NO 15
<211> LENGTH: 37
<212> TYPE: DNA
<213> ORGANISM: Artificial Sequence
<220> FEATURE:
<223> OTHER INFORMATION: CDK19 W105M: Trp105 (TGG)--->Met (ATG)
      (forward) Primer

<400> SEQUENCE: 15
gcagagcatg acttgatgca tattattaag tttcacc                           37

<210> SEQ ID NO 16
<211> LENGTH: 37
<212> TYPE: DNA
<213> ORGANISM: Artificial Sequence
<220> FEATURE:
<223> OTHER INFORMATION: CDK19 W105M: Trp105 (TGG)--->Met (ATG)
      (reverse) Primer

<400> SEQUENCE: 16
ggtgaaactt aataatatgc atcaagtcat gctctgc                           37
```